US011787844B2

(12) United States Patent
Salanti et al.

(10) Patent No.: US 11,787,844 B2
(45) Date of Patent: Oct. 17, 2023

(54) TARGETING OF CHONDROITIN SULFATE GLYCANS

(71) Applicant: VAR2 PHARMACEUTICALS APS, Copenhagen (DK)

(72) Inventors: Ali Salanti, Bronshoj (DK); Thor Grundtvig Theander, Greve (DK); Mads Daugaard, Vancouver (CA); Morten Nielsen, Birkerod (DK); Madeleine Dahlback, Swedala (SE); Thomas Mandel Clausen, Copenhagen (DK)

(73) Assignee: VAR2 Pharmaceuticals APS, Kobenhavn N (DK)

( * ) Notice: Subject to any disclaimer, the term of this patent is extended or adjusted under 35 U.S.C. 154(b) by 87 days.

(21) Appl. No.: 14/376,295

(22) PCT Filed: Feb. 8, 2013

(86) PCT No.: PCT/EP2013/052557
§ 371 (c)(1),
(2) Date: Aug. 1, 2014

(87) PCT Pub. No.: WO2013/117705
PCT Pub. Date: Aug. 15, 2013

(65) Prior Publication Data
US 2015/0004099 A1 Jan. 1, 2015

Related U.S. Application Data

(60) Provisional application No. 61/596,931, filed on Feb. 9, 2012.

(51) Int. Cl.
*A61K 39/015* (2006.01)
*A61K 35/68* (2006.01)
*C07K 14/445* (2006.01)
*G01N 33/574* (2006.01)
*A61K 38/16* (2006.01)
*A61K 38/45* (2006.01)
*A61K 49/00* (2006.01)
*A61K 51/08* (2006.01)
(Continued)

(52) U.S. Cl.
CPC ............ *C07K 14/445* (2013.01); *A61K 35/68* (2013.01); *A61K 38/16* (2013.01); *A61K 38/45* (2013.01); *A61K 39/015* (2013.01); *A61K 49/00* (2013.01); *A61K 49/0056* (2013.01); *A61K 51/088* (2013.01); *C07K 14/21* (2013.01); *C07K 14/34* (2013.01); *G01N 33/574* (2013.01); *G01N 33/57484* (2013.01); *A61K 38/00* (2013.01); *C07K 2319/33* (2013.01); *C12Y 204/02036* (2013.01); *G01N 2333/47* (2013.01); *G01N 2333/70585* (2013.01)

(58) Field of Classification Search
CPC .. C07K 2319/33; C07K 14/34; C07K 14/445; C07K 16/205; C07K 2317/33; C07K 16/084; C07K 2317/21; C07K 2317/622; C07K 2319/03; C07K 2319/21; C07K 2319/42; C07K 38/00; C07K 38/16; C07K 38/45; C07K 49/00; C07K 49/0056; C07K 51/088; C07K 39/015; C07K 2039/5158; C07K 2039/6075; C07K 35/17; C07K 35/76; C07K 39/0011; C07K 47/6803; C07K 47/6851; C07K 9/0019; C07K 14/21; G01N 2333/47; G01N 33/574; G01N 2333/70585; G01N 33/57484; G01N 33/56905; A61K 38/00; A61K 38/16; A61K 38/45; A61K 49/00; A61K 51/088; A61K 49/0056; A61K 39/015; A61K 2039/5158; A61K 2039/6075; A61K 35/17; A61K 35/76; A61K 39/0011; A61K 47/6803; A61K 47/6851; A61K 9/0019; C12Y 204/02036; A61P 35/00; Y02A 50/412; C12N 2710/20023; C12N 2710/20033
See application file for complete search history.

(56) References Cited

U.S. PATENT DOCUMENTS 5,225,584 A * 7/1993 Brooks ............... C07C 43/1747
549/221
7,253,333 B2 8/2007 Tanaka et al.
(Continued)

FOREIGN PATENT DOCUMENTS

| WO | WO 2004/067559 A1 | 8/2004 |
| WO | WO 2006/039652 A2 | 4/2006 |
| WO | WO 2012/014073 A2 | 2/2012 |

OTHER PUBLICATIONS

Farah HF. MedCrave J. Anal. Pharm. Res. 3: Jan. 10-Oct. 10, 2016.*
(Continued)

*Primary Examiner* — S. Devi
(74) *Attorney, Agent, or Firm* — Womble Bond Dickinson (US) LLP

(57) ABSTRACT

The present invention relates to functional binding fragments comprising the minimal binding fragments of VAR2CSA, to antibodies against such binding fragments of VAR2CSA, nucleic acids encoding such fragments of VAR2CSA as well as methods for their production. The invention further relates to conjugates and fusion proteins of VAR2CSA polypeptides including the minimal binding fragments and their use, in particular in the treatment of conditions associated with expression of chondroitin sulfate A (CSA), such as an inappropriate expression of chondroitin sulfate A (CSA).

13 Claims, No Drawings

Specification includes a Sequence Listing.

(51) Int. Cl.
  C07K 14/21    (2006.01)
  C07K 14/34    (2006.01)
  A61K 38/00    (2006.01)

(56) References Cited

U.S. PATENT DOCUMENTS

| | | | | |
|---|---|---|---|---|
| 7,745,580 | B2 | 6/2010 | Theander et al. | |
| 2004/0062769 | A1* | 4/2004 | Scherf | C07K 14/445 424/151.1 |
| 2006/0094649 | A1 | 5/2006 | Keogh et al. | |
| 2007/0053928 | A1* | 3/2007 | Theander | C07K 16/205 424/191.1 |
| 2009/0130136 | A1* | 5/2009 | Miller | C07K 14/445 424/192.1 |
| 2012/0277109 | A1* | 11/2012 | Singh | G01N 33/5011 506/9 |
| 2013/0129767 | A1* | 5/2013 | Tuikue Ndam | A61K 39/015 424/191.1 |
| 2014/0294930 | A1* | 10/2014 | Nizet | A61K 39/092 424/450 |

OTHER PUBLICATIONS

Oyewumi et al. Expert Rev. Vaccines 9: 1095-1107, 2010.*
Gangnard et al. J. Mol. Biol. 425: 1697-1711, ePub Feb. 18, 2013.*
O'Hagan et al. Methods 40: 10-19, 2006.*
Tayapiwatana et al. J. Immunol. Methods 317: 1-11, 2006.*
Fernandez et al. PLoS One 5: e12558, pp. 1-8, 2010.*
Chandrawanshi et al. J. Pharmacy Res. 2: 964-966, 2009.*
Skolnick et al. Trends in Biotechnology, 18: 34-39, 2000.*
Rudinger J. In: Peptide Hormones. (Ed) JA Parsons, University Park Press, pp. 1-7, 1976.*
Lazar et al. Mol. Cellular Biol. 8: 1247-1252, 1988.*
Document entitled Reconsideration Report by Examiner before Appeal, Jan. 5, 2018, pp. 1-2.*
Greenspan et al. Nature Biotechnology 17: 936-937, 1999.*
Alkhalil, A., et al., "Structural Requirements for the Adherence of *Plasmodium falciparum*-infected Erythrocytes to Chondroitin Sulfate Proteoglycans of Human Placenta," *The Journal Of Biological Chemistry*, 2000, vol. 275(51), pp. 40357-40364.
Avril, M., et al., "Antibodies to a Full-Length VAR2CSA Immunogen Are Broadly Strain-Transcendent but Do Not Cross-Inhibit Different Placental-Type Parasite Isolates," *PloS ONE*, 2011, vol. 6(2), pp. 1-10.
Bigey, P., et al., "The NTS-DBL2X Region of VAR2CSA Induces Cross-Reactive Antibodies That Inhibit Adehsion of Several *Plasmodium falciparum* Isolates to Chondroitin Sulfate A," *The Journal of Infectious Diseases*, 2011, vol. 204(7), pp. 1125-1133.
Bordbar, B., et al., "Identification of Id1-DBL2X of VAR2CSA as a key domain inducing highly inhibitory and cross-reactive antibodies," *Vaccine*, 2012, vol. 30, pp. 1343-1348.
Cardin, A., et anon., "Molecular Modeling of Protein-Glycosaminoglycan Interactions," *Arterioscler Throm Vasc Biol.*, 1989, vol. 9(1), pp. 21-32.
Clausen, T., et al., "Structural and Functional Insight into How the *Plasmodium falciparum* VAR2CSA Protein Mediates Binding to Chondroitin Sulfate A in Plancental Malaria," *Journal of Biological Chemisty*, 2012, vol. 287(28), pp. 23332-23345.
Dahlbäck, M., et al., "The Condroitin Sulfate A-binding Site of the VAR2CSA Protein Involves Multiple N-terminal Domains," *The Journal of Biological Chemistry*, 2011, vol. 286(18), pp. 15908-15917.
Faller, B., et al., "Heparin-Induced Confomational Change and Activation of Mucus Proteinase Inhibitor," *Biochemistry*, 1992, vol. 31, pp. 8285-8290.
Hileman, R., et al., "Glycosaminoglycan-protein interactions: definition of consensus sites in glycosaminoglycan binding proteins," *BioEssays*, 1998, vol. 20, pp. 156-167.
Khunrae, P., et al., "Full-Length Recombinant *Plasmodium falciparum* VAR2CSA Binds Specifically to CSPG and Induces Potent Parasite Adhesion-Blocking Antibodies," *J Mol Biol.*, 2010, vol. 397(3), pp. 826-834.
Resende, M., et al., "Chondroitin sulphate A (CSA)-binding of single recombinant Duffy-binding-like domains is not restricted to *Plasmodium falciparum* Erythrocyte Membrane Protein 1 expressed by CSA-binding parasites," *International Journal for Parasitology*, 2009, vol. 39(11), pp. 1195-1204.
Salanti, A., et al., "Selective upregulation of a single distinctly structured var gene in chondroitin sulphate A-adhering *Plasmodium falciparum* involved in pregnancy-associated malaria," *Molecular Microbiology*, 2003, vol. 49(1), pp. 179-191.
Sander, A., et al., "Multiple var2csa-Type PfEMP1 Genes Located at Different Chromosomal Loci Occur in Many *Plasmodium falciparum* Isolates," *PloS ONE*, 2009, vol. 4(8), pp. 1-12.
Srivastava, A., et al., "Full-length extracellular region of the var2CSA variant of PfEMP1 is required for specific, high-affinity binding to CSA," *PNAS*, 2010, vol. 107(11), pp. 4884-4889.
Srivastava, A., et al., "Var2CSA Minimal CSA Binding Region Is Located within the N-Terminal Region," *PloS ONE*, 2011, vol. 6(5), pp. 1-10.
Trimnell, A., et al., "Global genetic diversity and evolution of var genes associated with placental and severe childhood malaria," *Molecular & Biochemical Parasitology*, 2006, vol. 148, pp. 169-180.

* cited by examiner

```
                          SEQUENCE LISTING

<160> NUMBER OF SEQ ID NOS: 132

<210> SEQ ID NO 1
   <211> LENGTH: 640
   <212> TYPE: PRT
   <213> ORGANISM: Artificial
   <220> FEATURE:
   <223> OTHER INFORMATION: Artificial construct

<400> SEQUENCE: 1

Asn Tyr Ile Lys Gly Asp Pro Tyr Phe Ala Glu Tyr Ala Thr Lys Leu
   1               5                   10                  15

Ser Phe Ile Leu Asn Pro Ser Asp Ala Asn Asn Pro Ser Gly Glu Thr
                   20                  25                  30

Ala Asn His Asn Asp Glu Ala Cys Asn Cys Asn Glu Ser Gly Ile Ser
               35                  40                  45

Ser Val Gly Gln Ala Gln Thr Ser Gly Pro Ser Ser Asn Lys Thr Cys
       50                  55                  60

Ile Thr His Ser Ser Ile Lys Thr Asn Lys Lys Lys Glu Cys Lys Asp
   65                  70                  75                  80

Val Lys Leu Gly Val Arg Glu Asn Asp Lys Asp Leu Lys Ile Cys Val
                   85                  90                  95

Ile Glu Asp Thr Ser Leu Ser Gly Val Asp Asn Cys Cys Cys Gln Asp
               100                 105                 110

Leu Leu Gly Ile Leu Gln Glu Asn Cys Ser Asp Asn Lys Arg Gly Ser
               115                 120                 125

Ser Ser Asn Asp Ser Cys Asp Asn Lys Asn Gln Asp Glu Cys Gln Lys
       130                 135                 140

Lys Leu Glu Lys Val Phe Ala Ser Leu Thr Asn Gly Tyr Lys Cys Asp
   145                 150                 155                 160

Lys Cys Lys Ser Gly Thr Ser Arg Ser Lys Lys Lys Trp Ile Trp Lys
                   165                 170                 175

Lys Ser Ser Gly Asn Glu Glu Gly Leu Gln Glu Glu Tyr Ala Asn Thr
               180                 185                 190

Ile Gly Leu Pro Pro Arg Thr Gln Ser Leu Tyr Leu Gly Asn Leu Pro
               195                 200                 205

Lys Leu Glu Asn Val Cys Glu Asp Val Lys Asp Ile Asn Phe Asp Thr
       210                 215                 220

Lys Glu Lys Phe Leu Ala Gly Cys Leu Ile Val Ser Phe His Glu Gly
   225                 230                 235                 240

Lys Asn Leu Lys Lys Arg Tyr Pro Gln Asn Lys Asn Ser Gly Asn Lys
                   245                 250                 255
```

Glu Asn Leu Cys Lys Ala Leu Glu Tyr Ser Phe Ala Asp Tyr Gly Asp
            260                 265                 270

Leu Ile Lys Gly Thr Ser Ile Trp Asp Asn Glu Tyr Thr Lys Asp Leu
275                 280                 285

Glu Leu Asn Leu Gln Asn Asn Phe Gly Lys Leu Phe Gly Lys Tyr Ile
        290                 295                 300

Lys Lys Asn Asn Thr Ala Glu Gln Asp Thr Ser Tyr Ser Ser Leu Asp
305                 310                 315                 320

Glu Leu Arg Glu Ser Trp Trp Asn Thr Asn Lys Lys Tyr Ile Trp Thr
            325                 330                 335

Ala Met Lys His Gly Ala Glu Met Asn Ile Thr Thr Cys Asn Ala Asp
                340                 345                 350

Gly Ser Val Thr Gly Ser Gly Ser Ser Cys Asp Asp Ile Pro Thr Ile
            355                 360                 365

Asp Leu Ile Pro Gln Tyr Leu Arg Phe Leu Gln Glu Trp Val Glu Asn
370                 375                 380

Phe Cys Glu Gln Arg Gln Ala Lys Val Lys Asp Val Ile Thr Asn Cys
385                 390                 395                 400

Lys Ser Cys Lys Glu Ser Gly Asn Lys Cys Lys Thr Glu Cys Lys Thr
                405                 410                 415

Lys Cys Lys Asp Glu Cys Glu Lys Tyr Lys Lys Phe Ile Glu Ala Cys
            420                 425                 430

Gly Thr Ala Gly Gly Ile Gly Thr Ala Gly Ser Pro Trp Ser Lys
            435                 440                 445

Arg Trp Asp Gln Ile Tyr Lys Arg Tyr Ser Lys His Ile Glu Asp Ala
    450                 455                 460

Lys Arg Asn Arg Lys Ala Gly Thr Lys Asn Cys Gly Thr Ser Ser Thr
465                 470                 475                 480

Thr Asn Ala Ala Ala Ser Thr Asp Glu Asn Lys Cys Val Gln Ser Asp
                485                 490                 495

Ile Asp Ser Phe Phe Lys His Leu Ile Asp Ile Gly Leu Thr Thr Pro
            500                 505                 510

Ser Ser Tyr Leu Ser Asn Val Leu Asp Asp Asn Ile Cys Gly Ala Asp
            515                 520                 525

Lys Ala Pro Trp Thr Thr Tyr Thr Thr Tyr Thr Thr Thr Glu Lys Cys
530                 535                 540

Asn Lys Glu Arg Asp Lys Ser Lys Ser Gln Ser Ser Asp Thr Leu Val
545                 550                 555                 560

Val Val Asn Val Pro Ser Pro Leu Gly Asn Thr Pro Tyr Arg Tyr Lys
                565                 570                 575

Tyr Ala Cys Gln Cys Lys Ile Pro Thr Asn Glu Glu Thr Cys Asp Asp
            580                 585                 590

Arg Lys Glu Tyr Met Asn Gln Trp Ser Cys Gly Ser Ala Arg Thr Met
    595                 600                 605

Lys Arg Gly Tyr Lys Asn Asp Asn Tyr Glu Leu Cys Lys Tyr Asn Gly
            610                 615                 620

Val Asp Val Lys Pro Thr Thr Val Arg Ser Asn Ser Ser Lys Leu Asp
625                 630                 635                 640

<210> SEQ ID NO 2
<211> LENGTH: 341
<212> TYPE: PRT
<213> ORGANISM: Plasmodium falciparum

<400> SEQUENCE: 2

Lys Cys Asp Lys Cys Lys Ser Gly Thr Ser Arg Ser Arg Lys Ile Trp
1               5                   10                  15

Thr Trp Arg Lys Ser Ser Gly Asn Lys Glu Gly Leu Gln Glu Glu Tyr
            20                  25                  30

Ala Asn Thr Ile Gly Leu Ser Pro Arg Thr Gln Leu Leu Tyr Leu Gly
            35                  40                  45

Asn Leu Arg Lys Leu Glu Asn Val Cys Glu Asp Val Thr Asp Ile Asn
        50                  55                  60

Phe Asp Thr Lys Glu Lys Phe Leu Ala Gly Cys Leu Ile Ala Ala Phe
65                  70                  75                  80

His Glu Gly Lys Asn Leu Lys Lys Arg Tyr Leu Glu Lys Lys Lys Gly
                85                  90                  95

Asp Asn Asn Ser Lys Leu Cys Lys Asp Leu Lys Tyr Ser Phe Ala Asp
            100                 105                 110

Tyr Gly Asp Leu Ile Lys Gly Thr Ser Ile Trp Asp Asn Asp Phe Thr
            115                 120                 125

Lys Asp Leu Glu Leu Asn Leu Gln Gln Ile Phe Gly Lys Leu Phe Arg
130                 135                 140

Lys Tyr Ile Lys Lys Lys Asn Ile Ser Thr Glu Gln Asp Thr Ser Tyr
145                 150                 155                 160

Ser Ser Leu Asp Glu Leu Arg Glu Ser Trp Trp Asn Thr Asn Lys Lys
                165                 170                 175

Tyr Ile Trp Leu Ala Met Lys His Gly Ala Gly Met Asn Ser Thr Thr
            180                 185                 190

Cys Ser Cys Ser Gly Asp Ser Ser Gly Glu Asn Gln Thr Asn Ser
        195                 200                 205

Cys Asp Asp Ile Pro Thr Ile Asp Leu Ile Pro Gln Tyr Leu Arg Phe
210                 215                 220

Leu Gln Glu Trp Val Glu His Phe Cys Glu Gln Arg Gln Ala Lys Val
225                 230                 235                 240

Lys Asp Val Ile Thr Asn Cys Asn Ser Cys Lys Glu Ser Gly Gly Thr
                245                 250                 255

Cys Asn Ser Asp Cys Glu Lys Lys Cys Lys Asn Lys Cys Asp Ala Tyr
            260                 265                 270

Lys Thr Phe Ile Glu Asp Cys Lys Gly Val Gly Gly Thr Gly Thr Ala
            275                 280                 285

Gly Ser Ser Trp Val Lys Arg Trp Tyr Gln Ile Tyr Met Arg Tyr Ser
290                 295                 300

Lys Tyr Ile Glu Asp Ala Lys Arg Asn Arg Lys Ala Gly Thr Lys Ser
305                 310                 315                 320

Cys Gly Thr Ser Ser Thr Thr Asn Val Ser Val Ser Thr Asp Glu Asn
                325                 330                 335

Lys Cys Val Gln Ser
            340

<210> SEQ ID NO 3
<211> LENGTH: 656
<212> TYPE: PRT
<213> ORGANISM: Artificial
<220> FEATURE:
<223> OTHER INFORMATION: Artificial construct

<400> SEQUENCE: 3

Asp Tyr Ile Lys Gly Asp Pro Tyr Phe Ala Glu Tyr Ala Thr Lys Leu

```
1               5                   10                  15
Ser Phe Ile Leu Asn Ser Ser Asp Ala Asn Pro Ser Gly Glu Thr
            20                  25                  30

Ala Asn His Asn Asp Glu Val Cys Asn Pro Asn Glu Ser Glu Ile Ser
            35                  40                  45

Ser Val Gly Gln Ala Gln Thr Ser Asp Pro Ser Ser Asn Lys Thr Cys
50                      55                  60

Asn Thr His Ser Ser Ile Lys Ala Asn Lys Lys Val Cys Lys His
65                  70                  75                  80

Val Lys Leu Gly Ile Asn Asn Asn Asp Lys Val Leu Arg Val Cys Val
                85                  90                  95

Ile Glu Asp Thr Ser Leu Ser Gly Val Glu Asn Cys Cys Phe Lys Asp
            100                 105                 110

Leu Leu Gly Ile Leu Gln Glu Asn Cys Ser Asp Asn Lys Ser Gly Ser
            115                 120                 125

Ser Ser Asn Gly Ser Cys Asn Asn Lys Asn Gln Glu Ala Cys Glu Lys
130                 135                 140

Asn Leu Glu Lys Val Leu Ala Ser Leu Thr Asn Cys Tyr Lys Cys Asp
145                 150                 155                 160

Lys Cys Lys Ser Gly Thr Ser Thr Val Asn Lys Asn Trp Ile Trp Lys
                165                 170                 175

Lys Ser Ser Gly Asn Lys Glu Gly Leu Gln Lys Glu Tyr Ala Asn Thr
            180                 185                 190

Ile Gly Leu Pro Pro Arg Thr His Ser Leu Tyr Leu Gly Asn Leu Pro
            195                 200                 205

Lys Leu Glu Asn Val Cys Glu Asp Val Lys Asp Ile Asn Phe Asp Thr
210                 215                 220

Lys Glu Lys Phe Leu Ala Gly Cys Leu Ile Ala Ala Phe His Glu Gly
225                 230                 235                 240

Lys Asn Leu Lys Lys Arg Tyr Pro Gln Asn Lys Asn Asp Asp Asn Asn
                245                 250                 255

Ser Lys Leu Cys Lys Ala Leu Glu Tyr Ser Phe Ala Asp Tyr Gly Asp
            260                 265                 270

Leu Ile Lys Gly Thr Ser Ile Trp Asp Asn Glu Tyr Thr Lys Asp Leu
            275                 280                 285

Glu Leu Asn Leu Gln Gln Ile Phe Gly Lys Leu Phe Arg Lys Tyr Ile
290                 295                 300

Lys Lys Asn Ile Ser Thr Glu Gln Asp Thr Leu Tyr Ser Ser Leu Asp
305                 310                 315                 320

Glu Leu Arg Glu Ser Trp Trp Asn Thr Asn Lys Lys Tyr Ile Trp Leu
                325                 330                 335

Ala Met Lys His Gly Ala Gly Met Asn Ile Thr Thr Cys Cys Gly Asp
            340                 345                 350

Gly Ser Val Thr Gly Ser Gly Ser Cys Asp Asp Ile Pro Thr Ile
            355                 360                 365

Asp Leu Ile Pro Gln Tyr Leu Arg Phe Leu Gln Glu Trp Val Glu His
            370                 375                 380

Phe Cys Lys Gln Arg Gln Glu Lys Val Lys Asp Val Ile Asn Ser Cys
385                 390                 395                 400

Asn Ser Cys Lys Asn Thr Ser Ser Lys Thr Lys Leu Gly Asp Thr Cys
                405                 410                 415

Asn Ser Asp Cys Glu Lys Lys Cys Lys Ile Glu Cys Glu Lys Tyr Lys
            420                 425                 430
```

```
Lys Phe Ile Glu Glu Cys Arg Thr Ala Val Gly Gly Thr Ala Gly Ser
            435                 440                 445

Ser Trp Ser Lys Arg Trp Asp Gln Ile Tyr Lys Met Tyr Ser Lys His
    450                 455                 460

Ile Glu Asp Ala Lys Arg Asn Arg Lys Ala Gly Thr Lys Asn Cys Gly
465                 470                 475                 480

Ile Thr Thr Gly Thr Ile Ser Gly Ser Ser Gly Ala Asn Ser Gly
                    485                 490                 495

Val Thr Thr Thr Glu Asn Lys Cys Val Gln Ser Asp Ile Asp Ser Phe
                500                 505                 510

Phe Lys His Leu Ile Asp Ile Gly Leu Thr Thr Pro Ser Ser Tyr Leu
            515                 520                 525

Ser Ile Val Leu Asp Asp Asn Ile Cys Gly Asp Asp Lys Ala Pro Trp
        530                 535                 540

Thr Thr Tyr Thr Thr Tyr Thr Thr Tyr Thr Thr Thr Glu Lys Cys Asn
545                 550                 555                 560

Lys Glu Arg Asp Lys Ser Lys Ser Gln Gln Ser Asn Thr Ser Val Val
                565                 570                 575

Val Asn Val Pro Ser Pro Leu Gly Asn Thr Pro His Gly Tyr Lys Tyr
            580                 585                 590

Ala Cys Gln Cys Lys Ile Pro Thr Asn Glu Glu Thr Cys Asp Asp Arg
        595                 600                 605

Lys Glu Tyr Met Asn Gln Trp Ile Ser Asp Thr Ser Lys Asn Pro Lys
            610                 615                 620

Gly Ser Gly Ser Thr Asn Asn Asp Tyr Glu Leu Tyr Thr Tyr Asn Gly
625                 630                 635                 640

Val Lys Glu Thr Lys Leu Pro Lys Lys Leu Asn Ser Pro Lys Leu Asp
                645                 650                 655

<210> SEQ ID NO 4
<211> LENGTH: 643
<212> TYPE: PRT
<213> ORGANISM: Artificial
<220> FEATURE:
<223> OTHER INFORMATION: Artificial construct

<400> SEQUENCE: 4

Asp Tyr Ile Lys Asp Asp Pro Tyr Ser Lys Glu Tyr Thr Thr Lys Leu
1               5                   10                  15

Ser Phe Ile Leu Asn Ser Ser Asp Ala Asn Thr Ser Ser Gly Glu Thr
            20                  25                  30

Ala Asn His Asn Asp Glu Ala Cys Asn Cys Asn Glu Ser Glu Ile Ser
        35                  40                  45

Ser Val Gly Gln Ala Gln Thr Ser Gly Pro Ser Ser Asn Lys Thr Cys
    50                  55                  60

Ile Thr His Ser Phe Ile Lys Ala Asn Lys Lys Val Cys Lys Asp
65                  70                  75                  80

Val Lys Leu Gly Val Arg Glu Asn Asp Lys Val Leu Arg Val Cys Val
                85                  90                  95

Ile Glu Asp Thr Ser Leu Ser Gly Val Asp Asn Cys Cys Cys Gln Asp
            100                 105                 110

Leu Leu Gly Ile Leu Gln Glu Asn Cys Ser Asp Asn Lys Arg Gly Ser
        115                 120                 125

Ser Ser Asn Gly Ser Cys Asn Asn Lys Asn Gln Asp Glu Cys Gln Lys
    130                 135                 140
```

```
Lys Leu Glu Lys Val Phe Val Ser Leu Thr Asn Gly Tyr Lys Cys Asp
145                 150                 155                 160

Lys Cys Lys Ser Gly Thr Ser Thr Val Asn Lys Lys Trp Ile Trp Lys
                165                 170                 175

Lys Ser Ser Gly Asn Glu Lys Gly Leu Gln Lys Glu Tyr Ala Asn Thr
            180                 185                 190

Ile Gly Leu Pro Pro Arg Thr Gln Ser Leu Tyr Leu Gly Asn Leu Pro
            195                 200                 205

Lys Leu Gly Asn Val Cys Glu Asp Val Thr Asp Ile Asn Phe Asp Thr
210                 215                 220

Lys Glu Lys Phe Leu Ala Gly Cys Leu Ile Ala Ala Phe His Glu Gly
225                 230                 235                 240

Lys Asn Leu Lys Ile Ser His Glu Lys Lys Gly Asp Asn Gly Lys
                245                 250                 255

Lys Leu Cys Lys Ala Leu Glu Tyr Ser Phe Ala Asp Tyr Gly Asp Leu
            260                 265                 270

Ile Lys Gly Thr Ser Ile Trp Asp Asn Glu Tyr Thr Lys Asp Leu Glu
        275                 280                 285

Leu Asn Leu Gln Lys Ala Phe Gly Lys Leu Phe Gly Tyr Ile Lys
290                 295                 300

Lys Asn Ile Ala Ser Asp Glu Asn Thr Ser Tyr Ser Ser Leu Asp Glu
305                 310                 315                 320

Leu Arg Glu Ser Trp Trp Asn Thr Asn Lys Lys Tyr Ile Trp Thr Ala
                325                 330                 335

Met Lys His Gly Ala Glu Met Asn Ser Thr Met Cys Asn Ala Asp Gly
            340                 345                 350

Ser Val Thr Gly Ser Gly Ser Ser Cys Asp Asp Ile Pro Thr Thr Asp
            355                 360                 365

Phe Ile Pro Gln Tyr Leu Arg Phe Leu Gln Glu Trp Val Glu His Phe
            370                 375                 380

Cys Lys Gln Arg Gln Glu Lys Val Asn Ala Val Ile Glu Asn Cys Asn
385                 390                 395                 400

Ser Cys Lys Asn Thr Ser Gly Glu Arg Lys Ile Gly Thr Cys Asn
                405                 410                 415

Gly Asp Cys Lys Thr Glu Cys Lys Asn Lys Cys Glu Ala Tyr Lys Asn
            420                 425                 430

Phe Ile Glu Asp Cys Lys Gly Gly Asp Gly Thr Ala Gly Ser Ser Trp
            435                 440                 445

Val Lys Arg Trp Asp Gln Ile Tyr Lys Arg Tyr Ser Lys His Ile Glu
        450                 455                 460

Asp Ala Lys Arg Asn Arg Lys Ala Gly Thr Lys Ser Cys Gly Pro Ser
465                 470                 475                 480

Ser Ile Thr Asn Ala Ser Val Ser Thr Asp Glu Asn Lys Cys Val Gln
            485                 490                 495

Ser Asp Ile Asp Ser Phe Phe Lys His Leu Ile Asp Ile Gly Leu Thr
            500                 505                 510

Thr Pro Ser Ser Tyr Leu Ser Ile Val Leu Asp Glu Asn Asn Cys Gly
            515                 520                 525

Glu Asp Asn Ala Pro Trp Thr Thr Tyr Thr Thr Tyr Thr Thr Thr Glu
            530                 535                 540

Lys Cys Asn Lys Asp Lys Lys Ser Lys Ser Gln Ser Cys Asn Thr
545                 550                 555                 560
```

-continued

```
Ala Val Val Val Asn Val Pro Ser Pro Leu Gly Asn Thr Pro His Glu
            565                 570                 575

Tyr Lys Tyr Ala Cys Gln Cys Lys Ile Pro Thr Thr Glu Glu Thr Cys
            580                 585                 590

Asp Asp Arg Lys Glu Tyr Met Asn Gln Trp Ile Ser Asp Thr Ser Lys
            595                 600                 605

Lys Gln Lys Gly Ser Gly Ser Thr Asn Asn Asp Tyr Glu Leu Tyr Thr
            610                 615                 620

Tyr Thr Gly Val Lys Glu Thr Lys Leu Pro Lys Lys Leu Asn Ser Pro
625                 630                 635                 640

Lys Leu Asp

<210> SEQ ID NO 5
<211> LENGTH: 640
<212> TYPE: PRT
<213> ORGANISM: Artificial
<220> FEATURE:
<223> OTHER INFORMATION: Artificial construct

<400> SEQUENCE: 5

Ser Tyr Val Lys Asn Asp Pro Tyr Ser Lys Glu Tyr Val Thr Lys Leu
1               5                   10                  15

Ser Phe Ile Leu Asn Pro Ser Asp Ala Asn Asn Pro Ser Gly Glu Thr
            20                  25                  30

Ala Asn His Asn Asp Glu Ala Cys Asn Pro Asn Glu Ser Glu Ile Ala
            35                  40                  45

Ser Val Gly Gln Ala Gln Thr Ser Asp Arg Leu Ser Gln Lys Ala Cys
        50                  55                  60

Ile Thr His Ser Phe Ile Gly Ala Asn Lys Lys Ile Val Cys Lys Asp
65                  70                  75                  80

Val Lys Leu Gly Val Arg Glu Lys Asp Lys Asp Leu Lys Ile Cys Val
                85                  90                  95

Ile Glu Asp Asp Ser Leu Arg Gly Val Glu Asn Cys Cys Phe Lys Asp
            100                 105                 110

Leu Leu Gly Ile Leu Gln Glu Asn Cys Ser Asp Asn Lys Ser Gly Ser
        115                 120                 125

Ser Ser Asn Gly Ser Cys Asn Asn Lys Asn Gln Asp Glu Cys Gln Lys
130                 135                 140

Lys Leu Asp Glu Ala Leu Ala Ser Leu His Asn Gly Tyr Lys Cys Asp
145                 150                 155                 160

Lys Cys Lys Ser Gly Thr Ser Arg Ser Lys Lys Ile Trp Thr Trp Arg
                165                 170                 175

Lys Phe Pro Gly Asn Gly Glu Gly Leu Gln Lys Glu Tyr Ala Asn Thr
            180                 185                 190

Ile Gly Leu Pro Pro Arg Thr Gln Ser Leu Tyr Leu Gly Asn Leu Arg
        195                 200                 205

Lys Leu Glu Asn Val Cys Lys Gly Val Thr Asp Ile Asn Phe Asp Thr
210                 215                 220

Lys Glu Lys Phe Leu Ala Gly Cys Leu Ile Ala Ala Phe His Glu Gly
225                 230                 235                 240

Lys Asn Leu Lys Ile Ser Asn Lys Lys Asn Asp Asn Gly Lys
                245                 250                 255

Lys Leu Cys Lys Asp Leu Lys Tyr Ser Phe Ala Asp Tyr Gly Asp Leu
            260                 265                 270

Ile Lys Gly Thr Ser Ile Trp Asp Asn Glu Tyr Thr Lys Asp Leu Glu
```

```
            275                 280                 285
Leu Asn Leu Gln Lys Ile Phe Gly Lys Leu Phe Arg Lys Tyr Ile Lys
    290                 295                 300

Lys Asn Ile Ala Ser Asp Glu Asn Thr Leu Tyr Ser Ser Leu Asp Glu
305                 310                 315                 320

Leu Arg Glu Ser Trp Trp Asn Thr Asn Lys Tyr Ile Trp Leu Ala
                325                 330                 335

Met Lys His Gly Thr Thr Cys Ser Ser Gly Ser Gly Asp Asn Gly Asp
                340                 345                 350

Gly Ser Val Thr Gly Ser Gly Ser Ser Cys Asp Asp Met Ser Thr Ile
                355                 360                 365

Asp Leu Ile Pro Gln Tyr Leu Arg Phe Leu Gln Glu Trp Val Glu His
            370                 375                 380

Phe Cys Lys Gln Arg Gln Glu Lys Val Lys Asp Val Ile Glu Asn Cys
385                 390                 395                 400

Lys Ser Cys Lys Asn Thr Ser Gly Glu Arg Ile Ile Gly Gly Thr Cys
                405                 410                 415

Gly Ser Asp Cys Lys Thr Lys Cys Lys Gly Glu Cys Asp Ala Tyr Lys
                420                 425                 430

Asn Phe Ile Glu Glu Cys Lys Arg Gly Asp Gly Thr Ala Gly Ser Pro
            435                 440                 445

Trp Ser Lys Arg Trp Asp Gln Ile Tyr Met Arg Tyr Ser Lys Tyr Ile
    450                 455                 460

Glu Asp Ala Lys Arg Asn Arg Lys Ala Gly Thr Lys Asn Cys Gly Thr
465                 470                 475                 480

Ser Ser Thr Thr Asn Ala Ala Glu Asn Lys Cys Val Gln Ser Asp Ile
                485                 490                 495

Asp Ser Phe Phe Lys His Leu Ile Asp Ile Gly Leu Thr Thr Pro Ser
                500                 505                 510

Ser Tyr Leu Ser Ile Val Leu Asp Glu Asn Ile Cys Gly Asp Asp Lys
            515                 520                 525

Ala Pro Trp Thr Thr Tyr Thr Thr Tyr Thr Thr Thr Glu Lys Cys Asn
    530                 535                 540

Lys Glu Thr Asp Lys Ser Lys Ser Gln Ser Cys Asn Thr Ala Val Val
545                 550                 555                 560

Val Asn Val Pro Ser Pro Leu Gly Asn Thr Pro His Gly Tyr Lys Tyr
                565                 570                 575

Ala Cys Glu Cys Lys Ile Pro Thr Thr Glu Glu Thr Cys Asp Asp Arg
                580                 585                 590

Lys Glu Tyr Met Asn Gln Trp Ile Ser Asp Thr Ser Lys Lys Pro Lys
            595                 600                 605

Gly Gly Arg Ser Thr Asn Asn Asp Tyr Glu Leu Tyr Thr Tyr Asn Gly
    610                 615                 620

Val Lys Glu Thr Lys Leu Pro Lys Lys Ser Ser Ser Ser Lys Leu Asp
625                 630                 635                 640

<210> SEQ ID NO 6
<211> LENGTH: 358
<212> TYPE: PRT
<213> ORGANISM: Plasmodium falciparum

<400> SEQUENCE: 6

Lys Cys Glu Lys Cys Lys Ser Glu Gln Ser Lys Lys Asn Asn Asn Ile
1               5                   10                  15
```

-continued

```
Trp Ile Trp Arg Lys Phe Pro Gly Asn Gly Glu Gly Leu Gln Lys Glu
             20                  25                  30

Tyr Ala Asn Thr Ile Gly Leu Pro Pro Arg Thr His Ser Leu Tyr Leu
         35                  40                  45

Gly Asn Leu Pro Lys Leu Glu Asn Val Cys Lys Asp Val Lys Asp Ile
 50                  55                  60

Asn Phe Asp Thr Lys Glu Lys Phe Leu Ala Gly Cys Leu Ile Ala Ala
 65                  70                  75                  80

Phe His Glu Gly Lys Asn Leu Lys Thr Thr Tyr Pro Gln Asn Lys Asn
                 85                  90                  95

Ala Asp Asn Ser Lys Leu Cys Lys Asp Leu Lys Tyr Ser Phe Ala
             100                 105                 110

Asp Tyr Gly Asp Leu Ile Lys Gly Thr Ser Ile Trp Asp Asn Asp Phe
        115                 120                 125

Thr Lys Asp Leu Glu Leu Asn Leu Gln Lys Ile Phe Gly Lys Leu Phe
130                 135                 140

Arg Lys Tyr Ile Lys Lys Asn Ile Ala Ser Asp Glu Asn Thr Leu Tyr
145                 150                 155                 160

Ser Ser Leu Asp Glu Leu Arg Glu Ser Trp Trp Asn Thr Asn Lys Lys
                165                 170                 175

Tyr Ile Trp Leu Ala Met Lys His Gly Ala Glu Met Asn Ser Thr Met
            180                 185                 190

Cys Asn Gly Asp Gly Ser Val Thr Gly Ser Ser Asp Ser Gly Ser Thr
        195                 200                 205

Thr Cys Ser Gly Asp Asn Gly Ser Ile Ser Cys Asp Asp Ile Pro Thr
    210                 215                 220

Ile Asp Leu Ile Pro Gln Tyr Leu Arg Phe Leu Gln Glu Trp Val Glu
225                 230                 235                 240

His Phe Cys Lys Gln Arg Gln Glu Lys Val Lys Pro Val Ile Glu Asn
                245                 250                 255

Cys Lys Ser Cys Lys Asn Thr Ser Gly Glu Arg Ile Ile Gly Gly Thr
            260                 265                 270

Cys Gly Ser Asp Cys Glu Lys Lys Cys Lys Gly Glu Cys Asp Ala Tyr
        275                 280                 285

Lys Lys Phe Ile Glu Glu Cys Lys Gly Gly Gly Gly Thr Gly Thr
    290                 295                 300

Ala Gly Ser Pro Trp Ser Lys Arg Trp Asp Gln Ile Tyr Lys Arg Tyr
305                 310                 315                 320

Ser Lys Tyr Ile Glu Asp Ala Lys Arg Asn Arg Lys Ala Gly Thr Lys
                325                 330                 335

Ser Cys Gly Pro Ser Ser Thr Thr Asn Ala Ala Ala Ser Thr Thr Glu
            340                 345                 350

Ser Lys Cys Val Gln Ser
        355

<210> SEQ ID NO 7
<211> LENGTH: 333
<212> TYPE: PRT
<213> ORGANISM: Plasmodium falciparum

<400> SEQUENCE: 7

Lys Cys Asp Lys Cys Lys Ser Glu Gln Ser Lys Asn Asn Lys Asn
1               5                   10                  15

Trp Ile Trp Lys Gln Phe Pro Gly Asn Gly Glu Gly Leu Gln Lys Glu
             20                  25                  30
```

Tyr Ala Asn Thr Ile Gly Leu Pro Pro Arg Thr His Ser Leu Tyr Leu
            35                  40                  45

Gly Asn Leu Pro Lys Leu Glu Asn Val Cys Lys Gly Val Thr Asp Ile
    50                  55                  60

Asn Phe Asp Thr Lys Glu Lys Phe Leu Ala Gly Cys Leu Ile Ala Ala
65                  70                  75                  80

Phe His Glu Gly Lys Asn Leu Lys Thr Ser His Glu Lys Lys Lys Gly
                85                  90                  95

Asp Asn Gly Lys Lys Leu Cys Lys Asp Leu Lys Tyr Ser Phe Ala Asp
                100                 105                 110

Tyr Gly Asp Leu Ile Lys Gly Thr Ser Ile Trp Asp Asn Asp Phe Thr
            115                 120                 125

Lys Asp Leu Glu Leu Asn Leu Gln Gln Ile Phe Gly Lys Leu Phe Arg
130                 135                 140

Lys Tyr Ile Lys Lys Asn Ile Ser Ala Glu Gln Asp Thr Ser Tyr Ser
145                 150                 155                 160

Ser Leu Asp Glu Leu Arg Glu Ser Trp Trp Asn Thr Asn Lys Lys Tyr
                165                 170                 175

Ile Trp Leu Ala Met Lys His Gly Thr Thr Cys Ser Ser Gly Ser Gly
            180                 185                 190

Asp Asn Gly Asp Gly Ser Val Thr Gly Ser Gly Ser Ser Cys Asp Asp
            195                 200                 205

Met Pro Thr Thr Asp Phe Ile Pro Gln Tyr Leu Arg Phe Leu Gln Glu
            210                 215                 220

Trp Val Glu His Phe Cys Lys Gln Arg Gln Lys Val Asn Ala Val
225                 230                 235                 240

Ile Thr Asn Cys Lys Ser Cys Lys Glu Ser Gly Gly Thr Cys Asn Ser
                245                 250                 255

Asp Cys Glu Lys Lys Cys Lys Asp Glu Cys Glu Lys Tyr Lys Lys Phe
            260                 265                 270

Ile Glu Glu Cys Arg Thr Ala Ala Asp Gly Thr Ala Gly Ser Ser Trp
            275                 280                 285

Ser Lys Arg Trp Asp Gln Ile Tyr Lys Met Tyr Ser Lys His Ile Glu
            290                 295                 300

Asp Ala Lys Arg Asn Arg Lys Ala Gly Thr Lys Asn Cys Gly Thr Ser
305                 310                 315                 320

Ser Thr Thr Asn Ala Ala Glu Asn Lys Cys Val Gln Ser
                325                 330

<210> SEQ ID NO 8
<211> LENGTH: 269
<212> TYPE: PRT
<213> ORGANISM: Plasmodium falciparum

<400> SEQUENCE: 8

Asp Tyr Ile Lys Asp Asp Pro Tyr Ser Lys Glu Tyr Thr Thr Lys Leu
1               5                   10                  15

Ser Phe Ile Leu Asn Ser Ser Asp Ala Asn Thr Ser Ser Gly Glu Thr
            20                  25                  30

Ala Asn His Asn Asp Glu Ala Cys Asn Cys Asn Glu Ser Glu Ile Ala
            35                  40                  45

Ser Val Glu Gln Ala Ser Ile Ser Asp Arg Ser Ser Gln Lys Ala Tyr
        50                  55                  60

Ile Thr His Ser Ser Ile Lys Thr Asn Lys Lys Lys Val Cys Lys Tyr

```
                65                  70                  75                  80
Val Lys Leu Gly Ile Asn Asn Asn Asp Lys Val Leu Arg Val Cys Val
                    85                  90                  95

Ile Glu Asp Thr Ser Leu Ser Gly Val Glu Asn Cys Cys Phe Lys Asp
                    100                 105                 110

Leu Leu Gly Ile Leu Gln Glu Asn Cys Ser Asp Asn Lys Arg Gly Ser
                    115                 120                 125

Ser Phe Asn Asp Ser Cys Asn Asn Asn Glu Glu Ala Cys Gln Lys
                130                 135                 140

Lys Leu Glu Lys Val Leu Ala Ser Leu Thr Asn Gly Tyr Lys Cys Glu
145                 150                 155                 160

Lys Cys Lys Ser Gly Thr Ser Arg Ser Lys Lys Trp Ile Trp Lys
                    165                 170                 175

Lys Ser Ser Gly Lys Glu Gly Leu Gln Lys Glu Tyr Ala Asn Thr
                180                 185                 190

Ile Gly Leu Pro Pro Arg Thr Gln Ser Leu Tyr Leu Gly Asn Leu Pro
                195                 200                 205

Lys Leu Glu Asn Val Cys Lys Gly Val Thr Asp Ile Asn Phe Asp Thr
                210                 215                 220

Lys Glu Lys Phe Leu Ala Gly Cys Leu Ile Ala Ala Phe His Glu Gly
225                 230                 235                 240

Lys Asn Leu Lys Pro Ser His Gln Asn Lys Asn Asp Asp Asn Asn Ser
                    245                 250                 255

Lys Leu Cys Lys Asp Leu Lys Tyr Ser Phe Ala Asp Tyr
                260                 265

<210> SEQ ID NO 9
<211> LENGTH: 333
<212> TYPE: PRT
<213> ORGANISM: Plasmodium falciparum

<400> SEQUENCE: 9

Lys Cys Asp Lys Cys Lys Ser Gly Thr Ser Arg Ser Lys Lys Lys Trp
1               5                   10                  15

Thr Trp Arg Lys Ser Ser Gly Asn Lys Glu Gly Leu Gln Lys Glu Tyr
                20                  25                  30

Ala Asn Thr Ile Gly Leu Pro Pro Arg Thr His Ser Leu Tyr Leu Gly
            35                  40                  45

Asn Leu Arg Lys Leu Glu Asn Val Cys Glu Asp Val Thr Asp Ile Asn
        50                  55                  60

Phe Asp Thr Lys Glu Lys Phe Leu Ala Gly Cys Leu Ile Ala Ala Phe
65                  70                  75                  80

His Glu Gly Lys Asn Leu Lys Thr Thr Tyr Pro Gln Asn Lys Asn Asp
                    85                  90                  95

Asp Asn Asn Ser Lys Leu Cys Lys Ala Leu Lys Tyr Ser Phe Ala Asp
                100                 105                 110

Tyr Gly Asp Leu Ile Lys Gly Thr Ser Ile Trp Asp Asn Asp Phe Thr
            115                 120                 125

Lys Asp Leu Glu Leu Asn Leu Gln Lys Ile Phe Gly Lys Leu Phe Arg
        130                 135                 140

Lys Tyr Ile Lys Lys Asn Ile Ser Thr Glu Gln His Thr Ser Tyr Ser
145                 150                 155                 160

Ser Leu Asp Glu Leu Arg Glu Ser Trp Trp Asn Thr Asn Lys Lys Tyr
                    165                 170                 175
```

-continued

```
Ile Trp Leu Ala Met Lys His Gly Ala Glu Met Asn Gly Thr Thr Cys
            180                 185                 190

Ser Cys Ser Gly Asp Ser Ser Asp Ile Pro Thr Ile Asp Leu Ile
        195                 200                 205

Pro Gln Tyr Leu Arg Phe Leu Gln Glu Trp Val Glu His Phe Cys Lys
    210                 215                 220

Gln Arg Gln Ala Lys Val Asn Ala Val Ile Asn Ser Cys Asn Ser Cys
225                 230                 235                 240

Lys Asn Thr Ser Gly Glu Arg Lys Leu Gly Thr Cys Gly Ser Glu
                245                 250                 255

Cys Lys Thr Glu Cys Lys Asn Lys Cys Asp Ala Tyr Lys Glu Phe Ile
        260                 265                 270

Asp Gly Thr Gly Ser Gly Gly Thr Gly Thr Ala Gly Ser Ser Trp
                275                 280                 285

Val Lys Arg Trp Asp Gln Ile Tyr Lys Arg Tyr Ser Lys Tyr Ile Glu
    290                 295                 300

Asp Ala Lys Arg Asn Arg Lys Ala Gly Ser Lys Asn Cys Gly Thr Ser
305                 310                 315                 320

Ser Thr Thr Asn Ala Ala Glu Ser Lys Cys Val Gln Ser
                325                 330
```

<210> SEQ ID NO 10
<211> LENGTH: 650
<212> TYPE: PRT
<213> ORGANISM: Artificial
<220> FEATURE:
<223> OTHER INFORMATION: Artificial construct

<400> SEQUENCE: 10

```
Ser Tyr Val Lys Asn Asn Pro Tyr Ser Ala Glu Tyr Val Thr Lys Leu
1               5                   10                  15

Ser Phe Ile Leu Asn Ser Ser Asp Ala Asn Thr Ser Ser Glu Thr Pro
            20                  25                  30

Ser Lys Tyr Tyr Asp Glu Val Cys Asn Cys Asn Glu Ser Glu Ile Ser
        35                  40                  45

Ser Val Gly Gln Ala Gln Thr Ser Gly Pro Ser Ser Asn Lys Thr Cys
    50                  55                  60

Ile Thr His Ser Ser Ile Lys Thr Asn Lys Lys Val Cys Lys Asp
65                  70                  75                  80

Val Lys Leu Gly Ile Asn Asn Asn Asp Lys Val Leu Arg Val Cys Val
                85                  90                  95

Ile Glu Asp Thr Ser Leu Ser Gly Val Asp Asn Cys Cys Cys Gln Asp
            100                 105                 110

Leu Leu Gly Ile Leu Gln Glu Asn Cys Ser Asp Lys Asn Gln Ser Gly
        115                 120                 125

Ser Ser Ser Asn Gly Ser Cys Asn Asn Lys Asn Gln Asp Glu Cys Gln
130                 135                 140

Lys Lys Leu Glu Lys Val Phe Ala Ser Leu Thr Asn Gly Tyr Lys Cys
145                 150                 155                 160

Asp Lys Cys Lys Ser Gly Thr Ser Arg Ser Lys Lys Trp Ile Trp
                165                 170                 175

Arg Lys Ser Ser Gly Asn Glu Glu Gly Leu Gln Lys Glu Tyr Ala Asn
            180                 185                 190

Thr Ile Gly Leu Pro Pro Arg Thr Gln Ser Leu Tyr Leu Gly Asn Leu
        195                 200                 205
```

Arg Lys Leu Glu Asn Val Cys Lys Gly Val Thr Asp Ile Asn Phe Asp
210                 215                 220

Thr Lys Glu Lys Phe Leu Ala Gly Cys Leu Ile Ala Ala Phe His Glu
225                 230                 235                 240

Gly Lys Asn Leu Lys Thr Thr Tyr Pro Gln Asn Lys Lys Leu Cys
                245                 250                 255

Lys Asp Leu Lys Tyr Ser Phe Ala Asp Tyr Gly Asp Leu Ile Lys Gly
                260                 265                 270

Thr Ser Ile Trp Asp Asn Glu Tyr Thr Lys Asp Leu Glu Leu Asn Leu
            275                 280                 285

Gln Lys Ala Phe Gly Lys Leu Phe Arg Lys Tyr Ile Lys Lys Asn Ile
290                 295                 300

Ser Thr Glu Gln His Thr Leu Tyr Ser Ser Leu Asp Glu Leu Arg Glu
305                 310                 315                 320

Ser Trp Trp Asn Thr Asn Lys Lys Tyr Ile Trp Leu Ala Met Lys His
                325                 330                 335

Gly Ala Gly Met Asn Ser Thr Thr Cys Cys Gly Asp Gly Ser Val Thr
            340                 345                 350

Gly Ser Gly Ser Ser Cys Asp Asp Ile Pro Thr Ile Asp Leu Ile Pro
            355                 360                 365

Gln Tyr Leu Arg Phe Leu Gln Glu Trp Val Glu His Phe Cys Lys Gln
370                 375                 380

Arg Gln Glu Lys Val Asn Ala Val Ile Glu Asn Cys Asn Ser Cys Lys
385                 390                 395                 400

Glu Cys Gly Asp Thr Cys Asn Gly Glu Cys Lys Thr Glu Cys Glu Lys
                405                 410                 415

Lys Cys Lys Ile Glu Cys Glu Lys Tyr Lys Thr Phe Ile Glu Glu Cys
            420                 425                 430

Val Thr Ala Val Gly Thr Ser Gly Ser Pro Trp Ser Lys Arg Trp
                435                 440                 445

Asp Gln Ile Tyr Lys Arg Tyr Ser Lys Tyr Ile Glu Asp Ala Lys Arg
450                 455                 460

Asn Arg Lys Ala Gly Thr Lys Asn Cys Gly Ile Thr Thr Gly Thr Ile
465                 470                 475                 480

Ser Gly Glu Ser Ser Gly Ala Asn Ser Gly Val Thr Thr Glu Asn
                485                 490                 495

Lys Cys Val Gln Ser Asp Ile Asp Ser Phe Phe Lys His Leu Ile Asp
                500                 505                 510

Ile Gly Leu Thr Thr Pro Ser Ser Tyr Leu Ser Ile Val Leu Asp Asp
            515                 520                 525

Asn Ile Cys Gly Ala Asp Asn Ala Pro Trp Thr Thr Tyr Thr Thr Tyr
530                 535                 540

Thr Thr Tyr Thr Thr Thr Lys Asn Cys Asp Ile Lys Lys Lys Thr Pro
545                 550                 555                 560

Lys Ser Gln Pro Ile Asn Thr Ser Val Val Asn Val Pro Ser Pro
                565                 570                 575

Leu Gly Asn Thr Pro His Gly Tyr Lys Tyr Ala Cys Gln Cys Lys Ile
            580                 585                 590

Pro Thr Thr Glu Glu Ser Cys Asp Asp Arg Lys Glu Tyr Met Asn Gln
                595                 600                 605

Trp Ile Ile Asp Thr Ser Lys Lys Gln Lys Gly Ser Gly Ser Thr Asn
            610                 615                 620

Asn Asp Tyr Glu Leu Tyr Thr Tyr Asn Gly Val Lys Glu Thr Lys Leu

```
                625                 630                 635                 640
Pro Lys Lys Ser Ser Ser Lys Leu Asp
                645                 650

<210> SEQ ID NO 11
<211> LENGTH: 643
<212> TYPE: PRT
<213> ORGANISM: Artificial
<220> FEATURE:
<223> OTHER INFORMATION: Artificial construct

<400> SEQUENCE: 11

Ser Tyr Val Lys Asp Asp Pro Tyr Ser Ala Glu Tyr Val Thr Lys Leu
1               5                   10                  15

Ser Phe Ile Leu Asn Ser Ser Asp Ala Asn Thr Ser Ser Glu Thr Pro
            20                  25                  30

Ser Lys Tyr Tyr Asp Glu Val Cys Asn Cys Asn Glu Ser Glu Ile Ser
        35                  40                  45

Ser Val Gly Gln Ala Gln Thr Ser Gly Pro Ser Ser Asn Lys Thr Cys
    50                  55                  60

Ile Thr His Ser Ser Ile Lys Thr Asn Lys Lys Val Cys Lys Asp
65                  70                  75                  80

Val Lys Leu Gly Ile Asn Asn Asp Lys Val Leu Arg Val Cys Val
                85                  90                  95

Ile Glu Asp Thr Ser Leu Ser Gly Val Asp Asn Cys Cys Gln Asp
            100                 105                 110

Leu Leu Gly Ile Leu Gln Glu Asn Cys Ser Asp Lys Asn Gln Ser Gly
        115                 120                 125

Ser Ser Ser Asn Gly Ser Cys Asn Asn Lys Asn Gln Asp Glu Cys Gln
    130                 135                 140

Lys Lys Leu Glu Lys Val Phe Ala Ser Leu Thr Asn Gly Tyr Lys Cys
145                 150                 155                 160

Asp Lys Cys Lys Ser Gly Thr Ser Arg Ser Lys Lys Trp Ile Trp
                165                 170                 175

Arg Lys Ser Ser Gly Asn Glu Glu Gly Leu Gln Lys Glu Tyr Ala Asn
            180                 185                 190

Thr Ile Gly Leu Pro Pro Arg Thr Gln Ser Leu Tyr Leu Gly Asn Leu
        195                 200                 205

Pro Lys Leu Glu Asn Val Cys Lys Gly Val Thr Asp Ile Ile Tyr Asp
    210                 215                 220

Thr Lys Glu Lys Phe Leu Ser Gly Cys Leu Ile Ala Ala Phe His Glu
225                 230                 235                 240

Gly Lys Asn Leu Lys Thr Ser His Glu Lys Lys Asn Asp Asp Asn Gly
                245                 250                 255

Lys Lys Leu Cys Lys Ala Leu Glu Tyr Ser Phe Ala Asp Tyr Gly Asp
            260                 265                 270

Leu Ile Lys Gly Thr Ser Ile Trp Asp Asn Asp Phe Thr Lys Asp Leu
        275                 280                 285

Glu Leu Asn Leu Gln Lys Ile Phe Gly Lys Leu Phe Arg Lys Tyr Ile
    290                 295                 300

Lys Lys Asn Asn Thr Ala Glu Gln Asp Thr Ser Tyr Ser Ser Leu Asp
305                 310                 315                 320

Glu Leu Arg Glu Ser Trp Trp Asn Thr Asn Lys Lys Tyr Ile Trp Thr
                325                 330                 335

Ala Met Lys His Gly Ala Gly Met Asn Ser Thr Thr Cys Ser Gly Asp
```

```
                340                 345                 350
Gly Ser Val Thr Gly Ser Gly Ser Ser Cys Asp Asp Met Pro Thr Ile
            355                 360                 365
Asp Leu Ile Pro Gln Tyr Leu Arg Phe Leu Gln Glu Trp Val Glu His
        370                 375                 380
Phe Cys Lys Gln Arg Gln Glu Lys Val Lys Asp Val Ile Thr Asn Cys
385                 390                 395                 400
Asn Ser Cys Lys Glu Cys Gly Asp Thr Cys Asn Gly Glu Cys Lys Thr
                405                 410                 415
Glu Cys Lys Thr Lys Cys Lys Gly Glu Cys Glu Lys Tyr Lys Asn Phe
            420                 425                 430
Ile Glu Glu Cys Asn Gly Thr Ala Asp Gly Gly Thr Ser Gly Ser Ser
        435                 440                 445
Trp Ser Lys Arg Trp Asp Gln Ile Tyr Lys Arg Tyr Ser Lys Tyr Ile
    450                 455                 460
Glu Asp Ala Lys Arg Asn Arg Lys Ala Gly Thr Lys Asn Cys Gly Thr
465                 470                 475                 480
Ser Ser Thr Thr Asn Ala Ala Ala Ser Thr Thr Glu Asn Lys Cys Val
                485                 490                 495
Gln Ser Asp Ile Asp Ser Phe Phe Lys His Leu Ile Asp Ile Gly Leu
            500                 505                 510
Thr Thr Pro Ser Ser Tyr Leu Ser Asn Val Leu Asp Asp Asn Ile Cys
        515                 520                 525
Gly Glu Asp Lys Ala Pro Trp Thr Thr Tyr Thr Thr Tyr Thr Thr Lys
    530                 535                 540
Asn Cys Asp Ile Gln Lys Lys Thr Pro Lys Pro Gln Ser Cys Asp Thr
545                 550                 555                 560
Leu Val Val Val Asn Val Pro Ser Pro Leu Gly Asn Thr Pro His Gly
                565                 570                 575
Tyr Lys Tyr Val Cys Glu Cys Lys Ile Pro Thr Thr Glu Glu Thr Cys
            580                 585                 590
Asp Asp Arg Lys Glu Tyr Met Asn Gln Trp Ile Ile Asp Thr Ser Lys
        595                 600                 605
Lys Gln Lys Gly Ser Gly Ser Thr Asn Asn Asp Tyr Glu Leu Tyr Thr
    610                 615                 620
Tyr Asn Gly Val Gln Ile Lys Gln Ala Ala Gly Thr Leu Lys Asn Ser
625                 630                 635                 640
Lys Leu Asp

<210> SEQ ID NO 12
<211> LENGTH: 269
<212> TYPE: PRT
<213> ORGANISM: Plasmodium falciparum

<400> SEQUENCE: 12

Asn Tyr Ile Lys Gly Asp Pro Tyr Ser Ala Glu Tyr Ala Thr Lys Leu
1               5                   10                  15
Ser Phe Ile Leu Asn Ser Ser Asp Thr Glu Asn Ala Ser Glu Lys Ile
            20                  25                  30
Gln Lys Asn Asn Asp Glu Val Cys Asn Cys Asn Glu Ser Glu Ile Ala
        35                  40                  45
Ser Val Glu Gln Ala Pro Ile Ser Asp Arg Ser Gln Lys Ala Cys
    50                  55                  60
Ile Thr His Ser Ser Ile Lys Ala Asn Lys Lys Lys Val Cys Lys His
```

-continued

```
                65                  70                  75                  80
Val Lys Leu Gly Val Arg Glu Asn Asp Lys Asp Leu Lys Ile Cys Val
                        85                  90                  95

Ile Glu Asp Thr Ser Leu Ser Gly Val Asp Asn Cys Cys Gln Asp
                100                 105                 110

Leu Leu Gly Ile Leu Gln Glu Asn Cys Ser Asp Asn Lys Ser Gly Ser
                115                 120                 125

Ser Ser Asn Gly Ser Cys Asn Asn Asn Glu Glu Ile Cys Gln Lys
130                 135                 140

Lys Leu Glu Lys Val Leu Ala Ser Leu Thr Asn Gly Tyr Lys Cys Asp
145                 150                 155                 160

Lys Cys Lys Ser Gly Thr Ser Thr Val Asn Lys Asn Trp Ile Trp Lys
                165                 170                 175

Lys Tyr Ser Gly Lys Glu Gly Gly Leu Gln Glu Glu Tyr Ala Asn Thr
                180                 185                 190

Ile Gly Leu Pro Pro Arg Thr Gln Ser Leu Tyr Leu Gly Asn Leu Pro
                195                 200                 205

Lys Leu Glu Asn Val Cys Glu Asp Val Lys Asp Ile Asn Phe Asp Thr
210                 215                 220

Lys Glu Lys Phe Leu Ala Gly Cys Leu Ile Ala Ala Phe His Glu Gly
225                 230                 235                 240

Lys Asn Leu Lys Thr Ser Asn Lys Lys Asn Asp Asp Asn Asn Ser
                245                 250                 255

Lys Leu Cys Lys Ala Leu Lys Tyr Ser Phe Ala Asp Tyr
                260                 265

<210> SEQ ID NO 13
<211> LENGTH: 344
<212> TYPE: PRT
<213> ORGANISM: Plasmodium falciparum

<400> SEQUENCE: 13

Lys Cys Asp Lys Cys Lys Ser Gly Thr Ser Thr Val Asn Lys Lys Trp
1               5                   10                  15

Ile Trp Lys Lys Tyr Ser Gly Thr Glu Gly Leu Gln Glu Glu Tyr
                20                  25                  30

Ala Asn Thr Ile Ala Leu Pro Pro Arg Thr Gln Ser Leu Tyr Leu Gly
                35                  40                  45

Asn Leu Pro Lys Leu Glu Asn Val Cys Lys Asp Val Thr Asp Ile Asn
50                  55                  60

Phe Asp Thr Lys Glu Lys Phe Leu Ala Gly Cys Leu Ile Ala Ala Phe
65                  70                  75                  80

His Glu Gly Lys Asn Leu Lys Thr Thr Tyr Leu Glu Lys Lys Gly
                85                  90                  95

Asp Asn Gly Lys Lys Asn Asp Asp Asn Ser Lys Leu Cys Lys Ala
                100                 105                 110

Leu Lys Tyr Ser Phe Ala Asp Tyr Gly Asp Leu Ile Lys Gly Thr Ser
                115                 120                 125

Ile Trp Asp Asn Asp Phe Thr Lys Asp Leu Glu Leu Asn Leu Gln Gln
                130                 135                 140

Ile Phe Gly Lys Leu Phe Arg Lys Tyr Ile Lys Lys Asn Ile Ala Ser
145                 150                 155                 160

Asp Glu Asn Thr Leu Tyr Ser Ser Leu Asp Glu Leu Arg Glu Ser Trp
                165                 170                 175
```

```
Trp Asn Thr Asn Lys Lys Tyr Ile Trp Leu Ala Met Lys His Gly Ala
            180                 185                 190

Gly Met Asn Ser Thr Met Cys Asn Ala Asp Gly Ser Val Thr Gly Ser
        195                 200                 205

Gly Ser Ser Cys Asp Asp Ile Pro Thr Ile Asp Leu Ile Pro Gln Tyr
    210                 215                 220

Leu Arg Phe Leu Gln Glu Trp Val Glu His Phe Cys Lys Gln Arg Gln
225                 230                 235                 240

Ala Lys Val Lys Asp Val Ile Thr Asn Cys Asn Ser Cys Lys Glu Cys
                245                 250                 255

Gly Gly Thr Cys Asn Gly Glu Cys Lys Thr Glu Cys Glu Lys Lys Cys
            260                 265                 270

Lys Gly Glu Cys Asp Ala Tyr Lys Lys Phe Ile Glu Glu Cys Lys Gly
        275                 280                 285

Lys Ala Asp Glu Gly Thr Ser Gly Ser Ser Trp Ser Lys Arg Trp Asp
    290                 295                 300

Gln Ile Tyr Lys Arg Tyr Ser Tyr Ile Glu Asp Ala Lys Arg Asn
305                 310                 315                 320

Arg Lys Ala Gly Thr Lys Asn Cys Gly Pro Ser Ser Thr Thr Ser Thr
                325                 330                 335

Ala Glu Ser Lys Cys Val Gln Ser
            340

<210> SEQ ID NO 14
<211> LENGTH: 334
<212> TYPE: PRT
<213> ORGANISM: Plasmodium falciparum

<400> SEQUENCE: 14

Lys Cys Asp Lys Cys Lys Ser Glu Gln Ser Lys Lys Asn Asn Asn Ile
1               5                   10                  15

Trp Ile Trp Lys Lys Ser Ser Gly Thr Glu Gly Gly Leu Gln Lys Glu
            20                  25                  30

Tyr Ala Asn Thr Ile Ala Leu Pro Pro Arg Thr Gln Ser Leu Tyr Leu
        35                  40                  45

Gly Asn Leu Arg Lys Leu Glu Asn Val Cys Glu Asp Val Lys Asp Ile
    50                  55                  60

Asn Phe Asp Thr Lys Glu Lys Phe Leu Ala Gly Cys Leu Ile Ala Ala
65                  70                  75                  80

Phe His Glu Gly Lys Asn Leu Lys Lys Arg Tyr Leu Glu Lys Lys Asn
                85                  90                  95

Gly Asp Asn Asn Ser Lys Leu Cys Lys Ala Leu Lys Tyr Ser Phe Ala
            100                 105                 110

Asp Tyr Gly Asp Leu Ile Lys Gly Thr Ser Ile Trp Asp Asn Glu Tyr
        115                 120                 125

Thr Lys Asp Leu Glu Leu Asn Leu Gln Lys Ile Phe Gly Lys Leu Phe
    130                 135                 140

Arg Lys Tyr Ile Lys Lys Asn Asn Thr Ala Glu Gln His Thr Ser Tyr
145                 150                 155                 160

Ser Ser Leu Asp Glu Leu Arg Glu Ser Trp Trp Asn Thr Asn Lys Lys
                165                 170                 175

Tyr Ile Trp Leu Ala Met Lys His Gly Thr Thr Cys Ser Ser Gly Ser
            180                 185                 190

Gly Asp Asn Gly Ser Ile Ser Cys Asp Asp Ile Pro Thr Ile Asp Leu
        195                 200                 205
```

```
Ile Pro Gln Tyr Leu Arg Phe Leu Gln Glu Trp Val Glu His Phe Cys
    210                 215                 220

Glu Gln Arg Gln Gly Lys Val Asn Ala Val Ile Glu Asn Cys Asn Ser
225                 230                 235                 240

Cys Lys Asn Thr Ser Ser Lys Thr Lys Leu Gly Gly Thr Cys Asn Gly
                245                 250                 255

Glu Cys Lys Thr Glu Cys Lys Gly Glu Cys Asp Ala Tyr Lys Glu Phe
                260                 265                 270

Ile Glu Lys Cys Lys Gly Thr Ala Ala Glu Gly Thr Ser Gly Ser Ser
            275                 280                 285

Trp Val Lys Arg Trp Tyr Gln Ile Tyr Met Arg Tyr Ser Lys Tyr Ile
        290                 295                 300

Glu Asp Ala Lys Arg Asn Arg Lys Ala Gly Thr Lys Asn Cys Gly Thr
305                 310                 315                 320

Ser Ser Thr Thr Ser Thr Ala Glu Ser Lys Cys Val Gln Ser
                325                 330

<210> SEQ ID NO 15
<211> LENGTH: 332
<212> TYPE: PRT
<213> ORGANISM: Plasmodium falciparum

<400> SEQUENCE: 15

Lys Cys Asp Lys Cys Lys Ser Glu Gln Ser Lys Lys Asn Asn Asn Ile
1               5                   10                  15

Trp Ile Trp Lys Lys Ser Ser Gly Thr Glu Gly Gly Leu Gln Lys Glu
            20                  25                  30

Tyr Ala Asn Thr Ile Ala Leu Pro Pro Arg Thr Gln Ser Leu Tyr Leu
        35                  40                  45

Gly Asn Leu Arg Lys Leu Glu Asn Val Cys Glu Asp Val Lys Asp Ile
    50                  55                  60

Asn Phe Asp Thr Lys Glu Lys Phe Leu Ala Gly Cys Leu Ile Ala Ala
65                  70                  75                  80

Phe His Glu Gly Lys Asn Leu Lys Lys Arg Tyr Leu Glu Lys Lys Asn
                85                  90                  95

Gly Asp Asn Asn Ser Lys Leu Cys Lys Ala Leu Lys Tyr Ser Phe Ala
                100                 105                 110

Asp Tyr Gly Asp Leu Ile Lys Gly Thr Ser Ile Trp Asp Asn Glu Tyr
            115                 120                 125

Thr Lys Asp Leu Glu Leu Asn Leu Gln Lys Ile Phe Gly Lys Leu Phe
130                 135                 140

Arg Lys Tyr Ile Lys Lys Asn Asn Thr Ala Glu Gln Asp Thr Ser Tyr
145                 150                 155                 160

Ser Ser Leu Asp Glu Leu Arg Glu Ser Trp Trp Asn Thr Asn Lys Lys
                165                 170                 175

Tyr Ile Trp Thr Ala Met Lys His Gly Thr Thr Cys Ser Ser Gly Ser
            180                 185                 190

Gly Asp Asn Gly Ser Ile Ser Cys Asp Asp Ile Pro Thr Ile Asp Leu
        195                 200                 205

Ile Pro Gln Tyr Leu Arg Phe Leu Gln Glu Trp Val Glu His Phe Cys
    210                 215                 220

Glu Gln Arg Gln Glu Lys Val Lys Asp Val Ile Lys Asn Cys Asn Ser
225                 230                 235                 240

Cys Lys Glu Cys Gly Gly Thr Cys Asn Gly Glu Cys Lys Thr Glu Cys
```

```
                245                 250                 255
Lys Asn Lys Cys Lys Asp Glu Cys Asp Ala Tyr Lys Lys Phe Ile Glu
            260                 265                 270

Glu Cys Glu Gly Lys Ala Ala Glu Gly Thr Ser Gly Ser Ser Trp Ser
        275                 280                 285

Lys Arg Trp Asp Gln Ile Tyr Lys Arg Tyr Ser Lys Tyr Ile Glu Asp
    290                 295                 300

Ala Lys Arg Asn Arg Lys Ala Gly Thr Lys Asn Cys Gly Thr Ser Ser
305                 310                 315                 320

Thr Thr Ser Thr Ala Glu Asn Lys Cys Val Gln Ser
            325                 330

<210> SEQ ID NO 16
<211> LENGTH: 267
<212> TYPE: PRT
<213> ORGANISM: Plasmodium falciparum

<400> SEQUENCE: 16

Asn Tyr Ile Lys Asp Asp Pro Tyr Ser Ala Glu Tyr Thr Thr Lys Leu
1               5                   10                  15

Ser Phe Ile Leu Asn Ser Ser Asp Thr Glu Asn Ala Ser Glu Lys Ile
            20                  25                  30

Gln Lys Asn Asn Asp Glu Val Cys Asn Pro Asn Glu Ser Gly Ile Ala
        35                  40                  45

Cys Val Glu Leu Ala Gln Thr Ser Gly Ser Ser Asn Lys Thr Cys
    50                  55                  60

Asn Thr His Ser Phe Ile Lys Ala Asn Lys Lys Val Cys Lys Asp
65                  70                  75                  80

Val Lys Leu Gly Ile Asn Lys Lys Asp Lys Asp Leu Lys Ile Cys Val
                85                  90                  95

Ile Glu Asp Asp Ser Leu Arg Gly Val Asp Asn Cys Cys Cys Gln Asp
            100                 105                 110

Leu Leu Gly Ile Leu Gln Glu Asn Cys Ser Asp Lys Asn Gln Ser Gly
        115                 120                 125

Ser Ser Asn Gly Ser Cys Asn Asn Lys Asn Gln Glu Ala Cys Gln
    130                 135                 140

Lys Lys Leu Glu Asn Val Phe Ala Ser Leu Thr Asn Gly Tyr Lys Cys
145                 150                 155                 160

Glu Lys Cys Lys Ser Glu Gln Ser Lys Lys Asn Asn Lys Asn Trp Ile
                165                 170                 175

Trp Lys Lys Tyr Ser Val Lys Glu Glu Gly Leu Gln Lys Glu Tyr Ala
            180                 185                 190

Asn Thr Ile Ala Leu Pro Pro Arg Thr Gln Ser Leu Tyr Leu Gly Asn
        195                 200                 205

Leu Pro Lys Leu Gly Asn Val Cys Lys Gly Val Thr Asp Ile Asn Phe
    210                 215                 220

Asp Thr Lys Glu Lys Phe Leu Ala Gly Cys Leu Ile Ala Ala Phe His
225                 230                 235                 240

Glu Gly Lys Asn Leu Lys Thr Thr Tyr Leu Gln Asn Lys Lys Lys Leu
                245                 250                 255

Cys Lys Ala Leu Lys Tyr Ser Phe Ala Asp Tyr
            260                 265

<210> SEQ ID NO 17
<211> LENGTH: 263
```

```
<212> TYPE: PRT
<213> ORGANISM: Plasmodium falciparum

<400> SEQUENCE: 17

Asp Tyr Ile Lys Gly Asp Pro Tyr Phe Ala Glu Tyr Ala Thr Lys Leu
1               5                   10                  15

Ser Phe Ile Leu Asn Ser Ser Asp Ala Asn Thr Ser Ser Gly Glu Thr
            20                  25                  30

Ala Asn His Asn Asp Glu Ala Cys Asn Pro Asn Glu Ser Glu Ile Ala
        35                  40                  45

Ser Val Glu Gln Ala Ser Ile Ser Asp Arg Ser Ser Gln Lys Ala Cys
    50                  55                  60

Asn Thr His Ser Ser Ile Lys Ala Asn Lys Lys Glu Cys Lys His
65                  70                  75                  80

Val Lys Leu Gly Val Arg Glu Asn Asp Lys Asp Leu Lys Ile Cys Val
                85                  90                  95

Ile Glu Asp Thr Ser Leu Ser Gly Val Asp Asn Cys Cys Gln Asp
            100                 105                 110

Leu Leu Gly Ile Leu Gln Glu Asn Cys Ser Asp Asn Lys Arg Gly Ser
        115                 120                 125

Ser Ser Asn Gly Ser Cys Asp Lys Asn Ser Glu Glu Ile Cys Gln Lys
    130                 135                 140

Lys Leu Asp Glu Ala Leu Ala Ser Leu His Asn Gly Tyr Lys Asn Gln
145                 150                 155                 160

Lys Cys Lys Ser Glu Gln Ser Lys Lys Asn Lys Asn Lys Trp Ile Trp
                165                 170                 175

Lys Lys Ser Ser Gly Asn Glu Lys Gly Leu Gln Lys Glu Tyr Ala Asn
            180                 185                 190

Thr Ile Gly Leu Pro Pro Arg Thr Gln Ser Leu Tyr Leu Gly Asn Leu
        195                 200                 205

Pro Lys Leu Glu Asn Val Cys Glu Asp Val Thr Asp Ile Asn Phe Asp
    210                 215                 220

Thr Lys Glu Lys Phe Leu Ala Gly Cys Leu Ile Ala Ala Phe His Glu
225                 230                 235                 240

Gly Lys Asn Leu Lys Thr Thr Tyr Pro Gln Asn Lys Asn Asp Asp Asn
                245                 250                 255

Gly Lys Lys Leu Cys Lys Asp
            260

<210> SEQ ID NO 18
<211> LENGTH: 338
<212> TYPE: PRT
<213> ORGANISM: Plasmodium falciparum

<400> SEQUENCE: 18

Lys Cys Asp Lys Cys Lys Ser Glu Gln Ser Lys Lys Asn Asn Asn Ile
1               5                   10                  15

Trp Ile Trp Lys Lys Ser Ser Gly Asn Lys Lys Gly Leu Gln Lys Glu
            20                  25                  30

Tyr Ala Asn Thr Ile Gly Leu Pro Pro Arg Thr Gln Ser Leu Tyr Leu
        35                  40                  45

Gly Asn Leu Pro Lys Leu Glu Asn Val Cys Lys Asp Val Thr Asp Ile
    50                  55                  60

Asn Phe Asp Thr Lys Glu Lys Phe Leu Ala Gly Cys Leu Ile Ala Ala
65                  70                  75                  80
```

Phe His Glu Gly Lys Asn Leu Lys Ile Ser Asn Glu Lys Lys Asn Asp
            85                  90                  95

Asp Asn Gly Lys Lys Leu Cys Lys Asp Leu Lys Tyr Ser Phe Ala Asp
        100                 105                 110

Tyr Gly Asp Leu Ile Lys Gly Thr Ser Ile Trp Asp Asn Glu Tyr Thr
        115                 120                 125

Lys Asp Leu Glu Leu Asn Leu Gln Asn Asn Phe Gly Lys Leu Phe Arg
    130                 135                 140

Lys Tyr Ile Lys Lys Asn Asn Thr Ala Glu Gln His Thr Leu Tyr Ser
145                 150                 155                 160

Ser Leu Asp Glu Leu Arg Glu Ser Trp Trp Asn Thr Asn Lys Lys Tyr
                165                 170                 175

Ile Trp Leu Ala Met Lys His Gly Thr Thr Cys Ser Ser Gly Ser Gly
            180                 185                 190

Asp Asn Gly Asp Gly Ser Val Thr Gly Ser Gly Ser Ser Cys Asp Asp
        195                 200                 205

Met Ser Thr Ile Asp Leu Ile Pro Gln Tyr Leu Arg Phe Leu Gln Glu
    210                 215                 220

Trp Val Glu His Phe Cys Lys Gln Arg Gln Glu Lys Val Asn Ala Val
225                 230                 235                 240

Ile Glu Asn Cys Asn Ser Cys Lys Asn Thr Ser Ser Lys Thr Lys Leu
                245                 250                 255

Gly Gly Thr Cys Asn Gly Glu Cys Lys Thr Glu Cys Glu Lys Lys Cys
            260                 265                 270

Lys Asp Glu Cys Glu Lys Tyr Lys Glu Phe Ile Glu Glu Cys Lys Arg
        275                 280                 285

Gly Asp Gly Thr Ala Gly Ser Pro Trp Val Lys Arg Trp Asp Gln Ile
    290                 295                 300

Tyr Met Arg Tyr Ser Lys Tyr Ile Glu Asp Ala Lys Arg Asn Arg Lys
305                 310                 315                 320

Ala Gly Thr Lys Ser Cys Gly Thr Ser Ala Ala Glu Asn Lys Cys Val
                325                 330                 335

Gln Ser

<210> SEQ ID NO 19
<211> LENGTH: 341
<212> TYPE: PRT
<213> ORGANISM: Plasmodium falciparum

<400> SEQUENCE: 19

Lys Cys Asp Lys Cys Lys Ser Glu Gln Ser Lys Lys Asn Asn Asn Ile
1               5                   10                  15

Trp Ile Trp Lys Lys Ser Ser Gly Asp Glu Lys Gly Leu Gln Lys Glu
            20                  25                  30

Tyr Ala Asn Thr Ile Ala Leu Pro Pro Arg Thr Gln Ser Leu Tyr Leu
        35                  40                  45

Gly Asn Leu Pro Lys Leu Glu Asn Val Cys Lys Asp Val Thr Asp Ile
    50                  55                  60

Asn Phe Asp Thr Lys Glu Lys Phe Leu Ala Gly Cys Leu Ile Ala Ala
65                  70                  75                  80

Phe His Glu Gly Lys Asn Leu Lys Thr Ser His Gln Asn Lys Asn Ala
            85                  90                  95

Asp Asn Gly Lys Lys Asn Asp Asp Asn Gly Lys Lys Leu Cys Lys Ala
        100                 105                 110

```
Leu Lys Tyr Ser Phe Ala Asp Tyr Gly Asp Leu Ile Lys Gly Thr Ser
            115                 120                 125

Ile Trp Asp Asn Glu Tyr Thr Lys Asp Leu Glu Leu Asn Leu Gln Gln
        130                 135                 140

Ile Phe Gly Lys Leu Phe Arg Lys Tyr Ile Lys Arg Asn Asn Thr Ala
145                 150                 155                 160

Glu Gln His Thr Leu Tyr Ser Ser Leu Asp Glu Leu Arg Glu Ser Trp
                165                 170                 175

Trp Asn Thr Asn Lys Lys Tyr Ile Trp Leu Ala Met Lys His Gly Thr
            180                 185                 190

Thr Cys Ser Ser Gly Ser Gly Asp Asn Gly Asp Gly Ser Val Thr Gly
        195                 200                 205

Ser Gly Ser Ser Cys Asp Asp Met Ser Thr Ile Asp Leu Ile Pro Gln
210                 215                 220

Tyr Leu Arg Phe Leu Gln Glu Trp Val Glu His Phe Cys Lys Gln Arg
225                 230                 235                 240

Gln Glu Lys Val Lys Asp Val Ile Thr Asn Cys Asn Ser Cys Lys Glu
                245                 250                 255

Cys Gly Gly Thr Cys Gly Ser Asp Cys Lys Thr Lys Cys Glu Ala Tyr
            260                 265                 270

Lys Lys Phe Ile Glu Glu Cys Asn Gly Thr Ala Asp Gly Gly Thr Ser
        275                 280                 285

Gly Ser Ser Trp Ser Lys Arg Trp Asp Gln Ile Tyr Lys Arg Tyr Ser
    290                 295                 300

Lys Tyr Ile Glu Asp Ala Lys Arg Asn Arg Lys Ala Gly Thr Lys Asn
305                 310                 315                 320

Cys Gly Pro Ser Ser Gly Ala Asn Ser Gly Val Thr Thr Glu Asn
                325                 330                 335

Lys Cys Val Gln Ser
            340

<210> SEQ ID NO 20
<211> LENGTH: 352
<212> TYPE: PRT
<213> ORGANISM: Plasmodium falciparum

<400> SEQUENCE: 20

Lys Cys Glu Lys Cys Ser Glu Gln Ser Lys Asn Asn Lys Tyr
1               5                   10                  15

Trp Ile Trp Lys Lys Ser Ser Gly Asn Gly Glu Gly Leu Gln Glu Glu
            20                  25                  30

Tyr Ala Asn Thr Ile Ala Leu Pro Pro Arg Thr His Ser Leu Cys Leu
        35                  40                  45

Val Cys Leu His Glu Lys Gly Lys Lys Thr Gln Glu Leu Lys Asn
    50                  55                  60

Ile Arg Thr Asn Ser Glu Leu Leu Lys Glu Arg Ile Ile Ala Ala Phe
65                  70                  75                  80

His Glu Gly Lys Asn Leu Lys Thr Ser Pro Gln Asn Lys Asn Asp Asn
                85                  90                  95

Gly Lys Lys Leu Cys Lys Asp Leu Lys Tyr Ser Phe Ala Asp Tyr Gly
            100                 105                 110

Asp Leu Ile Lys Gly Thr Ser Ile Trp Asp Asn Glu Tyr Thr Lys Asp
        115                 120                 125

Leu Glu Leu Asn Leu Gln Lys Ile Phe Gly Lys Leu Phe Arg Lys Tyr
    130                 135                 140
```

```
Ile Lys Lys Asn Asn Thr Ala Glu Gln His Thr Leu Tyr Ser Ser Leu
145                 150                 155                 160

Asp Glu Leu Arg Glu Ser Trp Trp Asn Thr Asn Lys Lys Tyr Ile Trp
                165                 170                 175

Leu Ala Met Lys His Gly Ala Gly Met Asn Ser Thr Met Cys Asn Ala
            180                 185                 190

Asp Gly Ser Val Thr Gly Ser Ser Asp Ser Gly Ser Thr Thr Cys Cys
                195                 200                 205

Gly Asp Asn Gly Ser Ile Ser Cys Asp Asp Met Pro Thr Ile Asp Leu
            210                 215                 220

Ile Pro Gln Tyr Leu Arg Phe Leu Gln Glu Trp Val Glu His Phe Cys
225                 230                 235                 240

Glu Gln Arg Gln Glu Lys Val Asn Ala Val Ile Thr Asn Cys Lys Ser
                245                 250                 255

Cys Lys Glu Cys Gly Gly Thr Cys Asn Ser Asp Cys Glu Lys Lys Cys
                260                 265                 270

Lys Ala Tyr Lys Glu Phe Ile Glu Lys Cys Lys Gly Gly Gly Thr Glu
            275                 280                 285

Gly Thr Ser Gly Ser Ser Trp Ser Lys Arg Trp Asp Gln Ile Tyr Lys
            290                 295                 300

Arg His Ser Lys His Ile Glu Asp Ala Lys Arg Asn Arg Lys Ala Gly
305                 310                 315                 320

Thr Lys Asn Cys Gly Ile Thr Gly Thr Ile Ser Gly Glu Ser Ser
                325                 330                 335

Gly Ala Asn Ser Gly Val Thr Thr Thr Glu Asn Lys Cys Val Gln Ser
                340                 345                 350

<210> SEQ ID NO 21
<211> LENGTH: 344
<212> TYPE: PRT
<213> ORGANISM: Plasmodium falciparum

<400> SEQUENCE: 21

Lys Cys Asp Lys Cys Lys Ser Gly Thr Ser Arg Ser Arg Lys Ile Trp
1               5                   10                  15

Thr Trp Arg Lys Phe Arg Gly Asn Gly Glu Gly Leu Gln Lys Glu Tyr
                20                  25                  30

Ala Asn Thr Ile Gly Leu Ser Pro Arg Thr Gln Leu Leu Tyr Leu Val
            35                  40                  45

Cys Leu His Glu Lys Gly Lys Lys Thr Gln Glu Leu Lys Asn Ile Ser
50                  55                  60

Thr Asn Ser Glu Leu Leu Lys Glu Trp Ile Ile Ala Ala Phe His Glu
65                  70                  75                  80

Gly Lys Asn Leu Lys Thr Thr Tyr Pro Gln Lys Lys Asn Asp Asp Asn
                85                  90                  95

Gly Lys Lys Leu Cys Lys Ala Leu Lys Tyr Ser Phe Ala Asp Tyr Gly
            100                 105                 110

Asp Leu Ile Lys Gly Thr Ser Ile Trp Asp Asn Asp Phe Thr Lys Asp
            115                 120                 125

Leu Glu Leu Asn Leu Gln Lys Ile Phe Gly Lys Leu Phe Arg Lys Tyr
            130                 135                 140

Ile Lys Lys Asn Ile Ala Ser Asp Glu Asn Thr Ser Tyr Ser Ser Leu
145                 150                 155                 160

Asp Glu Leu Arg Glu Ser Trp Trp Asn Thr Asn Lys Lys Tyr Ile Trp
```

```
            165                 170                 175
Thr Ala Met Lys His Gly Ala Gly Met Asn Gly Thr Thr Cys Cys Gly
            180                 185                 190

Asp Gly Ser Val Thr Gly Ser Ser Asp Ser Gly Ser Thr Cys Cys
            195                 200                 205

Gly Asp Gly Ser Val Thr Gly Ser Gly Ser Ser Cys Asp Ile Pro
            210                 215                 220

Thr Ile Asp Leu Ile Pro Gln Tyr Leu Arg Phe Leu Gln Glu Trp Val
225                 230                 235                 240

Glu His Phe Cys Glu Gln Arg Gln Glu Lys Val Lys Asp Val Ile Thr
            245                 250                 255

Asn Cys Lys Ser Cys Lys Glu Ser Glu Lys Lys Cys Lys Asn Lys Cys
            260                 265                 270

Asp Ala Tyr Lys Glu Phe Ile Asp Gly Thr Gly Ser Gly Gly Gly Thr
            275                 280                 285

Gly Thr Ala Gly Ser Ser Trp Ser Lys Arg Trp Asp Gln Ile Tyr Met
            290                 295                 300

Arg Tyr Ser Lys Tyr Ile Glu Asp Ala Lys Arg Asn Arg Lys Ala Gly
305                 310                 315                 320

Thr Lys Asn Cys Gly Thr Ser Ser Gly Ala Asn Ser Gly Val Thr Thr
            325                 330                 335

Thr Glu Asn Lys Cys Val Gln Ser
            340

<210> SEQ ID NO 22
<211> LENGTH: 350
<212> TYPE: PRT
<213> ORGANISM: Plasmodium falciparum

<400> SEQUENCE: 22

Lys Cys Glu Lys Cys Lys Ser Glu Gln Ser Lys Lys Asn Asn Lys Ile
1               5                   10                  15

Trp Thr Trp Arg Lys Phe Pro Gly Asn Gly Glu Gly Leu Gln Lys Glu
            20                  25                  30

Tyr Ala Asn Thr Ile Gly Leu Ser Pro Arg Thr Gln Leu Leu Tyr Leu
            35                  40                  45

Val Cys Leu His Glu Lys Gly Lys Lys Thr Gln His Lys Thr Ile Ser
    50                  55                  60

Thr Asn Ser Glu Leu Leu Lys Glu Trp Ile Ile Ala Ala Phe His Glu
65                  70                  75                  80

Gly Lys Asn Leu Lys Lys Arg Tyr Leu Glu Lys Lys Gly Asp Asn
            85                  90                  95

Asn Ser Lys Leu Cys Lys Asp Leu Lys Tyr Ser Phe Ala Asp Tyr Gly
            100                 105                 110

Asp Leu Ile Lys Gly Thr Ser Ile Trp Asp Asn Asp Phe Thr Lys Asp
            115                 120                 125

Leu Glu Leu Asn Leu Gln Gln Ile Phe Gly Lys Leu Phe Arg Lys Tyr
130                 135                 140

Ile Lys Lys Asn Ile Ala Ser Asp Glu Asn Thr Ser Tyr Ser Ser Leu
145                 150                 155                 160

Asp Glu Leu Arg Glu Ser Trp Trp Asn Thr Asn Lys Lys Tyr Ile Trp
            165                 170                 175

Thr Ala Met Lys His Gly Ala Gly Met Asn Ser Thr Met Cys Asn Gly
            180                 185                 190
```

```
Asp Gly Ser Val Thr Gly Ser Ser Asp Ser Gly Ser Thr Thr Cys Ser
            195                 200                 205

Gly Asp Asn Gly Ser Ile Ser Cys Asp Ile Pro Thr Ile Asp Leu
        210                 215                 220

Ile Pro Gln Tyr Leu Arg Phe Leu Gln Glu Trp Val Glu His Phe Cys
225                 230                 235                 240

Glu Gln Arg Gln Glu Lys Val Lys Asp Val Ile Lys Asn Cys Asn Ser
                245                 250                 255

Cys Lys Glu Cys Gly Gly Thr Cys Asn Gly Cys Lys Thr Glu Cys
            260                 265                 270

Lys Asn Lys Cys Lys Asp Glu Cys Glu Lys Tyr Lys Asn Phe Ile Glu
        275                 280                 285

Val Cys Thr Gly Gly Asp Gly Thr Ala Gly Ser Pro Trp Ser Lys Arg
    290                 295                 300

Trp Tyr Gln Ile Tyr Met Arg Tyr Ser Lys Tyr Ile Glu Asp Ala Lys
305                 310                 315                 320

Arg Asn Arg Lys Ala Gly Thr Lys Ser Cys Gly Thr Ser Ser Gly Ala
                325                 330                 335

Asn Ser Gly Val Thr Thr Thr Glu Ser Lys Cys Val Gln Ser
            340                 345                 350

<210> SEQ ID NO 23
<211> LENGTH: 359
<212> TYPE: PRT
<213> ORGANISM: Plasmodium falciparum

<400> SEQUENCE: 23

Lys Cys Glu Lys Cys Lys Ser Glu Gln Ser Lys Lys Asn Asn Lys Asn
1               5                   10                  15

Trp Ile Trp Arg Lys Phe Pro Gly Asn Gly Glu Gly Leu Gln Lys Glu
                20                  25                  30

Tyr Ala Asn Thr Ile Gly Leu Pro Pro Arg Thr His Ser Leu Tyr Leu
            35                  40                  45

Val Cys Leu His Glu Lys Gly Lys Lys Thr Gln Glu Leu Lys Asn Ile
    50                  55                  60

Arg Thr Asn Ser Glu Leu Leu Lys Glu Trp Ile Ala Ala Phe His
65                  70                  75                  80

Glu Gly Lys Asn Leu Lys Lys Arg Tyr His Gln Asn Asn Asn Ser Gly
                85                  90                  95

Asn Lys Lys Lys Leu Cys Lys Ala Leu Glu Tyr Ser Phe Ala Asp Tyr
            100                 105                 110

Gly Asp Leu Ile Lys Gly Thr Ser Ile Trp Asp Asn Glu Tyr Thr Lys
        115                 120                 125

Asp Leu Glu Leu Asn Leu Gln Gln Ile Phe Gly Lys Leu Phe Arg Lys
    130                 135                 140

Tyr Ile Lys Lys Asn Ile Ser Thr Glu Gln Asp Thr Leu Tyr Ser Ser
145                 150                 155                 160

Leu Asp Glu Leu Arg Glu Ser Trp Trp Asn Thr Asn Lys Lys Tyr Ile
                165                 170                 175

Trp Leu Ala Met Lys His Gly Ala Gly Met Asn Ser Thr Thr Cys Cys
            180                 185                 190

Gly Asp Gly Ser Val Thr Gly Ser Ser Asp Ser Gly Ser Thr Thr Cys
        195                 200                 205

Ser Gly Asp Asn Gly Ser Ile Ser Cys Asp Asp Met Pro Thr Ile Asp
    210                 215                 220
```

-continued

Leu Ile Pro Gln Tyr Leu Arg Phe Leu Gln Glu Trp Val Glu His Phe
225                 230                 235                 240

Cys Glu Gln Arg Gln Glu Lys Val Lys Asp Val Ile Glu Asn Cys Lys
            245                 250                 255

Ser Cys Lys Asn Thr Ser Gly Glu Arg Ile Ile Gly Gly Thr Cys Asn
            260                 265                 270

Gly Glu Cys Lys Thr Glu Cys Glu Lys Cys Lys Ala Ala Cys Glu
            275                 280                 285

Ala Tyr Lys Thr Phe Ile Glu Glu Cys Glu Gly Lys Ala Ala Glu Gly
            290                 295                 300

Thr Ser Gly Ser Ser Trp Ser Lys Arg Trp Tyr Gln Ile Tyr Met Arg
305                 310                 315                 320

Tyr Ser Lys Tyr Ile Glu Asp Ala Lys Arg Asn Arg Lys Ala Gly Thr
                325                 330                 335

Lys Asn Cys Gly Lys Ser Ser Gly Ala Asn Ser Gly Val Thr Thr Thr
            340                 345                 350

Glu Asn Lys Cys Val Gln Ser
            355

<210> SEQ ID NO 24
<211> LENGTH: 270
<212> TYPE: PRT
<213> ORGANISM: Plasmodium falciparum

<400> SEQUENCE: 24

Asn Tyr Ile Lys Asp Asp Pro Tyr Ser Lys Glu Tyr Val Thr Lys Leu
1               5                   10                  15

Ser Phe Ile Pro Asn Ser Ser Asp Ala Asn Asn Pro Ser Gly Glu Thr
            20                  25                  30

Ala Asn His Asn Asp Glu Val Cys Asn Pro Asn Glu Ser Glu Ile Ser
        35                  40                  45

Ser Val Glu His Ala Gln Thr Ser Val Leu Leu Ser Gln Lys Ala Tyr
    50                  55                  60

Ile Thr His Ser Ser Ile Lys Ala Asn Lys Lys Val Cys Lys Tyr
65                  70                  75                  80

Val Lys Leu Gly Val Arg Glu Asn Asp Lys Asp Leu Lys Ile Cys Val
                85                  90                  95

Ile Glu Asp Asp Ser Leu Arg Gly Val Glu Asn Cys Cys Phe Lys Asp
            100                 105                 110

Phe Leu Arg Ile Leu Gln Glu Asn Cys Ser Asp Asn Lys Arg Glu Ser
        115                 120                 125

Ser Ser Asn Gly Ser Cys Asn Asn Asn Glu Glu Ala Cys Glu Lys
        130                 135                 140

Asn Leu Asp Glu Ala Leu Ala Ser Leu Thr Asn Cys Tyr Lys Asn Gln
145                 150                 155                 160

Lys Cys Lys Ser Gly Thr Ser Thr Val Asn Asn Lys Trp Ile Trp
                165                 170                 175

Lys Lys Ser Ser Gly Lys Glu Gly Gly Leu Gln Lys Glu Tyr Ala Asn
            180                 185                 190

Thr Ile Gly Leu Pro Pro Arg Thr Gln Ser Leu Cys Leu Val Val Cys
        195                 200                 205

Leu Asp Glu Lys Glu Gly Lys Thr Gln Glu Leu Lys Asn Ile Arg Thr
    210                 215                 220

Asn Ser Glu Leu Leu Lys Glu Trp Ile Ile Ala Ala Phe His Glu Gly

```
            225                 230                 235                 240
Lys Asn Leu Lys Lys Arg Tyr His Gln Asn Lys Asn Asp Asp Asn Asn
                    245                 250                 255
Ser Lys Leu Cys Lys Ala Leu Lys Tyr Ser Phe Ala Asp Tyr
                    260                 265                 270

<210> SEQ ID NO 25
<211> LENGTH: 334
<212> TYPE: PRT
<213> ORGANISM: Plasmodium falciparum

<400> SEQUENCE: 25

Lys Cys Asp Lys Cys Lys Ser Glu Gln Ser Lys Lys Asn Asn Lys Tyr
1               5                   10                  15
Trp Ile Trp Lys Lys Tyr Ser Val Lys Glu Gly Gly Leu Gln Lys Glu
                20                  25                  30
Tyr Ala Asn Thr Ile Ala Leu Pro Pro Arg Thr Gln Ser Leu Cys Leu
                35                  40                  45
Val Val Cys Leu Asp Glu Lys Glu Gly Lys Thr Gln Glu Leu Lys Asn
            50                  55                  60
Ile Arg Thr Asn Ser Glu Leu Leu Lys Glu Arg Ile Ile Ala Ala Phe
65                  70                  75                  80
His Glu Gly Lys Asn Leu Lys Thr Tyr His Glu Lys Lys Lys Gly Asp
                85                  90                  95
Asp Gly Lys Lys Leu Cys Lys Asp Leu Lys Tyr Ser Phe Ala Asp Tyr
                100                 105                 110
Gly Asp Leu Ile Lys Gly Thr Ser Ile Trp Asp Asn Asp Phe Thr Lys
            115                 120                 125
Asp Leu Glu Leu Asn Leu Gln Lys Ile Phe Gly Lys Leu Phe Arg Lys
130                 135                 140
Tyr Ile Lys Lys Asn Asn Thr Ala Glu Gln His Thr Ser Tyr Ser Ser
145                 150                 155                 160
Leu Asp Glu Leu Arg Glu Ser Trp Trp Asn Thr Asn Lys Lys Tyr Ile
                165                 170                 175
Trp Thr Ala Met Lys His Gly Ala Glu Met Asn Gly Thr Thr Cys Ser
                180                 185                 190
Cys Ser Gly Asp Ser Ser Asn Asp Ile Pro Thr Ile Asp Leu Ile Pro
            195                 200                 205
Gln Tyr Leu Arg Phe Leu Gln Glu Trp Val Glu His Phe Cys Glu Gln
            210                 215                 220
Arg Gln Ala Lys Val Asn Ala Val Ile Lys Asn Cys Lys Ser Cys Lys
225                 230                 235                 240
Glu Cys Gly Gly Thr Cys Asn Gly Glu Cys Lys Thr Glu Cys Lys Thr
                245                 250                 255
Lys Cys Lys Gly Glu Cys Glu Lys Tyr Lys Glu Phe Ile Glu Lys Cys
                260                 265                 270
Glu Gly Gln Ala Ala Glu Gly Thr Ser Gly Ser Ser Trp Ser Lys Arg
                275                 280                 285
Trp Tyr Gln Ile Tyr Met Arg Tyr Ser Lys Tyr Ile Glu Asp Ala Lys
            290                 295                 300
Arg Asn Arg Lys Ala Gly Thr Lys Asn Cys Gly Thr Ser Ser Gly Ala
305                 310                 315                 320
Asn Ser Gly Val Thr Thr Thr Glu Asn Lys Cys Val Gln Ser
                325                 330
```

<210> SEQ ID NO 26
<211> LENGTH: 351
<212> TYPE: PRT
<213> ORGANISM: Plasmodium falciparum

<400> SEQUENCE: 26

Lys Cys Asp Lys Cys Lys Ser Glu Gln Ser Lys Lys Asn Asn Lys Asn
1               5                   10                  15

Trp Ile Trp Lys Lys Tyr Ser Gly Thr Glu Gly Gly Leu Gln Lys Glu
            20                  25                  30

Tyr Ala Asn Thr Ile Ala Leu Pro Pro Arg Thr Gln Ser Leu Tyr Leu
        35                  40                  45

Val Cys Leu His Glu Lys Glu Glu Lys Thr Gln Glu Leu Lys Asn Ile
50                  55                  60

Ser Thr Asn Ser Glu Leu Leu Lys Glu Trp Ile Ala Ala Phe His
65                  70                  75                  80

Glu Gly Lys Asn Leu Lys Ile Ser Pro Gln Asn Lys Asn Asp Asn Gly
                85                  90                  95

Lys Asn Leu Cys Lys Asp Leu Lys Tyr Ser Phe Ala Asp Tyr Gly Asp
            100                 105                 110

Leu Ile Lys Gly Thr Ser Ile Trp Asp Asn Asp Phe Thr Lys Asp Leu
        115                 120                 125

Glu Leu Asn Leu Gln Gln Ile Phe Gly Lys Leu Phe Arg Lys Tyr Ile
130                 135                 140

Lys Lys Asn Asn Thr Ala Glu Gln Asp Thr Leu Tyr Ser Ser Leu Asp
145                 150                 155                 160

Glu Leu Arg Glu Ser Trp Trp Asn Thr Asn Lys Lys Tyr Ile Trp Thr
                165                 170                 175

Ala Met Lys His Gly Ala Gly Met Asn Gly Thr Thr Cys Cys Gly Asp
            180                 185                 190

Gly Ser Val Thr Gly Ser Ser Asp Ser Gly Ser Thr Thr Cys Cys Gly
        195                 200                 205

Asp Gly Ser Val Thr Gly Ser Gly Ser Ser Cys Asp Asp Ile Pro Thr
210                 215                 220

Ile Asp Leu Ile Pro Gln Tyr Leu Arg Phe Leu Gln Glu Trp Val Glu
225                 230                 235                 240

His Phe Cys Glu Gln Arg Gln Ala Lys Val Lys Asp Val Ile Lys Asn
                245                 250                 255

Cys Asn Ser Cys Lys Glu Cys Gly Gly Thr Cys Asn Gly Glu Cys Lys
            260                 265                 270

Thr Glu Cys Glu Lys Lys Cys Lys Gly Glu Cys Glu Ala Tyr Lys Lys
        275                 280                 285

Phe Ile Glu Lys Cys Asn Gly Gly Gly Gly Gly Thr Ser Gly Ser
290                 295                 300

Ser Trp Ser Lys Arg Trp Asp Gln Ile Tyr Met Arg Tyr Ser Lys Tyr
305                 310                 315                 320

Ile Glu Asp Ala Lys Arg Asn Arg Lys Ala Gly Thr Lys Asn Cys Gly
                325                 330                 335

Thr Ser Thr Thr Asn Ala Ala Glu Asn Lys Cys Val Gln Ser
            340                 345                 350

<210> SEQ ID NO 27
<211> LENGTH: 353
<212> TYPE: PRT
<213> ORGANISM: Plasmodium falciparum

```
<400> SEQUENCE: 27

Lys Cys Asp Lys Cys Lys Ser Gly Thr Ser Thr Val Asn Lys Lys Trp
1               5                   10                  15

Ile Trp Lys Lys Phe Pro Gly Lys Glu Gly Gly Leu Gln Glu Glu Tyr
            20                  25                  30

Ala Asn Thr Ile Ala Leu Pro Pro Arg Thr Gln Ser Leu Cys Leu Val
        35                  40                  45

Val Cys Leu Asp Glu Lys Glu Gly Lys Thr Gln His Lys Thr Ile Ser
50                  55                  60

Thr Asn Ser Glu Leu Leu Lys Glu Trp Ile Ile Ala Ala Phe His Glu
65                  70                  75                  80

Gly Lys Asn Leu Lys Ile Ser Asn Lys Lys Asn Asp Glu Asn Asn
                85                  90                  95

Ser Lys Leu Cys Lys Asp Leu Lys Tyr Ser Phe Ala Asp Tyr Gly Asp
            100                 105                 110

Leu Ile Lys Gly Thr Ser Ile Trp Asp Asn Asp Phe Thr Lys Asp Leu
            115                 120                 125

Glu Leu Asn Leu Gln Lys Ile Phe Gly Lys Leu Phe Arg Lys Tyr Ile
130                 135                 140

Lys Lys Asn Asn Thr Ala Glu Gln Asp Thr Ser Tyr Ser Ser Leu Asp
145                 150                 155                 160

Glu Leu Arg Glu Ser Trp Trp Asn Thr Asn Lys Lys Tyr Ile Trp Leu
                165                 170                 175

Ala Met Lys His Gly Thr Thr Cys Ser Ser Gly Ser Gly Asp Asn Gly
            180                 185                 190

Asp Gly Ser Val Thr Gly Ser Ser Asp Ser Gly Ser Thr Thr Cys Cys
        195                 200                 205

Gly Asp Gly Ser Val Thr Gly Ser Gly Ser Ser Cys Asp Asp Ile Pro
    210                 215                 220

Thr Ile Asp Leu Ile Pro Gln Tyr Leu Arg Phe Leu Gln Glu Trp Val
225                 230                 235                 240

Glu His Phe Cys Lys Gln Arg Gln Ala Lys Val Lys Asp Val Ile Glu
                245                 250                 255

Asn Cys Lys Ser Cys Lys Asn Thr Ser Ser Lys Thr Lys Leu Gly Asp
            260                 265                 270

Thr Cys Asn Ser Asp Cys Lys Thr Cys Lys Val Ala Cys Glu Lys
        275                 280                 285

Tyr Lys Glu Phe Ile Glu Lys Cys Val Ser Ala Ala Gly Gly Thr Ser
    290                 295                 300

Gly Ser Ser Trp Val Lys Arg Trp Asp Gln Ile Tyr Met Arg Tyr Ser
305                 310                 315                 320

Lys Tyr Ile Glu Asp Ala Lys Arg Asn Arg Lys Ala Gly Thr Lys Asn
                325                 330                 335

Cys Gly Pro Ser Ser Thr Thr Ser Thr Ala Glu Ser Lys Cys Val Gln
            340                 345                 350

Ser

<210> SEQ ID NO 28
<211> LENGTH: 327
<212> TYPE: PRT
<213> ORGANISM: Plasmodium falciparum

<400> SEQUENCE: 28
```

Lys Cys Asp Lys Cys Lys Ser Gly Thr Ser Thr Val Asn Lys Lys Trp
1               5                   10                  15

Ile Trp Lys Lys Tyr Ser Gly Lys Glu Gly Gly Leu Gln Lys Glu Tyr
            20                  25                  30

Ala Asn Thr Ile Gly Leu Pro Pro Arg Thr Gln Ser Leu Cys Leu Val
            35                  40                  45

Cys Leu His Glu Lys Glu Gly Lys Thr Gln Glu Leu Lys Asn Ile Ser
        50                  55                  60

Thr Asn Ser Glu Leu Leu Lys Glu Trp Ile Ile Ala Ala Phe His Glu
65                  70                  75                  80

Gly Lys Asn Leu Lys Ile Ser Asn Lys Lys Asn Asp Asp Asn Gly
            85                  90                  95

Lys Lys Leu Cys Lys Asp Leu Lys Tyr Ser Phe Ala Asp Tyr Gly Asp
            100                 105                 110

Leu Ile Lys Gly Thr Ser Ile Trp Asp Asn Asp Phe Thr Lys Asp Leu
            115                 120                 125

Glu Leu Asn Leu Gln Lys Ile Phe Gly Lys Leu Phe Arg Lys Tyr Ile
            130                 135                 140

Lys Lys Asn Asn Thr Ala Glu Gln Asp Thr Leu Tyr Ser Ser Leu Asp
145                 150                 155                 160

Glu Leu Arg Glu Ser Trp Trp Asn Thr Asn Lys Lys Tyr Ile Trp Thr
            165                 170                 175

Ala Met Lys His Gly Ala Gly Met Asn Ser Thr Thr Cys Ser Cys Ser
            180                 185                 190

Gly Asp Ser Ser Asn Asp Ile Pro Thr Ile Asp Leu Ile Pro Gln Tyr
            195                 200                 205

Leu Arg Phe Leu Gln Glu Trp Val Glu His Phe Cys Lys Gln Arg Gln
            210                 215                 220

Glu Lys Val Asn Ala Val Ile Thr Asn Cys Lys Ser Cys Lys Glu Ser
225                 230                 235                 240

Gly Gly Thr Cys Asn Ser Asp Cys Glu Lys Cys Lys Ile Glu Cys
            245                 250                 255

Glu Lys Tyr Lys Asn Phe Ile Glu Lys Cys Val Thr Ala Ala Gly Gly
            260                 265                 270

Thr Ser Gly Ser Ser Trp Ser Lys Arg Trp Asp Gln Ile Tyr Lys Met
            275                 280                 285

Tyr Ser Lys Tyr Ile Glu Asp Ala Lys Arg Asn Arg Lys Ala Gly Thr
            290                 295                 300

Lys Asn Cys Gly Pro Ser Ser Thr Thr Asn Ala Ala Ala Ser Thr Asp
305                 310                 315                 320

Glu Asn Lys Cys Val Gln Ser
                325

<210> SEQ ID NO 29
<211> LENGTH: 628
<212> TYPE: PRT
<213> ORGANISM: Artificial
<220> FEATURE:
<223> OTHER INFORMATION: Artificial construct

<400> SEQUENCE: 29

Asn Tyr Ile Lys Gly Asp Pro Tyr Phe Ala Glu Tyr Ala Thr Lys Leu
1               5                   10                  15

Ser Phe Ile Leu Asn Ser Asp Thr Glu Asn Ala Ser Glu Thr Pro
            20                  25                  30

-continued

```
Ser Lys Tyr Tyr Asp Glu Ala Cys Asn Cys Asn Glu Ser Glu Ile Ala
             35                  40                  45
Ser Val Gly Gln Ala Gln Thr Ser Gly Pro Ser Ser Asn Lys Thr Cys
 50                  55                  60
Ile Thr His Ser Ser Ile Lys Thr Asn Lys Lys Glu Cys Lys Asp
 65                  70                  75                  80
Val Lys Leu Gly Ile Asn Asn Asn Asp Lys Val Leu Arg Val Cys Val
                 85                  90                  95
Ile Glu Asp Thr Ser Leu Ser Gly Val Asp Asn Cys Cys Cys Gln Asp
                100                 105                 110
Leu Leu Gly Ile Leu Gln Glu Asn Cys Ser Asp Asn Lys Arg Gly Ser
                115                 120                 125
Ser Ser Asn Gly Ser Cys Asp Lys Asn Ser Glu Glu Ile Cys Gln Lys
 130                 135                 140
Lys Leu Glu Lys Val Phe Ala Ser Leu Thr Asn Gly Tyr Lys Cys Asp
 145                 150                 155                 160
Lys Cys Lys Ser Gly Thr Ser Arg Ser Lys Lys Trp Ile Trp Lys
                165                 170                 175
Lys Ser Ser Gly Asn Glu Glu Gly Leu Gln Lys Glu Tyr Ala Asn Thr
                180                 185                 190
Ile Gly Leu Pro Pro Arg Thr Gln Ser Leu Cys Leu Val Cys Leu His
                195                 200                 205
Glu Lys Glu Gly Lys Thr Gln His Lys Thr Ile Ser Thr Asn Ser Glu
                210                 215                 220
Leu Leu Lys Glu Trp Ile Ile Ala Ala Phe His Glu Gly Lys Asn Leu
 225                 230                 235                 240
Lys Thr Ser His Glu Lys Lys Asn Asp Asp Asn Gly Lys Lys Leu Cys
                245                 250                 255
Lys Ala Leu Glu Tyr Ser Phe Ala Asp Tyr Gly Asp Leu Ile Lys Gly
                260                 265                 270
Thr Ser Ile Trp Asp Asn Glu Tyr Thr Lys Asp Leu Glu Leu Asn Leu
                275                 280                 285
Gln Lys Ile Phe Gly Lys Leu Phe Arg Lys Tyr Ile Lys Lys Asn Asn
 290                 295                 300
Thr Ala Glu Gln His Thr Ser Tyr Ser Ser Leu Asp Glu Leu Arg Glu
 305                 310                 315                 320
Ser Trp Trp Asn Thr Asn Lys Lys Tyr Ile Trp Thr Ala Met Lys His
                325                 330                 335
Gly Ala Gly Met Asn Gly Thr Thr Cys Ser Cys Ser Gly Asp Ser Ser
                340                 345                 350
Asn Asp Met Pro Thr Ile Asp Leu Ile Pro Gln Tyr Leu Arg Phe Leu
                355                 360                 365
Gln Glu Trp Val Glu His Phe Cys Lys Gln Arg Gln Glu Lys Val Asn
                370                 375                 380
Ala Val Ile Glu Asn Cys Asn Cys Lys Glu Ser Gly Gly Thr Cys
 385                 390                 395                 400
Asn Ser Asp Cys Lys Thr Glu Cys Lys Asn Lys Cys Glu Ala Tyr Lys
                405                 410                 415
Glu Phe Ile Glu Asp Cys Lys Gly Gly Thr Gly Thr Ala Gly Ser
                420                 425                 430
Pro Trp Ser Lys Arg Trp Asp Gln Ile Tyr Lys Arg Tyr Ser Lys His
                435                 440                 445
Ile Glu Asp Ala Lys Arg Asn Arg Lys Ala Gly Thr Lys Asn Cys Gly
```

```
                 450             455             460
Thr Ser Ser Thr Thr Asn Ala Ala Ser Thr Asp Glu Asn Lys Cys
465                 470             475                 480

Val Gln Ser Asp Val Asp Ser Phe Phe Lys His Leu Ile Asp Ile Gly
                    485             490             495

Leu Thr Thr Pro Ser Ser Tyr Leu Ser Asn Val Leu Asp Asp Asn Ile
                500             505             510

Cys Gly Ala Asp Lys Ala Pro Trp Thr Thr Tyr Thr Thr Tyr Thr Thr
            515             520             525

Thr Lys Asn Cys Asp Ile Gln Lys Lys Thr Pro Lys Ser Gln Ser Cys
        530             535             540

Asp Thr Leu Val Val Val Asn Val Pro Ser Pro Leu Gly Asn Thr Pro
545             550             555             560

His Glu Tyr Lys Tyr Ala Cys Glu Cys Lys Ile Pro Thr Thr Glu Glu
                565             570             575

Thr Cys Asp Asp Arg Lys Glu Tyr Met Asn Gln Trp Ser Cys Gly Ser
            580             585             590

Ala Gln Thr Val Arg Gly Arg Ser Gly Lys Asp Asp Tyr Glu Leu Tyr
        595             600             605

Thr Tyr Asn Gly Val Lys Glu Thr Lys Pro Leu Gly Thr Leu Lys Asn
    610             615             620

Ser Lys Leu Asp
625

<210> SEQ ID NO 30
<211> LENGTH: 350
<212> TYPE: PRT
<213> ORGANISM: Plasmodium falciparum

<400> SEQUENCE: 30

Lys Cys Glu Lys Cys Lys Ser Glu Gln Ser Lys Lys Asn Asn Lys Asn
1               5                   10                  15

Trp Ile Trp Arg Lys Phe Arg Gly Thr Glu Gly Gly Leu Gln Glu Glu
                20                  25                  30

Tyr Ala Asn Thr Ile Gly Leu Pro Pro Arg Thr Gln Ser Leu Cys Leu
            35                  40                  45

Val Val Cys Leu Asp Glu Lys Gly Lys Lys Thr Gln Glu Leu Lys Asn
        50                  55                  60

Ile Arg Thr Asn Ser Glu Leu Leu Lys Glu Trp Ile Ile Ala Ala Phe
65                  70                  75                  80

His Glu Gly Lys Asn Leu Lys Pro Ser His Gln Asn Lys Asn Ser Gly
                85                  90                  95

Asn Lys Glu Asn Leu Cys Lys Ala Leu Lys Tyr Ser Phe Ala Asp Tyr
            100                 105                 110

Gly Asp Leu Ile Lys Gly Thr Ser Ile Trp Asp Asn Asp Phe Thr Lys
        115                 120                 125

Asp Leu Glu Leu Asn Leu Gln Lys Ile Phe Gly Lys Leu Phe Arg Lys
130                 135                 140

Tyr Ile Lys Lys Asn Asn Thr Ala Glu Gln His Thr Ser Tyr Ser Ser
145                 150                 155                 160

Leu Asp Glu Leu Arg Glu Ser Trp Trp Asn Thr Asn Lys Lys Tyr Ile
                165                 170                 175

Trp Thr Ala Met Lys His Gly Ala Glu Met Asn Gly Thr Thr Cys Asn
            180                 185                 190
```

```
Ala Asp Gly Ser Val Thr Gly Ser Ser Asp Ser Gly Ser Thr Thr Cys
            195                 200                 205

Ser Gly Asp Asn Gly Ser Ile Ser Cys Asp Asp Ile Pro Thr Ile Asp
210                 215                 220

Leu Ile Pro Gln Tyr Leu Arg Phe Leu Gln Glu Trp Val Glu His Phe
225                 230                 235                 240

Cys Lys Gln Arg Gln Glu Lys Val Asn Ala Val Ile Asn Ser Cys Asn
                245                 250                 255

Ser Cys Lys Asn Thr Ser Ser Lys Thr Lys Leu Gly Asp Thr Cys Asn
            260                 265                 270

Ser Asp Cys Lys Thr Lys Cys Lys Ile Glu Cys Glu Lys Tyr Lys Thr
            275                 280                 285

Phe Ile Glu Lys Cys Val Thr Ala Ala Gly Thr Ser Gly Ser Pro
290                 295                 300

Trp Ser Lys Arg Trp Asp Gln Ile Tyr Lys Arg Tyr Ser Lys Tyr Ile
305                 310                 315                 320

Glu Asp Ala Lys Arg Asn Arg Lys Ala Gly Thr Lys Asn Cys Gly Pro
                325                 330                 335

Ser Ser Thr Thr Ser Thr Ala Glu Ser Lys Cys Val Gln Ser
            340                 345                 350

<210> SEQ ID NO 31
<211> LENGTH: 330
<212> TYPE: PRT
<213> ORGANISM: Plasmodium falciparum

<400> SEQUENCE: 31

Lys Cys Asp Lys Cys Lys Ser Glu Gln Ser Lys Lys Asn Asn Lys Asn
1               5                   10                  15

Trp Ile Trp Arg Lys Tyr Ser Gly Asn Gly Gly Leu Gln Lys Glu
                20                  25                  30

Tyr Ala Asn Thr Ile Gly Leu Pro Pro Arg Thr His Ser Leu Tyr Leu
            35                  40                  45

Val Cys Leu His Glu Lys Glu Gly Lys Thr Gln Glu Leu Lys Asn Ile
50                  55                  60

Arg Thr Asn Ser Glu Leu Leu Lys Glu Trp Ile Ala Ala Phe His
65                  70                  75                  80

Glu Gly Lys Asn Leu Lys Thr Thr Tyr Leu Glu Asn Lys Asn Asp Glu
                85                  90                  95

Asn Lys Lys Lys Leu Cys Lys Ala Leu Lys Tyr Ser Phe Ala Asp Tyr
            100                 105                 110

Gly Asp Leu Ile Lys Gly Thr Ser Ile Trp Asp Asn Asp Phe Thr Lys
        115                 120                 125

Asp Leu Glu Leu Asn Leu Gln Lys Ile Phe Gly Lys Leu Phe Arg Lys
130                 135                 140

Tyr Ile Lys Lys Asn Ile Ala Ser Asp Glu Asn Thr Leu Tyr Ser Ser
145                 150                 155                 160

Leu Asp Glu Leu Arg Glu Ser Trp Trp Asn Thr Asn Lys Lys Tyr Ile
                165                 170                 175

Trp Thr Ala Met Lys His Gly Ala Glu Met Asn Gly Thr Thr Cys Ser
            180                 185                 190

Ser Gly Ser Gly Asp Asn Gly Ser Ile Ser Cys Asp Asp Ile Pro Thr
        195                 200                 205

Ile Asp Leu Ile Pro Gln Tyr Leu Arg Phe Leu Gln Glu Trp Val Gly
210                 215                 220
```

```
His Phe Cys Lys Gln Arg Gln Glu Lys Val Asn Ala Val Ile Thr Asn
225                 230                 235                 240

Cys Asn Ser Cys Lys Glu Ser Gly Gly Thr Cys Asn Ser Asp Cys Glu
            245                 250                 255

Lys Lys Cys Lys Ile Glu Cys Glu Lys Tyr Lys Lys Phe Ile Glu Glu
        260                 265                 270

Cys Arg Thr Ala Ala Gly Gly Thr Ser Gly Ser Pro Trp Ser Lys Arg
            275                 280                 285

Trp Asp Gln Ile Tyr Lys Met Tyr Ser Lys Tyr Ile Glu Asp Ala Lys
            290                 295                 300

Arg Asn Arg Lys Ala Gly Thr Lys Asn Cys Gly Pro Ser Ser Thr Thr
305                 310                 315                 320

Ser Thr Ala Glu Ser Lys Cys Val Gln Ser
                325                 330

<210> SEQ ID NO 32
<211> LENGTH: 334
<212> TYPE: PRT
<213> ORGANISM: Plasmodium falciparum

<400> SEQUENCE: 32

Lys Cys Asp Lys Cys Lys Ser Glu Gln Ser Lys Lys Asn Asn Lys Asn
1               5                   10                  15

Trp Ile Trp Arg Lys Tyr Ser Gly Asn Gly Glu Gly Leu Gln Lys Glu
            20                  25                  30

Tyr Ala Asn Thr Ile Gly Leu Pro Pro Arg Thr His Ser Leu Tyr Leu
            35                  40                  45

Val Cys Leu His Glu Lys Glu Gly Lys Thr Gln His Lys Thr Ile Ser
        50                  55                  60

Thr Asn Ser Glu Leu Leu Lys Glu Trp Ile Ile Ala Ala Phe His Glu
65                  70                  75                  80

Gly Lys Asn Leu Lys Lys Arg Tyr Pro Gln Asn Asn Asn Ser Gly Asn
                85                  90                  95

Lys Lys Lys Leu Cys Lys Asp Leu Lys Tyr Ser Phe Ala Asp Tyr Gly
            100                 105                 110

Asp Leu Ile Lys Gly Thr Ser Ile Trp Asp Asn Glu Tyr Thr Lys Asp
            115                 120                 125

Leu Glu Leu Asn Leu Gln Lys Ala Phe Gly Lys Leu Phe Arg Lys Tyr
        130                 135                 140

Ile Lys Lys Asn Ile Ala Ser Asp Glu Asn Thr Leu Tyr Ser Ser Leu
145                 150                 155                 160

Asp Glu Leu Arg Glu Ser Trp Trp Asn Thr Asn Lys Lys Tyr Ile Trp
                165                 170                 175

Leu Ala Met Lys His Gly Ala Glu Met Asn Gly Thr Met Cys Asn Ala
            180                 185                 190

Asp Gly Ser Val Thr Gly Ser Gly Ser Ser Cys Asp Asp Met Ser Thr
            195                 200                 205

Ile Asp Leu Ile Pro Gln Tyr Leu Arg Phe Leu Gln Glu Trp Val Glu
        210                 215                 220

His Phe Cys Glu Gln Arg Gln Ala Lys Val Lys Asp Val Ile Asn Ser
225                 230                 235                 240

Cys Lys Ser Cys Lys Glu Ser Gly Asp Thr Cys Asn Ser Asp Cys Glu
            245                 250                 255

Lys Lys Cys Lys Asn Lys Cys Asp Ala Tyr Lys Thr Phe Ile Glu Glu
```

```
                 260                 265                 270
Phe Cys Thr Ala Asp Gly Gly Thr Ala Gly Ser Pro Trp Ser Lys Arg
                275                 280                 285

Trp Asp Gln Ile Tyr Lys Arg Tyr Ser Lys Tyr Ile Glu Asp Ala Lys
290                 295                 300

Arg Asn Arg Lys Ala Gly Thr Lys Asn Cys Gly Thr Ser Ser Gly Ala
305                 310                 315                 320

Asn Ser Gly Val Thr Thr Thr Glu Asn Lys Cys Val Gln Ser
                325                 330

<210> SEQ ID NO 33
<211> LENGTH: 350
<212> TYPE: PRT
<213> ORGANISM: Plasmodium falciparum

<400> SEQUENCE: 33

Lys Cys Asp Lys Cys Lys Ser Gly Thr Ser Thr Val Asn Lys Asn Trp
1               5                   10                  15

Ile Trp Lys Lys Tyr Ser Gly Lys Glu Glu Gly Leu Gln Lys Glu Tyr
                20                  25                  30

Ala Asn Thr Ile Ala Leu Pro Pro Arg Thr His Ser Leu Tyr Leu Val
                35                  40                  45

Cys Leu His Glu Lys Gly Lys Lys Thr Gln Glu Leu Lys Asn Ile Arg
        50                  55                  60

Thr Asn Ser Glu Leu Leu Lys Glu Trp Ile Ile Ala Ala Phe His Glu
65                  70                  75                  80

Gly Lys Asn Leu Lys Thr Ser Pro Gln Asn Asn Asn Ser Gly Asn Lys
                85                  90                  95

Lys Lys Leu Cys Lys Ala Leu Lys Tyr Ser Phe Ala Asp Tyr Gly Asp
                100                 105                 110

Leu Ile Lys Gly Thr Ser Ile Trp Asp Asn Asp Phe Thr Lys Asp Leu
                115                 120                 125

Glu Leu Asn Leu Gln Lys Ile Phe Gly Lys Leu Phe Arg Lys Tyr Ile
        130                 135                 140

Lys Lys Asn Asn Thr Ala Glu Gln His Thr Ser Tyr Ser Ser Leu Asp
145                 150                 155                 160

Glu Leu Arg Glu Ser Trp Trp Asn Thr Asn Lys Lys Tyr Ile Trp Leu
                165                 170                 175

Ala Met Lys His Gly Ala Glu Met Asn Gly Thr Thr Cys Cys Gly Asp
                180                 185                 190

Gly Ser Val Thr Gly Ser Ser Asp Ser Gly Ser Thr Thr Cys Ser Gly
                195                 200                 205

Asp Asn Gly Ser Ile Ser Cys Asp Asp Met Pro Thr Thr Asp Phe Ile
        210                 215                 220

Pro Gln Tyr Leu Arg Phe Leu Gln Glu Trp Val Glu His Phe Cys Lys
225                 230                 235                 240

Gln Arg Gln Glu Lys Val Lys His Val Met Glu Ser Cys Lys Ser Cys
                245                 250                 255

Lys Glu Cys Gly Asp Thr Cys Asn Gly Glu Cys Lys Thr Glu Cys Glu
                260                 265                 270

Lys Lys Cys Lys Asn Lys Cys Glu Ala Tyr Lys Thr Phe Ile Glu Lys
                275                 280                 285

Cys Val Ser Ala Asp Gly Gly Thr Ser Gly Ser Ser Trp Ser Lys Arg
        290                 295                 300
```

```
Trp Asp Gln Ile Tyr Met Arg Tyr Ser Lys Tyr Ile Glu Asp Ala Lys
305                 310                 315                 320

Arg Asn Arg Lys Ala Gly Thr Lys Asn Cys Gly Thr Ser Ser Thr Thr
                325                 330                 335

Asn Ala Ala Ala Ser Thr Ala Glu Asn Lys Cys Val Gln Ser
            340                 345                 350

<210> SEQ ID NO 34
<211> LENGTH: 647
<212> TYPE: PRT
<213> ORGANISM: Artificial
<220> FEATURE:
<223> OTHER INFORMATION: Artificial construct

<400> SEQUENCE: 34

Asp Tyr Ile Lys Asp Asp Pro Tyr Ser Ala Glu Tyr Ala Thr Lys Leu
1               5                   10                  15

Ser Phe Ile Leu Asn Pro Ser Asp Ala Asn Thr Ser Ser Gly Glu Thr
                20                  25                  30

Ala Asn His Asn Asp Glu Val Cys Asn Cys Asn Glu Ser Glu Ile Ala
            35                  40                  45

Ser Val Glu Leu Ala Pro Ile Ser Asp Ser Ser Asn Lys Thr Cys
50                  55                  60

Ile Thr His Ser Phe Ile Gly Ala Asn Lys Lys Glu Cys Lys Asp
65                  70                  75                  80

Val Lys Leu Gly Val Arg Glu Lys Asp Lys Asp Leu Lys Ile Cys Val
                85                  90                  95

Ile Glu Asp Asp Ser Leu Arg Gly Val Glu Asn Cys Cys Cys Gln Asp
                100                 105                 110

Leu Leu Gly Ile Leu Gln Glu Asn Cys Ser Asp Asn Lys Ser Gly Ser
            115                 120                 125

Ser Ser Asn Gly Ser Cys Asp Lys Asn Ser Glu Asp Glu Cys Gln Lys
130                 135                 140

Lys Leu Glu Asn Val Phe Ala Ser Leu Lys Asn Gly Tyr Lys Cys Asp
145                 150                 155                 160

Lys Cys Lys Ser Gly Thr Ser Thr Val Asn Lys Lys Trp Ile Trp Arg
                165                 170                 175

Lys Tyr Ser Gly Asn Gly Glu Gly Leu Gln Lys Glu Tyr Ala Asn Thr
            180                 185                 190

Ile Gly Leu Pro Pro Arg Thr His Ser Leu Tyr Leu Val Cys Leu His
        195                 200                 205

Glu Lys Glu Gly Lys Thr Gln His Lys Thr Ile Ser Thr Asn Ser Glu
210                 215                 220

Leu Leu Lys Glu Trp Ile Ile Ala Ala Phe His Glu Gly Lys Asn Leu
225                 230                 235                 240

Lys Thr Ser His Gln Asn Asn Asn Ser Gly Asn Lys Lys Leu Cys
                245                 250                 255

Lys Ala Leu Lys Tyr Ser Phe Ala Asp Tyr Gly Asp Leu Ile Lys Gly
                260                 265                 270

Thr Ser Ile Trp Asp Asn Asp Phe Thr Lys Asp Leu Glu Leu Asn Leu
            275                 280                 285

Gln Lys Ile Phe Gly Lys Leu Phe Arg Lys Tyr Ile Lys Lys Asn Ile
        290                 295                 300

Ala Ser Asp Glu Asn Thr Ser Tyr Ser Ser Leu Asp Glu Leu Arg Glu
305                 310                 315                 320
```

```
Ser Trp Trp Asn Thr Asn Lys Lys Tyr Ile Trp Leu Ala Met Lys His
            325                 330                 335

Gly Ala Glu Met Asn Ser Thr Met Cys Asn Gly Asp Gly Ser Val Thr
            340                 345                 350

Gly Ser Ser Asp Ser Gly Ser Thr Thr Cys Ser Gly Asp Asn Gly Ser
            355                 360                 365

Ile Ser Cys Asp Asp Ile Pro Thr Ile Asp Leu Ile Pro Gln Tyr Leu
            370                 375                 380

Arg Phe Leu Gln Glu Trp Val Glu His Phe Cys Lys Gln Arg Gln Glu
385                 390                 395                 400

Lys Val Lys Asp Val Ile Thr Asn Cys Lys Ser Cys Lys Glu Ser Gly
            405                 410                 415

Asp Thr Cys Asn Ser Asp Cys Glu Lys Cys Lys Asn Lys Cys Glu
            420                 425                 430

Ala Tyr Lys Lys Phe Ile Glu Glu Arg Arg Thr Ala Ala Gln Gly Thr
            435                 440                 445

Ala Glu Ser Ser Trp Val Lys Arg Trp Asp Gln Ile Tyr Met Arg Tyr
            450                 455                 460

Ser Lys Tyr Ile Glu Asp Ala Lys Arg Asn Arg Lys Ala Gly Thr Lys
465                 470                 475                 480

Ser Cys Gly Pro Ser Ser Thr Thr Asn Ala Ala Ala Ser Thr Ala Glu
            485                 490                 495

Asn Lys Cys Val Gln Ser Asp Ile Asp Ser Phe Phe Lys His Leu Ile
            500                 505                 510

Asp Ile Gly Leu Thr Thr Pro Ser Ser Tyr Leu Ser Ile Val Leu Asp
            515                 520                 525

Asp Asn Ile Cys Gly Ala Asp Asn Ala Pro Trp Thr Thr Tyr Thr Thr
            530                 535                 540

Tyr Thr Thr Thr Lys Asn Cys Asp Ile Lys Lys Thr Pro Lys Pro
545                 550                 555                 560

Gln Ser Cys Asp Thr Leu Val Val Val Asn Val Pro Ser Pro Leu Gly
            565                 570                 575

Asn Thr Pro His Glu Tyr Lys Tyr Ala Cys Gln Cys Arg Thr Pro Asn
            580                 585                 590

Lys Gln Glu Ser Cys Asp Asp Arg Lys Glu Tyr Met Asn Gln Trp Ser
            595                 600                 605

Ser Gly Ser Ala Gln Thr Val Arg Gly Arg Ser Thr Asn Asn Asp Tyr
            610                 615                 620

Glu Leu Tyr Thr Tyr Asn Gly Val Lys Glu Thr Lys Pro Leu Gly Thr
625                 630                 635                 640

Leu Lys Asn Ser Lys Leu Asp
            645

<210> SEQ ID NO 35
<211> LENGTH: 341
<212> TYPE: PRT
<213> ORGANISM: Plasmodium falciparum

<400> SEQUENCE: 35

Lys Cys Asp Lys Cys Lys Ser Gly Thr Ser Thr Val Asn Lys Lys Trp
1               5                   10                  15

Ile Trp Arg Lys Ser Ser Gly Asn Lys Glu Gly Leu Gln Lys Glu Tyr
            20                  25                  30

Ala Asn Thr Ile Gly Leu Pro Pro Arg Thr Gln Ser Leu Tyr Leu Gly
            35                  40                  45
```

```
Asn Leu Pro Lys Leu Glu Asn Val Cys Glu Asp Val Lys Asp Ile Asn
 50                  55                  60
Phe Asp Thr Lys Glu Lys Phe Leu Ala Gly Cys Leu Ile Val Ser Phe
 65                  70                  75                  80
His Glu Gly Lys Asn Leu Lys Thr Ser His Glu Lys Lys Asn Asp Asp
                 85                  90                  95
Asn Gly Lys Lys Leu Cys Lys Ala Leu Glu Tyr Ser Phe Ala Asp Tyr
             100                 105                 110
Gly Asp Leu Ile Lys Gly Thr Ser Ile Trp Asp Asn Glu Tyr Thr Lys
             115                 120                 125
Asp Leu Glu Leu Asn Leu Gln Lys Ile Phe Gly Lys Leu Phe Arg Lys
130                 135                 140
Tyr Ile Lys Lys Asn Asn Thr Ala Glu Gln Asp Thr Ser Tyr Ser Ser
145                 150                 155                 160
Leu Asp Glu Leu Arg Glu Ser Trp Trp Asn Thr Asn Lys Lys Tyr Ile
                165                 170                 175
Trp Thr Ala Met Lys His Gly Ala Gly Met Asn Ile Thr Thr Cys Cys
                180                 185                 190
Gly Asp Gly Ser Ser Gly Glu Asn Gln Thr Asn Ser Cys Asp Asp Ile
             195                 200                 205
Pro Thr Ile Asp Leu Ile Pro Gln Tyr Leu Arg Phe Leu Gln Glu Trp
             210                 215                 220
Val Glu His Phe Cys Lys Gln Arg Gln Glu Lys Val Asn Ala Val Val
225                 230                 235                 240
Thr Asn Cys Lys Ser Cys Lys Glu Ser Gly Thr Cys Asn Gly Glu
                245                 250                 255
Cys Lys Thr Lys Cys Lys Asn Lys Cys Glu Val Tyr Lys Thr Phe Ile
                260                 265                 270
Asp Asn Val Gly Asp Gly Thr Ala Gly Ser Pro Trp Val Lys Arg Trp
             275                 280                 285
Asp Gln Ile Tyr Lys Arg Tyr Ser Lys His Ile Glu Asp Ala Lys Arg
             290                 295                 300
Asn Arg Lys Ala Gly Thr Lys Asn Cys Gly Ile Thr Thr Gly Thr Ile
305                 310                 315                 320
Ser Gly Glu Ser Ser Gly Ala Thr Ser Gly Val Thr Thr Thr Glu Asn
                325                 330                 335
Lys Cys Val Gln Ser
                340

<210> SEQ ID NO 36
<211> LENGTH: 632
<212> TYPE: PRT
<213> ORGANISM: Artificial
<220> FEATURE:
<223> OTHER INFORMATION: Artificial construct

<400> SEQUENCE: 36

Asn Tyr Ile Lys Asp Asp Pro Tyr Ser Lys Glu Tyr Val Thr Lys Leu
 1               5                  10                  15
Ser Phe Ile Pro Asn Ser Ser Asp Ala Asn Thr Ser Ser Glu Lys Ile
                 20                  25                  30
Gln Lys Asn Asn Asp Glu Val Cys Asn Pro Asn Glu Ser Gly Ile Ser
             35                  40                  45
Ser Val Glu Gln Ala Gln Thr Ser Gly Pro Ser Ser Asn Lys Thr Cys
 50                  55                  60
```

-continued

Ile Thr His Ser Ser Ile Lys Ala Asn Lys Lys Glu Cys Lys Asp
65                  70                  75                  80

Val Lys Leu Gly Val Arg Glu Asn Asp Lys Asp Leu Lys Ile Cys Val
            85                  90                  95

Ile Glu Asp Thr Ser Leu Ser Gly Val Asp Asn Cys Cys Cys Gln Asp
            100                 105                 110

Leu Leu Gly Ile Leu Gln Glu Asn Cys Ser Asp Asn Lys Arg Gly Ser
            115                 120                 125

Ser Ser Asn Asp Ser Cys Asp Asn Lys Asn Gln Asp Glu Cys Gln Lys
            130                 135                 140

Lys Leu Asp Glu Ala Leu Glu Ser Leu His Asn Gly Tyr Lys Asn Gln
145                 150                 155                 160

Lys Cys Lys Ser Gly Thr Ser Thr Val Asn Lys Lys Trp Ile Trp Lys
            165                 170                 175

Lys Ser Ser Gly Asn Lys Glu Gly Leu Gln Lys Glu Tyr Ala Asn Thr
            180                 185                 190

Ile Gly Leu Pro Pro Arg Thr Gln Ser Leu Tyr Leu Gly Asn Leu Pro
            195                 200                 205

Lys Leu Glu Asn Val Ser Lys Gly Val Thr Asp Ile Ile Tyr Asp Thr
210                 215                 220

Lys Glu Lys Phe Leu Ala Gly Cys Leu Ile Val Ser Phe His Glu Gly
225                 230                 235                 240

Lys Asn Leu Lys Thr Ser His Glu Lys Lys Asn Asp Asp Asn Gly Lys
            245                 250                 255

Lys Leu Cys Lys Ala Leu Glu Tyr Ser Phe Ala Asp Tyr Gly Asp Leu
            260                 265                 270

Ile Lys Gly Thr Ser Ile Trp Asp Asn Glu Tyr Thr Lys Asp Leu Glu
            275                 280                 285

Leu Asn Leu Gln Lys Ala Phe Gly Lys Leu Phe Arg Lys Tyr Ile Lys
            290                 295                 300

Lys Asn Ile Ser Ala Glu Gln Asp Thr Ser Tyr Ser Ser Leu Asp Glu
305                 310                 315                 320

Leu Arg Glu Ser Trp Trp Asn Thr Asn Lys Lys Tyr Ile Trp Ile Ala
            325                 330                 335

Met Lys His Gly Ala Gly Met Asn Gly Thr Thr Cys Cys Gly Asp Gly
            340                 345                 350

Ser Ser Gly Glu Asn Gln Thr Asn Ser Cys Asp Asp Ile Pro Thr Ile
            355                 360                 365

Asp Leu Ile Pro Gln Tyr Leu Arg Phe Leu Gln Glu Trp Val Glu His
            370                 375                 380

Phe Cys Glu Gln Arg Gln Ala Lys Val Lys Asp Val Ile Thr Asn Cys
385                 390                 395                 400

Lys Ser Cys Lys Asn Thr Ser Gly Glu Arg Lys Ile Gly Gly Thr Cys
            405                 410                 415

Asn Gly Glu Cys Lys Thr Lys Cys Lys Asn Lys Cys Glu Ala Tyr Lys
            420                 425                 430

Thr Phe Ile Glu His Cys Lys Gly Gly Asp Gly Thr Ala Gly Ser Ser
            435                 440                 445

Trp Val Lys Arg Trp Asp Gln Ile Tyr Lys Arg Tyr Ser Lys His Ile
            450                 455                 460

Glu Asp Ala Lys Arg Asn Arg Lys Ala Gly Thr Lys Ser Cys Gly Thr
465                 470                 475                 480

-continued

```
Ser Thr Ala Glu Asn Lys Cys Val Gln Ser Asp Ile Asp Ser Phe Phe
                485                 490                 495

Lys His Leu Ile Asp Ile Gly Leu Thr Thr Pro Ser Ser Tyr Leu Ser
            500                 505                 510

Ile Val Leu Asp Glu Asn Asn Cys Gly Glu Asp Lys Ala Pro Trp Thr
        515                 520                 525

Thr Tyr Thr Thr Thr Lys Asn Cys Asp Ile Gln Lys Asp Lys Ser Lys
    530                 535                 540

Ser Gln Ser Ser Asp Thr Leu Val Val Val Asn Val Pro Ser Pro Leu
545                 550                 555                 560

Gly Asn Thr Pro His Gly Tyr Lys Tyr Ala Cys Gln Cys Lys Ile Pro
                565                 570                 575

Thr Thr Glu Glu Thr Cys Asp Asp Arg Lys Glu Tyr Met Asn Gln Trp
            580                 585                 590

Ser Cys Gly Ser Ala Arg Thr Met Lys Arg Gly Tyr Lys Asn Asp Asn
        595                 600                 605

Tyr Glu Leu Cys Lys Tyr Asn Gly Val Asp Val Lys Pro Thr Thr Val
    610                 615                 620

Arg Ser Ser Ser Thr Lys Leu Asp
625                 630

<210> SEQ ID NO 37
<211> LENGTH: 639
<212> TYPE: PRT
<213> ORGANISM: Artificial
<220> FEATURE:
<223> OTHER INFORMATION: Artificial construct

<400> SEQUENCE: 37

Asp Tyr Ile Lys Gly Asp Pro Tyr Ser Ala Glu Tyr Val Thr Lys Leu
1               5                   10                  15

Ser Phe Ile Pro Asn Ser Ser Asp Ala Asn Asn Pro Ser Glu Lys Ile
            20                  25                  30

Gln Lys Asn Asn Asp Glu Val Cys Asn Cys Asn Glu Ser Glu Ile Ser
        35                  40                  45

Ser Val Gly Gln Ala Ser Ile Ser Asp Pro Ser Ser Asn Lys Thr Cys
    50                  55                  60

Asn Thr His Ser Ser Ile Lys Ala Asn Lys Lys Val Cys Lys Asp
65                  70                  75                  80

Val Lys Leu Gly Val Arg Glu Asn Asp Lys Val Leu Lys Ile Cys Val
                85                  90                  95

Ile Glu His Thr Ser Leu Arg Gly Val Asp Asn Cys Cys Phe Lys Asp
            100                 105                 110

Leu Leu Gly Ile Leu Gln Glu Pro Arg Ile Asp Lys Asn Gln Ser Gly
        115                 120                 125

Ser Ser Ser Asn Gly Ser Cys Asp Lys Asn Ser Glu Glu Ala Cys Glu
    130                 135                 140

Lys Asn Leu Glu Lys Val Leu Ala Ser Leu Thr Asn Gly Tyr Lys Cys
145                 150                 155                 160

Asp Lys Cys Lys Ser Gly Thr Ser Arg Ser Lys Lys Trp Ile Trp
                165                 170                 175

Lys Lys Tyr Ser Gly Lys Glu Gly Leu Gln Glu Glu Tyr Ala Asn
            180                 185                 190

Thr Ile Gly Leu Pro Pro Arg Thr Gln Ser Leu Cys Leu Val Val Cys
        195                 200                 205
```

```
Leu Asp Glu Lys Glu Gly Lys Thr Gln Glu Leu Lys Asn Ile Ser Thr
210                 215                 220
Asn Ser Glu Leu Leu Lys Glu Trp Ile Ile Ala Ala Phe Pro Glu Gly
225                 230                 235                 240
Lys Asn Leu Lys Pro Ser Pro Glu Lys Lys Gly Asp Asn Gly Lys
                245                 250                 255
Lys Leu Cys Lys Asp Leu Lys Tyr Ser Phe Ala Asp Tyr Gly Asp Leu
            260                 265                 270
Ile Lys Gly Thr Ser Ile Trp Asp Asn Glu Tyr Thr Lys Asp Leu Glu
                275                 280                 285
Leu Asn Leu Gln Lys Ile Phe Gly Lys Leu Phe Arg Lys Tyr Ile Lys
290                 295                 300
Lys Asn Ile Ala Ser Asp Glu Asn Thr Leu Tyr Ser Ser Leu Asp Glu
305                 310                 315                 320
Leu Arg Glu Ser Trp Trp Asn Thr Asn Lys Lys Tyr Ile Trp Leu Ala
                325                 330                 335
Met Lys His Gly Ala Gly Met Asn Ser Thr Met Cys Asn Ala Asp Gly
                340                 345                 350
Ser Val Thr Gly Ser Gly Ser Ser Cys Asp Asp Met Pro Thr Ile Asp
                355                 360                 365
Leu Ile Pro Gln Tyr Leu Arg Phe Leu Gln Glu Trp Val Glu His Phe
370                 375                 380
Cys Lys Gln Arg Gln Glu Lys Val Lys Pro Val Ile Glu Asn Cys Asn
385                 390                 395                 400
Ser Cys Lys Asn Thr Ser Ser Glu Arg Lys Ile Gly Gly Thr Cys Asn
                405                 410                 415
Ser Asp Cys Lys Thr Glu Cys Lys Asn Lys Cys Glu Val Tyr Lys Lys
                420                 425                 430
Phe Ile Glu Asp Cys Lys Gly Gly Asp Gly Thr Ala Gly Ser Ser Trp
                435                 440                 445
Ser Lys Arg Trp Asp Gln Ile Tyr Lys Arg Tyr Ser Lys Tyr Ile Glu
        450                 455                 460
Asp Ala Lys Arg Asn Arg Lys Ala Gly Thr Lys Asn Cys Gly Pro Ser
465                 470                 475                 480
Ser Thr Thr Asn Ala Ala Glu Asn Lys Cys Val Gln Ser Asp Ile Asp
                485                 490                 495
Ser Phe Phe Lys His Leu Ile Asp Ile Gly Leu Thr Thr Pro Ser Ser
                500                 505                 510
Tyr Leu Ser Thr Val Leu Asp Asp Asn Ile Cys Gly Glu Asp Asn Ala
        515                 520                 525
Pro Trp Thr Thr Tyr Thr Thr Tyr Thr Thr Lys Asn Cys Asp Lys
        530                 535                 540
Asp Lys Lys Lys Ser Lys Ser Gln Ser Cys Asp Thr Leu Val Val Val
545                 550                 555                 560
Asn Val Pro Ser Pro Leu Gly Asn Thr Pro His Glu Tyr Lys Tyr Ala
                565                 570                 575
Cys Glu Cys Arg Thr Pro Asn Lys Gln Glu Ser Cys Asp Asp Arg Lys
                580                 585                 590
Glu Tyr Met Asn Gln Trp Ile Ser Asp Asn Thr Lys Asn Pro Lys Gly
                595                 600                 605
Ser Gly Ser Gly Lys Asp Tyr Tyr Glu Leu Tyr Thr Tyr Asn Gly Val
        610                 615                 620
Asp Val Lys Pro Thr Thr Val Arg Ser Ser Ser Thr Lys Leu Asp
```

-continued

```
625                 630                 635
```

<210> SEQ ID NO 38
<211> LENGTH: 655
<212> TYPE: PRT
<213> ORGANISM: Artificial
<220> FEATURE:
<223> OTHER INFORMATION: Artificial construct

<400> SEQUENCE: 38

```
Asp Tyr Ile Lys Gly Asp Pro Tyr Phe Ala Glu Tyr Ala Thr Lys Leu
1               5                   10                  15

Ser Phe Ile Leu Asn Ser Ser Asp Ala Asn Thr Ser Ser Gly Glu Thr
            20                  25                  30

Ala Asn His Asn Asp Glu Ala Cys Asn Cys Asn Glu Ser Glu Ile Ser
        35                  40                  45

Ser Val Glu His Ala Ser Ile Ser Asp Pro Ser Ser Asn Lys Thr Cys
    50                  55                  60

Asn Thr His Ser Ser Ile Lys Ala Asn Lys Lys Val Cys Lys His
65                  70                  75                  80

Val Lys Leu Gly Val Arg Glu Asn Asp Lys Asp Leu Arg Val Cys Val
                85                  90                  95

Ile Glu His Thr Ser Leu Ser Gly Val Glu Asn Cys Cys Phe Lys Asp
            100                 105                 110

Phe Leu Arg Ile Leu Gln Glu Asn Cys Ser Asp Asn Lys Ser Gly Ser
        115                 120                 125

Ser Ser Asn Gly Ser Cys Asp Lys Asn Glu Glu Ala Cys Glu Lys
    130                 135                 140

Asn Leu Glu Lys Val Phe Ala Ser Leu Thr Asn Cys Tyr Lys Cys Glu
145                 150                 155                 160

Lys Cys Lys Ser Glu Gln Ser Lys Lys Asn Asn Lys Lys Trp Thr Trp
                165                 170                 175

Arg Lys Ser Ser Gly Asn Lys Gly Gly Leu Gln Glu Glu Tyr Ala Asn
            180                 185                 190

Thr Ile Gly Leu Pro Pro Arg Thr Gln Ser Leu Cys Leu Val Val Cys
        195                 200                 205

Leu Asp Glu Lys Glu Gly Lys Lys Thr Gln Glu Leu Lys Asn Ile Arg
    210                 215                 220

Thr Asn Ser Glu Leu Leu Lys Glu Trp Ile Ile Ala Ala Phe His Glu
225                 230                 235                 240

Gly Lys Asn Leu Lys Pro Ser His Glu Lys Lys Asn Asp Asp Asn Gly
                245                 250                 255

Lys Lys Asn Asp Asp Asn Asn Ser Lys Leu Cys Lys Asp Leu Lys Tyr
            260                 265                 270

Ser Phe Ala Asp Tyr Gly Asp Leu Ile Lys Gly Thr Ser Ile Trp Asp
        275                 280                 285

Asn Glu Tyr Thr Lys Asp Leu Glu Leu Asn Leu Gln Lys Ile Phe Gly
    290                 295                 300

Lys Leu Phe Arg Lys Tyr Ile Lys Lys Asn Ile Ala Ser Asp Glu Asn
305                 310                 315                 320

Thr Leu Tyr Ser Ser Leu Asp Glu Leu Arg Glu Ser Trp Trp Asn Thr
                325                 330                 335

Asn Lys Lys Tyr Ile Trp Leu Ala Met Lys His Gly Ala Glu Met Asn
            340                 345                 350

Gly Thr Thr Cys Asn Ala Asp Gly Ser Val Thr Gly Ser Gly Ser Ser
```

```
              355                 360                 365
Cys Asp Asp Ile Pro Thr Ile Asp Leu Ile Pro Gln Tyr Leu Arg Phe
370                 375                 380

Leu Gln Glu Trp Val Glu His Phe Cys Lys Gln Arg Gln Ala Lys Val
385                 390                 395                 400

Lys Asp Val Ile Glu Asn Cys Lys Ser Cys Lys Glu Ser Gly Asn Lys
                405                 410                 415

Cys Lys Thr Glu Cys Lys Asn Lys Cys Glu Ala Tyr Lys Lys Phe Ile
                420                 425                 430

Glu Asn Cys Lys Gly Gly Asp Gly Thr Ala Gly Ser Ser Trp Val Lys
                435                 440                 445

Arg Trp Asp Gln Ile Tyr Met Arg Tyr Ser Lys Tyr Ile Glu Asp Ala
                450                 455                 460

Lys Arg Asn Arg Lys Ala Gly Thr Lys Asn Cys Gly Pro Ser Ser Ile
465                 470                 475                 480

Thr Asn Val Ser Ala Ser Thr Asp Glu Asn Lys Cys Val Gln Ser Asp
                485                 490                 495

Ile Asp Ser Phe Phe Lys His Leu Ile Asp Ile Gly Leu Thr Thr Pro
                500                 505                 510

Ser Ser Tyr Leu Ser Ile Val Leu Asp Asp Asn Ile Cys Gly Asp Asp
                515                 520                 525

Lys Ala Pro Trp Thr Thr Tyr Thr Thr Tyr Thr Thr Tyr Thr Thr Tyr
                530                 535                 540

Thr Thr Tyr Thr Thr Tyr Thr Thr Tyr Thr Thr Lys Asn Cys Asp
545                 550                 555                 560

Lys Glu Arg Asp Lys Ser Lys Ser Gln Ser Cys Asn Thr Ala Val Val
                565                 570                 575

Val Asn Val Pro Ser Pro Leu Gly Asn Thr Pro His Glu Tyr Lys Tyr
                580                 585                 590

Ala Cys Glu Cys Arg Thr Pro Ser Asn Lys Glu Leu Cys Asp Asp Arg
                595                 600                 605

Lys Glu Tyr Met Asn Gln Trp Ser Ser Gly Ser Ala Gln Thr Val Arg
                610                 615                 620

Asp Arg Ser Gly Lys Asp Tyr Tyr Glu Leu Tyr Thr Tyr Asn Gly Val
625                 630                 635                 640

Lys Glu Thr Lys Leu Pro Lys Lys Leu Asn Ser Ser Lys Leu Asp
                645                 650                 655

<210> SEQ ID NO 39
<211> LENGTH: 347
<212> TYPE: PRT
<213> ORGANISM: Plasmodium falciparum

<400> SEQUENCE: 39

Lys Cys Asp Lys Cys Lys Ser Glu Gln Ser Lys Lys Asn Asn Lys Tyr
1               5                   10                  15

Trp Ile Trp Lys Lys Ser Ser Val Lys Glu Glu Gly Leu Gln Lys Glu
                20                  25                  30

Tyr Ala Asn Thr Ile Ala Leu Pro Pro Arg Thr His Ser Leu Cys Leu
                35                  40                  45

Val Val Cys Leu Asp Glu Lys Gly Lys Lys Thr Gln Glu Leu Lys Asn
                50                  55                  60

Ile Ser Thr Asn Ser Glu Leu Leu Lys Glu Arg Ile Ile Ala Ala Phe
65                  70                  75                  80
```

-continued

His Glu Gly Lys Asn Leu Lys Thr Thr Tyr Leu Glu Lys Lys Asn Ala
                85                  90                  95

Asp Asn Asn Ser Lys Leu Cys Lys Ala Leu Lys Tyr Ser Phe Ala Asp
            100                 105                 110

Tyr Gly Asp Leu Ile Lys Gly Thr Ser Ile Trp Asp Asn Glu Tyr Thr
        115                 120                 125

Lys Asp Leu Glu Leu Asn Leu Gln Gln Ile Phe Gly Lys Leu Phe Arg
    130                 135                 140

Lys Tyr Ile Lys Lys Asn Asn Thr Ala Glu Gln His Thr Leu Tyr Ser
145                 150                 155                 160

Ser Leu Asp Glu Leu Arg Glu Ser Trp Trp Asn Thr Asn Lys Lys Tyr
                165                 170                 175

Ile Trp Leu Ala Met Lys His Gly Ala Gly Met Asn Gly Thr Thr Cys
            180                 185                 190

Cys Gly Asp Gly Ser Val Thr Gly Ser Ser Asp Ser Gly Ser Thr Thr
        195                 200                 205

Cys Ser Gly Asp Asn Gly Ser Ile Ser Cys Asp Met Pro Thr Thr
    210                 215                 220

Asp Phe Ile Pro Gln Tyr Leu Arg Phe Leu Gln Glu Trp Val Glu His
225                 230                 235                 240

Phe Cys Lys Gln Arg Gln Glu Lys Val Lys Asp Val Ile Glu Asn Cys
                245                 250                 255

Asn Ser Cys Lys Asn Asn Leu Gly Lys Thr Glu Ile Asn Glu Lys Cys
            260                 265                 270

Lys Thr Glu Cys Lys Asn Lys Cys Glu Ala Tyr Lys Asn Phe Ile Glu
        275                 280                 285

Lys Phe Cys Thr Ala Asp Gly Gly Thr Ser Gly Ser Pro Trp Ser Lys
    290                 295                 300

Arg Trp Asp Gln Ile Tyr Lys Arg Tyr Ser Lys Tyr Ile Glu Asp Ala
305                 310                 315                 320

Lys Arg Asn Arg Lys Ala Gly Thr Lys Asn Cys Gly Thr Ser Ser Thr
                325                 330                 335

Thr Ser Thr Ala Glu Asn Lys Cys Val Gln Ser
            340                 345

<210> SEQ ID NO 40
<211> LENGTH: 335
<212> TYPE: PRT
<213> ORGANISM: Plasmodium falciparum

<400> SEQUENCE: 40

Lys Cys Glu Lys Cys Lys Ser Gly Thr Ser Thr Val Asn Lys Tyr Trp
1               5                   10                  15

Ile Trp Arg Lys Ser Ser Gly Asn Lys Glu Gly Leu Gln Lys Glu Tyr
            20                  25                  30

Ala Asn Thr Ile Ala Leu Pro Pro Arg Thr His Ser Leu Cys Leu Val
        35                  40                  45

Val Cys Leu Asp Glu Lys Glu Gly Lys Thr Gln Glu Leu Lys Asn Ile
    50                  55                  60

Ser Thr Asn Ser Glu Leu Leu Lys Glu Arg Ile Ile Ala Ala Phe His
65                  70                  75                  80

Glu Gly Glu Asn Leu Lys Thr Ser His Glu Lys Lys Gly Asp Asp
                85                  90                  95

Gly Lys Lys Asn Ala Asp Asn Asn Ser Lys Leu Cys Lys Ala Leu Lys
            100                 105                 110

```
Tyr Ser Phe Ala Asp Tyr Gly Asp Leu Ile Lys Gly Thr Ser Ile Trp
            115                 120                 125

Asp Asn Glu Tyr Thr Lys Asp Leu Glu Leu Asn Leu Gln Lys Ile Phe
        130                 135                 140

Gly Lys Leu Phe Arg Lys Tyr Ile Lys Asn Ile Ala Ser Asp Glu
145                 150                 155                 160

Asn Thr Ser Tyr Ser Ser Leu Asp Glu Leu Arg Glu Ser Trp Trp Asn
                165                 170                 175

Thr Asn Lys Lys Tyr Ile Trp Leu Ala Met Lys His Gly Ala Gly Met
            180                 185                 190

Asn Gly Thr Thr Cys Ser Cys Ser Gly Asp Ser Ser Asp Asp Met Pro
        195                 200                 205

Thr Thr Asp Phe Ile Pro Gln Tyr Leu Arg Phe Leu Gln Glu Trp Val
        210                 215                 220

Glu His Phe Cys Lys Gln Arg Gln Glu Asn Val Asn Ala Val Ile Glu
225                 230                 235                 240

Asn Cys Asn Ser Cys Lys Glu Cys Gly Gly Thr Cys Asn Ser Asp Cys
                245                 250                 255

Glu Lys Lys Cys Lys Thr Glu Cys Lys Asn Lys Cys Glu Ala Tyr Lys
            260                 265                 270

Asn Phe Ile Glu Lys Phe Cys Thr Ala Asp Gly Gly Thr Ser Gly Tyr
        275                 280                 285

Ser Trp Ser Lys Arg Trp Asp Gln Ile Tyr Lys Arg Tyr Ser Lys Tyr
        290                 295                 300

Ile Glu Asp Ala Lys Arg Asn Arg Lys Ala Gly Thr Lys Ser Cys Gly
305                 310                 315                 320

Thr Ser Ser Thr Thr Ser Thr Ala Glu Ser Lys Cys Val Gln Ser
                325                 330                 335

<210> SEQ ID NO 41
<211> LENGTH: 667
<212> TYPE: PRT
<213> ORGANISM: Artificial
<220> FEATURE:
<223> OTHER INFORMATION: Artificial construct

<400> SEQUENCE: 41

Ser Tyr Val Lys Asn Asn Pro Tyr Ser Lys Glu Tyr Val Thr Lys Leu
1               5                   10                  15

Ser Phe Ile Leu Asn Pro Ser Asp Ala Asn Asn Pro Ser Glu Thr Pro
            20                  25                  30

Ser Lys Tyr Tyr Asp Glu Val Cys Asn Cys Asn Glu Ser Gly Ile Ala
        35                  40                  45

Cys Val Gly Gln Ala Gln Thr Ser Gly Pro Ser Ser Asn Lys Thr Cys
    50                  55                  60

Ile Thr His Ser Phe Ile Gly Ala Asn Lys Lys Val Cys Lys Asp
65                  70                  75                  80

Val Lys Leu Gly Val Arg Glu Lys Asp Lys Asp Leu Lys Ile Cys Val
                85                  90                  95

Ile Glu Asp Thr Tyr Leu Ser Gly Val Asp Asn Cys Cys Phe Lys Asp
            100                 105                 110

Phe Leu Gly Met Leu Gln Glu Asn Cys Ser Asp Asn Lys Ser Gly Ser
        115                 120                 125

Ser Ser Asn Gly Ser Cys Asn Asn Lys Asn Gln Asp Glu Cys Glu Lys
    130                 135                 140
```

```
Asn Leu Asp Glu Ala Leu Ala Ser Leu Thr Asn Gly Tyr Lys Cys Glu
145                 150                 155                 160

Lys Cys Lys Ser Gly Thr Ser Thr Val Asn Lys Tyr Trp Ile Trp Arg
            165                 170                 175

Lys Ser Ser Gly Asn Lys Glu Gly Leu Gln Lys Glu Tyr Ala Asn Thr
            180                 185                 190

Ile Ala Leu Pro Pro Arg Thr His Ser Leu Cys Leu Val Val Cys Leu
            195                 200                 205

Asp Glu Lys Glu Gly Lys Thr Gln His Lys Thr Ile Ser Thr Asn Ser
            210                 215                 220

Glu Leu Leu Lys Glu Trp Ile Ile Ala Ala Phe His Glu Gly Lys Asn
225                 230                 235                 240

Leu Lys Thr Ser His Glu Lys Lys Gly Asp Asp Gly Lys Lys Asn
            245                 250                 255

Ala Asp Asn Asn Ser Lys Leu Cys Lys Ala Leu Lys Tyr Ser Phe Ala
            260                 265                 270

Asp Tyr Gly Asp Leu Ile Lys Gly Thr Ser Ile Trp Asp Asn Asp Phe
            275                 280                 285

Thr Lys Asp Leu Glu Leu Asn Leu Gln Lys Ile Phe Gly Lys Leu Phe
290                 295                 300

Arg Lys Tyr Ile Lys Lys Asn Ile Ala Ser Asp Glu Asn Thr Ser Tyr
305                 310                 315                 320

Ser Ser Leu Asp Glu Leu Arg Glu Ser Trp Trp Asn Thr Asn Lys Lys
            325                 330                 335

Tyr Ile Trp Leu Ala Met Lys His Gly Ala Gly Met Asn Ser Thr Thr
            340                 345                 350

Cys Cys Gly Asp Gly Ser Val Thr Gly Ser Ser Asp Ser Gly Ser Thr
            355                 360                 365

Thr Cys Cys Gly Asp Gly Ser Val Thr Gly Ser Gly Ser Ser Cys Asp
            370                 375                 380

Asp Met Pro Thr Thr Asp Phe Ile Pro Gln Tyr Leu Arg Phe Leu Gln
385                 390                 395                 400

Glu Trp Val Glu His Phe Cys Lys Gln Arg Gln Glu Asn Val Asn Ala
            405                 410                 415

Val Ile Glu Asn Cys Asn Ser Cys Lys Glu Cys Gly Gly Thr Cys Asn
            420                 425                 430

Ser Asp Cys Glu Lys Lys Cys Lys Thr Glu Cys Lys Gly Glu Cys Asp
            435                 440                 445

Ala Tyr Lys Glu Phe Ile Glu Lys Cys Asn Gly Gly Ala Ala Glu Gly
            450                 455                 460

Thr Ser Gly Ser Ser Trp Ser Lys Arg Trp Asp Gln Ile Tyr Lys Arg
465                 470                 475                 480

Tyr Ser Lys Tyr Ile Glu Asp Ala Lys Arg Asn Arg Lys Ala Gly Thr
            485                 490                 495

Lys Asn Cys Gly Thr Ser Ser Thr Ser Thr Ala Glu Ser Lys Cys
            500                 505                 510

Val Gln Ser Asp Ile Asp Ser Phe Phe Lys His Leu Ile Asp Ile Gly
            515                 520                 525

Leu Thr Thr Pro Ser Ser Tyr Leu Ser Ile Val Leu Asp Glu Asn Ile
            530                 535                 540

Cys Gly Ala Asp Asn Ala Pro Trp Thr Thr Tyr Thr Thr Tyr Thr Thr
545                 550                 555                 560
```

```
Tyr Thr Thr Tyr Thr Thr Glu Lys Cys Asn Lys Glu Thr Asp Lys
                565                 570                 575

Ser Lys Leu Gln Gln Cys Asn Thr Ser Val Val Asn Val Pro Ser
            580                 585                 590

Pro Leu Gly Asn Thr Pro His Gly Tyr Lys Tyr Val Cys Glu Cys Arg
            595                 600                 605

Thr Pro Asn Lys Gln Glu Thr Cys Asp Asp Arg Lys Glu Tyr Met Asn
        610                 615                 620

Gln Trp Ile Ser Asp Asn Thr Lys Asn Pro Lys Gly Ser Arg Ser Thr
625                 630                 635                 640

Asn Asn Asp Tyr Glu Leu Tyr Thr Tyr Asn Gly Val Gln Ile Lys Pro
            645                 650                 655

Thr Thr Val Arg Ser Asn Ser Thr Lys Leu Asp
            660                 665

<210> SEQ ID NO 42
<211> LENGTH: 348
<212> TYPE: PRT
<213> ORGANISM: Plasmodium falciparum

<400> SEQUENCE: 42

Lys Cys Asp Lys Cys Lys Ser Glu Gln Ser Lys Lys Asn Asn Lys Asn
1               5                   10                  15

Trp Ile Trp Lys Lys Ser Ser Gly Asn Glu Lys Gly Leu Gln Lys Glu
            20                  25                  30

Tyr Ala Asn Thr Ile Gly Leu Pro Pro Arg Thr Gln Ser Leu Cys Leu
        35                  40                  45

Val Val Cys Leu Asp Glu Lys Glu Gly Lys Thr Gln Glu Leu Lys Asn
    50                  55                  60

Ile Arg Thr Asn Ser Glu Leu Leu Lys Glu Trp Ile Ala Ala Phe
65                  70                  75                  80

His Glu Gly Lys Asn Leu Lys Thr Ser His Glu Lys Lys Gly Asp
                85                  90                  95

Asn Asn Ser Lys Leu Cys Lys Asp Leu Lys Tyr Ser Phe Ala Asp Tyr
            100                 105                 110

Gly Asp Leu Ile Lys Gly Thr Ser Ile Trp Asp Asn Glu Tyr Thr Lys
        115                 120                 125

Asp Leu Glu Leu Asn Leu Gln Asn Asn Phe Gly Lys Leu Phe Arg Lys
    130                 135                 140

Tyr Ile Lys Lys Asn Ile Ala Ser Asp Glu Asn Thr Ser Tyr Ser Ser
145                 150                 155                 160

Leu Asp Glu Leu Arg Glu Ser Trp Trp Asn Thr Asn Lys Lys Tyr Ile
                165                 170                 175

Trp Leu Ala Met Lys His Gly Ala Gly Met Asn Ser Thr Thr Cys Ser
            180                 185                 190

Ser Gly Ser Gly Ser Thr Thr Cys Ser Ser Gly Ser Gly Ser Thr Thr
        195                 200                 205

Cys Ser Ser Gly Ser Gly Asp Ser Cys Asp Asp Met Pro Thr Ile Asp
    210                 215                 220

Leu Ile Pro Gln Tyr Leu Arg Phe Leu Gln Glu Trp Val Glu His Phe
225                 230                 235                 240

Cys Lys Gln Arg Gln Glu Lys Val Asn Ala Val Ile Lys Asn Cys Asn
                245                 250                 255

Ser Cys Lys Glu Ser Gly Gly Thr Cys Asn Gly Glu Cys Lys Thr Glu
            260                 265                 270
```

```
Cys Lys Asn Lys Cys Glu Ala Tyr Lys Thr Phe Ile Glu Glu Phe Cys
            275                 280                 285

Thr Ala Asp Gly Gly Thr Ser Gly Ser Pro Trp Ser Lys Arg Trp Asp
        290                 295                 300

Gln Ile Tyr Lys Met Tyr Ser Lys His Ile Glu Asp Ala Lys Arg Asn
305                 310                 315                 320

Arg Lys Ala Gly Thr Lys Asn Cys Gly Pro Ser Ser Thr Thr Asn Val
                325                 330                 335

Ser Val Ser Thr Asp Glu Asn Lys Cys Val Gln Ser
            340                 345

<210> SEQ ID NO 43
<211> LENGTH: 652
<212> TYPE: PRT
<213> ORGANISM: Artificial
<220> FEATURE:
<223> OTHER INFORMATION: Artificial construct

<400> SEQUENCE: 43

Asp Tyr Ile Lys Asp Asp Pro Tyr Phe Ala Glu Tyr Val Thr Lys Leu
1               5                   10                  15

Ser Phe Ile Leu Asn Ser Ser Asp Ala Asn Asn Pro Ser Gly Glu Thr
            20                  25                  30

Ala Asn His Asn Asp Glu Val Cys Asn Pro Asn Glu Ser Gly Ile Ala
        35                  40                  45

Ser Val Glu Gln Ala Gln Thr Ser Asp Pro Ser Ser Asn Lys Thr Cys
    50                  55                  60

Asn Thr His Ser Ser Ile Lys Ala Asn Lys Lys Val Cys Lys His
65                  70                  75                  80

Val Lys Leu Gly Val Arg Glu Asn Asp Lys Asp Leu Lys Ile Cys Val
                85                  90                  95

Ile Glu His Thr Ser Leu Ser Gly Val Glu Asn Cys Cys Cys Gln Asp
            100                 105                 110

Phe Leu Arg Ile Leu Gln Glu Asn Cys Ser Asp Asn Lys Ser Gly Ser
        115                 120                 125

Ser Ser Asn Gly Ser Cys Asn Asn Lys Asn Gln Glu Ala Cys Glu Lys
    130                 135                 140

Asn Leu Glu Lys Val Leu Ala Ser Leu Thr Asn Cys Tyr Lys Cys Asp
145                 150                 155                 160

Lys Cys Lys Ser Glu Gln Ser Lys Lys Asn Lys Asn Trp Ile Trp
                165                 170                 175

Lys Lys Ser Ser Gly Asn Glu Lys Gly Leu Gln Lys Glu Tyr Ala Asn
            180                 185                 190

Thr Ile Gly Leu Pro Pro Arg Thr Gln Ser Leu Cys Leu Val Val Cys
        195                 200                 205

Leu Asp Glu Lys Glu Gly Lys Thr Gln Glu Leu Lys Asn Ile Arg Thr
    210                 215                 220

Asn Ser Glu Leu Leu Lys Glu Trp Ile Ile Ala Ala Phe His Glu Gly
225                 230                 235                 240

Lys Asn Leu Lys Lys Arg Tyr Pro Gln Asn Lys Asn Asp Asp Asn Asn
                245                 250                 255

Ser Lys Leu Cys Lys Asp Leu Lys Tyr Ser Phe Ala Asp Tyr Gly Asp
            260                 265                 270

Leu Ile Lys Gly Thr Ser Ile Trp Asp Asn Glu Tyr Thr Lys Asp Leu
        275                 280                 285
```

Glu Leu Asn Leu Gln Asn Asn Phe Gly Lys Leu Phe Arg Lys Tyr Ile
            290                 295                 300

Lys Lys Asn Ile Ser Thr Glu Gln Asp Thr Leu Tyr Ser Ser Leu Asp
305                 310                 315                 320

Glu Leu Arg Glu Ser Trp Trp Asn Thr Asn Lys Lys Tyr Ile Trp Leu
                325                 330                 335

Ala Met Lys His Gly Ala Gly Met Asn Ser Thr Thr Cys Ser Ser Gly
            340                 345                 350

Ser Gly Ser Thr Thr Cys Ser Ser Gly Ser Gly Ser Thr Thr Cys Ser
            355                 360                 365

Ser Gly Ser Gly Asp Ser Cys Asp Asp Met Pro Thr Thr Asp Phe Ile
            370                 375                 380

Pro Gln Tyr Leu Arg Phe Leu Gln Glu Trp Val Glu His Phe Cys Lys
385                 390                 395                 400

Gln Arg Gln Glu Lys Val Asn Ala Val Ile Lys Asn Cys Asn Ser Cys
                405                 410                 415

Lys Glu Ser Gly Gly Thr Cys Asn Gly Glu Cys Lys Thr Glu Cys Lys
                420                 425                 430

Asn Lys Cys Glu Ala Tyr Lys Thr Phe Ile Glu Glu Phe Cys Thr Ala
            435                 440                 445

Asp Gly Gly Thr Ser Gly Ser Pro Trp Ser Lys Arg Trp Asp Gln Ile
450                 455                 460

Tyr Lys Met Tyr Ser Lys His Ile Glu Asp Ala Lys Arg Asn Arg Lys
465                 470                 475                 480

Ala Gly Thr Lys Asn Cys Gly Pro Ser Ser Thr Thr Asn Val Ser Val
                485                 490                 495

Ser Thr Asp Glu Asn Lys Cys Val Gln Ser Asp Ile Asp Ser Phe Phe
            500                 505                 510

Lys His Leu Ile Asp Ile Gly Leu Thr Thr Pro Ser Ser Tyr Leu Ser
            515                 520                 525

Ile Val Leu Asp Asp Asn Ile Cys Gly Glu Asp Lys Ala Pro Trp Thr
530                 535                 540

Thr Tyr Thr Thr Tyr Thr Thr Thr Lys Lys Cys Asn Lys Glu Thr Asp
545                 550                 555                 560

Lys Ser Lys Ser Gln Ser Cys Asn Thr Ala Val Val Asn Val Pro
                565                 570                 575

Ser Pro Leu Gly Asn Thr Pro His Gly Tyr Lys Tyr Ala Cys Glu Cys
            580                 585                 590

Lys Ile Pro Thr Thr Glu Glu Thr Cys Asp Asp Arg Lys Glu Tyr Met
            595                 600                 605

Asn Gln Trp Ile Ile Asp Thr Ser Lys Lys Gln Lys Gly Ser Gly Ser
            610                 615                 620

Gly Lys Asp Asp Tyr Glu Leu Tyr Thr Tyr Asn Gly Val Asp Val Lys
625                 630                 635                 640

Pro Thr Thr Val Arg Ser Asn Ser Thr Lys Leu Asp
                645                 650

<210> SEQ ID NO 44
<211> LENGTH: 628
<212> TYPE: PRT
<213> ORGANISM: Artificial
<220> FEATURE:
<223> OTHER INFORMATION: Artificial construct

<400> SEQUENCE: 44

```
Asp Tyr Ile Lys Asp Pro Tyr Ser Ala Gln Tyr Thr Thr Lys Leu
1               5                   10                  15

Ser Phe Ile Leu Asn Pro Ser Asp Ala Asn Thr Ser Ser Glu Lys Ile
                20                  25                  30

Gln Lys Asn Asn Asp Glu Ala Cys Asn Cys Asn Glu Ser Gly Ile Ser
            35                  40                  45

Ser Val Gly Gln Ala Gln Thr Ser Gly Pro Ser Ser Asn Lys Thr Cys
    50                  55                  60

Ile Thr His Ser Ser Ile Lys Ala Asn Lys Lys Val Cys Lys Asp
65                  70                  75                  80

Val Lys Leu Gly Ile Asn Asn Asn Asp Lys Val Leu Arg Val Cys Val
                85                  90                  95

Ile Glu Asp Thr Ser Leu Ser Gly Val Asp Asn Cys Cys Cys Gln Asp
            100                 105                 110

Leu Leu Gly Ile Leu Gln Glu Asn Cys Ser Asp Asn Lys Arg Gly Ser
        115                 120                 125

Ser Ser Asn Gly Ser Cys Asn Asn Asn Glu Glu Ala Cys Glu Lys
    130                 135                 140

Asn Leu Asp Glu Ala Pro Ala Ser Leu His Asn Gly Tyr Lys Asn Gln
145                 150                 155                 160

Lys Cys Lys Ser Gly Thr Ser Arg Ser Lys Lys Trp Ile Trp Lys
                165                 170                 175

Lys Ser Ser Gly Asn Glu Lys Gly Leu Gln Glu Glu Tyr Ala Asn Thr
            180                 185                 190

Ile Gly Leu Pro Pro Arg Thr Gln Ser Leu Cys Leu Val Cys Leu His
        195                 200                 205

Glu Lys Glu Gly Lys Thr Gln His Lys Thr Ile Ser Thr Asn Ser Glu
210                 215                 220

Leu Leu Lys Glu Trp Ile Ile Ala Ala Phe His Glu Gly Lys Asn Leu
225                 230                 235                 240

Lys Thr Ser His Glu Lys Lys Asn Asp Asp Asn Gly Lys Lys Leu Cys
                245                 250                 255

Lys Ala Leu Glu Tyr Ser Phe Ala Asp Tyr Gly Asp Leu Ile Lys Gly
            260                 265                 270

Thr Ser Ile Trp Asp Asn Glu Tyr Thr Lys Asp Leu Glu Leu Asn Leu
        275                 280                 285

Gln Lys Ala Phe Gly Lys Leu Phe Arg Lys Tyr Ile Lys Lys Asn Asn
290                 295                 300

Thr Ala Glu Gln Asp Thr Ser Tyr Ser Ser Leu Asp Glu Leu Arg Glu
305                 310                 315                 320

Ser Trp Trp Asn Thr Asn Lys Lys Tyr Ile Trp Ile Ala Met Lys His
                325                 330                 335

Gly Ala Gly Met Asn Gly Thr Thr Cys Ser Cys Ser Gly Asp Ser Ser
            340                 345                 350

Asn Asp Met Pro Thr Ile Asp Leu Ile Pro Gln Tyr Leu Arg Phe Leu
        355                 360                 365

Gln Glu Trp Val Glu His Phe Cys Glu Gln Arg Gln Ala Lys Val Lys
370                 375                 380

Asp Val Ile Thr Asn Cys Lys Ser Cys Lys Glu Ser Gly Asn Lys Cys
385                 390                 395                 400

Lys Thr Glu Cys Lys Thr Lys Cys Lys Asp Glu Cys Glu Lys Tyr Lys
                405                 410                 415
```

```
Thr Phe Ile Glu Asp Cys Asn Gly Gly Thr Gly Thr Ala Gly Ser
            420                 425                 430

Ser Trp Val Lys Arg Trp Asp Gln Ile Tyr Lys Arg Tyr Ser Lys His
        435                 440                 445

Ile Glu Asp Ala Lys Arg Asn Arg Lys Ala Gly Thr Lys Asn Cys Gly
450                 455                 460

Pro Ser Ser Ile Thr Asn Ala Ala Ser Thr Asp Glu Asn Lys Cys
465                 470                 475                 480

Val Gln Ser Asp Ile Asp Ser Phe Phe Lys His Leu Ile Asp Ile Gly
                485                 490                 495

Leu Thr Thr Pro Ser Ser Tyr Leu Ser Asn Val Leu Asp Glu Asn Ser
            500                 505                 510

Cys Gly Asp Asp Lys Ala Pro Trp Thr Thr Tyr Thr Thr Tyr Thr Thr
            515                 520                 525

Thr Lys Asn Cys Asp Ile Gln Lys Asp Lys Ser Lys Ser Gln Pro Ile
        530                 535                 540

Asn Thr Ser Val Val Asn Val Pro Ser Pro Leu Gly Asn Thr Pro
545                 550                 555                 560

Tyr Arg Tyr Lys Tyr Ala Cys Glu Cys Lys Ile Pro Thr Thr Glu Glu
                565                 570                 575

Ser Cys Asp Asp Arg Lys Glu Tyr Met Asn Gln Trp Ser Cys Gly Ser
            580                 585                 590

Ala Arg Thr Met Lys Arg Gly Tyr Lys Asn Asp Asn Tyr Glu Leu Cys
                595                 600                 605

Lys Tyr Asn Gly Val Asp Val Lys Pro Thr Thr Val Arg Ser Asn Ser
        610                 615                 620

Ser Lys Leu Asp
625

<210> SEQ ID NO 45
<211> LENGTH: 653
<212> TYPE: PRT
<213> ORGANISM: Artificial
<220> FEATURE:
<223> OTHER INFORMATION: Artificial construct

<400> SEQUENCE: 45

Asp Tyr Ile Lys Gly Asp Pro Tyr Phe Ala Glu Tyr Ala Thr Lys Leu
1               5                   10                  15

Ser Phe Ile Leu Asn Pro Ser Asp Thr Glu Asn Ala Ser Glu Thr Pro
            20                  25                  30

Ser Lys Tyr Tyr Asp Glu Ala Cys Asn Pro Asn Glu Ser Glu Ile Ala
        35                  40                  45

Ser Val Glu Gln Ala Gln Thr Ser Gly Pro Ser Ser Asn Lys Thr Cys
    50                  55                  60

Ile Thr His Ser Ser Ile Lys Thr Asn Lys Lys Glu Cys Lys Asp
65                  70                  75                  80

Val Lys Leu Gly Val Arg Glu Asn Asp Lys Asp Leu Lys Ile Cys Val
                85                  90                  95

Ile Glu Asp Thr Ser Leu Ser Gly Val Asp Asn Cys Cys Phe Lys Asp
            100                 105                 110

Leu Leu Gly Ile Leu Gln Glu Asn Cys Ser Asp Asn Lys Arg Gly Ser
        115                 120                 125

Ser Ser Asn Asp Ser Cys Asn Asn Asn Glu Glu Ala Cys Glu Lys
    130                 135                 140
```

```
Asn Leu Asp Glu Ala Leu Ala Ser Leu Thr Asn Gly Tyr Lys Cys Asp
145                 150                 155                 160

Lys Cys Lys Ser Gly Thr Ser Thr Val Asn Lys Lys Trp Thr Trp Arg
            165                 170                 175

Lys Ser Ser Gly Asn Glu Glu Gly Leu Gln Lys Glu Tyr Ala Asn Thr
                180                 185                 190

Ile Gly Leu Pro Pro Arg Thr Gln Ser Leu Cys Leu Val Cys Leu His
    195                 200                 205

Glu Lys Glu Gly Lys Thr Lys His Lys Thr Ile Ser Thr Asn Ser Glu
210                 215                 220

Leu Leu Lys Glu Trp Ile Ile Ala Ala Phe His Glu Gly Lys Asn Leu
225                 230                 235                 240

Lys Thr Ser His Glu Lys Lys Asn Asp Asp Asn Gly Lys Lys Leu Cys
                245                 250                 255

Lys Ala Leu Glu Tyr Ser Phe Ala Asp Tyr Gly Asp Leu Ile Lys Gly
                260                 265                 270

Thr Ser Ile Trp Asp Asn Glu Tyr Thr Lys Asp Leu Glu Leu Asn Leu
            275                 280                 285

Gln Lys Ala Phe Gly Lys Leu Phe Arg Lys Tyr Ile Lys Lys Asn Asn
290                 295                 300

Thr Ala Glu Gln Asp Thr Ser Tyr Ser Ser Leu Asp Glu Leu Arg Glu
305                 310                 315                 320

Ser Trp Trp Asn Thr Asn Lys Lys Tyr Ile Trp Thr Ala Met Lys His
                325                 330                 335

Gly Ala Glu Met Asn Gly Thr Thr Cys Ser Ser Gly Ser Gly Asp Asn
                340                 345                 350

Gly Asp Ser Ser Ile Thr Gly Ser Asp Ser Gly Ser Thr Thr Cys
                355                 360                 365

Ser Gly Asp Asn Gly Ser Ile Ser Cys Asp Asp Ile Pro Thr Thr Asp
        370                 375                 380

Phe Ile Pro Gln Tyr Leu Arg Phe Leu Gln Glu Trp Val Glu His Phe
385                 390                 395                 400

Cys Glu Gln Arg Gln Ala Lys Val Lys Asp Val Ile Asn Ser Cys Asn
                405                 410                 415

Ser Cys Asn Glu Ser Gly Gly Thr Cys Asn Gly Glu Cys Lys Thr Lys
        420                 425                 430

Cys Lys Asp Glu Cys Glu Lys Tyr Lys Lys Phe Ile Glu Asp Cys Asn
        435                 440                 445

Gly Gly Asp Gly Thr Ala Gly Ser Ser Trp Val Lys Arg Trp Asp Gln
450                 455                 460

Ile Tyr Lys Arg Tyr Ser Lys His Ile Glu Asp Ala Lys Arg Asn Arg
465                 470                 475                 480

Lys Ala Gly Thr Lys Asn Cys Gly Pro Ser Ser Ile Thr Asn Ala Ala
                485                 490                 495

Ala Ser Thr Asp Glu Asn Lys Cys Val Gln Ser Asp Val Asp Ser Phe
        500                 505                 510

Phe Lys His Leu Ile Asp Ile Gly Leu Thr Thr Pro Ser Ser Tyr Leu
        515                 520                 525

Ser Ile Val Leu Asp Glu Asn Ser Cys Gly Asp Asp Lys Ala Pro Trp
        530                 535                 540

Thr Thr Tyr Thr Thr Tyr Thr Thr Glu Lys Cys Asn Lys Glu Arg
545                 550                 555                 560

Asp Lys Ser Lys Ser Gln Ser Ser Asp Thr Leu Val Val Val Asn Val
```

```
                    565                 570                 575

Pro Ser Pro Leu Gly Asn Thr Pro His Glu Tyr Lys Tyr Ala Cys Glu
            580                 585                 590

Cys Lys Ile Pro Thr Asn Glu Glu Thr Cys Asp Asp Arg Lys Asp Tyr
        595                 600                 605

Met Asn Gln Trp Ile Ser Asp Thr Ser Lys Lys Gln Lys Gly Ser Gly
    610                 615                 620

Ser Gly Lys Asp Tyr Tyr Glu Leu Tyr Thr Tyr Asn Gly Val Gln Ile
625                 630                 635                 640

Lys Gln Ala Ala Gly Arg Ser Ser Thr Lys Leu Asp
                645                 650

<210> SEQ ID NO 46
<211> LENGTH: 490
<212> TYPE: PRT
<213> ORGANISM: Plasmodium falciparum

<400> SEQUENCE: 46

Lys Cys Asp Lys Cys Lys Ser Glu Gln Ser Lys Lys Asn Asn Asn Lys
1               5                   10                  15

Trp Ile Trp Lys Lys Tyr Ser Gly Asn Gly Glu Gly Leu Gln Lys Glu
            20                  25                  30

Tyr Ala Asn Thr Ile Gly Leu Pro Pro Arg Thr Gln Ser Leu Cys Leu
        35                  40                  45

Val Cys Leu His Glu Lys Glu Gly Lys Thr Gln His Lys Thr Ile Ser
    50                  55                  60

Thr Asn Ser Glu Leu Leu Lys Glu Trp Ile Ile Ala Ala Phe His Glu
65                  70                  75                  80

Gly Lys Asn Leu Lys Lys Arg Tyr Pro Gln Asn Lys Asn Asp Asp Asn
                85                  90                  95

Asn Ser Lys Leu Cys Lys Ala Leu Glu Tyr Ser Phe Ala Asp Tyr Gly
            100                 105                 110

Asp Leu Ile Lys Gly Thr Ser Ile Trp Asp Asn Glu Tyr Thr Lys Asp
        115                 120                 125

Leu Glu Leu Asn Leu Gln Lys Ala Phe Gly Lys Leu Phe Arg Lys Tyr
    130                 135                 140

Ile Lys Lys Asn Asn Thr Ala Glu Gln Asp Thr Ser Tyr Ser Ser Leu
145                 150                 155                 160

Asp Glu Leu Arg Glu Ser Trp Trp Asn Thr Asn Lys Lys Tyr Ile Trp
                165                 170                 175

Thr Ala Met Lys His Gly Ala Glu Met Asn Gly Thr Thr Cys Ser Ser
            180                 185                 190

Gly Ser Gly Asp Asn Gly Asp Ser Ser Cys Asp Asp Ile Pro Thr Ile
        195                 200                 205

Asp Leu Ile Pro Gln Tyr Leu Arg Phe Leu Gln Glu Trp Val Glu His
    210                 215                 220

Phe Cys Lys Gln Arg Gln Ala Lys Val Lys Asp Val Ile Asn Ser Cys
225                 230                 235                 240

Asn Ser Cys Lys Asn Thr Ser Gly Glu Arg Lys Ile Gly Gly Thr Cys
                245                 250                 255

Asn Ser Asp Cys Glu Lys Lys Cys Lys Val Ala Cys Asp Ala Tyr Lys
            260                 265                 270

Thr Phe Ile Glu Glu Cys Arg Thr Ala Val Gly Gly Thr Ala Gly Ser
        275                 280                 285
```

```
Ser Trp Val Lys Arg Trp Asp Gln Ile Tyr Lys Arg Tyr Ser Lys His
    290                 295                 300
Ile Glu Asp Ala Lys Arg Asn Arg Lys Ala Gly Thr Lys Asn Cys Gly
305                 310                 315                 320
Pro Ser Ser Thr Thr Asn Ala Ala Glu Asn Lys Cys Val Gln Ser Asp
                325                 330                 335
Ile Asp Ser Phe Phe Lys His Leu Ile Asp Ile Gly Leu Thr Thr Pro
            340                 345                 350
Ser Ser Tyr Leu Ser Asn Val Leu Asp Glu Asn Ser Cys Gly Ala Asp
        355                 360                 365
Lys Ala Pro Trp Thr Thr Tyr Thr Thr Tyr Thr Thr Tyr Thr Thr Tyr
    370                 375                 380
Thr Thr Tyr Thr Thr Thr Glu Lys Cys Asn Lys Glu Arg Asp Lys Ser
385                 390                 395                 400
Lys Ser Gln Gln Ser Asn Thr Ser Val Val Asn Val Pro Ser Pro
                405                 410                 415
Leu Gly Asn Thr Pro His Glu Tyr Lys Tyr Ala Cys Glu Cys Lys Ile
            420                 425                 430
Pro Thr Thr Glu Glu Thr Cys Asp Asp Arg Lys Glu Tyr Met Asn Gln
        435                 440                 445
Trp Ile Ile Asp Asn Thr Lys Asn Pro Lys Gly Ser Gly Ser Thr Asp
    450                 455                 460
Asn Asp Tyr Glu Leu Tyr Thr Tyr Asn Gly Val Gln Ile Lys Gln Ala
465                 470                 475                 480
Ala Gly Arg Ser Ser Ser Thr Lys Leu Asp
                485                 490

<210> SEQ ID NO 47
<211> LENGTH: 335
<212> TYPE: PRT
<213> ORGANISM: Plasmodium falciparum

<400> SEQUENCE: 47

Lys Cys Glu Lys Cys Lys Ser Gly Thr Ser Thr Val Asn Asn Lys Trp
1               5                   10                  15
Ile Trp Arg Lys Ser Ser Gly Lys Glu Gly Gly Leu Gln Lys Glu Tyr
            20                  25                  30
Ala Asn Thr Ile Gly Leu Pro Pro Arg Thr Gln Ser Leu Tyr Leu Gly
        35                  40                  45
Asn Leu Pro Lys Leu Glu Asn Val Cys Lys Gly Val Thr Asp Ile Ile
    50                  55                  60
Tyr Asp Thr Lys Glu Lys Phe Leu Ser Gly Cys Leu Ile Ala Ala Phe
65                  70                  75                  80
His Glu Gly Lys Asn Leu Lys Thr Thr Tyr Leu Glu Lys Lys Asn Asp
                85                  90                  95
Asp Asn Gly Lys Lys Leu Cys Lys Ala Leu Glu Tyr Ser Phe Ala Asp
                100                 105                 110
Tyr Gly Asp Leu Ile Lys Gly Thr Ser Ile Trp Asp Asn Glu Tyr Thr
            115                 120                 125
Lys Asp Leu Glu Leu Asn Leu Gln Lys Ile Phe Gly Lys Leu Phe Arg
        130                 135                 140
Lys Tyr Ile Lys Lys Asn Asn Thr Ala Glu Gln Asp Thr Ser Tyr Ser
145                 150                 155                 160
Ser Leu Asp Glu Leu Arg Glu Ser Trp Trp Asn Thr Asn Lys Lys Tyr
                165                 170                 175
```

```
Ile Trp Ile Ala Met Lys His Gly Ala Gly Met Asn Gly Thr Thr Cys
            180                 185                 190
Ser Ser Gly Ser Gly Asp Ser Asn Asp Ile Pro Thr Thr Asp Phe
        195                 200                 205
Ile Pro Gln Tyr Leu Arg Phe Leu Gln Glu Trp Val Glu Asn Phe Cys
210                 215                 220
Glu Gln Arg Gln Ala Lys Val Lys Pro Val Ile Glu Asn Cys Asn Ser
225                 230                 235                 240
Cys Lys Glu Ser Gly Gly Thr Cys Asn Gly Glu Cys Lys Thr Lys Cys
                245                 250                 255
Lys Val Ala Cys Asp Ala Tyr Lys Lys Phe Ile Asp Gly Thr Gly Ser
            260                 265                 270
Gly Gly Gly Ser Arg Pro Thr Gly Ile Ala Gly Ser Ser Trp Ser Lys
            275                 280                 285
Arg Trp Asp Gln Ile Tyr Lys Arg Tyr Ser Lys His Ile Glu Asp Ala
        290                 295                 300
Lys Arg Asn Arg Lys Ala Gly Thr Lys Asn Cys Gly Pro Ser Ser Ile
305                 310                 315                 320
Thr Asn Val Ser Val Ser Thr Asp Glu Asn Lys Cys Val Gln Ser
                325                 330                 335
```

<210> SEQ ID NO 48
<211> LENGTH: 637
<212> TYPE: PRT
<213> ORGANISM: Artificial
<220> FEATURE:
<223> OTHER INFORMATION: Artificial construct

<400> SEQUENCE: 48

```
Asn Tyr Ile Lys Asp Asp Pro Tyr Ser Lys Glu Tyr Val Thr Lys Leu
1               5                   10                  15
Ser Phe Ile Pro Asn Ser Ser Asp Ala Asn Thr Ser Ser Glu Lys Ile
            20                  25                  30
Gln Lys Asn Asn Asp Glu Val Cys Asn Pro Asn Glu Ser Gly Ile Ser
        35                  40                  45
Ser Val Glu Gln Ala Gln Thr Ser Asp Pro Ser Ser Asn Lys Thr Cys
    50                  55                  60
Ile Thr His Ser Ser Ile Lys Ala Asn Lys Lys Glu Cys Lys Asp
65                  70                  75                  80
Val Lys Leu Gly Val Arg Glu Asn Asp Lys Asp Leu Lys Ile Cys Val
                85                  90                  95
Ile Glu His Thr Ser Leu Ser Gly Val Asp Asn Cys Cys Phe Lys Asp
            100                 105                 110
Phe Leu Arg Met Leu Gln Glu Pro Arg Ile Asp Lys Asn Gln Arg Gly
        115                 120                 125
Ser Ser Ser Asn Gly Ser Cys Asp Lys Asn Ser Glu Glu Ala Cys Glu
    130                 135                 140
Lys Asn Leu Asp Glu Ala Leu Ala Ser Leu Thr Asn Gly Tyr Lys Cys
145                 150                 155                 160
Asp Lys Cys Lys Ser Glu Gln Ser Lys Lys Asn Asn Asn Lys Trp Ile
                165                 170                 175
Trp Lys Lys Phe Pro Gly Lys Glu Gly Gly Leu Gln Glu Glu Tyr Ala
            180                 185                 190
Asn Thr Ile Gly Leu Pro Pro Arg Thr Gln Tyr Leu Cys Leu Val Val
        195                 200                 205
```

```
Cys Leu Asp Glu Lys Glu Gly Lys Thr Gln Glu Leu Lys Asn Ile Arg
    210                 215                 220

Thr Asn Ser Glu Leu Leu Lys Glu Trp Ile Ile Ala Ala Phe His Glu
225                 230                 235                 240

Gly Lys Asn Leu Lys Thr Thr Tyr Pro Gln Lys Lys Asn Asp Asp Asn
                245                 250                 255

Gly Lys Lys Leu Cys Lys Asp Leu Lys Tyr Ser Phe Ala Asp Tyr Gly
                260                 265                 270

Asp Leu Ile Lys Gly Thr Ser Ile Trp Asp Asn Glu Tyr Thr Lys Asn
                275                 280                 285

Val Glu Leu Asn Leu Gln Asn Asn Phe Gly Lys Leu Phe Arg Lys Tyr
    290                 295                 300

Ile Lys Lys Asn Asn Thr Ala Glu Gln Asp Thr Ser Tyr Ser Ser Leu
305                 310                 315                 320

Asp Glu Leu Arg Glu Ser Trp Trp Asn Thr Asn Lys Lys Tyr Ile Trp
                325                 330                 335

Leu Ala Met Lys His Gly Ala Glu Met Asn Ser Thr Thr Cys Cys Gly
                340                 345                 350

Asp Gly Ser Val Thr Gly Ser Gly Ser Ser Cys Asp Asp Ile Pro Thr
                355                 360                 365

Ile Asp Leu Ile Pro Gln Tyr Leu Arg Phe Leu Gln Glu Trp Val Glu
370                 375                 380

His Phe Cys Lys Gln Arg Gln Ala Lys Val Lys Asp Val Ile Thr Asn
385                 390                 395                 400

Cys Asn Ser Cys Lys Glu Ser Gly Asn Lys Cys Lys Thr Glu Cys Lys
                405                 410                 415

Asn Lys Cys Lys Asp Glu Cys Glu Lys Tyr Lys Lys Phe Ile Glu Ala
                420                 425                 430

Cys Gly Thr Ala Val Gly Gly Thr Gly Thr Ala Gly Ser Pro Trp Ser
                435                 440                 445

Lys Arg Trp Asp Gln Ile Tyr Lys Arg Tyr Ser Lys His Ile Glu Asp
                450                 455                 460

Ala Lys Arg Asn Arg Lys Ala Gly Thr Lys Asn Cys Gly Pro Ser Ser
465                 470                 475                 480

Thr Thr Asn Ala Ala Glu Asn Lys Cys Val Gln Ser Asp Ile Asp Ser
                485                 490                 495

Phe Phe Lys His Leu Ile Asp Ile Gly Leu Thr Thr Pro Ser Ser Tyr
                500                 505                 510

Leu Ser Ile Val Leu Asp Asp Asn Ile Cys Gly Ala Asp Lys Ala Pro
                515                 520                 525

Trp Thr Thr Tyr Thr Thr Tyr Thr Thr Glu Asn Cys Asp Ile Gln Lys
                530                 535                 540

Lys Thr Pro Lys Ser Gln Ser Cys Asp Thr Leu Val Val Asn Val
545                 550                 555                 560

Pro Ser Pro Leu Gly Asn Thr Pro His Gly Tyr Lys Tyr Ala Cys Gln
                565                 570                 575

Cys Arg Thr Pro Asn Lys Gln Glu Ser Cys Asp Asp Arg Lys Glu Tyr
                580                 585                 590

Met Asn Gln Trp Ile Ile Asp Asn Thr Lys Asn Pro Lys Gly Ser Gly
                595                 600                 605

Ser Gly Lys Asp Tyr Tyr Glu Leu Cys Lys Tyr Asn Gly Val Lys Glu
610                 615                 620
```

```
Thr Lys Pro Leu Gly Thr Leu Lys Asn Ser Lys Leu Asp
625                 630                 635
```

<210> SEQ ID NO 49
<211> LENGTH: 330
<212> TYPE: PRT
<213> ORGANISM: Plasmodium falciparum

<400> SEQUENCE: 49

```
Lys Cys Asp Lys Cys Lys Ser Glu Gln Ser Lys Asn Asn Asn Lys
1               5                   10                  15

Trp Ile Trp Arg Lys Phe Pro Gly Lys Glu Gly Leu Gln Lys Glu
                20                  25                  30

Tyr Ala Asn Thr Ile Gly Leu Pro Pro Arg Thr Gln Ser Leu Cys Leu
            35                  40                  45

Val Cys Leu His Glu Lys Glu Gly Lys Thr Gln His Lys Thr Ile Ser
50                  55                          60

Thr Asn Ser Glu Leu Leu Lys Glu Trp Ile Ile Ala Ala Phe His Glu
65                  70                  75                  80

Gly Lys Asn Leu Lys Thr Thr Tyr Leu Glu Lys Lys Asn Ala Glu Asn
                85                  90                  95

Lys Lys Lys Leu Cys Lys Ala Leu Lys Tyr Ser Phe Ala Asp Tyr Gly
                100                 105                 110

Asp Leu Ile Lys Gly Thr Ser Ile Trp Asp Asn Glu Tyr Thr Lys Asp
                115                 120                 125

Leu Glu Leu Asn Leu Gln Lys Ile Phe Gly Lys Leu Phe Arg Lys Tyr
                130                 135                 140

Ile Lys Lys Asn Asn Thr Ala Glu Gln Asp Thr Ser Tyr Ser Ser Leu
145                 150                 155                 160

Asp Glu Leu Arg Glu Ser Trp Trp Asn Thr Asn Lys Lys Tyr Ile Trp
                165                 170                 175

Thr Ala Met Lys His Gly Ala Gly Met Asn Gly Thr Met Cys Asn Ala
                180                 185                 190

Asp Gly Ser Val Thr Gly Ser Gly Ser Cys Asp Asp Met Pro Thr
                195                 200                 205

Thr Asp Phe Ile Pro Gln Tyr Leu Arg Phe Leu Gln Glu Trp Val Glu
210                 215                 220

His Phe Cys Lys Gln Arg Gln Ala Lys Val Lys Asp Val Ile Glu Asn
225                 230                 235                 240

Cys Lys Ser Cys Lys Glu Ser Gly Asn Lys Cys Lys Thr Glu Cys Lys
                245                 250                 255

Asn Lys Cys Asp Ala Tyr Lys Thr Phe Ile Glu Glu Cys Gly Thr Ala
                260                 265                 270

Val Gly Gly Thr Ala Gly Ser Ser Trp Val Lys Arg Trp Asp Gln Ile
                275                 280                 285

Tyr Lys Arg Tyr Ser Lys His Ile Glu Asp Ala Lys Arg Asn Arg Lys
                290                 295                 300

Ala Gly Thr Lys Asn Cys Gly Thr Ser Ser Thr Asn Ala Ala Ala
305                 310                 315                 320

Ser Thr Ala Glu Asn Lys Cys Val Gln Ser
                325                 330
```

<210> SEQ ID NO 50
<211> LENGTH: 269
<212> TYPE: PRT
<213> ORGANISM: Plasmodium falciparum

<400> SEQUENCE: 50

```
Asn Tyr Ile Lys Asp Asp Pro Tyr Ser Lys Glu Tyr Val Thr Lys Leu
1               5                   10                  15
Ser Phe Ile Leu Asn Ser Ser Asp Ala Glu Asn Ala Ser Glu Thr Pro
            20                  25                  30
Ser Lys Tyr Tyr Asp Glu Ala Cys Asn Cys Asn Glu Ser Gly Ile Ser
        35                  40                  45
Ser Val Glu Gln Ala Ser Ile Ser Asp Arg Ser Ser Gln Lys Ala Cys
    50                  55                  60
Asn Thr His Ser Phe Ile Gly Ala Asn Lys Lys Val Cys Lys His
65                  70                  75                  80
Val Lys Leu Gly Val Arg Glu Asn Asp Lys Asp Leu Lys Ile Cys Val
                85                  90                  95
Ile Glu Asp Asp Ser Leu Arg Gly Val Asn Cys Cys Phe Lys Asp
            100                 105                 110
Phe Leu Arg Met Leu Gln Glu Pro Arg Ile Asp Lys Asn Gln Arg Gly
        115                 120                 125
Ser Ser Ser Asn Asp Ser Cys Asn Asn Asn Glu Glu Ala Cys Glu
    130                 135                 140
Lys Asn Leu Asp Glu Ala Leu Ala Ser Leu His Asn Gly Tyr Lys Asn
145                 150                 155                 160
Gln Lys Cys Lys Ser Glu Gln Ser Lys Lys Asn Asn Lys Trp Ile
                165                 170                 175
Trp Lys Lys Ser Ser Gly Lys Glu Gly Gly Leu Gln Lys Glu Tyr Ala
            180                 185                 190
Asn Thr Ile Gly Leu Pro Pro Arg Thr Gln Ser Leu Cys Leu Val Cys
        195                 200                 205
Leu His Glu Lys Glu Gly Lys Thr Gln His Lys Thr Ile Ser Thr Asn
    210                 215                 220
Ser Glu Leu Leu Lys Glu Trp Ile Ile Asp Ala Phe His Glu Gly Lys
225                 230                 235                 240
Asn Leu Lys Thr Thr Tyr Leu Glu Lys Lys Gly Asp Asn Gly Lys
                245                 250                 255
Lys Leu Cys Lys Ala Leu Lys Tyr Ser Phe Ala Asp Tyr
            260                 265
```

```
<210> SEQ ID NO 51
<211> LENGTH: 347
<212> TYPE: PRT
<213> ORGANISM: Plasmodium falciparum
```

<400> SEQUENCE: 51

```
Lys Cys Asp Lys Cys Lys Ser Glu Gln Ser Lys Lys Asn Asn Lys Asn
1               5                   10                  15
Trp Ile Trp Lys Lys Ser Ser Gly Lys Glu Gly Gly Leu Gln Lys Glu
            20                  25                  30
Tyr Ala Asn Thr Ile Ala Leu Pro Pro Arg Thr Gln Ser Leu Cys Leu
        35                  40                  45
Val Val Cys Leu His Glu Lys Glu Gly Lys Thr Gln His Lys Thr Ile
    50                  55                  60
Ser Thr Asn Ser Glu Leu Leu Lys Glu Trp Ile Ile Asp Ala Phe His
65                  70                  75                  80
Glu Gly Lys Asn Leu Lys Thr Thr Tyr Leu Glu Lys Gln Asn Ala Asp
                85                  90                  95
```

```
Asn Gly Lys Lys Asn Ala Asp Asn Ser Lys Leu Cys Lys Asp Leu
            100                 105                 110
Lys Tyr Ser Phe Ala Asp Tyr Gly Asp Leu Ile Lys Gly Thr Ser Ile
            115                 120                 125
Trp Asp Asn Glu Tyr Thr Lys Asp Leu Glu Leu Asn Leu Gln Gln Ile
130                 135                 140
Phe Gly Lys Leu Phe Arg Lys Tyr Ile Lys Lys Asn Ile Ala Ser Asp
145                 150                 155                 160
Glu Asn Thr Leu Tyr Ser Ser Leu Asp Glu Leu Arg Glu Ser Trp Trp
            165                 170                 175
Asn Thr Asn Lys Lys Tyr Ile Trp Thr Ala Met Lys His Gly Ala Glu
            180                 185                 190
Met Asn Gly Thr Thr Cys Ser Ser Gly Ser Gly Asp Ser Ser Ser Gly
            195                 200                 205
Glu Asn Gln Thr Asn Ser Cys Asp Asp Ile Pro Thr Ile Asp Leu Ile
            210                 215                 220
Pro Gln Tyr Leu Arg Phe Leu Gln Glu Trp Val Glu His Phe Cys Glu
225                 230                 235                 240
Gln Arg Gln Ala Lys Val Lys Asp Val Ile Thr Asn Cys Lys Ser Cys
            245                 250                 255
Lys Glu Ser Gly Gly Thr Cys Asn Ser Asp Cys Lys Thr Lys Cys Lys
            260                 265                 270
Gly Glu Cys Glu Lys Tyr Lys Lys Phe Ile Glu Lys Cys Lys Gly Gly
            275                 280                 285
Gly Thr Glu Gly Thr Ser Gly Ser Ser Trp Val Lys Arg Trp Tyr Gln
            290                 295                 300
Ile Tyr Met Arg Tyr Ser Lys Tyr Ile Glu Asp Ala Lys Arg Asn Arg
305                 310                 315                 320
Lys Ala Gly Thr Lys Ser Cys Gly Thr Ser Ser Gly Ala Asn Ser Gly
            325                 330                 335
Val Thr Thr Thr Glu Ser Lys Cys Val Gln Ser
            340                 345

<210> SEQ ID NO 52
<211> LENGTH: 269
<212> TYPE: PRT
<213> ORGANISM: Plasmodium falciparum

<400> SEQUENCE: 52

Asp Tyr Ile Lys Asp Asp Pro Tyr Ser Lys Glu Tyr Thr Thr Lys Leu
1               5                   10                  15
Ser Phe Ile Leu Asn Ser Ser Asp Ala Asn Thr Ser Ser Glu Lys Ile
            20                  25                  30
Gln Lys Asn Asn Asp Glu Val Cys Asn Pro Asn Glu Ser Glu Ile Ser
            35                  40                  45
Ser Val Glu Gln Ala Gln Thr Ser Arg Pro Ser Ser Asn Lys Thr Cys
            50                  55                  60
Ile Thr His Ser Ser Ile Lys Ala Asn Lys Lys Val Cys Lys Asp
65                  70                  75                  80
Val Lys Leu Gly Val Arg Glu Asn Asp Lys Val Leu Arg Val Cys Val
            85                  90                  95
Ile Glu His Thr Ser Leu Ser Gly Val Glu Asn Cys Cys Gln Asp
            100                 105                 110
Leu Leu Gly Ile Leu Gln Glu Asn Cys Ser Asp Asn Lys Arg Gly Ser
```

```
            115                 120                 125
Ser Ser Asn Gly Ser Cys Asp Lys Asn Ser Glu Glu Ala Cys Glu Lys
130                 135                 140

Asn Leu Asp Glu Ala Leu Ala Ser Leu Thr Asn Cys Tyr Lys Asn Gln
145                 150                 155                 160

Lys Cys Lys Ser Glu Gln Ser Lys Lys Asn Asn Lys Trp Ile Trp
                165                 170                 175

Lys Lys Ser Ser Gly Asn Glu Lys Gly Leu Gln Lys Glu Tyr Ala Asn
                180                 185                 190

Thr Ile Gly Leu Pro Pro Arg Thr Gln Ser Leu Cys Leu Val Cys Leu
                195                 200                 205

His Glu Lys Glu Gly Lys Thr Gln Glu Leu Lys Asn Ile Ser Thr Asn
                210                 215                 220

Ser Glu Leu Leu Lys Glu Trp Ile Ile Ala Ala Phe His Glu Gly Lys
225                 230                 235                 240

Asn Leu Lys Thr Thr Tyr Pro Gln Asn Lys Asn Asp Asp Asn Gly Lys
                245                 250                 255

Lys Leu Phe Lys Asp Leu Lys Tyr Ser Phe Ala Asp Tyr
                260                 265

<210> SEQ ID NO 53
<211> LENGTH: 646
<212> TYPE: PRT
<213> ORGANISM: Artificial
<220> FEATURE:
<223> OTHER INFORMATION: Artificial construct

<400> SEQUENCE: 53

Asp Tyr Ile Lys Asp Asp Pro Tyr Ser Lys Glu Tyr Thr Thr Lys Leu
1               5                   10                  15

Ser Phe Ile Leu Asn Ser Ser Asp Ala Asn Thr Ser Ser Glu Lys Ile
                20                  25                  30

Gln Lys Asn Asn Asp Glu Val Cys Asn Pro Asn Glu Ser Glu Ile Ser
                35                  40                  45

Ser Val Glu Gln Ala Gln Thr Ser Arg Pro Ser Ser Asn Lys Thr Cys
50                  55                  60

Ile Thr His Ser Ser Ile Lys Ala Asn Lys Lys Val Cys Lys Asp
65                  70                  75                  80

Val Lys Leu Gly Val Arg Glu Asn Asp Lys Val Leu Arg Val Cys Val
                85                  90                  95

Ile Glu His Thr Ser Leu Ser Gly Val Glu Asn Cys Cys Cys Gln Asp
                100                 105                 110

Leu Leu Gly Ile Leu Gln Glu Asn Cys Ser Asp Asn Lys Arg Gly Ser
                115                 120                 125

Ser Ser Asn Gly Ser Cys Asp Lys Asn Ser Glu Glu Ala Cys Glu Lys
130                 135                 140

Asn Leu Asp Glu Ala Leu Ala Ser Leu Thr Asn Cys Tyr Lys Asn Gln
145                 150                 155                 160

Lys Cys Lys Ser Glu Gln Ser Lys Lys Asn Asn Lys Trp Ile Trp
                165                 170                 175

Lys Lys Ser Ser Gly Lys Glu Gly Gly Leu Gln Lys Glu Tyr Ala Asn
                180                 185                 190

Thr Ile Gly Leu Pro Pro Arg Thr Gln Ser Leu Tyr Leu Gly Asn Leu
                195                 200                 205

Pro Lys Leu Glu Asn Val Cys Lys Gly Val Thr Asp Ile Asn Phe Asp
```

```
            210                 215                 220
Thr Lys Glu Lys Phe Leu Ala Gly Cys Leu Ile Ala Ala Phe His Glu
225                 230                 235                 240

Gly Lys Asn Leu Lys Thr Thr Tyr Leu Glu Lys Lys Asn Asp Asp Asn
                245                 250                 255

Gly Lys Lys Leu Cys Lys Ala Leu Glu Tyr Ser Phe Ala Asp Tyr Gly
                260                 265                 270

Asp Leu Ile Lys Gly Thr Ser Ile Trp Asp Asn Glu Tyr Thr Lys Asp
            275                 280                 285

Leu Glu Leu Asn Leu Gln Lys Ala Phe Gly Lys Leu Phe Arg Lys Tyr
290                 295                 300

Ile Lys Lys Asn Asn Thr Ala Glu Gln Asp Thr Ser Tyr Ser Ser Leu
305                 310                 315                 320

Asp Glu Leu Arg Glu Ser Trp Trp Asn Thr Asn Lys Lys Tyr Ile Trp
                325                 330                 335

Thr Ala Met Lys His Gly Ala Gly Met Asn Gly Thr Thr Cys Ser Ser
                340                 345                 350

Gly Ser Gly Asp Ser Ser Asn Asp Ile Pro Thr Thr Asp Phe Ile Pro
            355                 360                 365

Gln Tyr Leu Arg Phe Leu Gln Glu Trp Val Glu Asn Phe Cys Glu Gln
                370                 375                 380

Arg Gln Ala Lys Val Lys Asp Val Ile Glu Asn Cys Asn Ser Cys Lys
385                 390                 395                 400

Asn Thr Ser Gly Glu Arg Lys Ile Gly Asp Thr Cys Asn Ser Asp Cys
                405                 410                 415

Glu Lys Lys Cys Lys Asp Glu Cys Glu Lys Tyr Lys Lys Phe Ile Glu
                420                 425                 430

Asp Cys Lys Gly Gly Asp Gly Thr Ala Gly Ser Ser Trp Val Lys Arg
            435                 440                 445

Trp Asp Gln Ile Tyr Lys Arg Tyr Ser Lys His Ile Glu Asp Ala Lys
450                 455                 460

Arg Asn Arg Lys Ala Gly Thr Lys Asn Cys Gly Ile Thr Thr Gly Thr
465                 470                 475                 480

Ile Ser Gly Glu Ser Ser Gly Ala Thr Ser Gly Val Thr Thr Thr Glu
                485                 490                 495

Asn Lys Cys Val Gln Ser Asp Ile Asp Ser Phe Phe Lys His Leu Ile
                500                 505                 510

Asp Ile Gly Leu Thr Thr Pro Ser Ser Tyr Leu Ser Asn Val Leu Asp
            515                 520                 525

Asp Asn Ile Cys Gly Glu Asp Asn Ala Pro Trp Thr Thr Tyr Thr Thr
530                 535                 540

Tyr Thr Thr Glu Lys Cys Asn Lys Glu Thr Asp Lys Ser Lys Ser Gln
545                 550                 555                 560

Gln Ser Asn Thr Ala Val Val Val Asn Val Pro Ser Pro Leu Gly Asn
                565                 570                 575

Thr Pro His Gly Tyr Lys Tyr Ala Cys Glu Cys Lys Ile Pro Thr Thr
            580                 585                 590

Glu Glu Thr Cys Asp Asp Arg Lys Glu Tyr Met Asn Gln Trp Ser Cys
                595                 600                 605

Gly Ser Ala Gln Thr Val Arg Asp Arg Ser Gly Lys Asp Asp Tyr Glu
            610                 615                 620

Leu Cys Lys Tyr Asn Gly Val Gln Ile Lys Gln Ala Ala Gly Thr Leu
625                 630                 635                 640
```

Lys Asn Ser Lys Leu Asp
            645

<210> SEQ ID NO 54
<211> LENGTH: 632
<212> TYPE: PRT
<213> ORGANISM: Plasmodium falciparum

<400> SEQUENCE: 54

Asn Tyr Ile Lys Gly Asp Pro Tyr Phe Ala Glu Tyr Ala Thr Lys Leu
1               5                   10                  15

Ser Phe Ile Leu Asn Ser Ser Asp Ala Asn Asn Pro Ser Glu Lys Ile
            20                  25                  30

Gln Lys Asn Asn Asp Glu Val Cys Asn Cys Asn Glu Ser Gly Ile Ala
        35                  40                  45

Ser Val Glu Gln Glu Gln Ile Ser Asp Pro Ser Ser Asn Lys Thr Cys
    50                  55                  60

Ile Thr His Ser Ser Ile Lys Ala Asn Lys Lys Val Cys Lys His
65                  70                  75                  80

Val Lys Leu Gly Val Arg Glu Asn Asp Lys Asp Leu Arg Val Cys Val
                85                  90                  95

Ile Glu His Thr Ser Leu Ser Gly Val Glu Asn Cys Cys Cys Gln Asp
            100                 105                 110

Phe Leu Arg Ile Leu Gln Glu Asn Cys Ser Asp Asn Lys Ser Gly Ser
        115                 120                 125

Ser Ser Asn Gly Ser Cys Asn Asn Lys Asn Gln Glu Ala Cys Glu Lys
    130                 135                 140

Asn Leu Glu Lys Val Leu Ala Ser Leu Thr Asn Cys Tyr Lys Cys Asp
145                 150                 155                 160

Lys Cys Lys Ser Glu Gln Ser Lys Lys Asn Asn Lys Asn Trp Ile Trp
                165                 170                 175

Lys Lys Ser Ser Gly Lys Glu Gly Gly Leu Gln Lys Glu Tyr Ala Asn
            180                 185                 190

Thr Ile Gly Leu Pro Pro Arg Thr Gln Ser Leu Cys Leu Val Val Cys
        195                 200                 205

Leu Asp Glu Lys Gly Lys Lys Thr Gln Glu Leu Lys Asn Ile Arg Thr
210                 215                 220

Asn Ser Glu Leu Leu Lys Glu Trp Ile Ile Ala Ala Phe His Glu Gly
225                 230                 235                 240

Lys Asn Leu Lys Pro Ser His Glu Lys Lys Asn Asp Asp Asn Gly Lys
                245                 250                 255

Lys Leu Cys Lys Ala Leu Glu Tyr Ser Phe Ala Asp Tyr Gly Asp Leu
            260                 265                 270

Ile Lys Gly Thr Ser Ile Trp Asp Asn Glu Tyr Thr Lys Asp Leu Glu
        275                 280                 285

Leu Asn Leu Gln Lys Ile Phe Gly Lys Leu Phe Arg Lys Tyr Ile Lys
    290                 295                 300

Lys Asn Asn Thr Ala Glu Gln Asp Thr Ser Tyr Ser Ser Leu Asp Glu
305                 310                 315                 320

Leu Arg Glu Ser Trp Trp Asn Thr Asn Lys Lys Tyr Ile Trp Leu Ala
                325                 330                 335

Met Lys His Gly Ala Gly Met Asn Ser Thr Thr Cys Cys Gly Asp Gly
            340                 345                 350

Ser Val Thr Gly Ser Gly Ser Ser Cys Asp Asp Ile Pro Thr Ile Asp

```
              355                 360                 365
Leu Ile Pro Gln Tyr Leu Arg Phe Leu Gln Glu Trp Val Glu His Phe
370                 375                 380

Cys Lys Gln Arg Gln Glu Lys Val Lys Pro Val Ile Glu Asn Cys Lys
385                 390                 395                 400

Ser Cys Lys Glu Ser Gly Gly Thr Cys Asn Gly Glu Cys Lys Thr Glu
                405                 410                 415

Cys Lys Asn Lys Cys Glu Val Tyr Lys Lys Phe Ile Glu Asp Cys Lys
            420                 425                 430

Gly Gly Asp Gly Thr Ala Gly Ser Ser Trp Val Lys Arg Trp Asp Gln
        435                 440                 445

Ile Tyr Lys Arg Tyr Ser Lys Tyr Ile Glu Asp Ala Lys Arg Asn Arg
    450                 455                 460

Lys Ala Gly Thr Lys Asn Cys Gly Pro Ser Ser Thr Thr Asn Ala Ala
465                 470                 475                 480

Glu Asn Lys Cys Val Gln Ser Asp Ile Asp Ser Phe Phe Lys His Leu
                485                 490                 495

Ile Asp Ile Gly Leu Thr Thr Pro Ser Ser Tyr Leu Ser Ile Val Leu
            500                 505                 510

Asp Asp Asn Ile Cys Gly Ala Asp Lys Ala Pro Trp Thr Thr Tyr Thr
        515                 520                 525

Thr Tyr Thr Thr Thr Glu Lys Cys Asn Lys Glu Thr Asp Lys Ser Lys
    530                 535                 540

Leu Gln Gln Cys Asn Thr Ala Val Val Val Asn Val Pro Ser Pro Leu
545                 550                 555                 560

Gly Asn Thr Pro His Gly Tyr Lys Tyr Ala Cys Gln Cys Lys Ile Pro
                565                 570                 575

Thr Asn Glu Glu Thr Cys Asp Asp Arg Lys Glu Tyr Met Asn Gln Trp
            580                 585                 590

Ser Cys Gly Ser Ala Arg Thr Met Lys Arg Gly Tyr Lys Asn Asp Asn
        595                 600                 605

Tyr Glu Leu Cys Lys Tyr Asn Gly Val Asp Val Lys Pro Thr Thr Val
    610                 615                 620

Arg Ser Asn Ser Ser Lys Leu Asp
625                 630

<210> SEQ ID NO 55
<211> LENGTH: 2730
<212> TYPE: PRT
<213> ORGANISM: Plasmodium falciparum

<400> SEQUENCE: 55

Met Asp Lys Ser Ser Ile Ala Asn Lys Ile Glu Ala Tyr Leu Gly Ala
1               5                   10                  15

Lys Ser Asp Asp Ser Lys Ile Asp Gln Ser Leu Lys Ala Asp Pro Ser
            20                  25                  30

Glu Val Gln Tyr Tyr Gly Ser Gly Asp Gly Tyr Tyr Leu Arg Lys
        35                  40                  45

Asn Ile Cys Lys Ile Thr Val Asn His Ser Asp Ser Gly Thr Asn Asp
    50                  55                  60

Pro Cys Asp Arg Ile Pro Pro Tyr Gly Asp Asn Asp Gln Trp Lys
65                  70                  75                  80

Cys Ala Ile Ile Leu Ser Lys Val Ser Glu Lys Pro Glu Asn Val Phe
                85                  90                  95
```

Val Pro Pro Arg Arg Gln Arg Met Cys Ile Asn Asn Leu Glu Lys Leu
            100                 105                 110

Asn Val Asp Lys Ile Arg Asp Lys His Ala Phe Leu Ala Asp Val Leu
        115                 120                 125

Leu Thr Ala Arg Asn Glu Gly Glu Arg Ile Val Gln Asn His Pro Asp
    130                 135                 140

Thr Asn Ser Ser Asn Val Cys Asn Ala Leu Glu Arg Ser Phe Ala Asp
145                 150                 155                 160

Ile Ala Asp Ile Ile Arg Gly Thr Asp Leu Trp Lys Gly Thr Asn Ser
                165                 170                 175

Asn Leu Glu Gln Asn Leu Lys Gln Met Phe Ala Lys Ile Arg Glu Asn
        180                 185                 190

Asp Lys Val Leu Gln Asp Lys Tyr Pro Lys Asp Gln Asn Tyr Arg Lys
        195                 200                 205

Leu Arg Glu Asp Trp Trp Asn Ala Asn Arg Gln Lys Val Trp Glu Val
    210                 215                 220

Ile Thr Cys Gly Ala Arg Ser Asn Asp Leu Leu Ile Lys Arg Gly Trp
225                 230                 235                 240

Arg Thr Ser Gly Lys Ser Asn Gly Asp Asn Lys Leu Glu Leu Cys Arg
                245                 250                 255

Lys Cys Gly His Tyr Glu Glu Lys Val Pro Thr Lys Leu Asp Tyr Val
        260                 265                 270

Pro Gln Phe Leu Arg Trp Leu Thr Glu Trp Ile Glu Asp Phe Tyr Arg
        275                 280                 285

Glu Lys Gln Asn Leu Ile Asp Asp Met Glu Arg His Arg Glu Glu Cys
    290                 295                 300

Thr Ser Glu Asp His Lys Ser Lys Gly Thr Ser Tyr Cys Ser Thr
305                 310                 315                 320

Cys Lys Asp Lys Cys Lys Lys Tyr Cys Glu Cys Val Lys Lys Trp Lys
                325                 330                 335

Ser Glu Trp Glu Asn Gln Lys Asn Lys Tyr Thr Glu Leu Tyr Gln Gln
        340                 345                 350

Asn Lys Asn Glu Thr Ser Gln Lys Asn Thr Ser Arg Tyr Asp Asp Tyr
        355                 360                 365

Val Lys Asp Phe Phe Lys Lys Leu Glu Ala Asn Tyr Ser Ser Leu Glu
    370                 375                 380

Asn Tyr Ile Lys Gly Asp Pro Tyr Phe Ala Glu Tyr Ala Thr Lys Leu
385                 390                 395                 400

Ser Phe Ile Leu Asn Ser Ser Asp Ala Asn Asn Pro Ser Glu Lys Ile
                405                 410                 415

Gln Lys Asn Asn Asp Glu Val Cys Asn Cys Asn Glu Ser Gly Ile Ala
        420                 425                 430

Ser Val Glu Gln Glu Gln Ile Ser Asp Pro Ser Ser Asn Lys Thr Cys
        435                 440                 445

Ile Thr His Ser Ser Ile Lys Ala Asn Lys Lys Val Cys Lys His
    450                 455                 460

Val Lys Leu Gly Val Arg Glu Asn Asp Lys Asp Leu Arg Val Cys Val
465                 470                 475                 480

Ile Glu His Thr Ser Leu Ser Gly Val Glu Asn Cys Cys Cys Gln Asp
                485                 490                 495

Phe Leu Arg Ile Leu Gln Glu Asn Cys Ser Asp Asn Lys Ser Gly Ser
        500                 505                 510

Ser Ser Asn Gly Ser Cys Asn Asn Lys Asn Gln Glu Ala Cys Glu Lys

-continued

```
            515                 520                 525

Asn Leu Glu Lys Val Leu Ala Ser Leu Thr Asn Cys Tyr Lys Cys Asp
            530                 535                 540

Lys Cys Lys Ser Glu Gln Ser Lys Lys Asn Asn Lys Asn Trp Ile Trp
545                 550                 555                 560

Lys Lys Ser Ser Gly Lys Glu Gly Gly Leu Gln Lys Glu Tyr Ala Asn
                565                 570                 575

Thr Ile Gly Leu Pro Pro Arg Thr Gln Ser Leu Cys Leu Val Val Cys
            580                 585                 590

Leu Asp Glu Lys Gly Lys Lys Thr Gln Glu Leu Lys Asn Ile Arg Thr
            595                 600                 605

Asn Ser Glu Leu Leu Lys Glu Trp Ile Ile Ala Ala Phe His Glu Gly
            610                 615                 620

Lys Asn Leu Lys Pro Ser His Glu Lys Lys Asn Asp Asp Asn Gly Lys
625                 630                 635                 640

Lys Leu Cys Lys Ala Leu Glu Tyr Ser Phe Ala Asp Tyr Gly Asp Leu
                645                 650                 655

Ile Lys Gly Thr Ser Ile Trp Asp Asn Glu Tyr Thr Lys Asp Leu Glu
            660                 665                 670

Leu Asn Leu Gln Lys Ile Phe Gly Lys Leu Phe Arg Lys Tyr Ile Lys
            675                 680                 685

Lys Asn Asn Thr Ala Glu Gln Asp Thr Ser Tyr Ser Ser Leu Asp Glu
            690                 695                 700

Leu Arg Glu Ser Trp Trp Asn Thr Asn Lys Lys Tyr Ile Trp Leu Ala
705                 710                 715                 720

Met Lys His Gly Ala Gly Met Asn Ser Thr Thr Cys Cys Gly Asp Gly
                725                 730                 735

Ser Val Thr Gly Ser Gly Ser Ser Cys Asp Asp Ile Pro Thr Ile Asp
            740                 745                 750

Leu Ile Pro Gln Tyr Leu Arg Phe Leu Gln Glu Trp Val Glu His Phe
            755                 760                 765

Cys Lys Gln Arg Gln Glu Lys Val Lys Pro Val Ile Glu Asn Cys Lys
            770                 775                 780

Ser Cys Lys Glu Ser Gly Gly Thr Cys Asn Gly Glu Cys Lys Thr Glu
785                 790                 795                 800

Cys Lys Asn Lys Cys Glu Val Tyr Lys Lys Phe Ile Glu Asp Cys Lys
                805                 810                 815

Gly Gly Asp Gly Thr Ala Gly Ser Ser Trp Val Lys Arg Trp Asp Gln
            820                 825                 830

Ile Tyr Lys Arg Tyr Ser Lys Tyr Ile Glu Asp Ala Lys Arg Asn Arg
            835                 840                 845

Lys Ala Gly Thr Lys Asn Cys Gly Pro Ser Ser Thr Thr Asn Ala Ala
            850                 855                 860

Glu Asn Lys Cys Val Gln Ser Asp Ile Asp Ser Phe Phe Lys His Leu
865                 870                 875                 880

Ile Asp Ile Gly Leu Thr Thr Pro Ser Ser Tyr Leu Ser Ile Val Leu
                885                 890                 895

Asp Asp Asn Ile Cys Gly Ala Asp Lys Ala Pro Trp Thr Thr Tyr Thr
            900                 905                 910

Thr Tyr Thr Thr Thr Glu Lys Cys Asn Lys Glu Thr Asp Lys Ser Lys
            915                 920                 925

Leu Gln Gln Cys Asn Thr Ala Val Val Val Asn Val Pro Ser Pro Leu
            930                 935                 940
```

```
Gly Asn Thr Pro His Gly Tyr Lys Tyr Ala Cys Gln Cys Lys Ile Pro
945                 950                 955                 960

Thr Asn Glu Glu Thr Cys Asp Asp Arg Lys Glu Tyr Met Asn Gln Trp
                965                 970                 975

Ser Cys Gly Ser Ala Arg Thr Met Lys Arg Gly Tyr Lys Asn Asp Asn
            980                 985                 990

Tyr Glu Leu Cys Lys Tyr Asn Gly Val Asp Val Lys Pro Thr Thr Val
        995                 1000                1005

Arg Ser Asn Ser Ser Lys Leu Asp Asp Lys Asp Val Thr Phe Phe
    1010                1015                1020

Asn Leu Phe Glu Gln Trp Asn Lys Glu Ile Gln Tyr Gln Ile Glu
    1025                1030                1035

Gln Tyr Met Thr Asn Thr Lys Ile Ser Cys Asn Asn Glu Lys Asn
    1040                1045                1050

Val Leu Ser Arg Val Ser Asp Glu Ala Ala Gln Pro Lys Phe Ser
    1055                1060                1065

Asp Asn Glu Arg Asp Arg Asn Ser Ile Thr His Glu Asp Lys Asn
    1070                1075                1080

Cys Lys Glu Lys Cys Lys Cys Tyr Ser Leu Trp Ile Glu Lys Ile
    1085                1090                1095

Asn Asp Gln Trp Asp Lys Gln Lys Asp Asn Tyr Asn Lys Phe Gln
    1100                1105                1110

Arg Lys Gln Ile Tyr Asp Ala Asn Lys Gly Ser Gln Asn Lys Lys
    1115                1120                1125

Val Val Ser Leu Ser Asn Phe Leu Phe Phe Ser Cys Trp Glu Glu
    1130                1135                1140

Tyr Ile Gln Lys Tyr Phe Asn Gly Asp Trp Ser Lys Ile Lys Asn
    1145                1150                1155

Ile Gly Ser Asp Thr Phe Glu Phe Leu Ile Lys Lys Cys Gly Asn
    1160                1165                1170

Asp Ser Gly Asp Gly Glu Thr Ile Phe Ser Glu Lys Leu Asn Asn
    1175                1180                1185

Ala Glu Lys Lys Cys Lys Glu Asn Glu Ser Thr Asn Asn Lys Met
    1190                1195                1200

Lys Ser Ser Glu Thr Ser Cys Asp Cys Ser Glu Pro Ile Tyr Ile
    1205                1210                1215

Arg Gly Cys Gln Pro Lys Ile Tyr Asp Gly Lys Ile Phe Pro Gly
    1220                1225                1230

Lys Gly Gly Glu Lys Gln Trp Ile Cys Lys Asp Thr Ile Ile His
    1235                1240                1245

Gly Asp Thr Asn Gly Ala Cys Ile Pro Pro Arg Thr Gln Asn Leu
    1250                1255                1260

Cys Val Gly Glu Leu Trp Asp Lys Arg Tyr Gly Gly Arg Ser Asn
    1265                1270                1275

Ile Lys Asn Asp Thr Lys Glu Ser Leu Lys Gln Lys Ile Lys Asn
    1280                1285                1290

Ala Ile Gln Lys Glu Thr Glu Leu Leu Tyr Glu Tyr His Asp Lys
    1295                1300                1305

Gly Thr Ala Ile Ile Ser Arg Asn Pro Met Lys Gly Gln Lys Glu
    1310                1315                1320

Lys Glu Glu Lys Asn Asn Asp Ser Asn Gly Leu Pro Lys Gly Phe
    1325                1330                1335
```

```
Cys His Ala Val Gln Arg Ser Phe Ile Asp Tyr Lys Asn Met Ile
1340                1345                1350

Leu Gly Thr Ser Val Asn Ile Tyr Glu Tyr Ile Gly Lys Leu Gln
    1355                1360                1365

Glu Asp Ile Lys Lys Ile Ile Glu Lys Gly Thr Thr Lys Gln Asn
        1370                1375                1380

Gly Lys Thr Val Gly Ser Gly Ala Glu Asn Val Asn Ala Trp Trp
            1385                1390                1395

Lys Gly Ile Glu Gly Glu Met Trp Asp Ala Val Arg Cys Ala Ile
    1400                1405                1410

Thr Lys Ile Asn Lys Lys Gln Lys Lys Asn Gly Thr Phe Ser Ile
    1415                1420                1425

Asp Glu Cys Gly Ile Phe Pro Pro Thr Gly Asn Asp Glu Asp Gln
    1430                1435                1440

Ser Val Ser Trp Phe Lys Glu Trp Ser Glu Gln Phe Cys Ile Glu
    1445                1450                1455

Arg Leu Gln Tyr Glu Lys Asn Ile Arg Asp Ala Cys Thr Asn Asn
    1460                1465                1470

Gly Gln Gly Asp Lys Ile Gln Gly Asp Cys Lys Arg Lys Cys Glu
    1475                1480                1485

Glu Tyr Lys Lys Tyr Ile Ser Glu Lys Lys Gln Glu Trp Asp Lys
    1490                1495                1500

Gln Lys Thr Lys Tyr Glu Asn Lys Tyr Val Gly Lys Ser Ala Ser
    1505                1510                1515

Asp Leu Leu Lys Glu Asn Tyr Pro Glu Cys Ile Ser Ala Asn Phe
    1520                1525                1530

Asp Phe Ile Phe Asn Asp Asn Ile Glu Tyr Lys Thr Tyr Tyr Pro
    1535                1540                1545

Tyr Gly Asp Tyr Ser Ser Ile Cys Ser Cys Glu Gln Val Lys Tyr
    1550                1555                1560

Tyr Glu Tyr Asn Asn Ala Glu Lys Lys Asn Asn Lys Ser Leu Cys
    1565                1570                1575

His Glu Lys Gly Asn Asp Arg Thr Trp Ser Lys Lys Tyr Ile Lys
    1580                1585                1590

Lys Leu Glu Asn Gly Arg Thr Leu Glu Gly Val Tyr Val Pro Pro
    1595                1600                1605

Arg Arg Gln Gln Leu Cys Leu Tyr Glu Leu Phe Pro Ile Ile Ile
    1610                1615                1620

Lys Asn Lys Asn Asp Ile Thr Asn Ala Lys Lys Glu Leu Leu Glu
    1625                1630                1635

Thr Leu Gln Ile Val Ala Glu Arg Glu Ala Tyr Tyr Leu Trp Lys
    1640                1645                1650

Gln Tyr His Ala His Asn Asp Thr Thr Tyr Leu Ala His Lys Lys
    1655                1660                1665

Ala Cys Cys Ala Ile Arg Gly Ser Phe Tyr Asp Leu Glu Asp Ile
    1670                1675                1680

Ile Lys Gly Asn Asp Leu Val His Asp Glu Tyr Thr Lys Tyr Ile
    1685                1690                1695

Asp Ser Lys Leu Asn Glu Ile Phe Asp Ser Ser Asn Lys Asn Asp
    1700                1705                1710

Ile Glu Thr Lys Arg Ala Arg Thr Asp Trp Trp Glu Asn Glu Ala
    1715                1720                1725

Ile Ala Val Pro Asn Ile Thr Gly Ala Asn Lys Ser Asp Pro Lys
```

1730                1735                1740

Thr Ile Arg Gln Leu Val Trp Asp Ala Met Gln Ser Gly Val Arg
    1745                1750                1755

Lys Ala Ile Asp Glu Glu Lys Glu Lys Lys Pro Asn Glu Asn
    1760                1765                1770

Phe Pro Pro Cys Met Gly Val Gln His Ile Gly Ile Ala Lys Pro
    1775                1780                1785

Gln Phe Ile Arg Trp Leu Glu Glu Trp Thr Asn Glu Phe Cys Glu
    1790                1795                1800

Lys Tyr Thr Lys Tyr Phe Glu Asp Met Lys Ser Asn Cys Asn Leu
    1805                1810                1815

Arg Lys Gly Ala Asp Asp Cys Asp Asp Asn Ser Asn Ile Glu Cys
    1820                1825                1830

Lys Lys Ala Cys Ala Asn Tyr Thr Asn Trp Leu Asn Pro Lys Arg
    1835                1840                1845

Ile Glu Trp Asn Gly Met Ser Asn Tyr Tyr Asn Lys Ile Tyr Arg
    1850                1855                1860

Lys Ser Asn Lys Glu Ser Glu Asp Gly Lys Asp Tyr Ser Met Ile
    1865                1870                1875

Met Glu Pro Thr Val Ile Asp Tyr Leu Asn Lys Arg Cys Asn Gly
    1880                1885                1890

Glu Ile Asn Gly Asn Tyr Ile Cys Cys Ser Cys Lys Asn Ile Gly
    1895                1900                1905

Glu Asn Ser Thr Ser Gly Thr Val Asn Lys Lys Leu Gln Lys Lys
    1910                1915                1920

Glu Thr Gln Cys Glu Asp Asn Lys Gly Pro Leu Asp Leu Met Asn
    1925                1930                1935

Lys Val Leu Asn Lys Met Asp Pro Lys Tyr Ser Glu His Lys Met
    1940                1945                1950

Lys Cys Thr Glu Val Tyr Leu Glu His Val Glu Gln Leu Lys
    1955                1960                1965

Glu Ile Asp Asn Ala Ile Lys Asp Tyr Lys Leu Tyr Pro Leu Asp
    1970                1975                1980

Arg Cys Phe Asp Asp Lys Ser Lys Met Lys Val Cys Asp Leu Ile
    1985                1990                1995

Gly Asp Ala Ile Gly Cys Lys His Lys Thr Lys Leu Asp Glu Leu
    2000                2005                2010

Asp Glu Trp Asn Asp Val Asp Met Arg Asp Pro Tyr Asn Lys Tyr
    2015                2020                2025

Lys Gly Val Leu Ile Pro Pro Arg Arg Arg Gln Leu Cys Phe Ser
    2030                2035                2040

Arg Ile Val Arg Gly Pro Ala Asn Leu Arg Asn Leu Lys Glu Phe
    2045                2050                2055

Lys Glu Glu Ile Leu Lys Gly Ala Gln Ser Glu Gly Lys Phe Leu
    2060                2065                2070

Gly Asn Tyr Tyr Asn Glu Asp Lys Asp Lys Glu Lys Ala Leu Glu
    2075                2080                2085

Ala Met Lys Asn Ser Phe Tyr Asp Tyr Glu Tyr Ile Ile Lys Gly
    2090                2095                2100

Ser Asp Met Leu Thr Asn Ile Gln Phe Lys Asp Ile Lys Arg Lys
    2105                2110                2115

Leu Asp Arg Leu Leu Glu Lys Glu Thr Asn Asn Thr Glu Lys Val
    2120                2125                2130

Asp Asp Trp Trp Glu Thr Asn Lys Lys Ser Ile Trp Asn Ala Met
2135                2140                2145

Leu Cys Gly Tyr Lys Lys Ser Gly Asn Lys Ile Ile Asp Pro Ser
2150                2155                2160

Trp Cys Thr Ile Pro Thr Thr Glu Thr Pro Pro Gln Phe Leu Arg
2165                2170                2175

Trp Ile Lys Glu Trp Gly Thr Asn Val Cys Ile Gln Lys Glu Glu
2180                2185                2190

His Lys Glu Tyr Val Lys Ser Lys Cys Ser Asn Val Thr Asn Leu
2195                2200                2205

Gly Ala Gln Glu Ser Glu Ser Lys Asn Cys Thr Ser Glu Ile Lys
2210                2215                2220

Lys Tyr Gln Glu Trp Ser Arg Lys Arg Ser Ile Gln Trp Glu Ala
2225                2230                2235

Ile Ser Glu Gly Tyr Lys Lys Tyr Lys Gly Met Asp Glu Phe Lys
2240                2245                2250

Asn Thr Phe Lys Asn Ile Lys Glu Pro Asp Ala Asn Glu Pro Asn
2255                2260                2265

Ala Asn Glu Tyr Leu Lys Lys His Cys Ser Lys Cys Pro Cys Gly
2270                2275                2280

Phe Asn Asp Met Gln Glu Ile Thr Lys Tyr Thr Asn Ile Gly Asn
2285                2290                2295

Glu Ala Phe Lys Gln Ile Lys Glu Gln Val Asp Ile Pro Ala Glu
2300                2305                2310

Leu Glu Asp Val Ile Tyr Arg Leu Lys His His Glu Tyr Asp Lys
2315                2320                2325

Gly Asn Asp Tyr Ile Cys Asn Lys Tyr Lys Asn Ile Asn Val Asn
2330                2335                2340

Met Lys Lys Asn Asn Asp Asp Thr Trp Thr Asp Leu Val Lys Asn
2345                2350                2355

Ser Ser Asp Ile Asn Lys Gly Val Leu Leu Pro Pro Arg Arg Lys
2360                2365                2370

Asn Leu Phe Leu Lys Ile Asp Glu Ser Asp Ile Cys Lys Tyr Lys
2375                2380                2385

Arg Asp Pro Lys Leu Phe Lys Asp Phe Ile Tyr Ser Ser Ala Ile
2390                2395                2400

Ser Glu Val Glu Arg Leu Lys Lys Val Tyr Gly Glu Ala Lys Thr
2405                2410                2415

Lys Val Val His Ala Met Lys Tyr Ser Phe Ala Asp Ile Gly Ser
2420                2425                2430

Ile Ile Lys Gly Asp Asp Met Met Glu Asn Asn Ser Ser Asp Lys
2435                2440                2445

Ile Gly Lys Ile Leu Gly Asp Gly Val Gly Gln Asn Glu Lys Arg
2450                2455                2460

Lys Lys Trp Trp Asp Met Asn Lys Tyr His Ile Trp Glu Ser Met
2465                2470                2475

Leu Cys Gly Tyr Lys His Ala Tyr Gly Asn Ile Ser Glu Asn Asp
2480                2485                2490

Arg Lys Met Leu Asp Ile Pro Asn Asn Asp Asp Glu His Gln Phe
2495                2500                2505

Leu Arg Trp Phe Gln Glu Trp Thr Glu Asn Phe Cys Thr Lys Arg
2510                2515                2520

```
Asn Glu Leu Tyr Glu Asn Met Val Thr Ala Cys Asn Ser Ala Lys
    2525                2530                2535

Cys Asn Thr Ser Asn Gly Ser Val Asp Lys Lys Glu Cys Thr Glu
    2540                2545                2550

Ala Cys Lys Asn Tyr Ser Asn Phe Ile Leu Ile Lys Lys Lys Glu
    2555                2560                2565

Tyr Gln Ser Leu Asn Ser Gln Tyr Asp Met Asn Tyr Lys Glu Thr
    2570                2575                2580

Lys Ala Glu Lys Lys Glu Ser Pro Glu Tyr Phe Lys Asp Lys Cys
    2585                2590                2595

Asn Gly Glu Cys Ser Cys Leu Ser Glu Tyr Phe Lys Asp Glu Thr
    2600                2605                2610

Arg Trp Lys Asn Pro Tyr Glu Thr Leu Asp Asp Thr Glu Val Lys
    2615                2620                2625

Asn Asn Cys Met Cys Lys Pro Pro Pro Ala Ser Asn Asn Thr
    2630                2635                2640

Ser Asp Ile Leu Gln Lys Thr Ile Pro Phe Gly Ile Ala Leu Ala
    2645                2650                2655

Leu Gly Ser Ile Ala Phe Leu Phe Met Lys Lys Lys Pro Lys Thr
    2660                2665                2670

Pro Val Asp Leu Leu Arg Val Leu Asp Ile Pro Lys Gly Asp Tyr
    2675                2680                2685

Gly Ile Pro Thr Pro Lys Ser Ser Asn Arg Tyr Ile Pro Tyr Ala
    2690                2695                2700

Ser Asp Arg Tyr Lys Gly Lys Thr Tyr Ile Tyr Met Glu Gly Asp
    2705                2710                2715

Thr Ser Gly Asp Asp Asp Lys Tyr Ile Trp Asp Leu
    2720                2725                2730

<210> SEQ ID NO 56
<211> LENGTH: 2734
<212> TYPE: PRT
<213> ORGANISM: Artificial
<220> FEATURE:
<223> OTHER INFORMATION: Artificial construct

<400> SEQUENCE: 56

Met Asp Ser Thr Ser Thr Ile Ala Asn Lys Ile Glu Glu Tyr Leu Gly
1               5                   10                  15

Ala Lys Ser Asp Asp Ser Lys Ile Asp Glu Leu Leu Lys Ala Asp Pro
                20                  25                  30

Ser Glu Val Glu Tyr Tyr Arg Ser Gly Asp Gly Asp Tyr Leu Lys
            35                  40                  45

Asn Asn Ile Cys Lys Ile Thr Val Asn His Ser Asp Ser Gly Lys Tyr
50                  55                  60

Asp Pro Cys Glu Lys Lys Leu Pro Pro Tyr Asp Asn Asp Gln Trp
65                  70                  75                  80

Lys Cys Gln Gln Asn Ser Ser Asp Gly Ser Gly Lys Pro Glu Asn Ile
                85                  90                  95

Cys Val Pro Pro Arg Arg Glu Arg Leu Cys Thr Tyr Asn Leu Glu Asn
                100                 105                 110

Leu Lys Phe Asp Lys Ile Arg Asp Asn Asn Ala Phe Leu Ala Asp Val
            115                 120                 125

Leu Leu Thr Ala Arg Asn Glu Gly Glu Lys Ile Val Gln Asn His Pro
        130                 135                 140
```

-continued

```
Asp Thr Asn Ser Ser Asn Val Cys Asn Ala Leu Glu Arg Ser Phe Ala
145                 150                 155                 160

Asp Leu Ala Asp Ile Ile Arg Gly Thr Asp Gln Trp Lys Gly Thr Asn
            165                 170                 175

Ser Asn Leu Glu Lys Asn Leu Lys Gln Met Phe Ala Lys Ile Arg Glu
        180                 185                 190

Asn Asp Lys Val Leu Gln Asp Lys Tyr Pro Lys Asp Gln Lys Tyr Thr
    195                 200                 205

Lys Leu Arg Glu Ala Trp Trp Asn Ala Asn Arg Gln Lys Val Trp Glu
    210                 215                 220

Val Ile Thr Cys Gly Ala Arg Ser Asn Asp Leu Leu Ile Lys Arg Gly
225                 230                 235                 240

Trp Arg Thr Ser Gly Lys Ser Asp Arg Lys Lys Asn Phe Glu Leu Cys
            245                 250                 255

Arg Lys Cys Gly His Tyr Glu Lys Glu Val Pro Thr Lys Leu Asp Tyr
        260                 265                 270

Val Pro Gln Phe Leu Arg Trp Leu Thr Glu Trp Ile Glu Asp Phe Tyr
    275                 280                 285

Arg Glu Lys Gln Asn Leu Ile Asp Asp Met Glu Arg His Arg Glu Glu
    290                 295                 300

Cys Thr Arg Glu Asp His Lys Ser Lys Glu Gly Thr Ser Tyr Cys Ser
305                 310                 315                 320

Thr Cys Lys Asp Lys Cys Lys Lys Tyr Cys Glu Cys Val Lys Lys Trp
            325                 330                 335

Lys Thr Glu Trp Glu Asn Gln Glu Asn Lys Tyr Lys Asp Leu Tyr Glu
        340                 345                 350

Gln Asn Lys Asn Lys Thr Ser Gln Lys Asn Thr Ser Arg Tyr Asp Asp
    355                 360                 365

Tyr Val Lys Asp Phe Phe Glu Lys Leu Glu Ala Asn Tyr Ser Ser Leu
    370                 375                 380

Glu Asn Tyr Ile Lys Gly Asp Pro Tyr Phe Ala Glu Tyr Ala Thr Lys
385                 390                 395                 400

Leu Ser Phe Ile Leu Asn Pro Ser Asp Ala Asn Asn Pro Ser Gly Glu
            405                 410                 415

Thr Ala Asn His Asn Asp Glu Ala Cys Asn Cys Asn Glu Ser Gly Ile
        420                 425                 430

Ser Ser Val Gly Gln Ala Gln Thr Ser Gly Pro Ser Ser Asn Lys Thr
    435                 440                 445

Cys Ile Thr His Ser Ser Ile Lys Thr Asn Lys Lys Glu Cys Lys
    450                 455                 460

Asp Val Lys Leu Gly Val Arg Glu Asn Asp Lys Asp Leu Lys Ile Cys
465                 470                 475                 480

Val Ile Glu Asp Thr Ser Leu Ser Gly Val Asp Asn Cys Cys Cys Gln
            485                 490                 495

Asp Leu Leu Gly Ile Leu Gln Glu Asn Cys Ser Asp Asn Lys Arg Gly
        500                 505                 510

Ser Ser Ser Asn Asp Ser Cys Asp Asn Lys Asn Gln Asp Glu Cys Gln
    515                 520                 525

Lys Lys Leu Glu Lys Val Phe Ala Ser Leu Thr Gly Tyr Lys Cys
    530                 535                 540

Asp Lys Cys Lys Ser Gly Thr Ser Arg Ser Lys Lys Lys Trp Ile Trp
545                 550                 555                 560

Lys Lys Ser Ser Gly Asn Glu Glu Gly Leu Gln Glu Glu Tyr Ala Asn
```

```
                565                 570                 575
Thr Ile Gly Leu Pro Arg Thr Gln Ser Leu Tyr Leu Gly Asn Leu
            580                 585                 590

Pro Lys Leu Glu Asn Val Cys Glu Asp Val Lys Asp Ile Asn Phe Asp
            595                 600                 605

Thr Lys Glu Lys Phe Leu Ala Gly Cys Leu Ile Val Ser Phe His Glu
            610                 615                 620

Gly Lys Asn Leu Lys Lys Arg Tyr Pro Gln Asn Lys Asn Ser Gly Asn
625                 630                 635                 640

Lys Glu Asn Leu Cys Lys Ala Leu Glu Tyr Ser Phe Ala Asp Tyr Gly
                645                 650                 655

Asp Leu Ile Lys Gly Thr Ser Ile Trp Asp Asn Glu Tyr Thr Lys Asp
            660                 665                 670

Leu Glu Leu Asn Leu Gln Asn Asn Phe Gly Lys Leu Phe Gly Lys Tyr
            675                 680                 685

Ile Lys Lys Asn Asn Thr Ala Glu Gln Asp Thr Ser Tyr Ser Ser Leu
            690                 695                 700

Asp Glu Leu Arg Glu Ser Trp Trp Asn Thr Asn Lys Lys Tyr Ile Trp
705                 710                 715                 720

Thr Ala Met Lys His Gly Ala Glu Met Asn Ile Thr Thr Cys Asn Ala
                725                 730                 735

Asp Gly Ser Val Thr Gly Ser Gly Ser Ser Cys Asp Asp Ile Pro Thr
            740                 745                 750

Ile Asp Leu Ile Pro Gln Tyr Leu Arg Phe Leu Gln Glu Trp Val Glu
            755                 760                 765

Asn Phe Cys Glu Gln Arg Gln Ala Lys Val Lys Asp Val Ile Thr Asn
770                 775                 780

Cys Lys Ser Cys Lys Glu Ser Gly Asn Lys Cys Lys Thr Glu Cys Lys
785                 790                 795                 800

Thr Lys Cys Lys Asp Glu Cys Glu Lys Tyr Lys Lys Phe Ile Glu Ala
                805                 810                 815

Cys Gly Thr Ala Gly Gly Gly Ile Gly Thr Ala Gly Ser Pro Trp Ser
            820                 825                 830

Lys Arg Trp Asp Gln Ile Tyr Lys Arg Tyr Ser Lys His Ile Glu Asp
            835                 840                 845

Ala Lys Arg Asn Arg Lys Ala Gly Thr Lys Asn Cys Gly Thr Ser Ser
            850                 855                 860

Thr Thr Asn Ala Ala Ala Ser Thr Asp Glu Asn Lys Cys Val Gln Ser
865                 870                 875                 880

Asp Ile Asp Ser Phe Phe Lys His Leu Ile Asp Ile Gly Leu Thr Thr
                885                 890                 895

Pro Ser Ser Tyr Leu Ser Asn Val Leu Asp Asp Asn Ile Cys Gly Ala
            900                 905                 910

Asp Lys Ala Pro Trp Thr Thr Tyr Thr Thr Tyr Thr Thr Thr Glu Lys
            915                 920                 925

Cys Asn Lys Glu Arg Asp Lys Ser Lys Ser Gln Ser Ser Asp Thr Leu
930                 935                 940

Val Val Val Asn Val Pro Ser Pro Leu Gly Asn Thr Pro Tyr Arg Tyr
945                 950                 955                 960

Lys Tyr Ala Cys Gln Cys Lys Ile Pro Thr Asn Glu Glu Thr Cys Asp
                965                 970                 975

Asp Arg Lys Glu Tyr Met Asn Gln Trp Ser Cys Gly Ser Ala Arg Thr
            980                 985                 990
```

-continued

```
Met Lys Arg Gly Tyr Lys Asn Asp Asn Tyr Glu Leu Cys Lys Tyr Asn
        995                 1000                1005

Gly Val Asp Val Lys Pro Thr Thr Val Arg Ser Asn Ser Ser Lys
    1010                1015                1020

Leu Asp Gly Asn Asp Val Thr Phe Phe Asn Leu Phe Glu Gln Trp
    1025                1030                1035

Asn Lys Glu Ile Gln Tyr Gln Ile Glu Gln Tyr Met Thr Asn Ala
    1040                1045                1050

Asn Ile Ser Cys Ile Asp Glu Lys Glu Val Leu Asp Ser Val Ser
    1055                1060                1065

Asp Glu Gly Thr Pro Lys Val Arg Gly Tyr Glu Asp Gly Arg
    1070                1075                1080

Asn Asn Asn Thr Asp Gln Gly Thr Asn Cys Lys Glu Lys Cys Lys
    1085                1090                1095

Cys Tyr Lys Leu Trp Ile Glu Lys Ile Asn Asp Gln Trp Gly Lys
    1100                1105                1110

Gln Lys Asp Asn Tyr Asn Lys Phe Arg Ser Lys Gln Ile Tyr Asp
    1115                1120                1125

Ala Asn Lys Gly Ser Gln Asn Lys Lys Val Val Ser Leu Ser Asn
    1130                1135                1140

Phe Leu Phe Phe Ser Cys Trp Glu Glu Tyr Ile Gln Lys Tyr Phe
    1145                1150                1155

Asn Gly Asp Trp Ser Lys Ile Lys Asn Ile Gly Ser Asp Thr Phe
    1160                1165                1170

Glu Phe Leu Ile Lys Lys Cys Gly Asn Asn Ser Ala His Gly Glu
    1175                1180                1185

Glu Ile Phe Asn Glu Lys Leu Lys Asn Ala Glu Lys Lys Cys Lys
    1190                1195                1200

Glu Asn Glu Ser Thr Asp Thr Asn Ile Asn Lys Ser Glu Thr Ser
    1205                1210                1215

Cys Asp Leu Asn Ala Thr Asn Tyr Ile Arg Gly Cys Gln Ser Lys
    1220                1225                1230

Thr Tyr Asp Gly Lys Ile Phe Pro Gly Lys Gly Glu Lys Gln
    1235                1240                1245

Trp Ile Cys Lys Asp Thr Ile Ile His Gly Asp Thr Asn Gly Ala
    1250                1255                1260

Cys Ile Pro Pro Arg Thr Gln Asn Leu Cys Val Gly Glu Leu Trp
    1265                1270                1275

Asp Lys Ser Tyr Gly Gly Arg Ser Asn Ile Lys Asn Asp Thr Lys
    1280                1285                1290

Glu Leu Leu Lys Glu Lys Ile Lys Asn Ala Ile His Lys Glu Thr
    1295                1300                1305

Glu Leu Leu Tyr Glu Tyr His Asp Thr Gly Thr Ala Ile Ile Ser
    1310                1315                1320

Lys Asn Asp Lys Lys Gly Gln Lys Gly Lys Asn Asp Pro Asn Gly
    1325                1330                1335

Leu Pro Lys Gly Phe Cys His Ala Val Gln Arg Ser Phe Ile Asp
    1340                1345                1350

Tyr Lys Asn Met Ile Leu Gly Thr Ser Val Asn Ile Tyr Glu His
    1355                1360                1365

Ile Gly Lys Leu Gln Glu Asp Ile Lys Lys Ile Ile Glu Lys Gly
    1370                1375                1380
```

Thr Pro Gln Gln Lys Asp Lys Ile Gly Gly Val Gly Ser Ser Thr
1385             1390                 1395

Glu Asn Val Asn Ala Trp Trp Lys Gly Ile Glu Arg Glu Met Trp
1400             1405                 1410

Asp Ala Val Arg Cys Ala Ile Thr Lys Ile Asn Lys Lys Asn Asn
1415             1420                 1425

Asn Ser Ile Phe Asn Gly Asp Glu Cys Gly Val Ser Pro Pro Thr
1430             1435                 1440

Gly Asn Asp Glu Asp Gln Ser Val Ser Trp Phe Lys Glu Trp Gly
1445             1450                 1455

Glu Gln Phe Cys Ile Glu Arg Leu Arg Tyr Glu Gln Asn Ile Arg
1460             1465                 1470

Glu Ala Cys Thr Ile Asn Gly Lys Asn Glu Lys Lys Cys Ile Asn
1475             1480                 1485

Ser Lys Ser Gly Gln Gly Asp Lys Ile Gln Gly Ala Cys Lys Arg
1490             1495                 1500

Lys Cys Glu Lys Tyr Lys Lys Tyr Ile Ser Glu Lys Lys Gln Glu
1505             1510                 1515

Trp Asp Lys Gln Lys Thr Lys Tyr Glu Asn Lys Tyr Val Gly Lys
1520             1525                 1530

Ser Ala Ser Asp Leu Leu Lys Glu Asn Tyr Pro Glu Cys Ile Ser
1535             1540                 1545

Ala Asn Phe Asp Phe Ile Phe Asn Asp Asn Ile Glu Tyr Lys Thr
1550             1555                 1560

Tyr Tyr Pro Tyr Gly Asp Tyr Ser Ser Ile Cys Ser Cys Glu Gln
1565             1570                 1575

Val Lys Tyr Tyr Lys Tyr Asn Asn Ala Glu Lys Lys Asn Asn Lys
1580             1585                 1590

Ser Leu Cys Tyr Glu Lys Asp Asn Asp Met Thr Trp Ser Lys Lys
1595             1600                 1605

Tyr Ile Lys Lys Leu Glu Asn Gly Arg Ser Leu Glu Gly Val Tyr
1610             1615                 1620

Val Pro Pro Arg Arg Gln Gln Leu Cys Leu Tyr Glu Leu Phe Pro
1625             1630                 1635

Ile Ile Ile Lys Asn Glu Glu Gly Met Glu Lys Ala Lys Glu Glu
1640             1645                 1650

Leu Leu Glu Thr Leu Gln Ile Val Ala Glu Arg Glu Ala Tyr Tyr
1655             1660                 1665

Leu Trp Lys Gln Tyr Asn Pro Thr Gly Lys Gly Ile Asp Asp Ala
1670             1675                 1680

Asn Lys Lys Ala Cys Cys Ala Ile Arg Gly Ser Phe Tyr Asp Leu
1685             1690                 1695

Glu Asp Ile Ile Lys Gly Asn Asp Leu Val His Asp Glu Tyr Thr
1700             1705                 1710

Lys Tyr Ile Asp Ser Lys Leu Asn Glu Ile Phe Gly Ser Ser Asp
1715             1720                 1725

Thr Asn Asp Ile Asp Thr Lys Arg Ala Arg Thr Asp Trp Trp Glu
1730             1735                 1740

Asn Glu Thr Ile Thr Asn Gly Thr Asp Arg Lys Thr Ile Arg Gln
1745             1750                 1755

Leu Val Trp Asp Ala Met Gln Ser Gly Val Arg Tyr Ala Val Glu
1760             1765                 1770

Glu Lys Asn Glu Asn Phe Pro Leu Cys Met Gly Val Glu His Ile

```
            1775                1780                1785

Gly Ile Ala Lys Pro Gln Phe Ile Arg Trp Leu Glu Glu Trp Thr
            1790                1795                1800

Asn Glu Phe Cys Glu Lys Tyr Thr Lys Tyr Phe Glu Asp Met Lys
            1805                1810                1815

Ser Lys Cys Asp Pro Pro Lys Arg Ala Asp Thr Cys Gly Asp Asn
            1820                1825                1830

Ser Asn Ile Glu Cys Lys Lys Ala Cys Ala Asn Tyr Thr Asn Trp
            1835                1840                1845

Leu Asn Pro Lys Arg Ile Glu Trp Asn Gly Met Ser Asn Tyr Tyr
            1850                1855                1860

Asn Lys Ile Tyr Arg Lys Ser Asn Lys Glu Ser Glu Gly Gly Lys
            1865                1870                1875

Asp Tyr Ser Met Ile Met Ala Pro Thr Val Ile Asp Tyr Leu Asn
            1880                1885                1890

Lys Arg Cys His Gly Glu Ile Asn Gly Asn Tyr Ile Cys Cys Ser
            1895                1900                1905

Cys Lys Asn Ile Gly Ala Tyr Asn Thr Thr Ser Gly Thr Val Asn
            1910                1915                1920

Lys Lys Leu Gln Lys Lys Glu Thr Glu Cys Glu Glu Lys Gly
            1925                1930                1935

Pro Leu Asp Leu Met Asn Glu Val Leu Asn Lys Met Asp Lys Lys
            1940                1945                1950

Tyr Ser Ala His Lys Met Lys Cys Thr Glu Val Tyr Leu Glu His
            1955                1960                1965

Val Glu Glu Gln Leu Asn Glu Ile Asp Asn Ala Ile Lys Asp Tyr
            1970                1975                1980

Lys Leu Tyr Pro Leu Asp Arg Cys Phe Asp Gln Thr Lys Met
            1985                1990                1995

Lys Val Cys Asp Leu Ile Ala Asp Ala Ile Gly Cys Lys Asp Lys
            2000                2005                2010

Thr Lys Leu Asp Glu Leu Asp Glu Trp Asn Asp Met Asp Leu Arg
            2015                2020                2025

Gly Thr Tyr Asn Lys His Lys Gly Val Leu Ile Pro Pro Arg Arg
            2030                2035                2040

Arg Gln Leu Cys Phe Ser Arg Ile Val Arg Gly Pro Ala Asn Leu
            2045                2050                2055

Arg Ser Leu Asn Glu Phe Lys Glu Glu Ile Leu Lys Gly Ala Gln
            2060                2065                2070

Ser Glu Gly Lys Phe Leu Gly Asn Tyr Tyr Lys Glu His Lys Asp
            2075                2080                2085

Lys Glu Lys Ala Leu Glu Ala Met Lys Asn Ser Phe Tyr Asp Tyr
            2090                2095                2100

Glu Asp Ile Ile Lys Gly Thr Asp Met Leu Thr Asn Ile Glu Phe
            2105                2110                2115

Lys Asp Ile Lys Ile Lys Leu Asp Arg Leu Leu Glu Lys Glu Thr
            2120                2125                2130

Asn Asn Thr Lys Lys Ala Glu Asp Trp Trp Lys Thr Asn Lys Lys
            2135                2140                2145

Ser Ile Trp Asn Ala Met Leu Cys Gly Tyr Lys Lys Ser Gly Asn
            2150                2155                2160

Lys Ile Ile Asp Pro Ser Trp Cys Thr Ile Pro Thr Thr Glu Thr
            2165                2170                2175
```

```
Pro Pro Gln Phe Leu Arg Trp Ile Lys Glu Trp Gly Thr Asn Val
2180              2185                  2190

Cys Ile Gln Lys Gln Glu His Lys Glu Tyr Val Lys Ser Lys Cys
2195              2200                  2205

Ser Asn Val Thr Asn Leu Gly Ala Gln Ala Ser Glu Ser Asn Asn
2210              2215                  2220

Cys Thr Ser Glu Ile Lys Lys Tyr Gln Glu Trp Ser Arg Lys Arg
2225              2230                  2235

Ser Ile Arg Trp Glu Thr Ile Ser Lys Arg Tyr Lys Lys Tyr Lys
2240              2245                  2250

Arg Met Asp Ile Leu Lys Asp Val Lys Glu Pro Asp Ala Asn Thr
2255              2260                  2265

Tyr Leu Arg Glu His Cys Ser Lys Cys Pro Cys Gly Phe Asn Asp
2270              2275                  2280

Met Glu Glu Met Asn Asn Asn Glu Asp Asn Lys Glu Ala Phe
2285              2290                  2295

Lys Gln Ile Lys Glu Gln Val Lys Ile Pro Ala Glu Leu Glu Asp
2300              2305                  2310

Val Ile Tyr Arg Ile Lys His His Glu Tyr Asp Lys Gly Asn Asp
2315              2320                  2325

Tyr Ile Cys Asn Lys Tyr Lys Asn Ile His Asp Arg Met Lys Lys
2330              2335                  2340

Asn Asn Gly Asn Phe Val Thr Asp Asn Phe Val Lys Lys Ser Trp
2345              2350                  2355

Glu Ile Ser Asn Gly Val Leu Ile Pro Pro Arg Arg Lys Asn Leu
2360              2365                  2370

Phe Leu Tyr Ile Asp Pro Ser Lys Ile Cys Glu Tyr Lys Lys Asp
2375              2380                  2385

Pro Lys Leu Phe Lys Asp Phe Ile Tyr Trp Ser Ala Phe Thr Glu
2390              2395                  2400

Val Glu Arg Leu Lys Lys Ala Tyr Gly Gly Ala Arg Ala Lys Val
2405              2410                  2415

Val His Ala Met Lys Tyr Ser Phe Thr Asp Ile Gly Ser Ile Ile
2420              2425                  2430

Lys Gly Asp Asp Met Met Glu Lys Asn Ser Ser Asp Lys Ile Gly
2435              2440                  2445

Lys Ile Leu Gly Asp Thr Asp Gly Gln Asn Glu Lys Arg Lys Lys
2450              2455                  2460

Trp Trp Asp Met Asn Lys Tyr His Ile Trp Glu Ser Met Leu Cys
2465              2470                  2475

Gly Tyr Arg Glu Ala Glu Gly Asp Thr Glu Thr Asn Glu Asn Cys
2480              2485                  2490

Arg Phe Pro Asp Ile Glu Ser Val Pro Gln Phe Leu Arg Trp Phe
2495              2500                  2505

Gln Glu Trp Ser Glu Asn Phe Cys Asp Arg Arg Gln Lys Leu Tyr
2510              2515                  2520

Asp Lys Leu Asn Ser Glu Cys Ile Ser Ala Glu Cys Thr Asn Gly
2525              2530                  2535

Ser Val Asp Asn Ser Lys Cys Thr His Ala Cys Val Asn Tyr Lys
2540              2545                  2550

Asn Tyr Ile Leu Thr Lys Lys Thr Glu Tyr Glu Ile Gln Thr Asn
2555              2560                  2565
```

```
Lys Tyr Asp Asn Glu Phe Lys Asn Lys Asn Ser Asn Asp Lys Asp
    2570                2575                2580

Ala Pro Asp Tyr Leu Lys Glu Lys Cys Asn Asp Asn Lys Cys Glu
2585                2590                2595

Cys Leu Asn Lys His Ile Asp Asp Lys Asn Lys Thr Trp Lys Asn
    2600                2605                2610

Pro Tyr Glu Thr Leu Glu Asp Thr Phe Lys Ser Lys Cys Asp Cys
    2615                2620                2625

Pro Lys Pro Leu Pro Ser Pro Ile Lys Pro Asp Asp Leu Pro Pro
    2630                2635                2640

Gln Ala Asp Glu Pro Phe Asp Pro Thr Ile Leu Gln Thr Thr Ile
    2645                2650                2655

Pro Phe Gly Ile Ala Leu Ala Leu Gly Ser Ile Ala Phe Leu Phe
    2660                2665                2670

Met Lys Val Ile Tyr Ile Tyr Ile Tyr Val Cys Cys Ile Cys Met
    2675                2680                2685

Tyr Val Cys Met Tyr Val Cys Met Tyr Val Cys Met Tyr Val Cys
    2690                2695                2700

Met Tyr Val Cys Met His Val Cys Met Leu Cys Val Tyr Val Ile
    2705                2710                2715

Tyr Val Phe Lys Ile Cys Ile Tyr Ile Glu Lys Glu Lys Arg Lys
    2720                2725                2730

Lys

<210> SEQ ID NO 57
<211> LENGTH: 58
<212> TYPE: PRT
<213> ORGANISM: Artificial
<220> FEATURE:
<223> OTHER INFORMATION: Artificial construct

<400> SEQUENCE: 57

Arg Pro Asp Phe Cys Leu Glu Pro Pro Tyr Thr Gly Pro Cys Lys Ala
1               5                   10                  15

Arg Ile Ile Arg Tyr Phe Tyr Asn Ala Lys Ala Gly Leu Cys Gln Thr
            20                  25                  30

Phe Val Tyr Gly Gly Cys Arg Ala Lys Arg Asn Asn Phe Lys Ser Ala
        35                  40                  45

Glu Asp Cys Met Arg Thr Cys Gly Gly Ala
        50                  55

<210> SEQ ID NO 58
<211> LENGTH: 324
<212> TYPE: PRT
<213> ORGANISM: Artificial
<220> FEATURE:
<223> OTHER INFORMATION: Artificial construct

<400> SEQUENCE: 58

Arg His Arg Gln Pro Arg Gly Trp Glu Gln Leu Glu Gln Cys Gly Tyr
1               5                   10                  15

Pro Val Gln Arg Leu Val Ala Leu Tyr Leu Ala Ala Arg Leu Ser Trp
            20                  25                  30

Asn Gln Val Asp Gln Val Ile Arg Asn Ala Leu Ala Ser Pro Gly Ser
        35                  40                  45

Gly Gly Asp Leu Gly Glu Ala Ile Arg Glu Gln Pro Glu Gln Ala Arg
    50                  55                  60
```

Leu Ala Leu Thr Leu Ala Ala Glu Ser Glu Arg Phe Val Arg Gln
65                  70                  75                  80

Gly Thr Gly Asn Asp Glu Ala Gly Ala Asn Gly Pro Ala Asp Ser
            85                  90                  95

Gly Asp Ala Leu Leu Glu Arg Asn Tyr Pro Thr Gly Ala Glu Phe Leu
        100                 105                 110

Gly Asp Gly Gly Asp Ile Ser Phe Ser Thr Arg Gly Thr Gln Asn Trp
        115                 120                 125

Thr Val Glu Arg Leu Leu Gln Ala His Arg Gln Leu Glu Glu Arg Gly
    130                 135                 140

Tyr Val Phe Val Gly Tyr His Gly Thr Phe Leu Glu Ala Ala Gln Ser
145                 150                 155                 160

Ile Val Phe Gly Gly Val Arg Ala Arg Ser Gln Asp Leu Asp Ala Ile
                165                 170                 175

Trp Arg Gly Phe Tyr Ile Ala Gly Asp Pro Ala Leu Ala Tyr Gly Tyr
            180                 185                 190

Ala Gln Asp Gln Glu Pro Asp Ala Arg Gly Arg Ile Arg Asn Gly Ala
        195                 200                 205

Leu Leu Arg Val Tyr Val Pro Arg Ser Ser Leu Pro Gly Phe Tyr Arg
    210                 215                 220

Thr Ser Leu Thr Leu Ala Ala Pro Glu Ala Ala Gly Glu Val Glu Arg
225                 230                 235                 240

Leu Ile Gly His Pro Leu Pro Leu Arg Leu Asp Ala Ile Thr Gly Pro
                245                 250                 255

Glu Glu Glu Gly Gly Arg Leu Glu Thr Ile Leu Gly Trp Pro Leu Ala
            260                 265                 270

Glu Arg Thr Val Val Ile Pro Ser Ala Ile Pro Thr Asp Pro Arg Asn
        275                 280                 285

Val Gly Gly Asp Leu Asp Pro Ser Ser Ile Pro Asp Lys Glu Gln Ala
    290                 295                 300

Ile Ser Ala Leu Pro Asp Tyr Ala Ser Gln Pro Gly Lys Pro Pro Arg
305                 310                 315                 320

Lys Asp Glu Leu

<210> SEQ ID NO 59
<211> LENGTH: 231
<212> TYPE: PRT
<213> ORGANISM: Artificial
<220> FEATURE:
<223> OTHER INFORMATION: Artificial construct

<400> SEQUENCE: 59

Arg His Arg Gln Pro Arg Gly Trp Glu Gln Leu Tyr Pro Thr Gly Ala
1               5                   10                  15

Glu Phe Leu Gly Asp Gly Gly Asp Ile Ser Phe Ser Thr Arg Gly Thr
            20                  25                  30

Gln Asn Trp Thr Val Glu Arg Leu Leu Gln Ala His Arg Gln Leu Glu
        35                  40                  45

Glu Arg Gly Tyr Val Phe Val Gly Tyr His Gly Thr Phe Leu Glu Ala
    50                  55                  60

Ala Gln Ser Ile Val Phe Gly Gly Val Arg Ala Arg Ser Gln Asp Leu
65                  70                  75                  80

Asp Ala Ile Trp Arg Gly Phe Tyr Ile Ala Gly Asp Pro Ala Leu Ala
                85                  90                  95

Tyr Gly Tyr Ala Gln Asp Gln Glu Pro Asp Ala Arg Gly Arg Ile Arg

```
            100                 105                 110
Asn Gly Ala Leu Leu Arg Val Tyr Val Pro Arg Ser Ser Leu Pro Gly
            115                 120                 125

Phe Tyr Arg Thr Ser Leu Thr Leu Ala Ala Pro Glu Ala Ala Gly Glu
            130                 135                 140

Val Glu Arg Leu Ile Gly His Pro Leu Pro Leu Arg Leu Asp Ala Ile
145                 150                 155                 160

Thr Gly Pro Glu Glu Gly Gly Arg Leu Glu Thr Ile Leu Gly Trp
                165                 170                 175

Pro Leu Ala Glu Arg Thr Val Val Ile Pro Ser Ala Ile Pro Thr Asp
            180                 185                 190

Pro Arg Asn Val Gly Gly Asp Leu Asp Pro Ser Ser Ile Pro Asp Lys
            195                 200                 205

Glu Gln Ala Ile Ser Ala Leu Pro Asp Tyr Ala Ser Gln Pro Gly Lys
            210                 215                 220

Pro Pro Arg Lys Asp Glu Leu
225                 230
```

<210> SEQ ID NO 60
<211> LENGTH: 929
<212> TYPE: PRT
<213> ORGANISM: Artificial
<220> FEATURE:
<223> OTHER INFORMATION: Artificial construct

<400> SEQUENCE: 60

```
Arg Pro Asp Phe Cys Leu Glu Pro Pro Tyr Thr Gly Pro Cys Lys Ala
1               5                   10                  15

Arg Ile Ile Arg Tyr Phe Tyr Asn Ala Lys Ala Gly Leu Cys Gln Thr
            20                  25                  30

Phe Val Tyr Gly Gly Cys Arg Ala Lys Arg Asn Asn Phe Lys Ser Ala
        35                  40                  45

Glu Asp Cys Met Arg Thr Cys Gly Gly Ala Asn Tyr Ile Lys Gly Asp
    50                  55                  60

Pro Tyr Phe Ala Glu Tyr Ala Thr Lys Leu Ser Phe Ile Leu Asn Pro
65              70                  75                  80

Ser Asp Ala Asn Asn Pro Ser Gly Glu Thr Ala Asn His Asn Asp Glu
            85                  90                  95

Ala Cys Asn Cys Asn Glu Ser Gly Ile Ser Ser Val Gly Gln Ala Gln
            100                 105                 110

Thr Ser Gly Pro Ser Ser Asn Lys Thr Cys Ile Thr His Ser Ser Ile
            115                 120                 125

Lys Thr Asn Lys Lys Lys Glu Cys Lys Asp Val Lys Leu Gly Val Arg
            130                 135                 140

Glu Asn Asp Lys Asp Leu Lys Ile Cys Val Ile Glu Asp Thr Ser Leu
145                 150                 155                 160

Ser Gly Val Asp Asn Cys Cys Cys Gln Asp Leu Leu Gly Ile Leu Gln
            165                 170                 175

Glu Asn Cys Ser Asp Asn Lys Arg Gly Ser Ser Ser Asn Asp Ser Cys
            180                 185                 190

Asp Asn Lys Asn Gln Asp Glu Cys Gln Lys Lys Leu Lys Val Phe
            195                 200                 205

Ala Ser Leu Thr Asn Gly Tyr Lys Cys Asp Lys Cys Lys Ser Gly Thr
            210                 215                 220

Ser Arg Ser Lys Lys Lys Trp Ile Trp Lys Lys Ser Ser Gly Asn Glu
```

```
            225                 230                 235                 240
Glu Gly Leu Gln Glu Glu Tyr Ala Asn Thr Ile Gly Leu Pro Pro Arg
                245                 250                 255
Thr Gln Ser Leu Tyr Leu Gly Asn Leu Pro Lys Leu Glu Asn Val Cys
                260                 265                 270
Glu Asp Val Lys Asp Ile Asn Phe Asp Thr Lys Glu Lys Phe Leu Ala
                275                 280                 285
Gly Cys Leu Ile Val Ser Phe His Glu Gly Lys Asn Leu Lys Lys Arg
                290                 295                 300
Tyr Pro Gln Asn Lys Asn Ser Gly Asn Lys Glu Asn Leu Cys Lys Ala
305                 310                 315                 320
Leu Glu Tyr Ser Phe Ala Asp Tyr Gly Asp Leu Ile Lys Gly Thr Ser
                325                 330                 335
Ile Trp Asp Asn Glu Tyr Thr Lys Asp Leu Glu Leu Asn Leu Gln Asn
                340                 345                 350
Asn Phe Gly Lys Leu Phe Gly Lys Tyr Ile Lys Lys Asn Asn Thr Ala
                355                 360                 365
Glu Gln Asp Thr Ser Tyr Ser Ser Leu Asp Glu Leu Arg Glu Ser Trp
                370                 375                 380
Trp Asn Thr Asn Lys Lys Tyr Ile Trp Thr Ala Met Lys His Gly Ala
385                 390                 395                 400
Glu Met Asn Ile Thr Thr Cys Asn Ala Asp Gly Ser Val Thr Gly Ser
                405                 410                 415
Gly Ser Ser Cys Asp Asp Ile Pro Thr Ile Asp Leu Ile Pro Gln Tyr
                420                 425                 430
Leu Arg Phe Leu Gln Glu Trp Val Glu Asn Phe Cys Glu Gln Arg Gln
                435                 440                 445
Ala Lys Val Lys Asp Val Ile Thr Asn Cys Lys Ser Cys Lys Glu Ser
                450                 455                 460
Gly Asn Lys Cys Lys Thr Glu Cys Lys Thr Lys Cys Lys Asp Glu Cys
465                 470                 475                 480
Glu Lys Tyr Lys Lys Phe Ile Glu Ala Cys Gly Thr Ala Gly Gly Gly
                485                 490                 495
Ile Gly Thr Ala Gly Ser Pro Trp Ser Lys Arg Trp Asp Gln Ile Tyr
                500                 505                 510
Lys Arg Tyr Ser Lys His Ile Glu Asp Ala Lys Arg Asn Arg Lys Ala
                515                 520                 525
Gly Thr Lys Asn Cys Gly Thr Ser Ser Thr Thr Asn Ala Ala Ala Ser
                530                 535                 540
Thr Asp Glu Asn Lys Cys Val Gln Ser Asp Ile Asp Ser Phe Phe Lys
545                 550                 555                 560
His Leu Ile Asp Ile Gly Leu Thr Thr Pro Ser Ser Tyr Leu Ser Asn
                565                 570                 575
Val Leu Asp Asp Asn Ile Cys Gly Ala Asp Lys Ala Pro Trp Thr Thr
                580                 585                 590
Tyr Thr Thr Tyr Thr Thr Thr Glu Lys Cys Asn Lys Glu Arg Asp Lys
                595                 600                 605
Ser Lys Ser Gln Ser Ser Asp Thr Leu Val Val Asn Val Pro Ser
                610                 615                 620
Pro Leu Gly Asn Thr Pro Tyr Arg Tyr Lys Tyr Ala Cys Gln Cys Lys
625                 630                 635                 640
Ile Pro Thr Asn Glu Glu Thr Cys Asp Asp Arg Lys Glu Tyr Met Asn
                645                 650                 655
```

```
Gln Trp Ser Cys Gly Ser Ala Arg Thr Met Lys Arg Gly Tyr Lys Asn
                660                 665                 670

Asp Asn Tyr Glu Leu Cys Lys Tyr Asn Gly Val Asp Val Lys Pro Thr
            675                 680                 685

Thr Val Arg Ser Asn Ser Ser Lys Leu Asp Arg His Arg Gln Pro Arg
        690                 695                 700

Gly Trp Glu Gln Leu Tyr Pro Thr Gly Ala Glu Phe Leu Gly Asp Gly
705                 710                 715                 720

Gly Asp Ile Ser Phe Ser Thr Arg Gly Thr Gln Asn Trp Thr Val Glu
                725                 730                 735

Arg Leu Leu Gln Ala His Arg Gln Leu Glu Arg Gly Tyr Val Phe
            740                 745                 750

Val Gly Tyr His Gly Thr Phe Leu Glu Ala Ala Gln Ser Ile Val Phe
        755                 760                 765

Gly Gly Val Arg Ala Arg Ser Gln Asp Leu Asp Ala Ile Trp Arg Gly
770                 775                 780

Phe Tyr Ile Ala Gly Asp Pro Ala Leu Ala Tyr Gly Tyr Ala Gln Asp
785                 790                 795                 800

Gln Glu Pro Asp Ala Arg Gly Arg Ile Arg Asn Gly Ala Leu Leu Arg
                805                 810                 815

Val Tyr Val Pro Arg Ser Ser Leu Pro Gly Phe Tyr Arg Thr Ser Leu
            820                 825                 830

Thr Leu Ala Ala Pro Glu Ala Ala Gly Glu Val Glu Arg Leu Ile Gly
        835                 840                 845

His Pro Leu Pro Leu Arg Leu Asp Ala Ile Thr Gly Pro Glu Glu Glu
        850                 855                 860

Gly Gly Arg Leu Glu Thr Ile Leu Gly Trp Pro Leu Ala Glu Arg Thr
865                 870                 875                 880

Val Val Ile Pro Ser Ala Ile Pro Thr Asp Pro Arg Asn Val Gly Gly
                885                 890                 895

Asp Leu Asp Pro Ser Ser Ile Pro Asp Lys Glu Gln Ala Ile Ser Ala
            900                 905                 910

Leu Pro Asp Tyr Ala Ser Gln Pro Gly Lys Pro Arg Lys Asp Glu
        915                 920                 925

Leu

<210> SEQ ID NO 61
<211> LENGTH: 1045
<212> TYPE: PRT
<213> ORGANISM: Artificial
<220> FEATURE:
<223> OTHER INFORMATION: Artificial construct

<400> SEQUENCE: 61

Arg Pro Asp Phe Cys Leu Glu Pro Pro Tyr Thr Gly Pro Cys Lys Ala
1               5                   10                  15

Arg Ile Ile Arg Tyr Phe Tyr Asn Ala Lys Ala Gly Leu Cys Gln Thr
                20                  25                  30

Phe Val Tyr Gly Gly Cys Arg Ala Lys Arg Asn Asn Phe Lys Ser Ala
            35                  40                  45

Glu Asp Cys Met Arg Thr Cys Gly Gly Ala Asn Tyr Ile Lys Gly Asp
        50                  55                  60

Pro Tyr Phe Ala Glu Tyr Ala Thr Lys Leu Ser Phe Ile Leu Asn Pro
65                  70                  75                  80
```

```
Ser Asp Ala Asn Asn Pro Ser Gly Glu Thr Ala Asn His Asn Asp Glu
                 85                  90                  95

Ala Cys Asn Cys Asn Glu Ser Gly Ile Ser Ser Val Gly Gln Ala Gln
            100                 105                 110

Thr Ser Gly Pro Ser Ser Asn Lys Thr Cys Ile Thr His Ser Ser Ile
        115                 120                 125

Lys Thr Asn Lys Lys Lys Glu Cys Lys Asp Val Lys Leu Gly Val Arg
    130                 135                 140

Glu Asn Asp Lys Asp Leu Lys Ile Cys Val Ile Glu Asp Thr Ser Leu
145                 150                 155                 160

Ser Gly Val Asp Asn Cys Cys Gln Asp Leu Leu Gly Ile Leu Gln
                165                 170                 175

Glu Asn Cys Ser Asp Asn Lys Arg Gly Ser Ser Ser Asn Asp Ser Cys
            180                 185                 190

Asp Asn Lys Asn Gln Asp Glu Cys Gln Lys Lys Leu Glu Lys Val Phe
        195                 200                 205

Ala Ser Leu Thr Asn Gly Tyr Lys Cys Asp Lys Cys Lys Ser Gly Thr
    210                 215                 220

Ser Arg Ser Lys Lys Lys Trp Ile Trp Lys Lys Ser Ser Gly Asn Glu
225                 230                 235                 240

Glu Gly Leu Gln Glu Glu Tyr Ala Asn Thr Ile Gly Leu Pro Pro Arg
                245                 250                 255

Thr Gln Ser Leu Tyr Leu Gly Asn Leu Pro Lys Leu Glu Asn Val Cys
            260                 265                 270

Glu Asp Val Lys Asp Ile Asn Phe Asp Thr Lys Glu Lys Phe Leu Ala
        275                 280                 285

Gly Cys Leu Ile Val Ser Phe His Glu Gly Lys Asn Leu Lys Lys Arg
    290                 295                 300

Tyr Pro Gln Asn Lys Asn Ser Gly Asn Lys Glu Asn Leu Cys Lys Ala
305                 310                 315                 320

Leu Glu Tyr Ser Phe Ala Asp Tyr Gly Asp Leu Ile Lys Gly Thr Ser
                325                 330                 335

Ile Trp Asp Asn Glu Tyr Thr Lys Asp Leu Glu Leu Asn Leu Gln Asn
            340                 345                 350

Asn Phe Gly Lys Leu Phe Gly Lys Tyr Ile Lys Lys Asn Asn Thr Ala
        355                 360                 365

Glu Gln Asp Thr Ser Tyr Ser Ser Leu Asp Glu Leu Arg Glu Ser Trp
    370                 375                 380

Trp Asn Thr Asn Lys Lys Tyr Ile Trp Thr Ala Met Lys His Gly Ala
385                 390                 395                 400

Glu Met Asn Ile Thr Thr Cys Asn Ala Asp Gly Ser Val Thr Gly Ser
                405                 410                 415

Gly Ser Ser Cys Asp Asp Ile Pro Thr Ile Asp Leu Ile Pro Gln Tyr
            420                 425                 430

Leu Arg Phe Leu Gln Glu Trp Val Glu Asn Phe Cys Glu Gln Arg Gln
        435                 440                 445

Ala Lys Val Lys Asp Val Ile Thr Asn Cys Lys Ser Cys Lys Glu Ser
    450                 455                 460

Gly Asn Lys Cys Lys Thr Glu Cys Lys Thr Cys Lys Asp Glu Cys
465                 470                 475                 480

Glu Lys Tyr Lys Lys Phe Ile Glu Ala Cys Gly Thr Ala Gly Gly Gly
                485                 490                 495

Ile Gly Thr Ala Gly Ser Pro Trp Ser Lys Arg Trp Asp Gln Ile Tyr
```

```
                500             505             510
Lys Arg Tyr Ser Lys His Ile Glu Asp Ala Lys Arg Asn Arg Lys Ala
            515                 520                 525
Gly Thr Lys Asn Cys Gly Thr Ser Ser Thr Thr Asn Ala Ala Ala Ser
        530                 535                 540
Thr Asp Glu Asn Lys Cys Val Gln Ser Asp Ile Asp Ser Phe Phe Lys
545                 550                 555                 560
His Leu Ile Asp Ile Gly Leu Thr Thr Pro Ser Ser Tyr Leu Ser Asn
                565                 570                 575
Val Leu Asp Asp Asn Ile Cys Gly Ala Asp Lys Ala Pro Trp Thr Thr
            580                 585                 590
Tyr Thr Thr Tyr Thr Thr Thr Glu Lys Cys Asn Lys Glu Arg Asp Lys
        595                 600                 605
Ser Lys Ser Gln Ser Ser Asp Thr Leu Val Val Asn Val Pro Ser
    610                 615                 620
Pro Leu Gly Asn Thr Pro Tyr Arg Tyr Lys Tyr Ala Cys Gln Cys Lys
625                 630                 635                 640
Ile Pro Thr Asn Glu Glu Thr Cys Asp Asp Arg Lys Glu Tyr Met Asn
                645                 650                 655
Gln Trp Ser Cys Gly Ser Ala Arg Thr Met Lys Arg Gly Tyr Lys Asn
            660                 665                 670
Asp Asn Tyr Glu Leu Cys Lys Tyr Asn Gly Val Asp Val Lys Pro Thr
        675                 680                 685
Thr Val Arg Ser Asn Ser Ser Lys Leu Asp Pro Glu Gly Gly Ser Leu
    690                 695                 700
Ala Ala Leu Thr Ala His Gln Ala Cys His Leu Pro Leu Glu Thr Phe
705                 710                 715                 720
Thr Arg His Arg Gln Pro Arg Gly Trp Glu Gln Leu Glu Gln Cys Gly
                725                 730                 735
Tyr Pro Val Gln Arg Leu Val Ala Leu Tyr Leu Ala Ala Arg Leu Ser
            740                 745                 750
Trp Asn Gln Val Asp Gln Val Ile Arg Asn Ala Leu Ala Ser Pro Gly
        755                 760                 765
Ser Gly Gly Asp Leu Gly Glu Ala Ile Arg Glu Gln Pro Glu Gln Ala
    770                 775                 780
Arg Leu Ala Leu Thr Leu Ala Ala Ala Glu Ser Glu Arg Phe Val Arg
785                 790                 795                 800
Gln Gly Thr Gly Asn Asp Glu Ala Gly Ala Ala Asn Gly Pro Ala Asp
                805                 810                 815
Ser Gly Asp Ala Leu Leu Glu Arg Asn Tyr Pro Thr Gly Ala Glu Phe
            820                 825                 830
Leu Gly Asp Gly Gly Asp Ile Ser Phe Ser Thr Arg Gly Thr Gln Asn
        835                 840                 845
Trp Thr Val Glu Arg Leu Leu Gln Ala His Arg Gln Leu Glu Glu Arg
    850                 855                 860
Gly Tyr Val Phe Val Gly Tyr His Gly Thr Phe Leu Glu Ala Ala Gln
865                 870                 875                 880
Ser Ile Val Phe Gly Gly Val Arg Ala Arg Ser Gln Asp Leu Asp Ala
                885                 890                 895
Ile Trp Arg Gly Phe Tyr Ile Ala Gly Asp Pro Ala Leu Ala Tyr Gly
            900                 905                 910
Tyr Ala Gln Asp Gln Glu Pro Asp Ala Arg Gly Arg Ile Arg Asn Gly
        915                 920                 925
```

```
Ala Leu Leu Arg Val Tyr Val Pro Arg Ser Ser Leu Pro Gly Phe Tyr
        930                 935                 940

Arg Thr Ser Leu Thr Leu Ala Ala Pro Glu Ala Ala Gly Glu Val Glu
945                 950                 955                 960

Arg Leu Ile Gly His Pro Leu Pro Leu Arg Leu Asp Ala Ile Thr Gly
                965                 970                 975

Pro Glu Glu Gly Gly Arg Leu Glu Thr Ile Leu Gly Trp Pro Leu
                980                 985                 990

Ala Glu Arg Thr Val Val Ile Pro  Ser Ala Ile Pro Thr Asp Pro Arg
        995                 1000                 1005

Asn Val  Gly Gly Asp Leu Asp  Pro Ser Ser Ile Pro  Asp Lys Glu
    1010                 1015                 1020

Gln Ala  Ile Ser Ala Leu Pro  Asp Tyr Ala Ser Gln  Pro Gly Lys
    1025                 1030                 1035

Pro Pro  Arg Lys Asp Glu Leu
    1040                 1045

<210> SEQ ID NO 62
<211> LENGTH: 987
<212> TYPE: PRT
<213> ORGANISM: Artificial
<220> FEATURE:
<223> OTHER INFORMATION: Artificial construct

<400> SEQUENCE: 62

Asn Tyr Ile Lys Gly Asp Pro Tyr Phe Ala Glu Tyr Ala Thr Lys Leu
1               5                   10                  15

Ser Phe Ile Leu Asn Pro Ser Asp Ala Asn Asn Pro Ser Gly Glu Thr
            20                  25                  30

Ala Asn His Asn Asp Glu Ala Cys Asn Cys Asn Glu Ser Gly Ile Ser
        35                  40                  45

Ser Val Gly Gln Ala Gln Thr Ser Gly Pro Ser Ser Asn Lys Thr Cys
    50                  55                  60

Ile Thr His Ser Ser Ile Lys Thr Asn Lys Lys Glu Cys Lys Asp
65                  70                  75                  80

Val Lys Leu Gly Val Arg Glu Asn Asp Lys Asp Leu Lys Ile Cys Val
                85                  90                  95

Ile Glu Asp Thr Ser Leu Ser Gly Val Asp Asn Cys Cys Cys Gln Asp
            100                 105                 110

Leu Leu Gly Ile Leu Gln Glu Asn Cys Ser Asp Asn Lys Arg Gly Ser
        115                 120                 125

Ser Ser Asn Asp Ser Cys Asp Asn Lys Asn Gln Asp Glu Cys Gln Lys
    130                 135                 140

Lys Leu Glu Lys Val Phe Ala Ser Leu Thr Asn Gly Tyr Lys Cys Asp
145                 150                 155                 160

Lys Cys Lys Ser Gly Thr Ser Arg Ser Lys Lys Lys Trp Ile Trp Lys
                165                 170                 175

Lys Ser Ser Gly Asn Glu Glu Gly Leu Gln Glu Glu Tyr Ala Asn Thr
            180                 185                 190

Ile Gly Leu Pro Pro Arg Thr Gln Ser Leu Tyr Leu Gly Asn Leu Pro
        195                 200                 205

Lys Leu Glu Asn Val Cys Glu Asp Val Lys Asp Ile Asn Phe Asp Thr
    210                 215                 220

Lys Glu Lys Phe Leu Ala Gly Cys Leu Ile Val Ser Phe His Glu Gly
225                 230                 235                 240
```

-continued

```
Lys Asn Leu Lys Lys Arg Tyr Pro Gln Asn Lys Asn Ser Gly Asn Lys
            245                 250                 255
Glu Asn Leu Cys Lys Ala Leu Glu Tyr Ser Phe Ala Asp Tyr Gly Asp
            260                 265                 270
Leu Ile Lys Gly Thr Ser Ile Trp Asp Asn Glu Tyr Thr Lys Asp Leu
            275                 280                 285
Glu Leu Asn Leu Gln Asn Asn Phe Gly Lys Leu Phe Gly Lys Tyr Ile
            290                 295                 300
Lys Lys Asn Asn Thr Ala Glu Gln Asp Thr Ser Tyr Ser Ser Leu Asp
305                 310                 315                 320
Glu Leu Arg Glu Ser Trp Trp Asn Thr Asn Lys Lys Tyr Ile Trp Thr
            325                 330                 335
Ala Met Lys His Gly Ala Glu Met Asn Ile Thr Thr Cys Asn Ala Asp
            340                 345                 350
Gly Ser Val Thr Gly Ser Gly Ser Cys Asp Asp Ile Pro Thr Ile
            355                 360                 365
Asp Leu Ile Pro Gln Tyr Leu Arg Phe Leu Gln Glu Trp Val Glu Asn
            370                 375                 380
Phe Cys Glu Gln Arg Gln Ala Lys Val Lys Asp Val Ile Thr Asn Cys
385                 390                 395                 400
Lys Ser Cys Lys Glu Ser Gly Asn Lys Cys Lys Thr Glu Cys Lys Thr
            405                 410                 415
Lys Cys Lys Asp Glu Cys Glu Lys Tyr Lys Lys Phe Ile Glu Ala Cys
            420                 425                 430
Gly Thr Ala Gly Gly Gly Ile Gly Thr Ala Gly Ser Pro Trp Ser Lys
            435                 440                 445
Arg Trp Asp Gln Ile Tyr Lys Arg Tyr Ser Lys His Ile Glu Asp Ala
            450                 455                 460
Lys Arg Asn Arg Lys Ala Gly Thr Lys Asn Cys Gly Thr Ser Ser Thr
465                 470                 475                 480
Thr Asn Ala Ala Ala Ser Thr Asp Glu Asn Lys Cys Val Gln Ser Asp
            485                 490                 495
Ile Asp Ser Phe Phe Lys His Leu Ile Asp Ile Gly Leu Thr Thr Pro
            500                 505                 510
Ser Ser Tyr Leu Ser Asn Val Leu Asp Asp Asn Ile Cys Gly Ala Asp
            515                 520                 525
Lys Ala Pro Trp Thr Thr Tyr Thr Thr Tyr Thr Thr Thr Glu Lys Cys
            530                 535                 540
Asn Lys Glu Arg Asp Lys Ser Lys Ser Gln Ser Ser Asp Thr Leu Val
545                 550                 555                 560
Val Val Asn Val Pro Ser Pro Leu Gly Asn Thr Pro Tyr Arg Tyr Lys
            565                 570                 575
Tyr Ala Cys Gln Cys Lys Ile Pro Thr Asn Glu Glu Thr Cys Asp Asp
            580                 585                 590
Arg Lys Glu Tyr Met Asn Gln Trp Ser Cys Gly Ser Ala Arg Thr Met
            595                 600                 605
Lys Arg Gly Tyr Lys Asn Asp Asn Tyr Glu Leu Cys Lys Tyr Asn Gly
            610                 615                 620
Val Asp Val Lys Pro Thr Thr Val Arg Ser Asn Ser Ser Lys Leu Asp
625                 630                 635                 640
Pro Glu Gly Gly Ser Leu Ala Ala Leu Thr Ala His Gln Ala Cys His
            645                 650                 655
```

-continued

Leu Pro Leu Glu Thr Phe Thr Arg His Arg Gln Pro Arg Gly Trp Glu
                655                 660                 665                 670

Gln Leu Glu Gln Cys Gly Tyr Pro Val Gln Arg Leu Val Ala Leu Tyr
            675                 680                 685

Leu Ala Ala Arg Leu Ser Trp Asn Gln Val Asp Gln Val Ile Arg Asn
        690                 695                 700

Ala Leu Ala Ser Pro Gly Ser Gly Gly Asp Leu Gly Glu Ala Ile Arg
705                 710                 715                 720

Glu Gln Pro Glu Gln Ala Arg Leu Ala Leu Thr Leu Ala Ala Ala Glu
                725                 730                 735

Ser Glu Arg Phe Val Arg Gln Gly Thr Gly Asn Asp Glu Ala Gly Ala
            740                 745                 750

Ala Asn Gly Pro Ala Asp Ser Gly Asp Ala Leu Leu Glu Arg Asn Tyr
        755                 760                 765

Pro Thr Gly Ala Glu Phe Leu Gly Asp Gly Gly Asp Ile Ser Phe Ser
770                 775                 780

Thr Arg Gly Thr Gln Asn Trp Thr Val Glu Arg Leu Leu Gln Ala His
785                 790                 795                 800

Arg Gln Leu Glu Glu Arg Gly Tyr Val Phe Val Gly Tyr His Gly Thr
                805                 810                 815

Phe Leu Glu Ala Ala Gln Ser Ile Val Phe Gly Gly Val Arg Ala Arg
            820                 825                 830

Ser Gln Asp Leu Asp Ala Ile Trp Arg Gly Phe Tyr Ile Ala Gly Asp
        835                 840                 845

Pro Ala Leu Ala Tyr Gly Tyr Ala Gln Asp Gln Glu Pro Asp Ala Arg
850                 855                 860

Gly Arg Ile Arg Asn Gly Ala Leu Leu Arg Val Tyr Val Pro Arg Ser
865                 870                 875                 880

Ser Leu Pro Gly Phe Tyr Arg Thr Ser Leu Thr Leu Ala Ala Pro Glu
                885                 890                 895

Ala Ala Gly Glu Val Glu Arg Leu Ile Gly His Pro Leu Pro Leu Arg
            900                 905                 910

Leu Asp Ala Ile Thr Gly Pro Glu Glu Gly Gly Arg Leu Glu Thr
        915                 920                 925

Ile Leu Gly Trp Pro Leu Ala Glu Arg Thr Val Val Ile Pro Ser Ala
930                 935                 940

Ile Pro Thr Asp Pro Arg Asn Val Gly Gly Asp Leu Asp Pro Ser Ser
945                 950                 955                 960

Ile Pro Asp Lys Glu Gln Ala Ile Ser Ala Leu Pro Asp Tyr Ala Ser
                965                 970                 975

Gln Pro Gly Lys Pro Pro Arg Lys Asp Glu Leu
            980                 985

<210> SEQ ID NO 63
<211> LENGTH: 871
<212> TYPE: PRT
<213> ORGANISM: Artificial
<220> FEATURE:
<223> OTHER INFORMATION: Artificial construct

<400> SEQUENCE: 63

Asn Tyr Ile Lys Gly Asp Pro Tyr Phe Ala Glu Tyr Ala Thr Lys Leu
1               5                   10                  15

Ser Phe Ile Leu Asn Pro Ser Asp Ala Asn Asn Pro Ser Gly Glu Thr
            20                  25                  30

-continued

Ala Asn His Asn Asp Glu Ala Cys Asn Cys Asn Glu Ser Gly Ile Ser
            35                  40                  45

Ser Val Gly Gln Ala Gln Thr Ser Gly Pro Ser Ser Asn Lys Thr Cys
 50                  55                  60

Ile Thr His Ser Ser Ile Lys Thr Asn Lys Lys Glu Cys Lys Asp
 65              70                  75                  80

Val Lys Leu Gly Val Arg Glu Asn Asp Lys Asp Leu Lys Ile Cys Val
                85                  90                  95

Ile Glu Asp Thr Ser Leu Ser Gly Val Asp Asn Cys Cys Cys Gln Asp
            100                 105                 110

Leu Leu Gly Ile Leu Gln Glu Asn Cys Ser Asp Asn Lys Arg Gly Ser
            115                 120                 125

Ser Ser Asn Asp Ser Cys Asp Asn Lys Asn Gln Asp Glu Cys Gln Lys
 130                 135                 140

Lys Leu Glu Lys Val Phe Ala Ser Leu Thr Asn Gly Tyr Lys Cys Asp
 145                 150                 155                 160

Lys Cys Lys Ser Gly Thr Ser Arg Ser Lys Lys Trp Ile Trp Lys
                165                 170                 175

Lys Ser Ser Gly Asn Glu Glu Gly Leu Gln Glu Glu Tyr Ala Asn Thr
            180                 185                 190

Ile Gly Leu Pro Pro Arg Thr Gln Ser Leu Tyr Leu Gly Asn Leu Pro
        195                 200                 205

Lys Leu Glu Asn Val Cys Glu Asp Val Lys Asp Ile Asn Phe Asp Thr
 210                 215                 220

Lys Glu Lys Phe Leu Ala Gly Cys Leu Ile Val Ser Phe His Glu Gly
 225                 230                 235                 240

Lys Asn Leu Lys Lys Arg Tyr Pro Gln Asn Lys Asn Ser Gly Asn Lys
                245                 250                 255

Glu Asn Leu Cys Lys Ala Leu Glu Tyr Ser Phe Ala Asp Tyr Gly Asp
            260                 265                 270

Leu Ile Lys Gly Thr Ser Ile Trp Asp Asn Glu Tyr Thr Lys Asp Leu
        275                 280                 285

Glu Leu Asn Leu Gln Asn Asn Phe Gly Lys Leu Phe Gly Lys Tyr Ile
 290                 295                 300

Lys Lys Asn Asn Thr Ala Glu Gln Asp Thr Ser Tyr Ser Ser Leu Asp
 305                 310                 315                 320

Glu Leu Arg Glu Ser Trp Trp Asn Thr Asn Lys Lys Tyr Ile Trp Thr
                325                 330                 335

Ala Met Lys His Gly Ala Glu Met Asn Ile Thr Thr Cys Asn Ala Asp
            340                 345                 350

Gly Ser Val Thr Gly Ser Gly Ser Cys Asp Asp Ile Pro Thr Ile
        355                 360                 365

Asp Leu Ile Pro Gln Tyr Leu Arg Phe Leu Gln Glu Trp Val Glu Asn
 370                 375                 380

Phe Cys Glu Gln Arg Gln Ala Lys Val Lys Asp Val Ile Thr Asn Cys
 385                 390                 395                 400

Lys Ser Cys Lys Glu Ser Gly Asn Lys Cys Lys Thr Glu Cys Lys Thr
                405                 410                 415

Lys Cys Lys Asp Glu Cys Glu Lys Lys Phe Ile Glu Ala Cys
            420                 425                 430

Gly Thr Ala Gly Gly Ile Gly Thr Ala Gly Ser Pro Trp Ser Lys
        435                 440                 445

Arg Trp Asp Gln Ile Tyr Lys Arg Tyr Ser Lys His Ile Glu Asp Ala

```
               450                 455                 460
Lys Arg Asn Arg Lys Ala Gly Thr Lys Asn Cys Gly Thr Ser Ser Thr
465                 470                 475                 480

Thr Asn Ala Ala Ala Ser Thr Asp Glu Asn Lys Cys Val Gln Ser Asp
                485                 490                 495

Ile Asp Ser Phe Phe Lys His Leu Ile Asp Ile Gly Leu Thr Thr Pro
                500                 505                 510

Ser Ser Tyr Leu Ser Asn Val Leu Asp Asp Asn Ile Cys Gly Ala Asp
                515                 520                 525

Lys Ala Pro Trp Thr Thr Tyr Thr Thr Tyr Thr Thr Thr Glu Lys Cys
530                 535                 540

Asn Lys Glu Arg Asp Lys Ser Lys Ser Gln Ser Ser Asp Thr Leu Val
545                 550                 555                 560

Val Val Asn Val Pro Ser Pro Leu Gly Asn Thr Pro Tyr Arg Tyr Lys
                565                 570                 575

Tyr Ala Cys Gln Cys Lys Ile Pro Thr Asn Glu Glu Thr Cys Asp Asp
                580                 585                 590

Arg Lys Glu Tyr Met Asn Gln Trp Ser Cys Gly Ser Ala Arg Thr Met
                595                 600                 605

Lys Arg Gly Tyr Lys Asn Asp Asn Tyr Glu Leu Cys Lys Tyr Asn Gly
610                 615                 620

Val Asp Val Lys Pro Thr Thr Val Arg Ser Asn Ser Ser Lys Leu Asp
625                 630                 635                 640

Arg His Arg Gln Pro Arg Gly Trp Glu Gln Leu Tyr Pro Thr Gly Ala
                645                 650                 655

Glu Phe Leu Gly Asp Gly Gly Asp Ile Ser Phe Ser Thr Arg Gly Thr
                660                 665                 670

Gln Asn Trp Thr Val Glu Arg Leu Leu Gln Ala His Arg Gln Leu Glu
                675                 680                 685

Glu Arg Gly Tyr Val Phe Val Gly Tyr His Gly Thr Phe Leu Glu Ala
                690                 695                 700

Ala Gln Ser Ile Val Phe Gly Gly Val Arg Ala Arg Ser Gln Asp Leu
705                 710                 715                 720

Asp Ala Ile Trp Arg Gly Phe Tyr Ile Ala Gly Asp Pro Ala Leu Ala
                725                 730                 735

Tyr Gly Tyr Ala Gln Asp Gln Glu Pro Asp Ala Arg Gly Arg Ile Arg
                740                 745                 750

Asn Gly Ala Leu Leu Arg Val Tyr Val Pro Arg Ser Ser Leu Pro Gly
                755                 760                 765

Phe Tyr Arg Thr Ser Leu Thr Leu Ala Ala Pro Glu Ala Ala Gly Glu
770                 775                 780

Val Glu Arg Leu Ile Gly His Pro Leu Pro Leu Arg Leu Asp Ala Ile
785                 790                 795                 800

Thr Gly Pro Glu Glu Glu Gly Gly Arg Leu Glu Thr Ile Leu Gly Trp
                805                 810                 815

Pro Leu Ala Glu Arg Thr Val Val Ile Pro Ser Ala Ile Pro Thr Asp
                820                 825                 830

Pro Arg Asn Val Gly Gly Asp Leu Asp Pro Ser Ser Ile Pro Asp Lys
                835                 840                 845

Glu Gln Ala Ile Ser Ala Leu Pro Asp Tyr Ala Ser Gln Pro Gly Lys
850                 855                 860

Pro Pro Arg Lys Asp Glu Leu
865                 870
```

<210> SEQ ID NO 64
<211> LENGTH: 1258
<212> TYPE: PRT
<213> ORGANISM: Artificial
<220> FEATURE:
<223> OTHER INFORMATION: Artificial construct

<400> SEQUENCE: 64

```
Arg Pro Asp Phe Cys Leu Glu Pro Pro Tyr Thr Gly Pro Cys Lys Ala
1               5                   10                  15

Arg Ile Ile Arg Tyr Phe Tyr Asn Ala Lys Ala Gly Leu Cys Gln Thr
            20                  25                  30

Phe Val Tyr Gly Gly Cys Arg Ala Lys Arg Asn Asn Phe Lys Ser Ala
        35                  40                  45

Glu Asp Cys Met Arg Thr Cys Gly Gly Ala Asn His Ser Asp Ser Gly
    50                  55                  60

Lys Tyr Asp Pro Cys Glu Lys Lys Leu Pro Pro Tyr Asp Asp Asn Asp
65                  70                  75                  80

Gln Trp Lys Cys Gln Gln Asn Ser Ser Asp Ser Gly Lys Pro Glu
                85                  90                  95

Asn Ile Cys Val Pro Pro Arg Arg Glu Arg Leu Cys Thr Tyr Asn Leu
            100                 105                 110

Glu Asn Leu Lys Phe Asp Lys Ile Arg Asp Asn Ala Phe Leu Ala
            115                 120                 125

Asp Val Leu Leu Thr Ala Arg Asn Glu Gly Glu Lys Ile Val Gln Asn
    130                 135                 140

His Pro Asp Thr Asn Ser Ser Asn Val Cys Asn Ala Leu Glu Arg Ser
145                 150                 155                 160

Phe Ala Asp Leu Ala Asp Ile Ile Arg Gly Thr Asp Gln Trp Lys Gly
                165                 170                 175

Thr Asn Ser Asn Leu Glu Lys Asn Leu Lys Gln Met Phe Ala Lys Ile
            180                 185                 190

Arg Glu Asn Asp Lys Val Leu Gln Asp Lys Tyr Pro Lys Asp Gln Lys
        195                 200                 205

Tyr Thr Lys Leu Arg Glu Ala Trp Trp Asn Ala Asn Arg Gln Lys Val
    210                 215                 220

Trp Glu Val Ile Thr Cys Gly Ala Arg Ser Asn Asp Leu Leu Ile Lys
225                 230                 235                 240

Arg Gly Trp Arg Thr Ser Gly Lys Ser Asp Arg Lys Lys Asn Phe Glu
                245                 250                 255

Leu Cys Arg Lys Cys Gly His Tyr Glu Lys Glu Val Pro Thr Lys Leu
            260                 265                 270

Asp Tyr Val Pro Gln Phe Leu Arg Trp Leu Thr Glu Trp Ile Glu Asp
        275                 280                 285

Phe Tyr Arg Glu Lys Gln Asn Leu Ile Asp Asp Met Glu Arg His Arg
    290                 295                 300

Glu Glu Cys Thr Arg Glu Asp His Lys Ser Lys Glu Gly Thr Ser Tyr
305                 310                 315                 320

Cys Ser Thr Cys Lys Asp Lys Cys Lys Lys Tyr Cys Glu Cys Val Lys
                325                 330                 335

Lys Trp Lys Thr Glu Trp Glu Asn Gln Glu Asn Lys Tyr Lys Asp Leu
            340                 345                 350

Tyr Glu Gln Asn Lys Asn Lys Thr Ser Gln Lys Asn Thr Ser Arg Tyr
        355                 360                 365
```

-continued

Asp Asp Tyr Val Lys Asp Phe Phe Glu Lys Leu Glu Ala Asn Tyr Ser
        370                 375                 380

Ser Leu Glu Asn Tyr Ile Lys Gly Asp Pro Tyr Phe Ala Glu Tyr Ala
385                 390                 395                 400

Thr Lys Leu Ser Phe Ile Leu Asn Pro Ser Asp Ala Asn Asn Pro Ser
                405                 410                 415

Gly Glu Thr Ala Asn His Asn Asp Glu Ala Cys Asn Cys Asn Glu Ser
                420                 425                 430

Gly Ile Ser Ser Val Gly Gln Ala Gln Thr Ser Gly Pro Ser Ser Asn
                435                 440                 445

Lys Thr Cys Ile Thr His Ser Ser Ile Lys Thr Asn Lys Lys Lys Glu
        450                 455                 460

Cys Lys Asp Val Lys Leu Gly Val Arg Glu Asn Asp Lys Asp Leu Lys
465                 470                 475                 480

Ile Cys Val Ile Glu Asp Thr Ser Leu Ser Gly Val Asp Asn Cys Cys
                485                 490                 495

Cys Gln Asp Leu Leu Gly Ile Leu Gln Glu Asn Cys Ser Asp Asn Lys
                500                 505                 510

Arg Gly Ser Ser Ser Asn Asp Ser Cys Asp Asn Lys Asn Gln Asp Glu
        515                 520                 525

Cys Gln Lys Lys Leu Glu Lys Val Phe Ala Ser Leu Thr Asn Gly Tyr
        530                 535                 540

Lys Cys Asp Lys Cys Lys Ser Gly Thr Ser Arg Ser Lys Lys Lys Trp
545                 550                 555                 560

Ile Trp Lys Lys Ser Ser Gly Asn Glu Glu Gly Leu Gln Glu Glu Tyr
                565                 570                 575

Ala Asn Thr Ile Gly Leu Pro Pro Arg Thr Gln Ser Leu Tyr Leu Gly
                580                 585                 590

Asn Leu Pro Lys Leu Glu Asn Val Cys Glu Asp Val Lys Asp Ile Asn
                595                 600                 605

Phe Asp Thr Lys Glu Lys Phe Leu Ala Gly Cys Leu Ile Val Ser Phe
        610                 615                 620

His Glu Gly Lys Asn Leu Lys Lys Arg Tyr Pro Gln Asn Lys Asn Ser
625                 630                 635                 640

Gly Asn Lys Glu Asn Leu Cys Lys Ala Leu Glu Tyr Ser Phe Ala Asp
                645                 650                 655

Tyr Gly Asp Leu Ile Lys Gly Thr Ser Ile Trp Asp Asn Glu Tyr Thr
                660                 665                 670

Lys Asp Leu Glu Leu Asn Leu Gln Asn Asn Phe Gly Lys Leu Phe Gly
        675                 680                 685

Lys Tyr Ile Lys Lys Asn Asn Thr Ala Glu Gln Asp Thr Ser Tyr Ser
        690                 695                 700

Ser Leu Asp Glu Leu Arg Glu Ser Trp Trp Asn Thr Asn Lys Lys Tyr
705                 710                 715                 720

Ile Trp Thr Ala Met Lys His Gly Ala Glu Met Asn Ile Thr Thr Cys
                725                 730                 735

Asn Ala Asp Gly Ser Val Thr Gly Ser Gly Ser Ser Cys Asp Asp Ile
                740                 745                 750

Pro Thr Ile Asp Leu Ile Pro Gln Tyr Leu Arg Phe Leu Gln Glu Trp
        755                 760                 765

Val Glu Asn Phe Cys Glu Gln Arg Gln Ala Lys Val Lys Asp Val Ile
        770                 775                 780

```
Thr Asn Cys Lys Ser Cys Lys Glu Ser Gly Asn Lys Cys Lys Thr Glu
785                 790                 795                 800

Cys Lys Thr Lys Cys Lys Asp Glu Cys Glu Lys Tyr Lys Lys Phe Ile
            805                 810                 815

Glu Ala Cys Gly Thr Ala Gly Gly Ile Gly Thr Ala Gly Ser Pro
        820                 825                 830

Trp Ser Lys Arg Trp Asp Gln Ile Tyr Lys Arg Tyr Ser Lys His Ile
            835                 840                 845

Glu Asp Ala Lys Arg Asn Arg Lys Ala Gly Thr Lys Asn Cys Gly Thr
    850                 855                 860

Ser Ser Thr Thr Asn Ala Ala Ala Ser Thr Asp Glu Asn Lys Cys Val
865                 870                 875                 880

Gln Ser Asp Ile Asp Ser Phe Phe Lys His Leu Ile Asp Ile Gly Leu
                885                 890                 895

Thr Thr Pro Ser Ser Tyr Leu Ser Asn Val Leu Asp Asp Asn Ile Cys
            900                 905                 910

Gly Ala Asp Lys Ala Pro Trp Thr Thr Tyr Thr Thr Tyr Thr Thr Thr
            915                 920                 925

Glu Lys Cys Asn Lys Glu Arg Asp Lys Ser Lys Ser Gln Ser Ser Asp
    930                 935                 940

Thr Leu Val Val Val Asn Val Pro Ser Pro Leu Gly Asn Thr Pro Tyr
945                 950                 955                 960

Arg Tyr Lys Tyr Ala Cys Gln Cys Lys Ile Pro Thr Asn Glu Glu Thr
                965                 970                 975

Cys Asp Asp Arg Lys Glu Tyr Met Asn Gln Trp Ser Cys Gly Ser Ala
            980                 985                 990

Arg Thr Met Lys Arg Gly Tyr Lys  Asn Asp Asn Tyr Glu  Leu Cys Lys
            995                 1000                1005

Tyr Asn  Gly Val Asp Val Lys  Pro Thr Thr Val Arg  Ser Asn Ser
    1010                1015                1020

Ser Lys  Leu Asp Arg His Arg  Gln Pro Arg Gly Trp  Glu Gln Leu
    1025                1030                1035

Tyr Pro  Thr Gly Ala Glu Phe  Leu Gly Asp Gly Gly  Asp Ile Ser
    1040                1045                1050

Phe Ser  Thr Arg Gly Thr Gln  Asn Trp Thr Val Glu  Arg Leu Leu
    1055                1060                1065

Gln Ala  His Arg Gln Leu Glu  Glu Arg Gly Tyr Val  Phe Val Gly
    1070                1075                1080

Tyr His  Gly Thr Phe Leu Glu  Ala Ala Gln Ser Ile  Val Phe Gly
    1085                1090                1095

Gly Val  Arg Ala Arg Ser Gln  Asp Leu Asp Ala Ile  Trp Arg Gly
    1100                1105                1110

Phe Tyr  Ile Ala Gly Asp Pro  Ala Leu Ala Tyr Gly  Tyr Ala Gln
    1115                1120                1125

Asp Gln  Glu Pro Asp Ala Arg  Gly Arg Ile Arg Asn  Gly Ala Leu
    1130                1135                1140

Leu Arg  Val Tyr Val Pro Arg  Ser Ser Leu Pro Gly  Phe Tyr Arg
    1145                1150                1155

Thr Ser  Leu Thr Leu Ala Ala  Pro Glu Ala Ala Gly  Glu Val Glu
    1160                1165                1170

Arg Leu  Ile Gly His Pro Leu  Pro Leu Arg Leu Asp  Ala Ile Thr
    1175                1180                1185

Gly Pro  Glu Glu Glu Gly Gly  Arg Leu Glu Thr Ile  Leu Gly Trp
```

```
                1190                1195                1200

Pro Leu Ala Glu Arg Thr Val Val Ile Pro Ser Ala Ile Pro Thr
                1205                1210                1215

Asp Pro Arg Asn Val Gly Gly Asp Leu Asp Pro Ser Ser Ile Pro
                1220                1225                1230

Asp Lys Glu Gln Ala Ile Ser Ala Leu Pro Asp Tyr Ala Ser Gln
                1235                1240                1245

Pro Gly Lys Pro Pro Arg Lys Asp Glu Leu
                1250                1255

<210> SEQ ID NO 65
<211> LENGTH: 1374
<212> TYPE: PRT
<213> ORGANISM: Artificial
<220> FEATURE:
<223> OTHER INFORMATION: Artificial construct

<400> SEQUENCE: 65

Arg Pro Asp Phe Cys Leu Glu Pro Pro Tyr Thr Gly Pro Cys Lys Ala
1               5                   10                  15

Arg Ile Ile Arg Tyr Phe Tyr Asn Ala Lys Ala Gly Leu Cys Gln Thr
            20                  25                  30

Phe Val Tyr Gly Gly Cys Arg Ala Lys Arg Asn Asn Phe Lys Ser Ala
        35                  40                  45

Glu Asp Cys Met Arg Thr Cys Gly Gly Ala Asn His Ser Asp Ser Gly
    50                  55                  60

Lys Tyr Asp Pro Cys Glu Lys Lys Leu Pro Pro Tyr Asp Asp Asn Asp
65                  70                  75                  80

Gln Trp Lys Cys Gln Gln Asn Ser Ser Asp Gly Ser Gly Lys Pro Glu
                85                  90                  95

Asn Ile Cys Val Pro Pro Arg Arg Glu Arg Leu Cys Thr Tyr Asn Leu
            100                 105                 110

Glu Asn Leu Lys Phe Asp Lys Ile Arg Asp Asn Asn Ala Phe Leu Ala
        115                 120                 125

Asp Val Leu Leu Thr Ala Arg Asn Glu Gly Glu Lys Ile Val Gln Asn
    130                 135                 140

His Pro Asp Thr Asn Ser Ser Asn Val Cys Asn Ala Leu Glu Arg Ser
145                 150                 155                 160

Phe Ala Asp Leu Ala Asp Ile Ile Arg Gly Thr Asp Gln Trp Lys Gly
                165                 170                 175

Thr Asn Ser Asn Leu Glu Lys Asn Leu Lys Gln Met Phe Ala Lys Ile
            180                 185                 190

Arg Glu Asn Asp Lys Val Leu Gln Asp Lys Tyr Pro Lys Asp Gln Lys
        195                 200                 205

Tyr Thr Lys Leu Arg Glu Ala Trp Trp Asn Ala Asn Arg Gln Lys Val
    210                 215                 220

Trp Glu Val Ile Thr Cys Gly Ala Arg Ser Asn Asp Leu Leu Ile Lys
225                 230                 235                 240

Arg Gly Trp Arg Thr Ser Gly Lys Ser Asp Arg Lys Lys Asn Phe Glu
                245                 250                 255

Leu Cys Arg Lys Cys Gly His Tyr Glu Lys Glu Val Pro Thr Lys Leu
            260                 265                 270

Asp Tyr Val Pro Gln Phe Leu Arg Trp Leu Thr Glu Trp Ile Glu Asp
        275                 280                 285

Phe Tyr Arg Glu Lys Gln Asn Leu Ile Asp Asp Met Glu Arg His Arg
```

-continued

```
            290                 295                 300
Glu Glu Cys Thr Arg Glu Asp His Lys Ser Lys Gly Thr Ser Tyr
305                 310                 315                 320
Cys Ser Thr Cys Lys Asp Lys Cys Lys Lys Tyr Cys Glu Cys Val Lys
                325                 330                 335
Lys Trp Lys Thr Glu Trp Glu Asn Gln Glu Asn Lys Tyr Lys Asp Leu
                340                 345                 350
Tyr Glu Gln Asn Lys Asn Lys Thr Ser Gln Lys Asn Thr Ser Arg Tyr
                355                 360                 365
Asp Asp Tyr Val Lys Asp Phe Phe Glu Lys Leu Glu Ala Asn Tyr Ser
        370                 375                 380
Ser Leu Glu Asn Tyr Ile Lys Gly Asp Pro Tyr Phe Ala Glu Tyr Ala
385                 390                 395                 400
Thr Lys Leu Ser Phe Ile Leu Asn Pro Ser Asp Ala Asn Asn Pro Ser
                405                 410                 415
Gly Glu Thr Ala Asn His Asn Asp Glu Ala Cys Asn Cys Asn Glu Ser
                420                 425                 430
Gly Ile Ser Ser Val Gly Gln Ala Gln Thr Ser Gly Pro Ser Ser Asn
                435                 440                 445
Lys Thr Cys Ile Thr His Ser Ser Ile Lys Thr Asn Lys Lys Lys Glu
                450                 455                 460
Cys Lys Asp Val Lys Leu Gly Val Arg Glu Asn Asp Lys Asp Leu Lys
465                 470                 475                 480
Ile Cys Val Ile Glu Asp Thr Ser Leu Ser Gly Val Asp Asn Cys Cys
                485                 490                 495
Cys Gln Asp Leu Leu Gly Ile Leu Gln Glu Asn Cys Ser Asp Asn Lys
                500                 505                 510
Arg Gly Ser Ser Ser Asn Asp Ser Cys Asp Asn Lys Asn Gln Asp Glu
                515                 520                 525
Cys Gln Lys Lys Leu Glu Lys Val Phe Ala Ser Leu Thr Asn Gly Tyr
                530                 535                 540
Lys Cys Asp Lys Cys Lys Ser Gly Thr Ser Arg Ser Lys Lys Lys Trp
545                 550                 555                 560
Ile Trp Lys Lys Ser Ser Gly Asn Glu Glu Gly Leu Gln Glu Glu Tyr
                565                 570                 575
Ala Asn Thr Ile Gly Leu Pro Pro Arg Thr Gln Ser Leu Tyr Leu Gly
                580                 585                 590
Asn Leu Pro Lys Leu Glu Asn Val Cys Glu Asp Val Lys Asp Ile Asn
                595                 600                 605
Phe Asp Thr Lys Glu Lys Phe Leu Ala Gly Cys Leu Ile Val Ser Phe
        610                 615                 620
His Glu Gly Lys Asn Leu Lys Lys Arg Tyr Pro Gln Asn Lys Asn Ser
625                 630                 635                 640
Gly Asn Lys Glu Asn Leu Cys Lys Ala Leu Glu Tyr Ser Phe Ala Asp
                645                 650                 655
Tyr Gly Asp Leu Ile Lys Gly Thr Ser Ile Trp Asp Asn Glu Tyr Thr
                660                 665                 670
Lys Asp Leu Glu Leu Asn Leu Gln Asn Asn Phe Gly Lys Leu Phe Gly
                675                 680                 685
Lys Tyr Ile Lys Lys Asn Asn Thr Ala Glu Gln Asp Thr Ser Tyr Ser
                690                 695                 700
Ser Leu Asp Glu Leu Arg Glu Ser Trp Trp Asn Thr Asn Lys Lys Tyr
705                 710                 715                 720
```

Ile Trp Thr Ala Met Lys His Gly Ala Glu Met Asn Ile Thr Thr Cys
            725                 730                 735

Asn Ala Asp Gly Ser Val Thr Gly Ser Gly Ser Ser Cys Asp Asp Ile
            740                 745                 750

Pro Thr Ile Asp Leu Ile Pro Gln Tyr Leu Arg Phe Leu Gln Glu Trp
            755                 760                 765

Val Glu Asn Phe Cys Glu Gln Arg Gln Ala Lys Val Lys Asp Val Ile
            770                 775                 780

Thr Asn Cys Lys Ser Cys Lys Glu Ser Gly Asn Lys Cys Lys Thr Glu
785                 790                 795                 800

Cys Lys Thr Lys Cys Lys Asp Glu Cys Glu Lys Tyr Lys Lys Phe Ile
            805                 810                 815

Glu Ala Cys Gly Thr Ala Gly Gly Ile Gly Thr Ala Gly Ser Pro
            820                 825                 830

Trp Ser Lys Arg Trp Asp Gln Ile Tyr Lys Arg Tyr Ser Lys His Ile
            835                 840                 845

Glu Asp Ala Lys Arg Asn Arg Lys Ala Gly Thr Lys Asn Cys Gly Thr
850                 855                 860

Ser Ser Thr Thr Asn Ala Ala Ser Thr Asp Glu Asn Lys Cys Val
865                 870                 875                 880

Gln Ser Asp Ile Asp Ser Phe Phe Lys His Leu Ile Asp Ile Gly Leu
            885                 890                 895

Thr Thr Pro Ser Ser Tyr Leu Ser Asn Val Leu Asp Asp Asn Ile Cys
            900                 905                 910

Gly Ala Asp Lys Ala Pro Trp Thr Thr Tyr Thr Thr Tyr Thr Thr Thr
            915                 920                 925

Glu Lys Cys Asn Lys Glu Arg Asp Lys Ser Lys Ser Gln Ser Ser Asp
930                 935                 940

Thr Leu Val Val Val Asn Val Pro Ser Pro Leu Gly Asn Thr Pro Tyr
945                 950                 955                 960

Arg Tyr Lys Tyr Ala Cys Gln Cys Lys Ile Pro Thr Asn Glu Glu Thr
            965                 970                 975

Cys Asp Asp Arg Lys Glu Tyr Met Asn Gln Trp Ser Cys Gly Ser Ala
            980                 985                 990

Arg Thr Met Lys Arg Gly Tyr Lys Asn Asp Asn Tyr Glu Leu Cys Lys
            995                 1000                1005

Tyr Asn Gly Val Asp Val Lys Pro Thr Thr Val Arg Ser Asn Ser
1010                1015                1020

Ser Lys Leu Asp Pro Glu Gly Gly Ser Leu Ala Ala Leu Thr Ala
1025                1030                1035

His Gln Ala Cys His Leu Pro Leu Glu Thr Phe Thr Arg His Arg
1040                1045                1050

Gln Pro Arg Gly Trp Glu Gln Leu Glu Gln Cys Gly Tyr Pro Val
1055                1060                1065

Gln Arg Leu Val Ala Leu Tyr Leu Ala Ala Arg Leu Ser Trp Asn
1070                1075                1080

Gln Val Asp Gln Val Ile Arg Asn Ala Leu Ala Ser Pro Gly Ser
1085                1090                1095

Gly Gly Asp Leu Gly Glu Ala Ile Arg Glu Gln Pro Glu Gln Ala
1100                1105                1110

Arg Leu Ala Leu Thr Leu Ala Ala Ala Glu Ser Glu Arg Phe Val
1115                1120                1125

-continued

Arg Gln Gly Thr Gly Asn Asp Glu Ala Gly Ala Ala Asn Gly Pro
    1130            1135            1140

Ala Asp Ser Gly Asp Ala Leu Leu Glu Arg Asn Tyr Pro Thr Gly
    1145            1150            1155

Ala Glu Phe Leu Gly Asp Gly Asp Ile Ser Phe Ser Thr Arg
    1160            1165            1170

Gly Thr Gln Asn Trp Thr Val Glu Arg Leu Leu Gln Ala His Arg
    1175            1180            1185

Gln Leu Glu Glu Arg Gly Tyr Val Phe Val Gly Tyr His Gly Thr
    1190            1195            1200

Phe Leu Glu Ala Ala Gln Ser Ile Val Phe Gly Val Arg Ala
    1205            1210            1215

Arg Ser Gln Asp Leu Asp Ala Ile Trp Arg Gly Phe Tyr Ile Ala
    1220            1225            1230

Gly Asp Pro Ala Leu Ala Tyr Gly Tyr Ala Gln Asp Gln Glu Pro
    1235            1240            1245

Asp Ala Arg Gly Arg Ile Arg Asn Gly Ala Leu Leu Arg Val Tyr
    1250            1255            1260

Val Pro Arg Ser Ser Leu Pro Gly Phe Tyr Arg Thr Ser Leu Thr
    1265            1270            1275

Leu Ala Ala Pro Glu Ala Ala Gly Glu Val Glu Arg Leu Ile Gly
    1280            1285            1290

His Pro Leu Pro Leu Arg Leu Asp Ala Ile Thr Gly Pro Glu Glu
    1295            1300            1305

Glu Gly Gly Arg Leu Glu Thr Ile Leu Gly Trp Pro Leu Ala Glu
    1310            1315            1320

Arg Thr Val Val Ile Pro Ser Ala Ile Pro Thr Asp Pro Arg Asn
    1325            1330            1335

Val Gly Gly Asp Leu Asp Pro Ser Ser Ile Pro Asp Lys Glu Gln
    1340            1345            1350

Ala Ile Ser Ala Leu Pro Asp Tyr Ala Ser Gln Pro Gly Lys Pro
    1355            1360            1365

Pro Arg Lys Asp Glu Leu
    1370

<210> SEQ ID NO 66
<211> LENGTH: 1200
<212> TYPE: PRT
<213> ORGANISM: Artificial
<220> FEATURE:
<223> OTHER INFORMATION: Artificial construct

<400> SEQUENCE: 66

Asn His Ser Asp Ser Gly Lys Tyr Asp Pro Cys Glu Lys Leu Pro
1               5               10              15

Pro Tyr Asp Asp Asn Asp Gln Trp Lys Cys Gln Gln Asn Ser Ser Asp
                20              25              30

Gly Ser Gly Lys Pro Glu Asn Ile Cys Val Pro Arg Arg Glu Arg
            35              40              45

Leu Cys Thr Tyr Asn Leu Glu Asn Leu Lys Phe Asp Lys Ile Arg Asp
    50              55              60

Asn Asn Ala Phe Leu Ala Asp Val Leu Leu Thr Ala Arg Asn Glu Gly
65              70              75              80

Glu Lys Ile Val Gln Asn His Pro Asp Thr Asn Ser Ser Asn Val Cys
                85              90              95

```
Asn Ala Leu Glu Arg Ser Phe Ala Asp Leu Ala Asp Ile Ile Arg Gly
                100                 105                 110

Thr Asp Gln Trp Lys Gly Thr Asn Ser Asn Leu Glu Lys Asn Leu Lys
        115                 120                 125

Gln Met Phe Ala Lys Ile Arg Glu Asn Asp Lys Val Leu Gln Asp Lys
    130                 135                 140

Tyr Pro Lys Asp Gln Lys Tyr Thr Lys Leu Arg Glu Ala Trp Trp Asn
145                 150                 155                 160

Ala Asn Arg Gln Lys Val Trp Glu Val Ile Thr Cys Gly Ala Arg Ser
                165                 170                 175

Asn Asp Leu Leu Ile Lys Arg Gly Trp Arg Thr Ser Gly Lys Ser Asp
        180                 185                 190

Arg Lys Lys Asn Phe Glu Leu Cys Arg Lys Cys Gly His Tyr Glu Lys
    195                 200                 205

Glu Val Pro Thr Lys Leu Asp Tyr Val Pro Gln Phe Leu Arg Trp Leu
    210                 215                 220

Thr Glu Trp Ile Glu Asp Phe Tyr Arg Glu Lys Gln Asn Leu Ile Asp
225                 230                 235                 240

Asp Met Glu Arg His Arg Glu Glu Cys Thr Arg Glu Asp His Lys Ser
                245                 250                 255

Lys Glu Gly Thr Ser Tyr Cys Ser Thr Cys Lys Asp Lys Cys Lys Lys
        260                 265                 270

Tyr Cys Glu Cys Val Lys Lys Trp Lys Thr Glu Trp Glu Asn Gln Glu
    275                 280                 285

Asn Lys Tyr Lys Asp Leu Tyr Glu Gln Asn Lys Asn Lys Thr Ser Gln
    290                 295                 300

Lys Asn Thr Ser Arg Tyr Asp Asp Tyr Val Lys Asp Phe Phe Glu Lys
305                 310                 315                 320

Leu Glu Ala Asn Tyr Ser Ser Leu Glu Asn Tyr Ile Lys Gly Asp Pro
                325                 330                 335

Tyr Phe Ala Glu Tyr Ala Thr Lys Leu Ser Phe Ile Leu Asn Pro Ser
        340                 345                 350

Asp Ala Asn Asn Pro Ser Gly Glu Thr Ala Asn His Asn Asp Glu Ala
    355                 360                 365

Cys Asn Cys Asn Glu Ser Gly Ile Ser Ser Val Gly Gln Ala Gln Thr
    370                 375                 380

Ser Gly Pro Ser Ser Asn Lys Thr Cys Ile Thr His Ser Ser Ile Lys
385                 390                 395                 400

Thr Asn Lys Lys Lys Glu Cys Lys Asp Val Lys Leu Gly Val Arg Glu
                405                 410                 415

Asn Asp Lys Asp Leu Lys Ile Cys Val Ile Glu Asp Thr Ser Leu Ser
        420                 425                 430

Gly Val Asp Asn Cys Cys Cys Gln Asp Leu Leu Gly Ile Leu Gln Glu
    435                 440                 445

Asn Cys Ser Asp Asn Lys Arg Gly Ser Ser Ser Asn Asp Ser Cys Asp
    450                 455                 460

Asn Lys Asn Gln Asp Glu Cys Gln Lys Lys Leu Glu Lys Val Phe Ala
465                 470                 475                 480

Ser Leu Thr Asn Gly Tyr Lys Cys Asp Lys Cys Lys Ser Gly Thr Ser
                485                 490                 495

Arg Ser Lys Lys Lys Trp Ile Trp Lys Lys Ser Ser Gly Asn Glu Glu
        500                 505                 510

Gly Leu Gln Glu Glu Tyr Ala Asn Thr Ile Gly Leu Pro Pro Arg Thr
```

-continued

```
            515                 520                 525
Gln Ser Leu Tyr Leu Gly Asn Leu Pro Lys Leu Glu Asn Val Cys Glu
530                 535                 540

Asp Val Lys Asp Ile Asn Phe Asp Thr Lys Glu Lys Phe Leu Ala Gly
545                 550                 555                 560

Cys Leu Ile Val Ser Phe His Glu Gly Lys Asn Leu Lys Arg Tyr
                565                 570                 575

Pro Gln Asn Lys Asn Ser Gly Asn Lys Glu Asn Leu Cys Lys Ala Leu
                580                 585                 590

Glu Tyr Ser Phe Ala Asp Tyr Gly Asp Leu Ile Lys Gly Thr Ser Ile
                595                 600                 605

Trp Asp Asn Glu Tyr Thr Lys Asp Leu Glu Leu Asn Leu Gln Asn Asn
610                 615                 620

Phe Gly Lys Leu Phe Gly Lys Tyr Ile Lys Lys Asn Asn Thr Ala Glu
625                 630                 635                 640

Gln Asp Thr Ser Tyr Ser Ser Leu Asp Glu Leu Arg Glu Ser Trp Trp
                645                 650                 655

Asn Thr Asn Lys Lys Tyr Ile Trp Thr Ala Met Lys His Gly Ala Glu
                660                 665                 670

Met Asn Ile Thr Thr Cys Asn Ala Asp Gly Ser Val Thr Gly Ser Gly
                675                 680                 685

Ser Ser Cys Asp Asp Ile Pro Thr Ile Asp Leu Ile Pro Gln Tyr Leu
690                 695                 700

Arg Phe Leu Gln Glu Trp Val Glu Asn Phe Cys Glu Gln Arg Gln Ala
705                 710                 715                 720

Lys Val Lys Asp Val Ile Thr Asn Cys Lys Ser Cys Lys Glu Ser Gly
                725                 730                 735

Asn Lys Cys Lys Thr Glu Cys Lys Thr Lys Cys Lys Asp Glu Cys Glu
                740                 745                 750

Lys Tyr Lys Lys Phe Ile Glu Ala Cys Gly Thr Ala Gly Gly Ile
                755                 760                 765

Gly Thr Ala Gly Ser Pro Trp Ser Lys Arg Trp Asp Gln Ile Tyr Lys
770                 775                 780

Arg Tyr Ser Lys His Ile Glu Asp Ala Lys Arg Asn Arg Lys Ala Gly
785                 790                 795                 800

Thr Lys Asn Cys Gly Thr Ser Ser Thr Thr Asn Ala Ala Ala Ser Thr
                805                 810                 815

Asp Glu Asn Lys Cys Val Gln Ser Asp Ile Asp Ser Phe Phe Lys His
                820                 825                 830

Leu Ile Asp Ile Gly Leu Thr Thr Pro Ser Ser Tyr Leu Ser Asn Val
835                 840                 845

Leu Asp Asp Asn Ile Cys Gly Ala Asp Lys Ala Pro Trp Thr Thr Tyr
850                 855                 860

Thr Thr Tyr Thr Thr Thr Glu Lys Cys Asn Lys Glu Arg Asp Lys Ser
865                 870                 875                 880

Lys Ser Gln Ser Ser Asp Thr Leu Val Val Asn Val Pro Ser Pro
                885                 890                 895

Leu Gly Asn Thr Pro Tyr Arg Tyr Lys Tyr Ala Cys Gln Cys Lys Ile
                900                 905                 910

Pro Thr Asn Glu Glu Thr Cys Asp Asp Arg Lys Glu Tyr Met Asn Gln
                915                 920                 925

Trp Ser Cys Gly Ser Ala Arg Thr Met Lys Arg Gly Tyr Lys Asn Asp
930                 935                 940
```

-continued

```
Asn Tyr Glu Leu Cys Lys Tyr Asn Gly Val Asp Val Lys Pro Thr Thr
945                 950                 955                 960

Val Arg Ser Asn Ser Ser Lys Leu Asp Arg His Arg Gln Pro Arg Gly
                965                 970                 975

Trp Glu Gln Leu Tyr Pro Thr Gly Ala Glu Phe Leu Gly Asp Gly Gly
            980                 985                 990

Asp Ile Ser Phe Ser Thr Arg Gly Thr Gln Asn Trp Thr Val Glu Arg
        995                 1000                1005

Leu Leu Gln Ala His Arg Gln Leu Glu Arg Gly Tyr Val Phe
    1010                1015                1020

Val Gly Tyr His Gly Thr Phe Leu Glu Ala Ala Gln Ser Ile Val
    1025                1030                1035

Phe Gly Gly Val Arg Ala Arg Ser Gln Asp Leu Asp Ala Ile Trp
    1040                1045                1050

Arg Gly Phe Tyr Ile Ala Gly Asp Pro Ala Leu Ala Tyr Gly Tyr
    1055                1060                1065

Ala Gln Asp Gln Glu Pro Asp Ala Arg Gly Arg Ile Arg Asn Gly
    1070                1075                1080

Ala Leu Leu Arg Val Tyr Val Pro Arg Ser Ser Leu Pro Gly Phe
    1085                1090                1095

Tyr Arg Thr Ser Leu Thr Leu Ala Ala Pro Glu Ala Ala Gly Glu
    1100                1105                1110

Val Glu Arg Leu Ile Gly His Pro Leu Pro Leu Arg Leu Asp Ala
    1115                1120                1125

Ile Thr Gly Pro Glu Glu Gly Gly Arg Leu Glu Thr Ile Leu
    1130                1135                1140

Gly Trp Pro Leu Ala Glu Arg Thr Val Val Ile Pro Ser Ala Ile
    1145                1150                1155

Pro Thr Asp Pro Arg Asn Val Gly Gly Asp Leu Asp Pro Ser Ser
    1160                1165                1170

Ile Pro Asp Lys Glu Gln Ala Ile Ser Ala Leu Pro Asp Tyr Ala
    1175                1180                1185

Ser Gln Pro Gly Lys Pro Pro Arg Lys Asp Glu Leu
    1190                1195                1200

<210> SEQ ID NO 67
<211> LENGTH: 1316
<212> TYPE: PRT
<213> ORGANISM: Artificial
<220> FEATURE:
<223> OTHER INFORMATION: Artificial construct

<400> SEQUENCE: 67

Asn His Ser Asp Ser Gly Lys Tyr Asp Pro Cys Glu Lys Lys Leu Pro
1               5                   10                  15

Pro Tyr Asp Asp Asn Asp Gln Trp Lys Cys Gln Gln Asn Ser Ser Asp
            20                  25                  30

Gly Ser Gly Lys Pro Glu Asn Ile Cys Val Pro Pro Arg Arg Glu Arg
        35                  40                  45

Leu Cys Thr Tyr Asn Leu Glu Asn Leu Lys Phe Asp Lys Ile Arg Asp
    50                  55                  60

Asn Asn Ala Phe Leu Ala Asp Val Leu Leu Thr Ala Arg Asn Glu Gly
65                  70                  75                  80

Glu Lys Ile Val Gln Asn His Pro Asp Thr Asn Ser Ser Asn Val Cys
                85                  90                  95
```

-continued

```
Asn Ala Leu Glu Arg Ser Phe Ala Asp Leu Ala Asp Ile Ile Arg Gly
            100                 105                 110

Thr Asp Gln Trp Lys Gly Thr Asn Ser Asn Leu Glu Lys Asn Leu Lys
        115                 120                 125

Gln Met Phe Ala Lys Ile Arg Glu Asn Asp Lys Val Leu Gln Asp Lys
    130                 135                 140

Tyr Pro Lys Asp Gln Lys Tyr Thr Lys Leu Arg Glu Ala Trp Trp Asn
145                 150                 155                 160

Ala Asn Arg Gln Lys Val Trp Glu Val Ile Thr Cys Gly Ala Arg Ser
                165                 170                 175

Asn Asp Leu Leu Ile Lys Arg Gly Trp Arg Thr Ser Gly Lys Ser Asp
            180                 185                 190

Arg Lys Lys Asn Phe Glu Leu Cys Arg Lys Cys Gly His Tyr Glu Lys
        195                 200                 205

Glu Val Pro Thr Lys Leu Asp Tyr Val Pro Gln Phe Leu Arg Trp Leu
    210                 215                 220

Thr Glu Trp Ile Glu Asp Phe Tyr Arg Glu Lys Gln Asn Leu Ile Asp
225                 230                 235                 240

Asp Met Glu Arg His Arg Glu Glu Cys Thr Arg Glu Asp His Lys Ser
                245                 250                 255

Lys Glu Gly Thr Ser Tyr Cys Ser Thr Cys Lys Asp Lys Cys Lys Lys
            260                 265                 270

Tyr Cys Glu Cys Val Lys Lys Trp Lys Thr Glu Trp Glu Asn Gln Glu
        275                 280                 285

Asn Lys Tyr Lys Asp Leu Tyr Glu Gln Asn Lys Asn Lys Thr Ser Gln
    290                 295                 300

Lys Asn Thr Ser Arg Tyr Asp Asp Tyr Val Lys Asp Phe Phe Glu Lys
305                 310                 315                 320

Leu Glu Ala Asn Tyr Ser Ser Leu Glu Asn Tyr Ile Lys Gly Asp Pro
                325                 330                 335

Tyr Phe Ala Glu Tyr Ala Thr Lys Leu Ser Phe Ile Leu Asn Pro Ser
            340                 345                 350

Asp Ala Asn Asn Pro Ser Gly Glu Thr Ala Asn His Asn Asp Glu Ala
        355                 360                 365

Cys Asn Cys Asn Glu Ser Gly Ile Ser Ser Val Gly Gln Ala Gln Thr
    370                 375                 380

Ser Gly Pro Ser Ser Asn Lys Thr Cys Ile Thr His Ser Ser Ile Lys
385                 390                 395                 400

Thr Asn Lys Lys Lys Glu Cys Lys Asp Val Lys Leu Gly Val Arg Glu
                405                 410                 415

Asn Asp Lys Asp Leu Lys Ile Cys Val Ile Glu Asp Thr Ser Leu Ser
            420                 425                 430

Gly Val Asp Asn Cys Cys Cys Gln Asp Leu Leu Gly Ile Leu Gln Glu
        435                 440                 445

Asn Cys Ser Asp Asn Lys Arg Gly Ser Ser Ser Asn Asp Ser Cys Asp
    450                 455                 460

Asn Lys Asn Gln Asp Glu Cys Gln Lys Lys Leu Glu Lys Val Phe Ala
465                 470                 475                 480

Ser Leu Thr Asn Gly Tyr Lys Cys Asp Lys Cys Lys Ser Gly Thr Ser
                485                 490                 495

Arg Ser Lys Lys Lys Trp Ile Trp Lys Lys Ser Ser Gly Asn Glu Glu
            500                 505                 510
```

-continued

Gly Leu Gln Glu Glu Tyr Ala Asn Thr Ile Gly Leu Pro Pro Arg Thr
            515                 520                 525

Gln Ser Leu Tyr Leu Gly Asn Leu Pro Lys Leu Glu Asn Val Cys Glu
530                 535                 540

Asp Val Lys Asp Ile Asn Phe Asp Thr Lys Glu Lys Phe Leu Ala Gly
545                 550                 555                 560

Cys Leu Ile Val Ser Phe His Glu Gly Lys Asn Leu Lys Lys Arg Tyr
                565                 570                 575

Pro Gln Asn Lys Asn Ser Gly Asn Glu Asn Leu Cys Lys Ala Leu
            580                 585                 590

Glu Tyr Ser Phe Ala Asp Tyr Gly Asp Leu Ile Lys Gly Thr Ser Ile
    595                 600                 605

Trp Asp Asn Glu Tyr Thr Lys Asp Leu Glu Leu Asn Leu Gln Asn Asn
    610                 615                 620

Phe Gly Lys Leu Phe Gly Lys Tyr Ile Lys Lys Asn Asn Thr Ala Glu
625                 630                 635                 640

Gln Asp Thr Ser Tyr Ser Ser Leu Asp Glu Leu Arg Glu Ser Trp Trp
                645                 650                 655

Asn Thr Asn Lys Lys Tyr Ile Trp Thr Ala Met Lys His Gly Ala Glu
            660                 665                 670

Met Asn Ile Thr Thr Cys Asn Ala Asp Gly Ser Val Thr Gly Ser Gly
        675                 680                 685

Ser Ser Cys Asp Asp Ile Pro Thr Ile Asp Leu Ile Pro Gln Tyr Leu
    690                 695                 700

Arg Phe Leu Gln Glu Trp Val Glu Asn Phe Cys Glu Gln Arg Gln Ala
705                 710                 715                 720

Lys Val Lys Asp Val Ile Thr Asn Cys Lys Ser Cys Lys Glu Ser Gly
                725                 730                 735

Asn Lys Cys Lys Thr Glu Cys Lys Thr Lys Cys Lys Asp Glu Cys Glu
            740                 745                 750

Lys Tyr Lys Lys Phe Ile Glu Ala Cys Gly Thr Ala Gly Gly Gly Ile
    755                 760                 765

Gly Thr Ala Gly Ser Pro Trp Ser Lys Arg Trp Asp Gln Ile Tyr Lys
770                 775                 780

Arg Tyr Ser Lys His Ile Glu Asp Ala Lys Arg Asn Arg Lys Ala Gly
785                 790                 795                 800

Thr Lys Asn Cys Gly Thr Ser Ser Thr Thr Asn Ala Ala Ala Ser Thr
                805                 810                 815

Asp Glu Asn Lys Cys Val Gln Ser Asp Ile Asp Ser Phe Phe Lys His
            820                 825                 830

Leu Ile Asp Ile Gly Leu Thr Thr Pro Ser Ser Tyr Leu Ser Asn Val
    835                 840                 845

Leu Asp Asp Asn Ile Cys Gly Ala Asp Lys Ala Pro Trp Thr Thr Tyr
850                 855                 860

Thr Thr Tyr Thr Thr Thr Glu Lys Cys Asn Lys Glu Arg Asp Lys Ser
865                 870                 875                 880

Lys Ser Gln Ser Ser Asp Thr Leu Val Val Val Asn Val Pro Ser Pro
                885                 890                 895

Leu Gly Asn Thr Pro Tyr Arg Tyr Lys Tyr Ala Cys Gln Cys Lys Ile
            900                 905                 910

Pro Thr Asn Glu Glu Thr Cys Asp Asp Arg Lys Glu Tyr Met Asn Gln
    915                 920                 925

Trp Ser Cys Gly Ser Ala Arg Thr Met Lys Arg Gly Tyr Lys Asn Asp

```
            930                 935                 940
Asn Tyr Glu Leu Cys Lys Tyr Asn Gly Val Asp Val Lys Pro Thr Thr
945                 950                 955                 960

Val Arg Ser Asn Ser Ser Lys Leu Asp Pro Glu Gly Ser Leu Ala
            965                 970                 975

Ala Leu Thr Ala His Gln Ala Cys His Leu Pro Leu Glu Thr Phe Thr
                980                 985                 990

Arg His Arg Gln Pro Arg Gly Trp Glu Gln Leu Glu Gln Cys Gly Tyr
            995                 1000                1005

Pro Val Gln Arg Leu Val Ala Leu Tyr Leu Ala Ala Arg Leu Ser
    1010                1015                1020

Trp Asn Gln Val Asp Gln Val Ile Arg Asn Ala Leu Ala Ser Pro
    1025                1030                1035

Gly Ser Gly Gly Asp Leu Gly Glu Ala Ile Arg Glu Gln Pro Glu
    1040                1045                1050

Gln Ala Arg Leu Ala Leu Thr Leu Ala Ala Ala Glu Ser Glu Arg
    1055                1060                1065

Phe Val Arg Gln Gly Thr Gly Asn Asp Glu Ala Gly Ala Ala Asn
    1070                1075                1080

Gly Pro Ala Asp Ser Gly Asp Ala Leu Leu Glu Arg Asn Tyr Pro
    1085                1090                1095

Thr Gly Ala Glu Phe Leu Gly Asp Gly Gly Asp Ile Ser Phe Ser
    1100                1105                1110

Thr Arg Gly Thr Gln Asn Trp Thr Val Glu Arg Leu Leu Gln Ala
    1115                1120                1125

His Arg Gln Leu Glu Glu Arg Gly Tyr Val Phe Val Gly Tyr His
    1130                1135                1140

Gly Thr Phe Leu Glu Ala Ala Gln Ser Ile Val Phe Gly Gly Val
    1145                1150                1155

Arg Ala Arg Ser Gln Asp Leu Asp Ala Ile Trp Arg Gly Phe Tyr
    1160                1165                1170

Ile Ala Gly Asp Pro Ala Leu Ala Tyr Gly Tyr Ala Gln Asp Gln
    1175                1180                1185

Glu Pro Asp Ala Arg Gly Arg Ile Arg Asn Gly Ala Leu Leu Arg
    1190                1195                1200

Val Tyr Val Pro Arg Ser Ser Leu Pro Gly Phe Tyr Arg Thr Ser
    1205                1210                1215

Leu Thr Leu Ala Ala Pro Glu Ala Ala Gly Glu Val Glu Arg Leu
    1220                1225                1230

Ile Gly His Pro Leu Pro Leu Arg Leu Asp Ala Ile Thr Gly Pro
    1235                1240                1245

Glu Glu Glu Gly Gly Arg Leu Glu Thr Ile Leu Gly Trp Pro Leu
    1250                1255                1260

Ala Glu Arg Thr Val Val Ile Pro Ser Ala Ile Pro Thr Asp Pro
    1265                1270                1275

Arg Asn Val Gly Gly Asp Leu Asp Pro Ser Ser Ile Pro Asp Lys
    1280                1285                1290

Glu Gln Ala Ile Ser Ala Leu Pro Asp Tyr Ala Ser Gln Pro Gly
    1295                1300                1305

Lys Pro Pro Arg Lys Asp Glu Leu
    1310                1315

<210> SEQ ID NO 68
```

```
<211> LENGTH: 964
<212> TYPE: PRT
<213> ORGANISM: Artificial
<220> FEATURE:
<223> OTHER INFORMATION: Artificial construct

<400> SEQUENCE: 68

Leu Ser Phe Ile Leu Asn Ser Ser Asp Ala Asn Asn Pro Ser Glu Lys
1               5                   10                  15

Ile Gln Lys Asn Asn Asp Glu Val Cys Asn Cys Asn Glu Ser Gly Ile
            20                  25                  30

Ala Ser Val Glu Gln Glu Gln Ile Ser Asp Pro Ser Ser Asn Lys Thr
        35                  40                  45

Cys Ile Thr His Ser Ser Ile Lys Ala Asn Lys Lys Lys Val Cys Lys
    50                  55                  60

His Val Lys Leu Gly Val Arg Glu Asn Asp Lys Asp Leu Arg Val Cys
65                  70                  75                  80

Val Ile Glu His Thr Ser Leu Ser Gly Val Glu Asn Cys Cys Cys Gln
                85                  90                  95

Asp Phe Leu Arg Ile Leu Gln Glu Asn Cys Ser Asp Asn Lys Ser Gly
            100                 105                 110

Ser Ser Ser Asn Gly Ser Cys Asn Asn Lys Asn Gln Glu Ala Cys Glu
        115                 120                 125

Lys Asn Leu Glu Lys Val Leu Ala Ser Leu Thr Asn Cys Tyr Lys Cys
130                 135                 140

Asp Lys Cys Lys Ser Glu Gln Ser Lys Asn Asn Lys Asn Trp Ile
145                 150                 155                 160

Trp Lys Lys Ser Ser Gly Lys Glu Gly Leu Gln Lys Glu Tyr Ala
                165                 170                 175

Asn Thr Ile Gly Leu Pro Pro Arg Thr Gln Ser Leu Cys Leu Val Val
            180                 185                 190

Cys Leu Asp Glu Lys Gly Lys Lys Thr Gln Glu Leu Lys Asn Ile Arg
        195                 200                 205

Thr Asn Ser Glu Leu Leu Lys Glu Trp Ile Ile Ala Ala Phe His Glu
210                 215                 220

Gly Lys Asn Leu Lys Pro Ser His Glu Lys Lys Asn Asp Asp Asn Gly
225                 230                 235                 240

Lys Lys Leu Cys Lys Ala Leu Glu Tyr Ser Phe Ala Asp Tyr Gly Asp
                245                 250                 255

Leu Ile Lys Gly Thr Ser Ile Trp Asp Asn Glu Tyr Thr Lys Asp Leu
            260                 265                 270

Glu Leu Asn Leu Gln Lys Ile Phe Gly Lys Leu Phe Arg Lys Tyr Ile
        275                 280                 285

Lys Lys Asn Asn Thr Ala Glu Gln Asp Thr Ser Tyr Ser Ser Leu Asp
290                 295                 300

Glu Leu Arg Glu Ser Trp Trp Asn Thr Asn Lys Lys Tyr Ile Trp Leu
305                 310                 315                 320

Ala Met Lys His Gly Ala Gly Met Asn Ser Thr Thr Cys Cys Gly Asp
                325                 330                 335

Gly Ser Val Thr Gly Ser Gly Ser Ser Cys Asp Asp Ile Pro Thr Ile
            340                 345                 350

Asp Leu Ile Pro Gln Tyr Leu Arg Phe Leu Gln Glu Trp Val Glu His
        355                 360                 365

Phe Cys Lys Gln Arg Gln Glu Lys Val Lys Pro Val Ile Glu Asn Cys
370                 375                 380
```

```
Lys Ser Cys Lys Glu Ser Gly Gly Thr Cys Asn Gly Glu Cys Lys Thr
385                 390                 395                 400

Glu Cys Lys Asn Lys Cys Glu Val Tyr Lys Phe Ile Glu Asp Cys
            405                 410                 415

Lys Gly Gly Asp Gly Thr Ala Gly Ser Ser Trp Val Lys Arg Trp Asp
            420                 425                 430

Gln Ile Tyr Lys Arg Tyr Ser Lys Tyr Ile Glu Asp Ala Lys Arg Asn
            435                 440                 445

Arg Lys Ala Gly Thr Lys Asn Cys Gly Pro Ser Ser Thr Thr Asn Ala
        450                 455                 460

Ala Glu Asn Lys Cys Val Gln Ser Asp Ile Asp Ser Phe Phe Lys His
465                 470                 475                 480

Leu Ile Asp Ile Gly Leu Thr Thr Pro Ser Ser Tyr Leu Ser Ile Val
                485                 490                 495

Leu Asp Asp Asn Ile Cys Gly Ala Asp Lys Ala Pro Trp Thr Thr Tyr
            500                 505                 510

Thr Thr Tyr Thr Thr Thr Glu Lys Cys Asn Lys Glu Thr Asp Lys Ser
            515                 520                 525

Lys Leu Gln Gln Cys Asn Thr Ala Val Val Asn Val Pro Ser Pro
530                 535                 540

Leu Gly Asn Thr Pro His Gly Tyr Lys Tyr Ala Cys Gln Cys Lys Ile
545                 550                 555                 560

Pro Thr Asn Glu Glu Thr Cys Asp Asp Arg Lys Glu Tyr Met Asn Gln
                565                 570                 575

Trp Ser Cys Gly Ser Ala Arg Thr Met Lys Arg Gly Tyr Lys Asn Asp
            580                 585                 590

Asn Tyr Glu Leu Cys Lys Tyr Asn Gly Val Asp Val Lys Pro Thr Thr
            595                 600                 605

Val Arg Ser Asn Ser Ser Lys Leu Asp Pro Glu Gly Gly Ser Leu Ala
        610                 615                 620

Ala Leu Thr Ala His Gln Ala Cys His Leu Pro Leu Glu Thr Phe Thr
625                 630                 635                 640

Arg His Arg Gln Pro Arg Gly Trp Glu Gln Leu Glu Gln Cys Gly Tyr
                645                 650                 655

Pro Val Gln Arg Leu Val Ala Leu Tyr Leu Ala Ala Arg Leu Ser Trp
            660                 665                 670

Asn Gln Val Asp Gln Val Ile Arg Asn Ala Leu Ala Ser Pro Gly Ser
            675                 680                 685

Gly Gly Asp Leu Gly Glu Ala Ile Arg Glu Gln Pro Glu Gln Ala Arg
            690                 695                 700

Leu Ala Leu Thr Leu Ala Ala Ala Glu Ser Glu Arg Phe Val Arg Gln
705                 710                 715                 720

Gly Thr Gly Asn Asp Glu Ala Gly Ala Ala Asn Gly Pro Ala Asp Ser
            725                 730                 735

Gly Asp Ala Leu Leu Glu Arg Asn Tyr Pro Thr Gly Ala Glu Phe Leu
            740                 745                 750

Gly Asp Gly Gly Asp Ile Ser Phe Ser Thr Arg Gly Thr Gln Asn Trp
            755                 760                 765

Thr Val Glu Arg Leu Leu Gln Ala His Arg Gln Leu Glu Glu Arg Gly
        770                 775                 780

Tyr Val Phe Val Gly Tyr His Gly Thr Phe Leu Glu Ala Ala Gln Ser
785                 790                 795                 800
```

```
Ile Val Phe Gly Gly Val Arg Ala Arg Ser Gln Asp Leu Asp Ala Ile
            805                 810                 815

Trp Arg Gly Phe Tyr Ile Ala Gly Asp Pro Ala Leu Ala Tyr Gly Tyr
        820                 825                 830

Ala Gln Asp Gln Glu Pro Asp Ala Arg Gly Arg Ile Arg Asn Gly Ala
    835                 840                 845

Leu Leu Arg Val Tyr Val Pro Arg Ser Ser Leu Pro Gly Phe Tyr Arg
850                 855                 860

Thr Ser Leu Thr Leu Ala Ala Pro Glu Ala Ala Gly Glu Val Glu Arg
865                 870                 875                 880

Leu Ile Gly His Pro Leu Pro Leu Arg Leu Asp Ala Ile Thr Gly Pro
                885                 890                 895

Glu Glu Glu Gly Gly Arg Leu Glu Thr Ile Leu Gly Trp Pro Leu Ala
            900                 905                 910

Glu Arg Thr Val Val Ile Pro Ser Ala Ile Pro Thr Asp Pro Arg Asn
        915                 920                 925

Val Gly Gly Asp Leu Asp Pro Ser Ser Ile Pro Asp Lys Glu Gln Ala
    930                 935                 940

Ile Ser Ala Leu Pro Asp Tyr Ala Ser Gln Pro Gly Lys Pro Pro Arg
945                 950                 955                 960

Lys Asp Glu Leu

<210> SEQ ID NO 69
<211> LENGTH: 848
<212> TYPE: PRT
<213> ORGANISM: Artificial
<220> FEATURE:
<223> OTHER INFORMATION: Artificial construct

<400> SEQUENCE: 69

Leu Ser Phe Ile Leu Asn Ser Ser Asp Ala Asn Asn Pro Ser Glu Lys
1               5                   10                  15

Ile Gln Lys Asn Asn Asp Glu Val Cys Asn Cys Asn Glu Ser Gly Ile
            20                  25                  30

Ala Ser Val Glu Gln Glu Gln Ile Ser Asp Pro Ser Ser Asn Lys Thr
        35                  40                  45

Cys Ile Thr His Ser Ser Ile Lys Ala Asn Lys Lys Val Cys Lys
50                  55                  60

His Val Lys Leu Gly Val Arg Glu Asn Asp Lys Asp Leu Arg Val Cys
65                  70                  75                  80

Val Ile Glu His Thr Ser Leu Ser Gly Val Glu Asn Cys Cys Cys Gln
                85                  90                  95

Asp Phe Leu Arg Ile Leu Gln Glu Asn Cys Ser Asp Asn Lys Ser Gly
            100                 105                 110

Ser Ser Ser Asn Gly Ser Cys Asn Asn Lys Asn Gln Glu Ala Cys Glu
        115                 120                 125

Lys Asn Leu Glu Lys Val Leu Ala Ser Leu Thr Asn Cys Tyr Lys Cys
    130                 135                 140

Asp Lys Cys Lys Ser Glu Gln Ser Lys Lys Asn Asn Lys Asn Trp Ile
145                 150                 155                 160

Trp Lys Lys Ser Ser Gly Lys Glu Gly Gly Leu Gln Lys Glu Tyr Ala
                165                 170                 175

Asn Thr Ile Gly Leu Pro Pro Arg Thr Gln Ser Leu Cys Leu Val Val
            180                 185                 190

Cys Leu Asp Glu Lys Gly Lys Lys Thr Gln Glu Leu Lys Asn Ile Arg
```

```
            195                 200                 205
Thr Asn Ser Glu Leu Leu Lys Glu Trp Ile Ile Ala Ala Phe His Glu
210                 215                 220

Gly Lys Asn Leu Lys Pro Ser His Glu Lys Lys Asn Asp Asp Asn Gly
225                 230                 235                 240

Lys Lys Leu Cys Lys Ala Leu Glu Tyr Ser Phe Ala Asp Tyr Gly Asp
                    245                 250                 255

Leu Ile Lys Gly Thr Ser Ile Trp Asp Asn Glu Tyr Thr Lys Asp Leu
                260                 265                 270

Glu Leu Asn Leu Gln Lys Ile Phe Gly Lys Leu Phe Arg Lys Tyr Ile
                275                 280                 285

Lys Lys Asn Asn Thr Ala Glu Gln Asp Thr Ser Tyr Ser Ser Leu Asp
290                 295                 300

Glu Leu Arg Glu Ser Trp Trp Asn Thr Asn Lys Lys Tyr Ile Trp Leu
305                 310                 315                 320

Ala Met Lys His Gly Ala Gly Met Asn Ser Thr Thr Cys Cys Gly Asp
                    325                 330                 335

Gly Ser Val Thr Gly Ser Gly Ser Ser Cys Asp Asp Ile Pro Thr Ile
                340                 345                 350

Asp Leu Ile Pro Gln Tyr Leu Arg Phe Leu Gln Glu Trp Val Glu His
                355                 360                 365

Phe Cys Lys Gln Arg Gln Glu Lys Val Lys Pro Val Ile Glu Asn Cys
370                 375                 380

Lys Ser Cys Lys Glu Ser Gly Gly Thr Cys Asn Gly Glu Cys Lys Thr
385                 390                 395                 400

Glu Cys Lys Asn Lys Cys Glu Val Tyr Lys Lys Phe Ile Glu Asp Cys
                    405                 410                 415

Lys Gly Gly Asp Gly Thr Ala Gly Ser Ser Trp Val Lys Arg Trp Asp
                420                 425                 430

Gln Ile Tyr Lys Arg Tyr Ser Lys Tyr Ile Glu Asp Ala Lys Arg Asn
                435                 440                 445

Arg Lys Ala Gly Thr Lys Asn Cys Gly Pro Ser Ser Thr Thr Asn Ala
450                 455                 460

Ala Glu Asn Lys Cys Val Gln Ser Asp Ile Asp Ser Phe Phe Lys His
465                 470                 475                 480

Leu Ile Asp Ile Gly Leu Thr Thr Pro Ser Ser Tyr Leu Ser Ile Val
                    485                 490                 495

Leu Asp Asp Asn Ile Cys Gly Ala Asp Lys Ala Pro Trp Thr Thr Tyr
                500                 505                 510

Thr Thr Tyr Thr Thr Thr Glu Lys Cys Asn Lys Glu Thr Asp Lys Ser
                515                 520                 525

Lys Leu Gln Gln Cys Asn Thr Ala Val Val Val Asn Val Pro Ser Pro
530                 535                 540

Leu Gly Asn Thr Pro His Gly Tyr Lys Tyr Ala Cys Gln Cys Lys Ile
545                 550                 555                 560

Pro Thr Asn Glu Glu Thr Cys Asp Asp Arg Lys Glu Tyr Met Asn Gln
                    565                 570                 575

Trp Ser Cys Gly Ser Ala Arg Thr Met Lys Arg Gly Tyr Lys Asn Asp
                580                 585                 590

Asn Tyr Glu Leu Cys Lys Tyr Asn Gly Val Asp Val Lys Pro Thr Thr
                595                 600                 605

Val Arg Ser Asn Ser Ser Lys Leu Asp Arg His Arg Gln Pro Arg Gly
610                 615                 620
```

Trp Glu Gln Leu Tyr Pro Thr Gly Ala Glu Phe Leu Gly Asp Gly Gly
625                 630                 635                 640

Asp Ile Ser Phe Ser Thr Arg Gly Thr Gln Asn Trp Thr Val Glu Arg
                645                 650                 655

Leu Leu Gln Ala His Arg Gln Leu Glu Glu Arg Gly Tyr Val Phe Val
            660                 665                 670

Gly Tyr His Gly Thr Phe Leu Glu Ala Ala Gln Ser Ile Val Phe Gly
        675                 680                 685

Gly Val Arg Ala Arg Ser Gln Asp Leu Asp Ala Ile Trp Arg Gly Phe
690                 695                 700

Tyr Ile Ala Gly Asp Pro Ala Leu Ala Tyr Gly Tyr Ala Gln Asp Gln
705                 710                 715                 720

Glu Pro Asp Ala Arg Gly Arg Ile Arg Asn Gly Ala Leu Leu Arg Val
                725                 730                 735

Tyr Val Pro Arg Ser Ser Leu Pro Gly Phe Tyr Arg Thr Ser Leu Thr
            740                 745                 750

Leu Ala Ala Pro Glu Ala Ala Gly Glu Val Glu Arg Leu Ile Gly His
        755                 760                 765

Pro Leu Pro Leu Arg Leu Asp Ala Ile Thr Gly Pro Glu Glu Glu Gly
770                 775                 780

Gly Arg Leu Glu Thr Ile Leu Gly Trp Pro Leu Ala Glu Arg Thr Val
785                 790                 795                 800

Val Ile Pro Ser Ala Ile Pro Thr Asp Pro Arg Asn Val Gly Gly Asp
                805                 810                 815

Leu Asp Pro Ser Ser Ile Pro Asp Lys Glu Gln Ala Ile Ser Ala Leu
            820                 825                 830

Pro Asp Tyr Ala Ser Gln Pro Gly Lys Pro Pro Arg Lys Asp Glu Leu
        835                 840                 845

<210> SEQ ID NO 70
<211> LENGTH: 808
<212> TYPE: PRT
<213> ORGANISM: Artificial
<220> FEATURE:
<223> OTHER INFORMATION: Artificial construct

<400> SEQUENCE: 70

Asn Tyr Ile Lys Gly Asp Pro Tyr Phe Ala Glu Tyr Ala Thr Lys Leu
1               5                   10                  15

Ser Phe Ile Leu Asn Pro Ser Asp Ala Asn Pro Ser Gly Glu Thr
            20                  25                  30

Ala Asn His Asn Asp Glu Ala Cys Asn Cys Asn Glu Ser Gly Ile Ser
        35                  40                  45

Ser Val Gly Gln Ala Gln Thr Ser Gly Pro Ser Ser Asn Lys Thr Cys
    50                  55                  60

Ile Thr His Ser Ser Ile Lys Thr Asn Lys Lys Glu Cys Lys Asp
65                  70                  75                  80

Val Lys Leu Gly Val Arg Glu Asn Asp Lys Asp Leu Lys Ile Cys Val
                85                  90                  95

Ile Glu Asp Thr Ser Leu Ser Gly Val Asp Asn Cys Cys Cys Gln Asp
            100                 105                 110

Leu Leu Gly Ile Leu Gln Glu Asn Cys Ser Asp Asn Lys Arg Gly Ser
        115                 120                 125

Ser Ser Asn Asp Ser Cys Asp Asn Lys Asn Gln Asp Glu Cys Gln Lys
    130                 135                 140

```
Lys Leu Glu Lys Val Phe Ala Ser Leu Thr Asn Gly Tyr Lys Cys Asp
145                 150                 155                 160

Lys Cys Lys Ser Gly Thr Ser Arg Ser Lys Lys Trp Ile Trp Lys
            165                 170                 175

Lys Ser Ser Gly Asn Glu Glu Gly Leu Gln Glu Glu Tyr Ala Asn Thr
            180                 185                 190

Ile Gly Leu Pro Pro Arg Thr Gln Ser Leu Tyr Leu Gly Asn Leu Pro
            195                 200                 205

Lys Leu Glu Asn Val Cys Glu Asp Val Lys Asp Ile Asn Phe Asp Thr
210                 215                 220

Lys Glu Lys Phe Leu Ala Gly Cys Leu Ile Val Ser Phe His Glu Gly
225                 230                 235                 240

Lys Asn Leu Lys Lys Arg Tyr Pro Gln Asn Lys Asn Ser Gly Asn Lys
            245                 250                 255

Glu Asn Leu Cys Lys Ala Leu Glu Tyr Ser Phe Ala Asp Tyr Gly Asp
            260                 265                 270

Leu Ile Lys Gly Thr Ser Ile Trp Asp Asn Glu Tyr Thr Lys Asp Leu
            275                 280                 285

Glu Leu Asn Leu Gln Asn Asn Phe Gly Lys Leu Phe Gly Lys Tyr Ile
            290                 295                 300

Lys Lys Asn Asn Thr Ala Glu Gln Asp Thr Ser Tyr Ser Ser Leu Asp
305                 310                 315                 320

Glu Leu Arg Glu Ser Trp Trp Asn Thr Asn Lys Lys Tyr Ile Trp Thr
            325                 330                 335

Ala Met Lys His Gly Ala Glu Met Asn Ile Thr Thr Cys Asn Ala Asp
            340                 345                 350

Gly Ser Val Thr Gly Ser Gly Ser Ser Cys Asp Asp Ile Pro Thr Ile
            355                 360                 365

Asp Leu Ile Pro Gln Tyr Leu Arg Phe Leu Gln Glu Trp Val Glu Asn
370                 375                 380

Phe Cys Glu Gln Arg Gln Ala Lys Val Lys Asp Val Ile Thr Asn Cys
385                 390                 395                 400

Lys Ser Cys Lys Glu Ser Gly Asn Lys Cys Lys Thr Glu Cys Lys Thr
            405                 410                 415

Lys Cys Lys Asp Glu Cys Glu Lys Tyr Lys Lys Phe Ile Glu Ala Cys
            420                 425                 430

Gly Thr Ala Gly Gly Ile Gly Thr Ala Gly Ser Pro Trp Ser Lys
            435                 440                 445

Arg Trp Asp Gln Ile Tyr Lys Arg Tyr Ser Lys His Ile Glu Asp Ala
    450                 455                 460

Lys Arg Asn Arg Lys Ala Gly Thr Lys Asn Cys Gly Thr Ser Ser Thr
465                 470                 475                 480

Thr Asn Ala Ala Ala Ser Thr Asp Glu Asn Lys Cys Val Gln Ser Asp
                485                 490                 495

Ile Asp Ser Phe Phe Lys His Leu Ile Asp Ile Gly Leu Thr Thr Pro
            500                 505                 510

Ser Ser Tyr Leu Ser Asn Val Leu Asp Asp Asn Ile Cys Gly Ala Asp
            515                 520                 525

Lys Ala Pro Trp Thr Thr Tyr Thr Thr Tyr Thr Thr Glu Lys Cys
530                 535                 540

Asn Lys Glu Arg Asp Lys Ser Lys Ser Gln Ser Ser Asp Thr Leu Val
545                 550                 555                 560
```

Val Val Asn Val Pro Ser Pro Leu Gly Asn Thr Pro Tyr Arg Tyr Lys
            565                 570                 575

Tyr Arg His Arg Gln Pro Arg Gly Trp Glu Gln Leu Tyr Pro Thr Gly
        580                 585                 590

Ala Glu Phe Leu Gly Asp Gly Gly Asp Ile Ser Phe Ser Thr Arg Gly
        595                 600                 605

Thr Gln Asn Trp Thr Val Glu Arg Leu Leu Gln Ala His Arg Gln Leu
    610                 615                 620

Glu Glu Arg Gly Tyr Val Phe Val Gly Tyr His Gly Thr Phe Leu Glu
625                 630                 635                 640

Ala Ala Gln Ser Ile Val Phe Gly Gly Val Arg Ala Arg Ser Gln Asp
                645                 650                 655

Leu Asp Ala Ile Trp Arg Gly Phe Tyr Ile Ala Gly Asp Pro Ala Leu
            660                 665                 670

Ala Tyr Gly Tyr Ala Gln Asp Gln Glu Pro Asp Ala Arg Gly Arg Ile
        675                 680                 685

Arg Asn Gly Ala Leu Leu Arg Val Tyr Val Pro Arg Ser Ser Leu Pro
    690                 695                 700

Gly Phe Tyr Arg Thr Ser Leu Thr Leu Ala Ala Pro Glu Ala Ala Gly
705                 710                 715                 720

Glu Val Glu Arg Leu Ile Gly His Pro Leu Pro Leu Arg Leu Asp Ala
                725                 730                 735

Ile Thr Gly Pro Glu Glu Gly Gly Arg Leu Glu Thr Ile Leu Gly
            740                 745                 750

Trp Pro Leu Ala Glu Arg Thr Val Val Ile Pro Ser Ala Ile Pro Thr
        755                 760                 765

Asp Pro Arg Asn Val Gly Gly Asp Leu Asp Pro Ser Ser Ile Pro Asp
    770                 775                 780

Lys Glu Gln Ala Ile Ser Ala Leu Pro Asp Tyr Ala Ser Gln Pro Gly
785                 790                 795                 800

Lys Pro Pro Arg Lys Asp Glu Leu
                805

<210> SEQ ID NO 71
<211> LENGTH: 393
<212> TYPE: PRT
<213> ORGANISM: Artificial
<220> FEATURE:
<223> OTHER INFORMATION: Artificial construct

<400> SEQUENCE: 71

Met Gly Ala Asp Asp Val Val Asp Ser Ser Lys Ser Phe Val Met Glu
1               5                   10                  15

Asn Phe Ser Ser Tyr His Gly Thr Lys Pro Gly Tyr Val Asp Ser Ile
            20                  25                  30

Gln Lys Gly Ile Gln Lys Pro Lys Ser Gly Thr Gln Gly Asn Tyr Asp
        35                  40                  45

Asp Asp Trp Lys Gly Phe Tyr Ser Thr Asp Asn Lys Tyr Asp Ala Ala
    50                  55                  60

Gly Tyr Ser Val Asp Asn Glu Asn Pro Leu Ser Gly Lys Ala Gly Gly
65                  70                  75                  80

Val Val Lys Val Thr Tyr Pro Gly Leu Thr Lys Val Leu Ala Leu Lys
                85                  90                  95

Val Asp Asn Ala Glu Thr Ile Lys Lys Glu Leu Gly Leu Ser Leu Thr
            100                 105                 110

```
Glu Pro Leu Met Glu Gln Val Gly Thr Glu Phe Ile Lys Arg Phe
            115                 120                 125

Gly Asp Gly Ala Ser Arg Val Val Leu Ser Leu Pro Phe Ala Glu Gly
130                 135                 140

Ser Ser Ser Val Glu Tyr Ile Asn Asn Trp Glu Gln Ala Lys Ala Leu
145                 150                 155                 160

Ser Val Glu Leu Glu Ile Asn Phe Glu Thr Arg Gly Lys Arg Gly Gln
                165                 170                 175

Asp Ala Met Tyr Glu Tyr Met Ala Gln Ala Cys Ala Gly Asn Arg Val
            180                 185                 190

Arg Arg Ser Val Gly Ser Ser Leu Ser Cys Ile Asn Leu Asp Trp Asp
        195                 200                 205

Val Ile Arg Asp Lys Thr Lys Thr Lys Ile Glu Ser Leu Lys Glu His
    210                 215                 220

Gly Pro Ile Lys Asn Lys Met Ser Glu Ser Pro Asn Lys Thr Val Ser
225                 230                 235                 240

Glu Glu Lys Ala Lys Gln Tyr Leu Glu Glu Phe His Gln Thr Ala Leu
                245                 250                 255

Glu His Pro Glu Leu Ser Glu Leu Lys Thr Val Thr Gly Thr Asn Pro
            260                 265                 270

Val Phe Ala Gly Ala Asn Tyr Ala Ala Trp Ala Val Asn Val Ala Gln
        275                 280                 285

Val Ile Asp Ser Glu Thr Ala Asp Asn Leu Glu Lys Thr Thr Ala Ala
    290                 295                 300

Leu Ser Ile Leu Pro Gly Ile Gly Ser Val Met Gly Ile Ala Asp Gly
305                 310                 315                 320

Ala Val His His Asn Thr Glu Glu Ile Val Ala Gln Ser Ile Ala Leu
                325                 330                 335

Ser Ser Leu Met Val Ala Gln Ala Ile Pro Leu Val Gly Glu Leu Val
            340                 345                 350

Asp Ile Gly Phe Ala Ala Tyr Asn Phe Val Glu Ser Ile Ile Asn Leu
        355                 360                 365

Phe Gln Val Val His Asn Ser Tyr Asn Arg Pro Ala Tyr Ser Pro Gly
    370                 375                 380

His Lys Thr Gln Pro Met His Glu Phe
385                 390

<210> SEQ ID NO 72
<211> LENGTH: 1356
<212> TYPE: PRT
<213> ORGANISM: Artificial
<220> FEATURE:
<223> OTHER INFORMATION: Artificial construct

<400> SEQUENCE: 72

Met Gly Ala Asp Asp Val Val Asp Ser Ser Lys Ser Phe Val Met Glu
1               5                   10                  15

Asn Phe Ser Ser Tyr His Gly Thr Lys Pro Gly Tyr Val Asp Ser Ile
                20                  25                  30

Gln Lys Gly Ile Gln Lys Pro Lys Ser Gly Thr Gln Gly Asn Tyr Asp
            35                  40                  45

Asp Asp Trp Lys Gly Phe Tyr Ser Thr Asp Asn Lys Tyr Asp Ala Ala
        50                  55                  60

Gly Tyr Ser Val Asp Asn Glu Asn Pro Leu Ser Gly Lys Ala Gly Gly
65                  70                  75                  80
```

```
Val Val Lys Val Thr Tyr Pro Gly Leu Thr Lys Val Leu Ala Leu Lys
             85                  90                  95

Val Asp Asn Ala Glu Thr Ile Lys Lys Glu Leu Gly Leu Ser Leu Thr
            100                 105                 110

Glu Pro Leu Met Glu Gln Val Gly Thr Glu Glu Phe Ile Lys Arg Phe
            115                 120                 125

Gly Asp Gly Ala Ser Arg Val Val Leu Ser Leu Pro Phe Ala Glu Gly
            130                 135                 140

Ser Ser Ser Val Glu Tyr Ile Asn Asn Trp Glu Gln Ala Lys Ala Leu
145                 150                 155                 160

Ser Val Glu Leu Glu Ile Asn Phe Glu Thr Arg Gly Lys Arg Gly Gln
                165                 170                 175

Asp Ala Met Tyr Glu Tyr Met Ala Gln Ala Cys Ala Gly Asn Arg Val
            180                 185                 190

Arg Arg Ser Val Gly Ser Ser Leu Ser Cys Ile Asn Leu Asp Trp Asp
            195                 200                 205

Val Ile Arg Asp Lys Thr Lys Thr Lys Ile Glu Ser Leu Lys Glu His
            210                 215                 220

Gly Pro Ile Lys Asn Lys Met Ser Glu Ser Pro Asn Lys Thr Val Ser
225                 230                 235                 240

Glu Glu Lys Ala Lys Gln Tyr Leu Glu Glu Phe His Gln Thr Ala Leu
                245                 250                 255

Glu His Pro Glu Leu Ser Glu Leu Lys Thr Val Thr Gly Thr Asn Pro
            260                 265                 270

Val Phe Ala Gly Ala Asn Tyr Ala Ala Trp Ala Val Asn Val Ala Gln
            275                 280                 285

Val Ile Asp Ser Glu Thr Ala Asp Asn Leu Glu Lys Thr Thr Ala Ala
            290                 295                 300

Leu Ser Ile Leu Pro Gly Ile Gly Ser Val Met Gly Ile Ala Asp Gly
305                 310                 315                 320

Ala Val His His Asn Thr Glu Glu Ile Val Ala Gln Ser Ile Ala Leu
                325                 330                 335

Ser Ser Leu Met Val Ala Gln Ala Ile Pro Leu Val Gly Glu Leu Val
            340                 345                 350

Asp Ile Gly Phe Ala Ala Tyr Asn Phe Val Glu Ser Ile Ile Asn Leu
            355                 360                 365

Phe Gln Val Val His Asn Ser Tyr Asn Arg Pro Ala Tyr Ser Pro Gly
            370                 375                 380

His Lys Thr Gln Pro Met His Glu Phe His Ser Asp Ser Gly Thr Asn
385                 390                 395                 400

Asp Pro Cys Asp Arg Ile Pro Pro Tyr Gly Asp Asn Asp Gln Trp
            405                 410                 415

Lys Cys Ala Ile Ile Leu Ser Lys Val Ser Glu Lys Pro Glu Asn Val
            420                 425                 430

Phe Val Pro Pro Arg Arg Gln Arg Met Cys Ile Asn Asn Leu Glu Lys
            435                 440                 445

Leu Asn Val Asp Lys Ile Arg Asp Lys His Ala Phe Leu Ala Asp Val
            450                 455                 460

Leu Leu Thr Ala Arg Asn Glu Gly Glu Arg Ile Val Gln Asn His Pro
465                 470                 475                 480

Asp Thr Asn Ser Ser Asn Val Cys Asn Ala Leu Glu Arg Ser Phe Ala
                485                 490                 495

Asp Ile Ala Asp Ile Ile Arg Gly Thr Asp Leu Trp Lys Gly Thr Asn
```

-continued

```
                500                 505                 510
Ser Asn Leu Glu Gln Asn Leu Lys Gln Met Phe Ala Lys Ile Arg Glu
            515                 520                 525

Asn Asp Lys Val Leu Gln Asp Lys Tyr Pro Lys Asp Gln Asn Tyr Arg
530                 535                 540

Lys Leu Arg Glu Asp Trp Trp Asn Ala Asn Arg Gln Lys Val Trp Glu
545                 550                 555                 560

Val Ile Thr Cys Gly Ala Arg Ser Asn Asp Leu Leu Ile Lys Arg Gly
                565                 570                 575

Trp Arg Thr Ser Gly Lys Ser Asn Gly Asp Asn Lys Leu Glu Leu Cys
            580                 585                 590

Arg Lys Cys Gly His Tyr Glu Glu Lys Val Pro Thr Lys Leu Asp Tyr
            595                 600                 605

Val Pro Gln Phe Leu Arg Trp Leu Thr Glu Trp Ile Glu Asp Phe Tyr
        610                 615                 620

Arg Glu Lys Gln Asn Leu Ile Asp Asp Met Glu Arg His Arg Glu Glu
625                 630                 635                 640

Cys Thr Ser Glu Asp His Lys Ser Lys Glu Gly Thr Ser Tyr Cys Ser
                645                 650                 655

Thr Cys Lys Asp Lys Cys Lys Lys Tyr Cys Glu Cys Val Lys Lys Trp
                660                 665                 670

Lys Ser Glu Trp Glu Asn Gln Lys Asn Lys Tyr Thr Glu Leu Tyr Gln
            675                 680                 685

Gln Asn Lys Asn Glu Thr Ser Gln Lys Asn Thr Ser Arg Tyr Asp Asp
        690                 695                 700

Tyr Val Lys Asp Phe Phe Lys Lys Leu Glu Ala Asn Tyr Ser Ser Leu
705                 710                 715                 720

Glu Asn Tyr Ile Lys Gly Asp Pro Tyr Phe Ala Glu Tyr Ala Thr Lys
                725                 730                 735

Leu Ser Phe Ile Leu Asn Ser Ser Asp Ala Asn Asn Pro Ser Glu Lys
            740                 745                 750

Ile Gln Lys Asn Asn Asp Glu Val Cys Asn Cys Asn Glu Ser Gly Ile
        755                 760                 765

Ala Ser Val Glu Gln Glu Gln Ile Ser Asp Pro Ser Ser Asn Lys Thr
        770                 775                 780

Cys Ile Thr His Ser Ser Ile Lys Ala Asn Lys Lys Val Cys Lys
785                 790                 795                 800

His Val Lys Leu Gly Val Arg Glu Asn Asp Lys Asp Leu Arg Val Cys
                805                 810                 815

Val Ile Glu His Thr Ser Leu Ser Gly Val Glu Asn Cys Cys Cys Gln
                820                 825                 830

Asp Phe Leu Arg Ile Leu Gln Glu Asn Cys Ser Asp Asn Lys Ser Gly
            835                 840                 845

Ser Ser Ser Asn Gly Ser Cys Asn Asn Lys Asn Gln Glu Ala Cys Glu
            850                 855                 860

Lys Asn Leu Glu Lys Val Leu Ala Ser Leu Thr Asn Cys Tyr Lys Cys
865                 870                 875                 880

Asp Lys Cys Lys Ser Glu Gln Ser Lys Lys Asn Asn Lys Asn Trp Ile
                885                 890                 895

Trp Lys Lys Ser Ser Gly Lys Glu Gly Gly Leu Gln Lys Glu Tyr Ala
            900                 905                 910

Asn Thr Ile Gly Leu Pro Pro Arg Thr Gln Ser Leu Cys Leu Val Val
            915                 920                 925
```

-continued

```
Cys Leu Asp Glu Lys Gly Lys Thr Gln Glu Leu Lys Asn Ile Arg
    930                 935                 940

Thr Asn Ser Glu Leu Leu Lys Glu Trp Ile Ile Ala Ala Phe His Glu
945                 950                 955                 960

Gly Lys Asn Leu Lys Pro Ser His Glu Lys Asn Asp Asp Asn Gly
                965                 970                 975

Lys Lys Leu Cys Lys Ala Leu Glu Tyr Ser Phe Ala Asp Tyr Gly Asp
            980                 985                 990

Leu Ile Lys Gly Thr Ser Ile Trp Asp Asn Glu Tyr Thr Lys Asp Leu
        995                 1000                1005

Glu Leu Asn Leu Gln Lys Ile Phe Gly Lys Leu Phe Arg Lys Tyr
    1010                1015                1020

Ile Lys Lys Asn Asn Thr Ala Glu Gln Asp Thr Ser Tyr Ser Ser
    1025                1030                1035

Leu Asp Glu Leu Arg Glu Ser Trp Trp Asn Thr Asn Lys Lys Tyr
    1040                1045                1050

Ile Trp Leu Ala Met Lys His Gly Ala Gly Met Asn Ser Thr Thr
    1055                1060                1065

Cys Cys Gly Asp Gly Ser Val Thr Gly Ser Gly Ser Ser Cys Asp
    1070                1075                1080

Asp Ile Pro Thr Ile Asp Leu Ile Pro Gln Tyr Leu Arg Phe Leu
    1085                1090                1095

Gln Glu Trp Val Glu His Phe Cys Lys Gln Arg Gln Glu Lys Val
    1100                1105                1110

Lys Pro Val Ile Glu Asn Cys Lys Ser Cys Lys Glu Ser Gly Gly
    1115                1120                1125

Thr Cys Asn Gly Glu Cys Lys Thr Glu Cys Lys Asn Lys Cys Glu
    1130                1135                1140

Val Tyr Lys Lys Phe Ile Glu Asp Cys Lys Gly Gly Asp Gly Thr
    1145                1150                1155

Ala Gly Ser Ser Trp Val Lys Arg Trp Asp Gln Ile Tyr Lys Arg
    1160                1165                1170

Tyr Ser Lys Tyr Ile Glu Asp Ala Lys Arg Asn Arg Lys Ala Gly
    1175                1180                1185

Thr Lys Asn Cys Gly Pro Ser Ser Thr Thr Asn Ala Ala Glu Asn
    1190                1195                1200

Lys Cys Val Gln Ser Asp Ile Asp Ser Phe Phe Lys His Leu Ile
    1205                1210                1215

Asp Ile Gly Leu Thr Thr Pro Ser Ser Tyr Leu Ser Ile Val Leu
    1220                1225                1230

Asp Asp Asn Ile Cys Gly Ala Asp Lys Ala Pro Trp Thr Thr Tyr
    1235                1240                1245

Thr Thr Tyr Thr Thr Thr Glu Lys Cys Asn Lys Glu Thr Asp Lys
    1250                1255                1260

Ser Lys Leu Gln Gln Cys Asn Thr Ala Val Val Val Asn Val Pro
    1265                1270                1275

Ser Pro Leu Gly Asn Thr Pro His Gly Tyr Lys Tyr Ala Cys Gln
    1280                1285                1290

Cys Lys Ile Pro Thr Asn Glu Glu Thr Cys Asp Asp Arg Lys Glu
    1295                1300                1305

Tyr Met Asn Gln Trp Ser Cys Gly Ser Ala Arg Thr Met Lys Arg
    1310                1315                1320
```

-continued

Gly Tyr Lys Asn Asp Asn Tyr Glu Leu Cys Lys Tyr Asn Gly Val
    1325                1330                1335

Asp Val Lys Pro Thr Thr Val Arg Ser Asn Ser Ser Lys Leu Asp
    1340                1345                1350

Ser Gly Arg
    1355

<210> SEQ ID NO 73
<211> LENGTH: 1364
<212> TYPE: PRT
<213> ORGANISM: Artificial
<220> FEATURE:
<223> OTHER INFORMATION: Artificial construct

<400> SEQUENCE: 73

Met Gly Ala Asp Asp Val Val Asp Ser Ser Lys Ser Phe Val Met Glu
1               5                   10                  15

Asn Phe Ser Ser Tyr His Gly Thr Lys Pro Gly Tyr Val Asp Ser Ile
            20                  25                  30

Gln Lys Gly Ile Gln Lys Pro Lys Ser Gly Thr Gln Gly Asn Tyr Asp
        35                  40                  45

Asp Asp Trp Lys Gly Phe Tyr Ser Thr Asp Asn Lys Tyr Asp Ala Ala
    50                  55                  60

Gly Tyr Ser Val Asp Asn Glu Asn Pro Leu Ser Gly Lys Ala Gly Gly
65                  70                  75                  80

Val Val Lys Val Thr Tyr Pro Gly Leu Thr Lys Val Leu Ala Leu Lys
                85                  90                  95

Val Asp Asn Ala Glu Thr Ile Lys Lys Glu Leu Gly Leu Ser Leu Thr
            100                 105                 110

Glu Pro Leu Met Glu Gln Val Gly Thr Glu Glu Phe Ile Lys Arg Phe
        115                 120                 125

Gly Asp Gly Ala Ser Arg Val Val Leu Ser Leu Pro Phe Ala Glu Gly
    130                 135                 140

Ser Ser Ser Val Glu Tyr Ile Asn Asn Trp Glu Gln Ala Lys Ala Leu
145                 150                 155                 160

Ser Val Glu Leu Glu Ile Asn Phe Glu Thr Arg Gly Lys Arg Gly Gln
                165                 170                 175

Asp Ala Met Tyr Glu Tyr Met Ala Gln Ala Cys Ala Gly Asn Arg Val
            180                 185                 190

Arg Arg Ser Val Gly Ser Ser Leu Ser Cys Ile Asn Leu Asp Trp Asp
        195                 200                 205

Val Ile Arg Asp Lys Thr Lys Thr Lys Ile Glu Ser Leu Lys Glu His
    210                 215                 220

Gly Pro Ile Lys Asn Lys Met Ser Glu Ser Pro Asn Lys Thr Val Ser
225                 230                 235                 240

Glu Glu Lys Ala Lys Gln Tyr Leu Glu Glu Phe His Gln Thr Ala Leu
                245                 250                 255

Glu His Pro Glu Leu Ser Glu Leu Lys Thr Val Thr Gly Thr Asn Pro
            260                 265                 270

Val Phe Ala Gly Ala Asn Tyr Ala Ala Trp Ala Val Asn Val Ala Gln
        275                 280                 285

Val Ile Asp Ser Glu Thr Ala Asp Asn Leu Glu Lys Thr Thr Ala Ala
    290                 295                 300

Leu Ser Ile Leu Pro Gly Ile Gly Ser Val Met Gly Ile Ala Asp Gly
305                 310                 315                 320

-continued

```
Ala Val His His Asn Thr Glu Glu Ile Val Ala Gln Ser Ile Ala Leu
                325                 330                 335

Ser Ser Leu Met Val Ala Gln Ala Ile Pro Leu Val Gly Glu Leu Val
            340                 345                 350

Asp Ile Gly Phe Ala Ala Tyr Asn Phe Val Glu Ser Ile Ile Asn Leu
        355                 360                 365

Phe Gln Val Val His Asn Ser Tyr Asn Arg Pro Ala Tyr Ser Pro Gly
    370                 375                 380

His Lys Thr Gln Pro Met His Glu Phe His Ser Asp Ser Gly Lys Tyr
385                 390                 395                 400

Asp Pro Cys Glu Lys Lys Leu Pro Pro Tyr Asp Asp Asn Asp Gln Trp
                405                 410                 415

Lys Cys Gln Gln Asn Ser Ser Asp Gly Ser Gly Lys Pro Glu Asn Ile
            420                 425                 430

Cys Val Pro Pro Arg Arg Glu Arg Leu Cys Thr Tyr Asn Leu Glu Asn
        435                 440                 445

Leu Lys Phe Asp Lys Ile Arg Asp Asn Asn Ala Phe Leu Ala Asp Val
    450                 455                 460

Leu Leu Thr Ala Arg Asn Glu Gly Glu Lys Ile Val Gln Asn His Pro
465                 470                 475                 480

Asp Thr Asn Ser Ser Asn Val Cys Asn Ala Leu Glu Arg Ser Phe Ala
                485                 490                 495

Asp Leu Ala Asp Ile Ile Arg Gly Thr Asp Gln Trp Lys Gly Thr Asn
            500                 505                 510

Ser Asn Leu Glu Lys Asn Leu Lys Gln Met Phe Ala Lys Ile Arg Glu
        515                 520                 525

Asn Asp Lys Val Leu Gln Asp Lys Tyr Pro Lys Asp Gln Lys Tyr Thr
    530                 535                 540

Lys Leu Arg Glu Ala Trp Trp Asn Ala Asn Arg Gln Lys Val Trp Glu
545                 550                 555                 560

Val Ile Thr Cys Gly Ala Arg Ser Asn Asp Leu Leu Ile Lys Arg Gly
                565                 570                 575

Trp Arg Thr Ser Gly Lys Ser Asp Arg Lys Lys Asn Phe Glu Leu Cys
            580                 585                 590

Arg Lys Cys Gly His Tyr Glu Lys Glu Val Pro Thr Lys Leu Asp Tyr
        595                 600                 605

Val Pro Gln Phe Leu Arg Trp Leu Thr Glu Trp Ile Glu Asp Phe Tyr
    610                 615                 620

Arg Glu Lys Gln Asn Leu Ile Asp Asp Met Glu Arg His Arg Glu Glu
625                 630                 635                 640

Cys Thr Arg Glu Asp His Lys Ser Lys Glu Gly Thr Ser Tyr Cys Ser
                645                 650                 655

Thr Cys Lys Asp Lys Cys Lys Lys Tyr Cys Glu Cys Val Lys Lys Trp
            660                 665                 670

Lys Thr Glu Trp Glu Asn Gln Glu Asn Lys Tyr Lys Asp Leu Tyr Glu
        675                 680                 685

Gln Asn Lys Asn Lys Thr Ser Gln Lys Asn Thr Ser Arg Tyr Asp Asp
    690                 695                 700

Tyr Val Lys Asp Phe Phe Glu Lys Leu Glu Ala Asn Tyr Ser Ser Leu
705                 710                 715                 720

Glu Asn Tyr Ile Lys Gly Asp Pro Tyr Phe Ala Glu Tyr Ala Thr Lys
                725                 730                 735

Leu Ser Phe Ile Leu Asn Pro Ser Asp Ala Asn Asn Pro Ser Gly Glu
```

```
                    740                 745                 750
Thr Ala Asn His Asn Asp Glu Ala Cys Asn Cys Asn Glu Ser Gly Ile
                755                 760                 765
Ser Ser Val Gly Gln Ala Gln Thr Ser Gly Pro Ser Ser Asn Lys Thr
        770                 775                 780
Cys Ile Thr His Ser Ser Ile Lys Thr Asn Lys Lys Glu Cys Lys
785                 790                 795                 800
Asp Val Lys Leu Gly Val Arg Glu Asn Asp Lys Asp Leu Lys Ile Cys
                805                 810                 815
Val Ile Glu Asp Thr Ser Leu Ser Gly Val Asp Asn Cys Cys Cys Gln
            820                 825                 830
Asp Leu Leu Gly Ile Leu Gln Glu Asn Cys Ser Asp Asn Lys Arg Gly
            835                 840                 845
Ser Ser Ser Asn Asp Ser Cys Asp Asn Lys Asn Gln Asp Glu Cys Gln
        850                 855                 860
Lys Lys Leu Glu Lys Val Phe Ala Ser Leu Thr Asn Gly Tyr Lys Cys
865                 870                 875                 880
Asp Lys Cys Lys Ser Gly Thr Ser Arg Ser Lys Lys Trp Ile Trp
                885                 890                 895
Lys Lys Ser Ser Gly Asn Glu Glu Gly Leu Gln Glu Glu Tyr Ala Asn
                900                 905                 910
Thr Ile Gly Leu Pro Pro Arg Thr Gln Ser Leu Tyr Leu Gly Asn Leu
            915                 920                 925
Pro Lys Leu Glu Asn Val Cys Glu Asp Val Lys Asp Ile Asn Phe Asp
        930                 935                 940
Thr Lys Glu Lys Phe Leu Ala Gly Cys Leu Ile Val Ser Phe His Glu
945                 950                 955                 960
Gly Lys Asn Leu Lys Lys Arg Tyr Pro Gln Asn Lys Asn Ser Gly Asn
                965                 970                 975
Lys Glu Asn Leu Cys Lys Ala Leu Glu Tyr Ser Phe Ala Asp Tyr Gly
            980                 985                 990
Asp Leu Ile Lys Gly Thr Ser Ile Trp Asp Asn Glu Tyr Thr Lys Asp
        995                 1000                1005
Leu Glu Leu Asn Leu Gln Asn Asn Phe Gly Lys Leu Phe Gly Lys
    1010                1015                1020
Tyr Ile Lys Lys Asn Asn Thr Ala Glu Gln Asp Thr Ser Tyr Ser
    1025                1030                1035
Ser Leu Asp Glu Leu Arg Glu Ser Trp Trp Asn Thr Asn Lys Lys
    1040                1045                1050
Tyr Ile Trp Thr Ala Met Lys His Gly Ala Glu Met Asn Ile Thr
    1055                1060                1065
Thr Cys Asn Ala Asp Gly Ser Val Thr Gly Ser Gly Ser Ser Cys
    1070                1075                1080
Asp Asp Ile Pro Thr Ile Asp Leu Ile Pro Gln Tyr Leu Arg Phe
    1085                1090                1095
Leu Gln Glu Trp Val Glu Asn Phe Cys Glu Gln Arg Gln Ala Lys
    1100                1105                1110
Val Lys Asp Val Ile Thr Asn Cys Lys Ser Cys Lys Glu Ser Gly
    1115                1120                1125
Asn Lys Cys Lys Thr Glu Cys Lys Thr Lys Cys Lys Asp Glu Cys
    1130                1135                1140
Glu Lys Tyr Lys Lys Phe Ile Glu Ala Cys Gly Thr Ala Gly Gly
    1145                1150                1155
```

Gly Ile Gly Thr Ala Gly Ser Pro Trp Ser Lys Arg Trp Asp Gln
1160                1165                1170

Ile Tyr Lys Arg Tyr Ser Lys His Ile Glu Asp Ala Lys Arg Asn
    1175                1180                1185

Arg Lys Ala Gly Thr Lys Asn Cys Gly Thr Ser Ser Thr Thr Asn
1190                1195                1200

Ala Ala Ala Ser Thr Asp Glu Asn Lys Cys Val Gln Ser Asp Ile
1205                1210                1215

Asp Ser Phe Phe Lys His Leu Ile Asp Ile Gly Leu Thr Thr Pro
1220                1225                1230

Ser Ser Tyr Leu Ser Asn Val Leu Asp Asp Asn Ile Cys Gly Ala
1235                1240                1245

Asp Lys Ala Pro Trp Thr Thr Tyr Thr Thr Tyr Thr Thr Thr Glu
1250                1255                1260

Lys Cys Asn Lys Glu Arg Asp Lys Ser Lys Ser Gln Ser Ser Asp
1265                1270                1275

Thr Leu Val Val Val Asn Val Pro Ser Pro Leu Gly Asn Thr Pro
1280                1285                1290

Tyr Arg Tyr Lys Tyr Ala Cys Gln Cys Lys Ile Pro Thr Asn Glu
1295                1300                1305

Glu Thr Cys Asp Asp Arg Lys Glu Tyr Met Asn Gln Trp Ser Cys
1310                1315                1320

Gly Ser Ala Arg Thr Met Lys Arg Gly Tyr Lys Asn Asp Asn Tyr
1325                1330                1335

Glu Leu Cys Lys Tyr Asn Gly Val Asp Val Lys Pro Thr Thr Val
1340                1345                1350

Arg Ser Asn Ser Ser Lys Leu Asp Ser Gly Arg
1355                1360

<210> SEQ ID NO 74
<211> LENGTH: 1013
<212> TYPE: PRT
<213> ORGANISM: Artificial
<220> FEATURE:
<223> OTHER INFORMATION: Artificial construct

<400> SEQUENCE: 74

Met Gly Ala Asp Asp Val Val Asp Ser Ser Lys Ser Phe Val Met Glu
1               5                   10                  15

Asn Phe Ser Ser Tyr His Gly Thr Lys Pro Gly Tyr Val Asp Ser Ile
                20                  25                  30

Gln Lys Gly Ile Gln Lys Pro Lys Ser Gly Thr Gln Gly Asn Tyr Asp
        35                  40                  45

Asp Asp Trp Lys Gly Phe Tyr Ser Thr Asp Asn Lys Tyr Asp Ala Ala
    50                  55                  60

Gly Tyr Ser Val Asp Asn Glu Asn Pro Leu Ser Gly Lys Ala Gly Gly
65                  70                  75                  80

Val Val Lys Val Thr Tyr Pro Gly Leu Thr Lys Val Leu Ala Leu Lys
                85                  90                  95

Val Asp Asn Ala Glu Thr Ile Lys Lys Glu Leu Gly Leu Ser Leu Thr
            100                 105                 110

Glu Pro Leu Met Glu Gln Val Gly Thr Glu Glu Phe Ile Lys Arg Phe
        115                 120                 125

Gly Asp Gly Ala Ser Arg Val Val Leu Ser Leu Pro Phe Ala Glu Gly
    130                 135                 140

```
Ser Ser Ser Val Glu Tyr Ile Asn Asn Trp Glu Gln Ala Lys Ala Leu
145                 150                 155                 160

Ser Val Glu Leu Glu Ile Asn Phe Glu Thr Arg Gly Lys Arg Gly Gln
                165                 170                 175

Asp Ala Met Tyr Glu Tyr Met Ala Gln Ala Cys Ala Gly Asn Arg Val
            180                 185                 190

Arg Arg Ser Val Gly Ser Ser Leu Ser Cys Ile Asn Leu Asp Trp Asp
        195                 200                 205

Val Ile Arg Asp Lys Thr Lys Thr Lys Ile Glu Ser Leu Lys Glu His
    210                 215                 220

Gly Pro Ile Lys Asn Lys Met Ser Glu Ser Pro Asn Lys Thr Val Ser
225                 230                 235                 240

Glu Glu Lys Ala Lys Gln Tyr Leu Glu Glu Phe His Gln Thr Ala Leu
                245                 250                 255

Glu His Pro Glu Leu Ser Glu Leu Lys Thr Val Thr Gly Thr Asn Pro
            260                 265                 270

Val Phe Ala Gly Ala Asn Tyr Ala Ala Trp Ala Val Asn Val Ala Gln
        275                 280                 285

Val Ile Asp Ser Glu Thr Ala Asp Asn Leu Glu Lys Thr Thr Ala Ala
    290                 295                 300

Leu Ser Ile Leu Pro Gly Ile Gly Ser Val Met Gly Ile Ala Asp Gly
305                 310                 315                 320

Ala Val His His Asn Thr Glu Glu Ile Val Ala Gln Ser Ile Ala Leu
                325                 330                 335

Ser Ser Leu Met Val Ala Gln Ala Ile Pro Leu Val Gly Glu Leu Val
            340                 345                 350

Asp Ile Gly Phe Ala Ala Tyr Asn Phe Val Glu Ser Ile Ile Asn Leu
        355                 360                 365

Phe Gln Val Val His Asn Ser Tyr Asn Arg Pro Ala Tyr Ser Pro Gly
    370                 375                 380

His Lys Thr Gln Pro Met His Glu Phe Leu Ser Phe Ile Leu Asn Ser
385                 390                 395                 400

Ser Asp Ala Asn Asn Pro Ser Glu Lys Ile Gln Lys Asn Asn Asp Glu
                405                 410                 415

Val Cys Asn Cys Asn Glu Ser Gly Ile Ala Ser Val Glu Gln Glu Gln
            420                 425                 430

Ile Ser Asp Pro Ser Ser Asn Lys Thr Cys Ile Thr His Ser Ser Ile
        435                 440                 445

Lys Ala Asn Lys Lys Val Cys Lys His Val Lys Leu Gly Val Arg
    450                 455                 460

Glu Asn Asp Lys Asp Leu Arg Val Cys Val Ile Glu His Thr Ser Leu
465                 470                 475                 480

Ser Gly Val Glu Asn Cys Cys Cys Gln Asp Phe Leu Arg Ile Leu Gln
                485                 490                 495

Glu Asn Cys Ser Asp Asn Lys Ser Gly Ser Ser Asn Gly Ser Cys
            500                 505                 510

Asn Asn Lys Asn Gln Glu Ala Cys Glu Lys Asn Leu Glu Lys Val Leu
        515                 520                 525

Ala Ser Leu Thr Asn Cys Tyr Lys Cys Asp Lys Cys Lys Ser Glu Gln
    530                 535                 540

Ser Lys Lys Asn Asn Lys Asn Trp Ile Trp Lys Lys Ser Ser Gly Lys
545                 550                 555                 560
```

-continued

```
Glu Gly Gly Leu Gln Lys Glu Tyr Ala Asn Thr Ile Gly Leu Pro Pro
                565                 570                 575

Arg Thr Gln Ser Leu Cys Leu Val Val Cys Leu Asp Glu Lys Gly Lys
                580                 585                 590

Lys Thr Gln Glu Leu Lys Asn Ile Arg Thr Asn Ser Glu Leu Leu Lys
                595                 600                 605

Glu Trp Ile Ile Ala Ala Phe His Glu Gly Lys Asn Leu Lys Pro Ser
                610                 615                 620

His Glu Lys Lys Asn Asp Asp Asn Gly Lys Lys Leu Cys Lys Ala Leu
625                 630                 635                 640

Glu Tyr Ser Phe Ala Asp Tyr Gly Asp Leu Ile Lys Gly Thr Ser Ile
                645                 650                 655

Trp Asp Asn Glu Tyr Thr Lys Asp Leu Glu Leu Asn Leu Gln Lys Ile
                660                 665                 670

Phe Gly Lys Leu Phe Arg Lys Tyr Ile Lys Lys Asn Asn Thr Ala Glu
                675                 680                 685

Gln Asp Thr Ser Tyr Ser Ser Leu Asp Glu Leu Arg Glu Ser Trp Trp
                690                 695                 700

Asn Thr Asn Lys Lys Tyr Ile Trp Leu Ala Met Lys His Gly Ala Gly
705                 710                 715                 720

Met Asn Ser Thr Thr Cys Cys Gly Asp Gly Ser Val Thr Gly Ser Gly
                725                 730                 735

Ser Ser Cys Asp Asp Ile Pro Thr Ile Asp Leu Ile Pro Gln Tyr Leu
                740                 745                 750

Arg Phe Leu Gln Glu Trp Val Glu His Phe Cys Lys Gln Arg Gln Glu
                755                 760                 765

Lys Val Lys Pro Val Ile Glu Asn Cys Lys Ser Cys Lys Glu Ser Gly
                770                 775                 780

Gly Thr Cys Asn Gly Glu Cys Lys Thr Glu Cys Lys Asn Lys Cys Glu
785                 790                 795                 800

Val Tyr Lys Lys Phe Ile Glu Asp Cys Lys Gly Gly Asp Gly Thr Ala
                805                 810                 815

Gly Ser Ser Trp Val Lys Arg Trp Asp Gln Ile Tyr Lys Arg Tyr Ser
                820                 825                 830

Lys Tyr Ile Glu Asp Ala Lys Arg Asn Arg Lys Ala Gly Thr Lys Asn
                835                 840                 845

Cys Gly Pro Ser Ser Thr Thr Asn Ala Ala Glu Asn Lys Cys Val Gln
850                 855                 860

Ser Asp Ile Asp Ser Phe Phe Lys His Leu Ile Asp Ile Gly Leu Thr
865                 870                 875                 880

Thr Pro Ser Ser Tyr Leu Ser Ile Val Leu Asp Asp Asn Ile Cys Gly
                885                 890                 895

Ala Asp Lys Ala Pro Trp Thr Thr Tyr Thr Thr Tyr Thr Thr Thr Glu
                900                 905                 910

Lys Cys Asn Lys Glu Thr Asp Lys Ser Lys Leu Gln Gln Cys Asn Thr
                915                 920                 925

Ala Val Val Val Asn Val Pro Ser Pro Leu Gly Asn Thr Pro His Gly
                930                 935                 940

Tyr Lys Tyr Ala Cys Gln Cys Lys Ile Pro Thr Asn Glu Glu Thr Cys
945                 950                 955                 960

Asp Asp Arg Lys Glu Tyr Met Asn Gln Trp Ser Cys Gly Ser Ala Arg
                965                 970                 975

Thr Met Lys Arg Gly Tyr Lys Asn Asp Asn Tyr Glu Leu Cys Lys Tyr
```

-continued

```
                980               985               990
Asn Gly Val Asp Val Lys Pro Thr Thr Val Arg Ser Asn Ser Ser Lys
            995                1000               1005

Leu Asp Ser Gly Arg
    1010
```

<210> SEQ ID NO 75
<211> LENGTH: 1036
<212> TYPE: PRT
<213> ORGANISM: Artificial
<220> FEATURE:
<223> OTHER INFORMATION: Artificial construct

<400> SEQUENCE: 75

```
Met Gly Ala Asp Asp Val Val Asp Ser Ser Lys Ser Phe Val Met Glu
1               5                   10                  15

Asn Phe Ser Ser Tyr His Gly Thr Lys Pro Gly Tyr Val Asp Ser Ile
            20                  25                  30

Gln Lys Gly Ile Gln Lys Pro Lys Ser Gly Thr Gln Gly Asn Tyr Asp
        35                  40                  45

Asp Asp Trp Lys Gly Phe Tyr Ser Thr Asp Asn Lys Tyr Asp Ala Ala
    50                  55                  60

Gly Tyr Ser Val Asp Asn Glu Asn Pro Leu Ser Gly Lys Ala Gly Gly
65                  70                  75                  80

Val Val Lys Val Thr Tyr Pro Gly Leu Thr Lys Val Leu Ala Leu Lys
                85                  90                  95

Val Asp Asn Ala Glu Thr Ile Lys Lys Glu Leu Gly Leu Ser Leu Thr
            100                 105                 110

Glu Pro Leu Met Glu Gln Val Gly Thr Glu Glu Phe Ile Lys Arg Phe
        115                 120                 125

Gly Asp Gly Ala Ser Arg Val Val Leu Ser Leu Pro Phe Ala Glu Gly
    130                 135                 140

Ser Ser Ser Val Glu Tyr Ile Asn Asn Trp Glu Gln Ala Lys Ala Leu
145                 150                 155                 160

Ser Val Glu Leu Glu Ile Asn Phe Glu Thr Arg Gly Lys Arg Gly Gln
                165                 170                 175

Asp Ala Met Tyr Glu Tyr Met Ala Gln Ala Cys Ala Gly Asn Arg Val
            180                 185                 190

Arg Arg Ser Val Gly Ser Ser Leu Ser Cys Ile Asn Leu Asp Trp Asp
        195                 200                 205

Val Ile Arg Asp Lys Thr Lys Thr Lys Ile Glu Ser Leu Lys Glu His
    210                 215                 220

Gly Pro Ile Lys Asn Lys Met Ser Glu Ser Pro Asn Lys Thr Val Ser
225                 230                 235                 240

Glu Glu Lys Ala Lys Gln Tyr Leu Glu Glu Phe His Gln Thr Ala Leu
                245                 250                 255

Glu His Pro Glu Leu Ser Glu Leu Lys Thr Val Thr Gly Thr Asn Pro
            260                 265                 270

Val Phe Ala Gly Ala Asn Tyr Ala Ala Trp Ala Val Asn Val Ala Gln
        275                 280                 285

Val Ile Asp Ser Glu Thr Ala Asp Asn Leu Glu Lys Thr Thr Ala Ala
    290                 295                 300

Leu Ser Ile Leu Pro Gly Ile Gly Ser Val Met Gly Ile Ala Asp Gly
305                 310                 315                 320

Ala Val His His Asn Thr Glu Glu Ile Val Ala Gln Ser Ile Ala Leu
```

-continued

```
                325                 330                 335
Ser Ser Leu Met Val Ala Gln Ala Ile Pro Leu Val Gly Glu Leu Val
            340                 345                 350

Asp Ile Gly Phe Ala Ala Tyr Asn Phe Val Glu Ser Ile Ile Asn Leu
            355                 360                 365

Phe Gln Val Val His Asn Ser Tyr Asn Arg Pro Ala Tyr Ser Pro Gly
    370                 375                 380

His Lys Thr Gln Pro Met His Glu Phe Asn Tyr Ile Lys Gly Asp Pro
385                 390                 395                 400

Tyr Phe Ala Glu Tyr Ala Thr Lys Leu Ser Phe Ile Leu Asn Pro Ser
                405                 410                 415

Asp Ala Asn Asn Pro Ser Gly Glu Thr Ala Asn His Asn Asp Glu Ala
            420                 425                 430

Cys Asn Cys Asn Glu Ser Gly Ile Ser Ser Val Gly Gln Ala Gln Thr
            435                 440                 445

Ser Gly Pro Ser Ser Asn Lys Thr Cys Ile Thr His Ser Ser Ile Lys
        450                 455                 460

Thr Asn Lys Lys Lys Glu Cys Lys Asp Val Lys Leu Gly Val Arg Glu
465                 470                 475                 480

Asn Asp Lys Asp Leu Lys Ile Cys Val Ile Glu Asp Thr Ser Leu Ser
                485                 490                 495

Gly Val Asp Asn Cys Cys Gln Asp Leu Leu Gly Ile Leu Gln Glu
            500                 505                 510

Asn Cys Ser Asp Asn Lys Arg Gly Ser Ser Asn Asp Ser Cys Asp
            515                 520                 525

Asn Lys Asn Gln Asp Glu Cys Gln Lys Lys Leu Glu Lys Val Phe Ala
    530                 535                 540

Ser Leu Thr Asn Gly Tyr Lys Cys Asp Lys Cys Lys Ser Gly Thr Ser
545                 550                 555                 560

Arg Ser Lys Lys Lys Trp Ile Trp Lys Lys Ser Ser Gly Asn Glu Glu
                565                 570                 575

Gly Leu Gln Glu Glu Tyr Ala Asn Thr Ile Gly Leu Pro Pro Arg Thr
            580                 585                 590

Gln Ser Leu Tyr Leu Gly Asn Leu Pro Lys Leu Glu Asn Val Cys Glu
        595                 600                 605

Asp Val Lys Asp Ile Asn Phe Asp Thr Lys Glu Lys Phe Leu Ala Gly
        610                 615                 620

Cys Leu Ile Val Ser Phe His Glu Gly Lys Asn Leu Lys Lys Arg Tyr
625                 630                 635                 640

Pro Gln Asn Lys Asn Ser Gly Asn Lys Glu Asn Leu Cys Lys Ala Leu
                645                 650                 655

Glu Tyr Ser Phe Ala Asp Tyr Gly Asp Leu Ile Lys Gly Thr Ser Ile
            660                 665                 670

Trp Asp Asn Glu Tyr Thr Lys Asp Leu Glu Leu Asn Leu Gln Asn Asn
            675                 680                 685

Phe Gly Lys Leu Phe Gly Lys Tyr Ile Lys Lys Asn Thr Ala Glu
    690                 695                 700

Gln Asp Thr Ser Tyr Ser Ser Leu Asp Glu Leu Arg Glu Ser Trp Trp
705                 710                 715                 720

Asn Thr Asn Lys Lys Tyr Ile Trp Thr Ala Met Lys His Gly Ala Glu
                725                 730                 735

Met Asn Ile Thr Thr Cys Asn Ala Asp Gly Ser Val Thr Gly Ser Gly
            740                 745                 750
```

```
Ser Ser Cys Asp Asp Ile Pro Thr Ile Asp Leu Ile Pro Gln Tyr Leu
        755                 760                 765

Arg Phe Leu Gln Glu Trp Val Glu Asn Phe Cys Glu Gln Arg Gln Ala
        770                 775                 780

Lys Val Lys Asp Val Ile Thr Asn Cys Lys Ser Cys Lys Glu Ser Gly
785                 790                 795                 800

Asn Lys Cys Lys Thr Glu Cys Lys Thr Lys Cys Lys Asp Glu Cys Glu
            805                 810                 815

Lys Tyr Lys Lys Phe Ile Glu Ala Cys Gly Thr Ala Gly Gly Gly Ile
                820                 825                 830

Gly Thr Ala Gly Ser Pro Trp Ser Lys Arg Trp Asp Gln Ile Tyr Lys
            835                 840                 845

Arg Tyr Ser Lys His Ile Glu Asp Ala Lys Arg Asn Arg Lys Ala Gly
        850                 855                 860

Thr Lys Asn Cys Gly Thr Ser Ser Thr Thr Asn Ala Ala Ala Ser Thr
865                 870                 875                 880

Asp Glu Asn Lys Cys Val Gln Ser Asp Ile Asp Ser Phe Phe Lys His
            885                 890                 895

Leu Ile Asp Ile Gly Leu Thr Thr Pro Ser Ser Tyr Leu Ser Asn Val
                900                 905                 910

Leu Asp Asp Asn Ile Cys Gly Ala Asp Lys Ala Pro Trp Thr Thr Tyr
        915                 920                 925

Thr Thr Tyr Thr Thr Thr Glu Lys Cys Asn Lys Glu Arg Asp Lys Ser
        930                 935                 940

Lys Ser Gln Ser Ser Asp Thr Leu Val Val Asn Val Pro Ser Pro
945                 950                 955                 960

Leu Gly Asn Thr Pro Tyr Arg Tyr Lys Tyr Ala Cys Gln Cys Lys Ile
            965                 970                 975

Pro Thr Asn Glu Glu Thr Cys Asp Asp Arg Lys Glu Tyr Met Asn Gln
                980                 985                 990

Trp Ser Cys Gly Ser Ala Arg Thr  Met Lys Arg Gly Tyr  Lys Asn Asp
            995                 1000                 1005

Asn Tyr  Glu Leu Cys Lys Tyr  Asn Gly Val Asp Val  Lys Pro Thr
        1010                 1015                 1020

Thr Val  Arg Ser Asn Ser Ser  Lys Leu Asp Ser Gly  Arg
        1025                 1030                 1035

<210> SEQ ID NO 76
<211> LENGTH: 18
<212> TYPE: DNA
<213> ORGANISM: Artificial
<220> FEATURE:
<223> OTHER INFORMATION: Primer sequence

<400> SEQUENCE: 76
aactacatca agggcgac                                                 18

<210> SEQ ID NO 77
<211> LENGTH: 21
<212> TYPE: DNA
<213> ORGANISM: Artificial
<220> FEATURE:
<223> OTHER INFORMATION: Primer sequence

<400> SEQUENCE: 77
cttgttgata ttggtgtcgg t                                             21
```

```
<210> SEQ ID NO 78
<211> LENGTH: 18
<212> TYPE: DNA
<213> ORGANISM: Artificial
<220> FEATURE:
<223> OTHER INFORMATION: Primer sequence

<400> SEQUENCE: 78
cacagcgata gcggcaag                                                 18

<210> SEQ ID NO 79
<211> LENGTH: 18
<212> TYPE: DNA
<213> ORGANISM: Artificial
<220> FEATURE:
<223> OTHER INFORMATION: Primer sequence

<400> SEQUENCE: 79
gtccagcttg ctggagtt                                                 18

<210> SEQ ID NO 80
<211> LENGTH: 18
<212> TYPE: DNA
<213> ORGANISM: Artificial
<220> FEATURE:
<223> OTHER INFORMATION: Primer sequence

<400> SEQUENCE: 80
aactacatca agggcgac                                                 18

<210> SEQ ID NO 81
<211> LENGTH: 18
<212> TYPE: DNA
<213> ORGANISM: Artificial
<220> FEATURE:
<223> OTHER INFORMATION: Primer sequence

<400> SEQUENCE: 81
gtccagcttg ctggagtt                                                 18

<210> SEQ ID NO 82
<211> LENGTH: 18
<212> TYPE: DNA
<213> ORGANISM: Artificial
<220> FEATURE:
<223> OTHER INFORMATION: Primer sequence

<400> SEQUENCE: 82
aactacatca agggcgac                                                 18

<210> SEQ ID NO 83
<211> LENGTH: 18
<212> TYPE: DNA
<213> ORGANISM: Artificial
<220> FEATURE:
<223> OTHER INFORMATION: Primer sequence

<400> SEQUENCE: 83
agcggcgttg gtggtgga                                                 18

<210> SEQ ID NO 84
<211> LENGTH: 18
<212> TYPE: DNA
<213> ORGANISM: Artificial
<220> FEATURE:
<223> OTHER INFORMATION: Primer sequence
```

```
<400> SEQUENCE: 84
aactacatca agggcgac                                                 18

<210> SEQ ID NO 85
<211> LENGTH: 18
<212> TYPE: DNA
<213> ORGANISM: Artificial
<220> FEATURE:
<223> OTHER INFORMATION: Primer sequence

<400> SEQUENCE: 85
gtacttgtac cggtaggg                                                 18

<210> SEQ ID NO 86
<211> LENGTH: 18
<212> TYPE: DNA
<213> ORGANISM: Artificial
<220> FEATURE:
<223> OTHER INFORMATION: Primer sequence

<400> SEQUENCE: 86
cacagcgata gcggcaag                                                 18

<210> SEQ ID NO 87
<211> LENGTH: 18
<212> TYPE: DNA
<213> ORGANISM: Artificial
<220> FEATURE:
<223> OTHER INFORMATION: Primer sequence

<400> SEQUENCE: 87
gtacttgtac cggtaggg                                                 18

<210> SEQ ID NO 88
<211> LENGTH: 18
<212> TYPE: DNA
<213> ORGANISM: Artificial
<220> FEATURE:
<223> OTHER INFORMATION: Primer sequence

<400> SEQUENCE: 88
ctgaccaact gctacaag                                                 18

<210> SEQ ID NO 89
<211> LENGTH: 19
<212> TYPE: DNA
<213> ORGANISM: Artificial
<220> FEATURE:
<223> OTHER INFORMATION: Primer sequence

<400> SEQUENCE: 89
ggtccagagg gtacagctt                                                19

<210> SEQ ID NO 90
<211> LENGTH: 18
<212> TYPE: DNA
<213> ORGANISM: Artificial
<220> FEATURE:
<223> OTHER INFORMATION: Primer sequence

<400> SEQUENCE: 90
ctgtccttca tcctgaac                                                 18

<210> SEQ ID NO 91
```

```
<211> LENGTH: 21
<212> TYPE: DNA
<213> ORGANISM: Artificial
<220> FEATURE:
<223> OTHER INFORMATION: Primer sequence

<400> SEQUENCE: 91
ttcagcgttg ttgtactcgt a                                      21

<210> SEQ ID NO 92
<211> LENGTH: 18
<212> TYPE: DNA
<213> ORGANISM: Artificial
<220> FEATURE:
<223> OTHER INFORMATION: Primer sequence

<400> SEQUENCE: 92
ctgtccttca tcctgaac                                          18

<210> SEQ ID NO 93
<211> LENGTH: 18
<212> TYPE: DNA
<213> ORGANISM: Artificial
<220> FEATURE:
<223> OTHER INFORMATION: Primer sequence

<400> SEQUENCE: 93
gtccagaggg tacagctt                                          18

<210> SEQ ID NO 94
<211> LENGTH: 18
<212> TYPE: DNA
<213> ORGANISM: Artificial
<220> FEATURE:
<223> OTHER INFORMATION: Primer sequence

<400> SEQUENCE: 94
cactctgact ctggcacc                                          18

<210> SEQ ID NO 95
<211> LENGTH: 24
<212> TYPE: DNA
<213> ORGANISM: Artificial
<220> FEATURE:
<223> OTHER INFORMATION: Primer sequence

<400> SEQUENCE: 95
agaggacttc atcttgttgt tggt                                   24

<210> SEQ ID NO 96
<211> LENGTH: 18
<212> TYPE: DNA
<213> ORGANISM: Artificial
<220> FEATURE:
<223> OTHER INFORMATION: Primer sequence

<400> SEQUENCE: 96
ctgtccttca tcctgaac                                          18

<210> SEQ ID NO 97
<211> LENGTH: 24
<212> TYPE: DNA
<213> ORGANISM: Artificial
<220> FEATURE:
<223> OTHER INFORMATION: Primer sequence

<400> SEQUENCE: 97
```
agaggacttc atcttgttgt tggt                                                  24

<210> SEQ ID NO 98
<211> LENGTH: 18
<212> TYPE: DNA
<213> ORGANISM: Artificial
<220> FEATURE:
<223> OTHER INFORMATION: Primer sequence

<400> SEQUENCE: 98
cactctgact ctggcacc                                                         18

<210> SEQ ID NO 99
<211> LENGTH: 18
<212> TYPE: DNA
<213> ORGANISM: Artificial
<220> FEATURE:
<223> OTHER INFORMATION: Primer sequence

<400> SEQUENCE: 99
gtccagctta gaggagtt                                                         18

<210> SEQ ID NO 100
<211> LENGTH: 18
<212> TYPE: DNA
<213> ORGANISM: Artificial
<220> FEATURE:
<223> OTHER INFORMATION: Primer sequence

<400> SEQUENCE: 100
ctgtccttca tcctgaac                                                         18

<210> SEQ ID NO 101
<211> LENGTH: 18
<212> TYPE: DNA
<213> ORGANISM: Artificial
<220> FEATURE:
<223> OTHER INFORMATION: Primer sequence

<400> SEQUENCE: 101
gtccagctta gaggagtt                                                         18

<210> SEQ ID NO 102
<211> LENGTH: 18
<212> TYPE: DNA
<213> ORGANISM: Artificial
<220> FEATURE:
<223> OTHER INFORMATION: Primer sequence

<400> SEQUENCE: 102
cactctgact ctggcacc                                                         18

<210> SEQ ID NO 103
<211> LENGTH: 18
<212> TYPE: DNA
<213> ORGANISM: Artificial
<220> FEATURE:
<223> OTHER INFORMATION: Primer sequence

<400> SEQUENCE: 103
ggcggcgttg gtggtaga                                                         18

<210> SEQ ID NO 104
<211> LENGTH: 18
<212> TYPE: DNA

```
<213> ORGANISM: Artificial
<220> FEATURE:
<223> OTHER INFORMATION: Primer sequence

<400> SEQUENCE: 104
ctgtccttca tcctgaac                                                18

<210> SEQ ID NO 105
<211> LENGTH: 18
<212> TYPE: DNA
<213> ORGANISM: Artificial
<220> FEATURE:
<223> OTHER INFORMATION: Primer sequence

<400> SEQUENCE: 105
ggcggcgttg gtggtaga                                                18

<210> SEQ ID NO 106
<211> LENGTH: 18
<212> TYPE: DNA
<213> ORGANISM: Artificial
<220> FEATURE:
<223> OTHER INFORMATION: Primer sequence

<400> SEQUENCE: 106
cactctgact ctggcacc                                                18

<210> SEQ ID NO 107
<211> LENGTH: 18
<212> TYPE: DNA
<213> ORGANISM: Artificial
<220> FEATURE:
<223> OTHER INFORMATION: Primer sequence

<400> SEQUENCE: 107
gtacttgtat ccgtgggg                                                18

<210> SEQ ID NO 108
<211> LENGTH: 18
<212> TYPE: DNA
<213> ORGANISM: Artificial
<220> FEATURE:
<223> OTHER INFORMATION: Primer sequence

<400> SEQUENCE: 108
ctgtccttca tcctgaac                                                18

<210> SEQ ID NO 109
<211> LENGTH: 18
<212> TYPE: DNA
<213> ORGANISM: Artificial
<220> FEATURE:
<223> OTHER INFORMATION: Primer sequence

<400> SEQUENCE: 109
gtacttgtat ccgtgggg                                                18

<210> SEQ ID NO 110
<211> LENGTH: 18
<212> TYPE: DNA
<213> ORGANISM: Artificial
<220> FEATURE:
<223> OTHER INFORMATION: Primer sequence

<400> SEQUENCE: 110
cacagcgata gcggcaag                                                18
```

<210> SEQ ID NO 111
<211> LENGTH: 36
<212> TYPE: DNA
<213> ORGANISM: Artificial
<220> FEATURE:
<223> OTHER INFORMATION: Primer sequence

<400> SEQUENCE: 111
ggtgtcgaag ttgatgtcgg gcagattgcc caggta                              36

<210> SEQ ID NO 112
<211> LENGTH: 18
<212> TYPE: DNA
<213> ORGANISM: Artificial
<220> FEATURE:
<223> OTHER INFORMATION: Primer sequence

<400> SEQUENCE: 112
cacagcgata gcggcaag                                                  18

<210> SEQ ID NO 113
<211> LENGTH: 36
<212> TYPE: DNA
<213> ORGANISM: Artificial
<220> FEATURE:
<223> OTHER INFORMATION: Primer sequence

<400> SEQUENCE: 113
agctgcggcc agattagcgc cctcgtggaa ggacac                              36

<210> SEQ ID NO 114
<211> LENGTH: 18
<212> TYPE: DNA
<213> ORGANISM: Artificial
<220> FEATURE:
<223> OTHER INFORMATION: Primer sequence

<400> SEQUENCE: 114
cacagcgata gcggcaag                                                  18

<210> SEQ ID NO 115
<211> LENGTH: 36
<212> TYPE: DNA
<213> ORGANISM: Artificial
<220> FEATURE:
<223> OTHER INFORMATION: Primer sequence

<400> SEQUENCE: 115
agcgcattca gctgcggcgt tggtcttgat ggagct                              36

<210> SEQ ID NO 116
<211> LENGTH: 18
<212> TYPE: DNA
<213> ORGANISM: Artificial
<220> FEATURE:
<223> OTHER INFORMATION: Primer sequence

<400> SEQUENCE: 116
cacagcgata gcggcaag                                                  18

<210> SEQ ID NO 117
<211> LENGTH: 18
<212> TYPE: DNA
<213> ORGANISM: Artificial
<220> FEATURE:

```
<223> OTHER INFORMATION: Primer sequence

<400> SEQUENCE: 117
gtccagcttg ctggagtt                                                        18

<210> SEQ ID NO 118
<211> LENGTH: 36
<212> TYPE: DNA
<213> ORGANISM: Artificial
<220> FEATURE:
<223> OTHER INFORMATION: Primer sequence

<400> SEQUENCE: 118
gctaatctgg ccgcagctta cccccagaat aagaac                                    36

<210> SEQ ID NO 119
<211> LENGTH: 18
<212> TYPE: DNA
<213> ORGANISM: Artificial
<220> FEATURE:
<223> OTHER INFORMATION: Primer sequence

<400> SEQUENCE: 119
gtccagcttg ctggagtt                                                        18

<210> SEQ ID NO 120
<211> LENGTH: 36
<212> TYPE: DNA
<213> ORGANISM: Artificial
<220> FEATURE:
<223> OTHER INFORMATION: Primer sequence

<400> SEQUENCE: 120
gccgcagctg aatgcgctga cgtgaagctg ggcgtg                                    36

<210> SEQ ID NO 121
<211> LENGTH: 18
<212> TYPE: DNA
<213> ORGANISM: Artificial
<220> FEATURE:
<223> OTHER INFORMATION: Primer sequence

<400> SEQUENCE: 121
gtccagcttg ctggagtt                                                        18

<210> SEQ ID NO 122
<211> LENGTH: 18
<212> TYPE: DNA
<213> ORGANISM: Artificial
<220> FEATURE:
<223> OTHER INFORMATION: Primer sequence

<400> SEQUENCE: 122
cacagcgata gcggcaag                                                        18

<210> SEQ ID NO 123
<211> LENGTH: 18
<212> TYPE: DNA
<213> ORGANISM: Artificial
<220> FEATURE:
<223> OTHER INFORMATION: Primer sequence

<400> SEQUENCE: 123
gtccagcttg ctggagtt                                                        18
```

```
<210> SEQ ID NO 124
<211> LENGTH: 18
<212> TYPE: DNA
<213> ORGANISM: Artificial
<220> FEATURE:
<223> OTHER INFORMATION: Primer sequence

<400> SEQUENCE: 124
cacagcgata gcggcaag                                                 18

<210> SEQ ID NO 125
<211> LENGTH: 18
<212> TYPE: DNA
<213> ORGANISM: Artificial
<220> FEATURE:
<223> OTHER INFORMATION: Primer sequence

<400> SEQUENCE: 125
gtccagcttg ctggagtt                                                 18

<210> SEQ ID NO 126
<211> LENGTH: 18
<212> TYPE: DNA
<213> ORGANISM: Artificial
<220> FEATURE:
<223> OTHER INFORMATION: Primer sequence

<400> SEQUENCE: 126
cacagcgata gcggcaag                                                 18

<210> SEQ ID NO 127
<211> LENGTH: 18
<212> TYPE: DNA
<213> ORGANISM: Artificial
<220> FEATURE:
<223> OTHER INFORMATION: Primer sequence

<400> SEQUENCE: 127
gtccagcttg ctggagtt                                                 18

<210> SEQ ID NO 128
<211> LENGTH: 8
<212> TYPE: PRT
<213> ORGANISM: Artificial
<220> FEATURE:
<223> OTHER INFORMATION: Artificial construct
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (5)..(6)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid

<400> SEQUENCE: 128

Xaa Asx Asx Asx Xaa Xaa Asx Xaa
 1               5

<210> SEQ ID NO 129
<211> LENGTH: 8
<212> TYPE: PRT
<213> ORGANISM: Artificial
<220> FEATURE:
<223> OTHER INFORMATION: Artificial construct
```

```
<400> SEQUENCE: 129

Asn Lys Lys Lys Glu Cys Lys Asp
1               5

<210> SEQ ID NO 130
<211> LENGTH: 8
<212> TYPE: PRT
<213> ORGANISM: Artificial
<220> FEATURE:
<223> OTHER INFORMATION: Artificial construct

<400> SEQUENCE: 130

Gly Lys Asn Leu Lys Lys Arg Tyr
1               5

<210> SEQ ID NO 131
<211> LENGTH: 10
<212> TYPE: PRT
<213> ORGANISM: Artificial
<220> FEATURE:
<223> OTHER INFORMATION: Artificial construct

<400> SEQUENCE: 131

Lys Leu Glu Asn Val Cys Glu Asp Val Lys
1               5                   10

<210> SEQ ID NO 132
<211> LENGTH: 6
<212> TYPE: PRT
<213> ORGANISM: Artificial
<220> FEATURE:
<223> OTHER INFORMATION: Artificial construct
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid

<400> SEQUENCE: 132

Xaa Asx Asx Xaa Asx Xaa
1               5
```

TARGETING OF CHONDROITIN SULFATE GLYCANS

CROSS-REFERENCE TO RELATED APPLICATIONS

This application is the U.S. National Stage of International Application PCT/EP2013/052557 filed Feb. 8, 2013, which designates the U.S. and was published by the International Bureau in English on Aug. 15, 2013, and which claims the benefit of U.S. Provisional Application No. 61/596,931, filed Feb. 9, 2012, both of which are hereby incorporated by reference in their entirety.

FIELD OF THE INVENTION

The present invention relates to functional binding fragments comprising the minimal binding fragments of VAR2CSA, to antibodies against such binding fragments of VAR2CSA, nucleic acids encoding such fragments of VAR2CSA as well as methods for their production. The invention further relates to conjugates and fusion proteins of VAR2CSA polypeptides including the minimal binding fragments and their use, in particular in the treatment of conditions associated with expression of chondroitin sulfate A (CSA), such as an inappropriate expression of chondroitin sulfate A (CSA).

BACKGROUND OF THE INVENTION

Proteoglycans are proteins conjugated to one or more glycosaminoglycan (GAG) chains. These proteins are distributed inside cells, on the cell membrane and in the extracellular matrix serving a variety of functions: cartilage matrix formation; the structural organization of tissues; organizations of basement membranes; regulating the role of secretory vesicles; binding of cytokines, chemokines, growth factors, and morphogens; protease receptors and protease inhibitors; co-receptors, tyrosine-kinase-type growth factor receptors; as endocytic receptors; facilitate cell attachment, cell-cell interactions, and cell motility as well as cell migration.

The malaria parasite *Plasmodium falciparum* utilizes host cell proteoglycans in almost all stages of its complex life cycle. The sporozoite infects hepatocytes in the liver through surface-expressed circumsporozoite protein interacting with highly sulfated heparan sulfate proteoglycans (HSPG). Merozoite infection of the erythrocytes is mediated by EBA-175 binding to sialic acid on glycophorin A. In addition, a number of *Plasmodium falciparum* Erythrocyte Membrane Protein 1 (PfEMP1) proteins, mediating host endothelial adhesion, have been described as glycan-binding. One of these is VAR2CSA, which is a unique member of the PfEMP1 protein family. VAR2CSA binds with high affinity to an unusual, low-sulfated form of chondroitin sulfate A (CSA), attached to proteoglycans, so called Chondroitin Sulfate Proteoglycan (CSPG), in the intervillous spaces of the placenta. VAR2CSA is a large multi-domain protein (350 kDa) expressed on the surface of *P. falciparum*-infected erythrocytes (IEs), and the VAR2CSA-CSA interaction is responsible for placenta specific sequestration in placental malaria (PM). Importantly, recombinant full-length VAR2CSA ecto-domain from FCR3 and 3D7 type parasites has shown affinity for CSA in the low nano-molar range.

CSA belongs to the family of glycosaminoglycans (GAGs), which are linear polymers of alternating amino sugars and hexuronic acid residues, attached to proteoglycans. There are several types of GAGs including; chondroitin sulfate (CS), dermatan sulfate (DS or CSB), heparan sulfate (HS) and heparin. While the polysaccharide backbone of these GAGs is simple, considerable diversity arises in modifications such as sulfation and uronate epimerization. This is the basis for the wide variety in domain structure and biological activities of different GAGs.

CS interacts with many important factors such as growth hormones, cytokines, chemokines, and adhesion molecules and is thought to be involved in structural stabilization, cytokinesis, cell proliferation, differentiation, cell migration, tissue morphogenesis, organogenesis, infection, and wound repair. CS chains are composed of alternating units of N-acetyl-D-galactosamine (GalNAc) and glucuronic acid residues. Glucuronic acid can be sulfated at its C2 position and GalNAc can be sulfated at C4 and/or C6, giving rise to various disaccharide units. Varying modifications of the sugar backbone allows structural and functional heterogeneity of the CS chains. Placenta adhering *P. falciparum* parasites specifically associate with low sulfated CSA with sulfation only at C4 of GalNAc.

Early studies pinpointed CSA as being responsible for IE sequestration in the placenta. The specific receptor was however not known. Upon further research it was found that the human placenta contained three distinct types of chondroitin sulfate proteoglycans (CSPG), but that the IE adhered specifically to low sulfated CSPG in the intervillous spaces. What is special for this type of CSPG is that only 2-8% of the disaccharide units are C4 sulfated. In an accompanying study, aimed to identify the specific structural requirements for the CSA, it was found that parasite adhesion to CSPG is inhibited by CSA containing between 30-50% C4 sulfation, with the remaining 50-70% disaccharide units being unsulfated. The minimal inhibition of binding requirements for CSA was shown to be a dodecasaccharide (six disaccharides) containing a minimum of 2-3 or 4-5 C4 sulfated disaccharide units.

Chondroitin sulfate proteoglycan 4 (CSPG4), also known as High Molecular Weight-Melanoma Associated Antigen (HMW-MAA) or melanoma-associated chondroitin sulfate proteoglycan (MSCP), is a cell surface proteoglycan which has been shown to be expressed by melanoma cells.

CSPG4/MSCP/HMV-MAA is a large proteoglycan characterized by having CS chains on the protein backbone. The sulfation of these CS chains seems to be primarily on C4 of GalNAc (CSA), although the degree of sulfation is not known.

OBJECT OF THE INVENTION

It is an object of embodiments of the invention to provide minimal functional binding fragments of VAR2CSA suitable for the targeting and/or detection of chondroitin sulfate glycans. Other objects of embodiments of the invention is to provide methods for treating conditions associated with expression, such as inappropriate expression of the chondroitin sulfate glycans, such as CSA, wherein VAR2CSA polypeptides or fragments thereof, either alone or as part of conjugates or fusion proteins are used to target and/or detect tissue or cells having an expression, such as inappropriate expression of the chondroitin sulfate glycans.

SUMMARY OF THE INVENTION

It has been found by the present inventors that VAR2CSA retains its ability to bind with high affinity and specificity to certain chondroitin sulfate proteoglycans with minimal structural elements of the polypeptide sequence. More importantly, the present inventors have found that VAR2CSA polypeptides bind with high and specific affinity to cancer cells and tissues, which binding by the present inventors is suggested to be through a specific interaction with chondroitin sulfate proteoglycans expressed on the surface of the cancer cells or in the surrounding extracellular matrix. Accordingly, the present inventors suggest to use this specific and high affinity binding for the targeting of cancer cells or other tissues or cells with high or otherwise expression, such as inappropriate expression of this particular type of chondroitin sulfate proteoglycans.

So, in a first aspect the present invention relates to an isolated protein fragment of VAR2CSA, which fragment consists of a sequential amino acid sequence of
  a) ID1, and
  b) DBL2Xb, and optionally
  c) ID2a.

In some embodiments the isolated protein fragment of VAR2CSA according to the present invention comprises ID2a.

In a second aspect the present invention relates to an antibody that specifically binds a protein fragment of VAR2CSA, which fragment consists of a sequential amino acid sequence of a) ID1, and b) DBL2Xb, and optionally c) ID2a. In some embodiments, the antibody according to the present invention does not bind full length VAR2CSA polypeptides.

In a third aspect the present invention relates to nucleic acid molecules encoding a protein fragment of VAR2CSA, which fragment consist of a sequential amino acid sequence of a) ID1, and b) DBL2Xb, and optionally c) ID2a. The invention further relates to a nucleic acid probe capable of hybridizing to such nucleic acid sequence under stringent conditions.

In a further aspect the present invention relates to a vector comprising an isolated nucleic acid molecule according to the invention.

In a further aspect the present invention relates to a host cell comprising a vector comprising an isolated nucleic acid molecule according to the invention.

In a further aspect the present invention relates to a method for producing the protein fragment according to the invention, the method comprising cultivating a cell as defined herein in an appropriate growth medium under conditions allowing expression of the polynucleotide construct and recovering the resulting protein fragment from the culture medium.

In a further aspect the present invention relates to a conjugate or fusion protein comprising a VAR2CSA polypeptide, and a therapeutic or diagnostic effector moiety, such as a cytotoxic moiety, fluorescent label, and/or a radiolabel.

It is to be understood that for a conjugate, fusion or chimeric protein comprising a VAR2CSA polypeptide, any VAR2CSA polypeptide as defined herein may be used. Accordingly, this aspect is not limited to the use of minimal binding fragments. This applies whenever the term VAR2CSA polypeptide is used and are accordingly equally relevant when used for medical treatment, targeting or diagnosing.

In a further aspect the present invention relates to a composition comprising the protein fragment as defined herein, the antibody according to the invention, or a conjugate according to the invention.

In a further aspect the present invention relates to a protein fragment as defined herein, the antibody according to the invention, a VAR2CSA polypeptide, or a conjugate according to the invention for use as a medicament or diagnostic agent.

In a further aspect the present invention relates to a protein fragment as defined herein, the antibody according to the invention, a VAR2CSA polypeptide, or a conjugate according to the invention for use in diagnosis.

In a further aspect the present invention relates to a pharmaceutical composition comprising the protein fragment as defined herein, a VAR2CSA polypeptide, or a conjugate according to the invention.

In a further aspect the present invention relates to a method for detecting a protein fragment as defined herein, or a conjugate according to the invention in a biological sample, said method comprising: a) obtaining a biological sample; b) contacting said biological sample with an antibody according to the invention; and c) detecting complexes of said antibody and said protein fragment or conjugate, if any; as an indication of the presence of said protein fragment or conjugate in said sample.

Accordingly, methods are provided to measure the level of protein fragments of VAR2CSA in a biological sample. This may be used and applied as part of a treatment, for monitoring the progress of a treatment, or alternatively as part of a production method producing VAR2CSA polypeptides according to the present invention.

In a further aspect the present invention relates to the use of a protein fragment as defined herein, a VAR2CSA polypeptide, or a conjugate according to the invention; for the preparation of a medicament.

In a further aspect the present invention relates to a protein fragment as defined herein, a VAR2CSA polypeptide, or a conjugate according to the invention for the treatment of any indications associated with a condition involving expression, such as inappropriate expression of CSA, such as in cancer, arthritis, arthrosis, multiple sclerosis, healing after neural damage, cartilage repair, wound healing, and in psoriasis.

In a further aspect the present invention relates to a method for the treatment of any indication associated with expression, such as inappropriate expression of CSA, such as in cancer, arthritis, arthrosis, multiple sclerosis, pathological conditions caused by neural damage, conditions of the cartilage and scar tissue, such as in rheumatism, cartilage repair or wound healing, or in psoriasis; the method comprising administering a therapeutically or prophylactically effective amount of a protein fragment as defined herein, a VAR2CSA polypeptide, or a conjugate according to the invention to a subject in need thereof.

In a further aspect the present invention relates to a method for preventing the occurrence of an indication or condition associated with expression, such as inappropriate expression of CSA, such as in cancer, multiple sclerosis, arthritis, arthrosis, pathological conditions caused by neural damage, conditions of the cartilage and scar tissue, such as in rheumatism, cartilage repair or wound healing, or in psoriasis; the method comprising administering a therapeutically or prophylactically effective amount of a protein fragment as defined herein, a VAR2CSA polypeptide, or a conjugate according to the invention to a subject in need thereof.

In a further aspect the present invention relates to the use of a protein fragment as defined herein, a VAR2CSA polypeptide, or a conjugate according to the invention, as a biomarker, such as tool to detect expression, such as inappropriate expression of CSA in body fluids such as blood, plasma, urine, saliva, feces, cerebrospinal fluid, lymph, gastric fluid, pleural fluid, cartilage fluid, sperm, and/or tissue for the diagnosis and/or prognosis of an indication or condition associated with expression, such as inappropriate expression of CSA, such as a malignant disease, arthritis, arthrosis, pathological conditions caused by neural damage, conditions of the cartilage and scar tissue, such as in rheumatism or wound healing, or a cancer disease, such as brain tumors, liver tumors and tumors in the reproductive tract.

It is to be understood that as used herein the term biomarker is intended to refer to the use of VAR2CSA polypeptides, conjugates and fusion proteins according to the present invention when introduced into an organism to detect CSA expression as a mean for diagnosis and/or prognosis of an indication or condition associated with expression of CSA, such as inappropriate expression of CSA.

In a further aspect the present invention relates to the use of a protein fragment as defined herein, a VAR2CSA polypeptide, or a conjugate according to the invention for the immunization of a subject, such as in a vaccine.

In a further aspect the present invention relates to the use of a protein fragment as defined herein, a VAR2CSA polypeptide, or a conjugate according to the invention, as a targeting moiety for the isolation of a cell expressing CD44 and/or CSPG4, and/or any other proteoglycan, such as a proteoglycan listed in Table 1.

TABLE 1

Potential molecules targeted by a VAR2CSA polypeptide

| Protein ID 1 | Protein ID 2 | Gene name |
|---|---|---|
| NG2 | CSPG4 | cspg4 |
| Neuroglycan and Neuroglycan-C | CSPG5 | ngc |
| Neuropilin-1 CS | NRP-1-CS | NRP1 |
| APLP2 and APP (and when CSA is added the proteins are called Appicans) | amyloid precursor-like protein 2 | APLP2 |
| Snorc | | Snorc |
| Tomoregulin-2 | TENB2 | TMEFF2 |
| Thrombomodulin, | CD141 | THBD |
| Betaglycan | Transforming growth factor beta receptor III | TGFBR3 |
| Syndecan 1 | CD138 | SDC1 |
| Syndecan 2 | CD362 | SDC2 |
| Syndecan 3 | | SDC3 |
| Syndecan 4 | Amphiglycan | SDC4 |
| CSPG8 | CSPG8 | Cd44 |
| Glypican1-6 (kun 1 og 5) | | GPC1-6 |
| Brevican | CSPG7 | bcan |
| lubricin | Proteoglycan 4 | PRG4 |
| Dentin matrix protein 1 | | DMP1 |
| Neurocan | CSPG3 | ncan |
| Versican | CSPG2 | vcan |
| Aggrecan | CSPG1 | acan |
| Bamecan | CSPG6 | smc3 |
| SRPX2 | Sushi repeat-containing protein | SRPX2 |
| Serglycin | Hematopoietic proteoglycan core protein | SRGN |
| Decorin | Small leucine-rich proteoglycan (SLRP) family | dcn |
| Biglycan | Small leucine-rich proteoglycan (SLRP) family | bgn |
| Lumican | Small leucine-rich proteoglycan (SLRP) family | lum |
| Fibromodulin | Small leucine-rich proteoglycan (SLRP) family | fmod |

TABLE 1-continued

Potential molecules targeted by a VAR2CSA polypeptide

| Protein ID 1 | Protein ID 2 | Gene name |
|---|---|---|
| Keratocan | Small leucine-rich proteoglycan (SLRP) family | kera |
| Mimecan | osteoglycin | ogn |
| Testican 1-3 | BM-40/SPARC/osteonectin family of extracellular calcium-binding proteins. | SPOCK1 |
| phosphacan | Receptor-type tyrosine-protein phosphatase zeta | PTPRZ1 |
| Leprecan | Leucine Proline-Enriched Proteoglycan 1 | LEPRE1 |
| Perlecan | basement membrane-specific heparan sulfate proteoglycan core protein | HSPG2 |

In a further aspect the present invention relates to a method for the isolation of cells expressing CD44, and/or CSPG4 and/or any other proteoglycan, such as a proteoglycan listed in Table 1, such as cancer stem cells in a biological sample, said method comprising:

a) obtaining a biological sample comprising cells expressing CD44, and/or CSPG4 and/or any other proteoglycan, such as a proteoglycan listed in Table 1;
b) contacting said biological sample with a protein fragment as defined herein, a VAR2CSA polypeptide, or a conjugate according to the invention, optionally coupled to a solid support; and
c) purifying or isolating the complexes of said cells expressing CD44, and/or CSPG4 and/or any other proteoglycan, such as a proteoglycan listed in Table 1 and said protein fragment or conjugate.

In a further aspect the present invention relates to a diagnostic method for detecting elevated CSA levels in a body fluid, such as blood, plasma, urine, spinal fluid, pleura effusions, joint fluid, bone marrow, gastric fluid, faeces, semen, sperm, prostate fluid, saliva, eye fluid, lung aspirate, and lymph, in response to malignancy or other conditions associated with inappropriate CSA expression, the method comprising the steps of contacting said body fluid with a protein fragment as defined herein, a VAR2CSA polypeptide, or a conjugate according to the invention and detecting the complexes formed with CSA in said body fluid.

In a further aspect the present invention relates to a method for the purification of CD44, and/or CSPG4, and/or any other proteoglycan, such as a proteoglycan listed in Table 1 in a biological sample, said method comprising:

a) obtaining a biological sample comprising CD44, and/or CSPG4 and/or any other proteoglycan, such as a proteoglycan listed in Table 1;
b) contacting said biological sample with a protein fragment as defined herein, a VAR2CSA polypeptide, or a conjugate according to the invention, optionally coupled to a solid support; and
c) purifying or isolating the complexes of said CD44, and/or CSPG4, and/or any other proteoglycan, such as a proteoglycan listed in Table 1 and said protein fragment or conjugate.

In a further aspect the present invention relates to a protein fragment as defined herein, a VAR2CSA polypeptide, or a conjugate according to the invention, or pharmaceutical composition according to the invention in combination with any other suitable anticancer agent.

DETAILED DISCLOSURE OF THE INVENTION

This invention is based on the fact that a part of a malaria protein, the so-called VAR2CSA, can bind to a cancer specific antigen and extra-cellular CSPG with very high specificity and very high binding strength.

VAR2CSA mediates parasite adhesion exclusively to low-sulfated chondroitin sulfate A (CSA) attached to proteoglycans (CSPG) in the placenta of pregnant women. Recombinant protein has been shown to bind with unprecedented high affinity and specificity to CSA. This may be due to an interaction with CSA that is not only dependent on the charged sulfates but also on the CS backbone. The inventors of the present invention envision that CS present in the placenta is very similar to the CS presented on various cancer cells including cancer stem cells. This is substantiated by the fact that VAR2CSA expressing malaria parasites adhere specifically to CSA on C32 melanoma cells and to human brain cancer cells.

Accordingly, the current invention relies on the high affinity and specificity between VAR2CSA recombinant proteins and low-sulfated CSA. By tagging this protein the invention can be used in a wide range of applications including the tracking of metastases in vivo and to diagnose metastatic disease. By coupling VAR2CSA to an apoptotic or cytotoxic reagent the invention can be used to specifically target and eliminate cancer cells and cancer stem cells. By simple therapy using VAR2CSA recombinant protein it will be possible to neutralize the activity of CSA thereby inhibiting tumorigenesis and/or metastasis of CSA-expressing cancer cells. CSA can be present on a number of protein backbones, e.g. CSPG4, CD44, biglycan, decorin, versican, aggrecan (the major CSPG in cartilage), perlecan, syndecan, and others listed in Table 1.

The present invention is envisioned to be particularly relevant to malignant melanoma cancer including cutaneous, ocular and conjuctival melanoma having CSPG4 with CSA chains on the surface of the melanoma cells. This GAG chain is believed to be involved in mitoses and metastases. However, CSPG4 is not only specific to melanoma. Micro- and tissue array analyses, performed by the inventors on data from large panels of human tissue and cell lines, suggest that CSPG4 and other types of CSA-containing proteoglycans may be present on a wide range of cancer types originating from all three cellular germ layers. These cancer types include carcinomas (Breast carcinoma, Pancreatic carcinoma, Ovarian carcinoma, Endometrial carcinoma, Hepatocellular carcinoma, Lung carcinoma, Colon carcinoma, Prostate carcinoma, Cervix carcinoma, Testis carcinoma, Basal cell skin carcinoma, Clear cell renal cell carcinoma, Kreatinized head and neck squamous cell carcinoma, Skin squamous cell carcinoma, Vulvar kreatinized squamous cell carcinoma and Vulvar basal cell carcinoma), sarcomas (Breast liposarcoma, Fibrosarcoma, Dedifferentiated chondro- and liposarcoma, Leiomyosarcoma, Liposarcoma, Myxoid liposarcoma, Uterine corpus leiomyosarcoma, Osteosarcoma, Ewing sarcoma and Rhabdomyosarcoma), hematopoietic cancers (Chronic lymphatic leukaemia (CLL), Acute lymphatic leukaemia (ALL), Acute myeloid leukaemia (AML), B-cell, T-cell and large granular lymphoma), tumours of neuroepithelial tissue, such as Astrocytomas (Pleomorphic Xanthoastrocytoma, Fibrillary Astrocytomas, Anaplastic astrocytoma, Glioblastoma Multiforme), Oligodendroglioma, Ependymoma, Choroid plexus tumor, Oligoastrocytoma, gliosarcoma, Ganglioglioma, Retinoblastoma, Neurocytoma, Neuroblastomas (Esthesioneuroblastoma and Ganglioneuroblastoma), Medulloblastoma, Atypical Teratoid Rhabdoid tumors and all types of neuroendocrine cancer.

Chondroitin sulfate proteoglycans (CSPG) also constitute an important component of the extracellular matrix of the central nerve system (CNS) including the eye and of joint cartilage. Extra-cellular CSPG is critically involved in the pathogenesis of arthritis and the lack of regeneration after neural damage. Loss of extra-cellular CSPG is critical for the development of arthritis and arthrosis, and high local concentrations of extra-cellular CSPG prevents neural out growth after neural damage.

VAR2CSA recombinant proteins may not only be used in the treatment of indications associated with malignant growth, such as in cancers. Therapies to either increase or decrease CSPG presence in the extracellular environment may be used to treat arthritis, arthrosis and to enhance neural recovery after neurite damage, including multiple sclerosis. For these strategies the inventors of the present invention envision that VAR2CSA may be used either as a direct inhibitor or as a molecule targeting and maintaining drugs changing CSPG metabolism to the affected tissues.

The inventors of the present invention have identified a malaria protein that binds CSA in the intervillous spaces of the placenta with an affinity below 10 nM. Smaller recombinant parts of VAR2CSA have been produced at high yields that bind CSA with characteristics similar to that of the full-length and native VAR2CSA protein. The recombinant VAR2CSA protein does not bind other CS such as chondroitin sulfate C (C6S) or highly sulfated GAGs such as heparan sulfate (HS). Recombinant proteins can be produced to bind with high affinity to CSA in various expression systems, here among S2 cells, T.Ni cells, CHO cells and *E. coli* strains including BL21 and SHUFFLE cells (tm Lifetechnologies).

The inventors of the present invention have also identified a single small (75 kDa) antigen that binds CSA with very high affinity (nM) and high specificity. Table 3 (See example 2) lists the CSA affinity of all the analyzed VAR2CSA proteins using biosensor technology.

The inventors of the present invention have shown that this VAR2CSA recombinant protein binds strongly at low concentrations to a wide range of cancer cell lines including cutaneous Melanoma (C32, MeWo), Lung carcinoma (A549), Breast carcinoma (HCC1395), Osterosarcoma (U2OS, MNNG/HOS), Rhabdomyosarcoma (RH30) and cutaneous T-cell lymphoma (Table 4 and 5). As a control molecule another VAR2CSA protein was used, which is identical to the minimal binding VAR2CSA construct except for a 151 amino acids truncation in the C-terminal part of the molecule. This truncation removes the CSA binding. Recombinant VAR2CSA binds all CSPG4 expressing cell lines and cancer cell lines expressing other CSPG molecules having CSA chains (e.g. T-cell lymphoma). Recombinant VAR2CSA protein fails to interact with human red blood cells and peripheral blood mononuclear cells (PBMC) (Table 4).

The inventors of the present invention have shown herein that malaria parasites adhere to C32 melanoma cells, probably through a specific interaction between CSPG4 and VAR2CSA. Thus, it is envisioned that recombinant VAR2CSA and conjugates thereof may be used as a therapeutic compound targeting CSA on various cancer cells.

The advantages of targeting CSA on cancer cells with VAR2CSA over other current therapies in development are numerous:

1) The interaction between VAR2CSA and CSA is of unprecedented high affinity and highly specific.

2) VAR2CSA is an evolutionary refined malaria protein and it is thus unlikely that therapy will break tolerance and cause autoimmune reactions in the patient.

3) VAR2CSA is a stable protein that is well characterized and can be highly expressed in organisms compatible with large-scale protein production.

4) VAR2CSA is a polymorphic protein with a number of serovariants. Repeated therapy could be offered by different serovariants to avoid issues with neutralizing antibodies.

5) VAR2CSA is naturally exposed extracellularly on the *P. falciparum*-infected the red blood cell and is thus by nature a stable protein in human serum and has been shown to be highly protease resistant.

The present invention is centred on the interaction between VAR2CSA and CSA. This interaction is a high affinity interaction and the main use is to target CSA expressing cancer cells.

CSA may also be involved in other diseases and pathological conditions like for example arthritis, arthrosis, multiple sclerosis and healing after neural damage, cartilage repair, wound healing, and in psoriasis. Accordingly, VAR2CSA polypeptides or conjugates may be used in the treatment of any such disease or condition.

In addition the interaction between VAR2CSA and CSA could be used as a biotechnological tool, for example for protein purification and cell sorting assays.

Accordingly, the inventors of the present invention envision several uses of this invention:

1) Traceable recombinant VAR2CSA polypeptides or conjugates may be used to track tumors and metastases in cancer patients.

2) Recombinant VAR2CSA polypeptides or conjugates may be used to directly target and neutralize CSA activity in cancer cells.

3) Recombinant VAR2CSA polypeptides or conjugates, such as VAR2CSA polypeptides coupled to a cytotoxic molecule may be used to target cancer cells with minimal adverse toxicity to CSA-negative tissue.

4) Tagged recombinant VAR2CSA polypeptides or conjugates may be used as a research or clinically developmental tool studying CSA on cancer cells.

5) A tagged recombinant VAR2CSA polypeptides or conjugates may be used in assays to sort CSA-positive cells in biotechnology and life sciences. This could be done by coupling recombinant VAR2CSA to resins so that it can be used to purify CSPG4-expressing cells, such as cancer stem cells, providing a novel and efficient biotechnological tool.

6) VAR2CSA polypeptides or conjugates may be used for in vitro depletion of CSPG4-expressing cells, such as cancer cells, as part of autologous transplantations.

7) VAR2CSA polypeptides or conjugates could be used in an anti-CSPG4 vaccine. By immunizing animals with CSPG4-VAR2CSA complexes or conjugates, VAR2CSA might act as a carrier and enhancer for an immune response towards CSPG4 with the aim of breaking tolerance to CSPG4.

8) VAR2CSA polypeptides or conjugates could be used in monitoring increased CSA levels in body fluids (i.e. urine, spinal fluid, pleural effusions, joints, bone marrow, and lymph) in response to malignancy. This is based on the fact that VAR2CSA polypeptides have specificity for low sulfated CSA and could detect tumor progression as a function of an increased proportion of un-sulfated CS (COS).

9) VAR2CSA polypeptides or conjugates could be used in treatment of arthritis and arthrosis. The VAR2CSA polypeptides could block or target drugs that block protease mediated degradation of aggrecan during arthritis and arthrosis. VAR2CSA polypeptides could also be used to target anti-inflammatory drugs to the affected tissues and to deliver inhibitors such as ADAMTS4 and -5 inhibitors. VAR2CSA polypeptides could be used to target drugs that stimulate the production of aggrecan by chondrocytes. Repeated i.v. injections of aggrecan coupled to VAR2CSA polypeptides could be used to induce tolerance to aggrecan.

10) VAR2CSA polypeptides or conjugates could by binding to extracellular CSPG in neural tissue inactivate the CSPGs effect on neurite outgrowth for instance by blocking the signaling through the tyrosine phosphatase-sigma receptor. VAR2CSA peptides could target drugs degrading CSPG or inhibiting CSPG production in affected neural tissue. For examples the following drugs could be considered to be coupled to VAR2CSA: chondroitinase ABC, which cut the sugar chains of the protein core of CSPG molecules. Xylocides, which reduce CSPG production, or drugs that inhibit enzymes important foe CSPG production such as chondroitin synthase or chondroitin polymerizing factor. Examples for such drugs include: 4-fluoro-glucosamine, p-nitrophenyl-beta-D-xyloxide, 4-methyl-umbelliferyl-beta-D-xylopyranoside.

11) VAR2CSA polypeptides or conjugates could also be used to target and maintain cytokines such as IL1-alfa, which stimulate production of ADAMTS4, which subsequently cleave CSPG.

12) CSPG4 expression on cancer cells can influence drug resistance. Tumors in many patients usually initially respond to therapy but chemoresistance develops over time and cancer progresses. CSPG4 expression is associated with multidrug resistance and is mediated by its association with integrin-induced activation of PI3K pathways. Recombinant VAR2CSA polypeptide targeting CSPG4 on cancer cells can reduce or hinder chemoresistance and could thus be used in combination therapies with for example PLX4032, a BRAFV600E inhibitor.

Definitions

The term "VAR2CSA polypeptide" as used herein refers to the extracellular part of a specific Erythrocyte Membrane Protein 1 (PfEMP1) protein expressed by *Plasmodium falciparum* interacting with chondroitin sulfate proteoglycans (CSPG) and characterized by having a sequence of SEQ ID NO:55 or SEQ ID NO:56 or fragments or variants thereof with the ability to bind chondroitin sulfate A (CSA) that could be presented on a proteoglycans (CSPG).

In some embodiments, the VAR2CSA polypeptide according to the present invention at least comprises the protein fragment of VAR2CSA, which fragment consist of a sequential amino acid sequence of a) ID1, and b) DBL2Xb.

In some embodiments, the VAR2CSA polypeptide according to the present invention at least comprises the protein fragment of VAR2CSA, which fragment consist of a sequential amino acid sequence of a) ID1, and b) DBL2Xb, and c) ID2a.

Included within the definition of a VAR2CSA polypeptide is polypeptides described in Salanti A. et al Mol. Micro 2003 July; 49(1):179-91, in Khunrae P. et al, J Mol Biol. 2010 Apr. 2; 397(3):826-34, in Srivastava A. et al, Proc Natl Acad Sci USA. 2010 Mar. 16; 107(11):4884-9, in Dahlback M. et al, J Biol Chem. 2011 May 6; 286(18):15908-17, or in Srivastava A. et al, PLoS One. 2011; 6(5):e20270.

The term "ID1" as used herein refers to a domain of VAR2CSA characterized by having an amino acid sequence with at least 70% sequence identity to an amino acid sequence identified by 1-152 of SEQ ID NO:1.

The term "DBL2Xb" as used herein refers to a domain of VAR2CSA characterized by having an amino acid sequence with at least 70% sequence identity with to amino acid sequence identified by 153-577 of SEQ ID NO:1.

The term "ID2a" as used herein refers to a domain of VAR2CSA characterized by having an amino acid sequence of at least 20, at least 21, at least 22, at least 23, at least 24, at least 25, at least 26, at least 27, at least 28, at least 29, at least 30, at least 31, at least 32, at least 33, at least 34, at least 35, at least 36, at least 37, at least 38, at least 39, at least 40, at least 41, at least 42, at least 43, at least 44, at least 45, at least 46, at least 47, at least 48, at least 49, at least 50, at least 51, at least 52, at least 53, at least 54, at least 55, at least 56, at least 57, at least 58, at least 59, at least 60, at least 61, or at least 62, such as the 63 consecutive amino acids from the N-terminal of amino acids 578-640 of SEQ ID NO:1 and with at least 70% sequence identity to such a sequence of consecutive amino acids.

In some embodiments an amino acid sequence identity referred to herein of at least 70% of any one sequence identified by SEQ ID NO:1-75 or a fragment thereof, refers to a sequence with at least 71, 72, 73, 74, 75, 76, 77, 78, 79, 80, 81, 8, 83, 84, 85, 86, 87, 88, 89, 90, 91, 92, 93, 94, 95, 96, 97, 98, or 99% sequence identity to this sequence.

The terms "variant" or "variants", as used herein, refers to a VAR2CSA polypeptide having an amino acid sequence of SEQ ID NO:55 or SEQ ID NO:56 or a fragments a VAR2CSA polypeptide comprising an amino acid sequence of SEQ ID NO:1-54, which fragments or variants retain the ability to bind chondroitin sulfate A (CSA) on proteoglycans (CSPG), wherein one or more amino acids have been substituted by another amino acid and/or wherein one or more amino acids have been deleted and/or wherein one or more amino acids have been inserted in the polypeptide and/or wherein one or more amino acids have been added to the polypeptide. Such addition can take place either at the N-terminal end or at the C-terminal end or both. The "variant" or "variants" within this definition still have functional activity in terms of being able to bind chondroitin sulfate A (CSA). In some embodiment a variant has at least 70%, such as at least 71, 72, 73, 74, 75, 76, 77, 78, 79, 80, 81, 8, 83, 84, 85, 86, 87, 88, 89, 90, 91, 92, 93, 94, 95, 96, 97, 98, or 99% sequence identity with the sequence of SEQ ID NO:1-75, such as the sequence of SEQ ID NO:1, 3-5, 10, 11, 29, 34, 36-38, 41, 43-45, 48, 53-56, 60-70, 72-75.

The phrases "functional variant", "functional fragment", and "functional derivatives" as used herein refers to variants, fragments, truncated versions, as well as derivatives of SEQ ID NO:55 or SEQ ID NO:56, such as any one of SEQ ID NO:1, 3-5, 10, 11, 29, 34, 36-38, 41, 43-45, 48, 53-56, 60-70, 72-75, which polypeptides comprises essential binding sequence parts of SEQ ID NO:55 or SEQ ID NO:56 and at least posses the ability to bind chondroitin sulfate A (CSA). It is to be understood that a VAR2CSA functional variant or functional fragment may have two or three features selected from being a both a variant, and/or a fragment and/or a derivative.

A functional variant or fragment of a VAR2CSA polypeptide encompass those that exhibit at least about 25%, such as at least about 50%, such as at least about 75%, such as at least about 90% of the binding affinity of wild-type VAR2CSA polypeptide that has been produced in the same cell type, when tested in the assays as described herein.

The term "immunologic fragment" as used herein refers to fragment of an amino acid sequence that posses essentially the same functional activities and the same spatial orientation to be recognized by an antibody. Accordingly a specific antibody will bind both the polypeptide and immunologic fragments thereof.

The term "another amino acid" as used herein means one amino acid that is different from that amino acid naturally present at that position. This includes but is not limited to amino acids that can be encoded by a polynucleotide. In some embodiments the different amino acid is in natural L-form and can be encoded by a polynucleotide.

The term "derivative" as used herein, is intended to designate a VAR2CSA polypeptide exhibiting substantially the same or improved biological activity relative to wild-type VAR2CSA identified by SEQ ID NO:55 or SEQ ID NO:56, or a fragment thereof, in which one or more of the amino acids of the parent peptide have been chemically modified, e.g. by alkylation, PEGylation, acylation, ester formation or amide formation or the like.

The term "construct" is intended to indicate a polynucleotide segment which may be based on a complete or partial naturally occurring nucleotide sequence encoding the polypeptide of interest. The construct may optionally contain other polynucleotide segments. In a similar way, the term "amino acids which can be encoded by polynucleotide constructs" covers amino acids which can be encoded by the polynucleotide constructs defined above, i.e. amino acids such as Ala, Val, Leu, Ile, Met, Phe, Trp, Pro, Gly, Ser, Thr, Cys, Tyr, Asn, Glu, Lys, Arg, His, Asp and Gln.

The term "vector", as used herein, means any nucleic acid entity capable of the amplification in a host cell. Thus, the vector may be an autonomously replicating vector, i.e. a vector, which exists as an extra-chromosomal entity, the replication of which is independent of chromosomal replication, e.g. a plasmid. Alternatively, the vector may be one which, when introduced into a host cell, is integrated into the host cell genome and replicated together with the chromosome(s) into which it has been integrated. The choice of vector will often depend on the host cell into which it is to be introduced. Vectors include, but are not limited to plasmid vectors, phage vectors, viruses or cosmid vectors. Vectors usually contain a replication origin and at least one selectable gene, i.e., a gene which encodes a product which is readily detectable or the presence of which is essential for cell growth.

As used herein the term "appropriate growth medium" means a medium containing nutrients and other components required for the growth of cells and the expression of the nucleic acid sequence encoding the VAR2CSA polypeptide of the invention.

In the present context, the term "treatment" is meant to include prevention, curing and alleviating the symptoms of a disease, disorder or condition involving expression, such as inappropriate expression of CSA, such as in cancer. Prophylactic and therapeutic administration of VAR2CSA polypeptide, conjugate or derivative according to the invention is thus included in the term "treatment".

The term "subject" as used herein means any animal, in particular mammals, such as humans, and may, where appropriate, be used interchangeably with the term "patient".

The term "sequence identity" as known in the art, refers to a relationship between the sequences of two or more polypeptide molecules or two or more nucleic acid molecules, as determined by comparing the sequences. In the art, "identity" also means the degree of sequence relatedness between nucleic acid molecules or between polypeptides, as the case may be, as determined by the number of matches between strings of two or more nucleotide residues or two or more amino acid residues. "Identity" measures the percent of identical matches between the smaller of two or more sequences with gap alignments (if any) addressed by a particular mathematical model or computer program (i.e., "algorithms").

The term "similarity" is a related concept, but in contrast to "identity", refers to a sequence relationship that includes both identical matches and conservative substitution matches. If two polypeptide sequences have, for example, (fraction ($^{10}\!/_{20}$)) identical amino acids, and the remainder are all non-conservative substitutions, then the percent identity and similarity would both be 50%. If, in the same example, there are 5 more positions where there are conservative substitutions, then the percent identity remains 50%, but the percent similarity would be 75% ((fraction ($^{15}\!/_{20}$))). Therefore, in cases where there are conservative substitutions, the degree of similarity between two polypeptides will be higher than the percent identity between those two polypeptides.

Conservative modifications to the amino acid sequence of SEQ ID NO: 1-56, 60-70, and 72-75 (and the corresponding modifications to the encoding nucleotides) will produce VAR2CSA polypeptides having functional and chemical characteristics similar to those of naturally occurring VAR2CSA polypeptides. In contrast, substantial modifications in the functional and/or chemical characteristics of a VAR2CSA polypeptide may be accomplished by selecting substitutions in the amino acid sequence of SEQ ID NO: 1-56, 60-70, and 72-75 that differ significantly in their effect on maintaining (a) the structure of the molecular backbone in the area of the substitution, for example, as a sheet or helical conformation, (b) the charge or hydrophobicity of the molecule at the target site, or (c) the bulk of the side chain.

For example, a "conservative amino acid substitution" may involve a substitution of a native amino acid residue with a nonnative residue such that there is little or no effect on the polarity or charge of the amino acid residue at that position. Furthermore, any native residue in the polypeptide may also be substituted with alanine, as has been previously described for "alanine scanning mutagenesis" (see, for example, MacLennan et al., 1998, Acta Physiol. Scand. Suppl. 643:55-67; Sasaki et al., 1998, Adv. Biophys. 35:1-24, which discuss alanine scanning mutagenesis).

Desired amino acid substitutions (whether conservative or non-conservative) can be determined by those skilled in the art at the time such substitutions are desired. For example, amino acid substitutions can be used to identify important residues of a VAR2CSA polypeptide, or to increase or decrease the affinity of a VAR2CSA polypeptide described herein.

Naturally occurring residues may be divided into classes based on common side chain properties:
1) hydrophobic: norleucine, Met, Ala, Val, Leu, Ile;
2) neutral hydrophilic: Cys, Ser, Thr, Asn, Gln;
3) acidic: Asp, Glu;
4) basic: His, Lys, Arg;
5) residues that influence chain orientation: Gly, Pro; and
6) aromatic: Trp, Tyr, Phe.

For example, non-conservative substitutions may involve the exchange of a member of one of these classes for a member from another class. Such substituted residues may be introduced into regions of the *Plasmodium falciparum* VAR2CSA polypeptide that are homologous with non-*Plasmodium falciparum* VAR2CSA polypeptides, or into the non-homologous regions of the molecule.

In making such changes, the hydropathic index of amino acids may be considered. Each amino acid has been assigned a hydropathic index on the basis of their hydrophobicity and charge characteristics, these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

The importance of the hydropathic amino acid index in conferring interactive biological function on a protein is understood in the art. Kyte et al., J. Mol. Biol., 157:105-131 (1982). It is known that certain amino acids may be substituted for other amino acids having a similar hydropathic index or score and still retain a similar biological activity. In making changes based upon the hydropathic index, the substitution of amino acids whose hydropathic indexes are within ±2 is preferred, those that are within ±1 are particularly preferred, and those within ±0.5 are even more particularly preferred.

It is also understood in the art that the substitution of like amino acids can be made effectively on the basis of hydrophilicity, particularly where the biologically functionally equivalent protein or peptide thereby created is intended for use in immunological embodiments, as in the present case. The greatest local average hydrophilicity of a protein, as governed by the hydrophilicity of its adjacent amino acids, correlates with its immunogenicity and antigenicity, i.e., with a biological property of the protein.

The following hydrophilicity values have been assigned to amino acid residues: arginine (+3.0); lysine ('3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). In making changes based upon similar hydrophilicity values, the substitution of amino acids whose hydrophilicity values are within ±2 is preferred, those that are within ±1 are particularly preferred, and those within ±0.5 are even more particularly preferred. One may also identify epitopes from primary amino acid sequences on the basis of hydrophilicity. These regions are also referred to as "epitopic core regions."

A skilled artisan will be able to determine suitable variants of the polypeptide as set forth in SEQ ID NO:1-75 using well known techniques. For identifying suitable areas of the molecule that may be changed without destroying activity, one skilled in the art may target areas not believed to be important for activity. For example, when similar polypeptides with similar activities from the same species or from other species are known, one skilled in the art may compare the amino acid sequence of a VAR2CSA polypeptide to such similar polypeptides. With such a comparison, one can identify residues and portions of the molecules that are conserved among similar polypeptides. It will be appreciated that changes in areas of a VAR2CSA polypeptide that are not conserved relative to such similar polypeptides would be less likely to adversely affect the biological activity and/or structure of the VAR2CSA polypeptide. One skilled in the art would also know that, even in relatively conserved regions, one may substitute chemically similar amino acids for the naturally occurring residues while retaining activity (conservative amino acid residue substitutions). Therefore, even areas that may be important for biological activity or for structure may be subject to conservative amino acid substitutions without destroying the biological activity or without adversely affecting the polypeptide structure.

Additionally, one skilled in the art can review structure-function studies identifying residues in similar polypeptides that are important for activity or structure. In view of such a comparison, one can predict the importance of amino acid residues in a VAR2CSA polypeptide that correspond to amino acid residues that are important for activity or structure in similar polypeptides. One skilled in the art may opt for chemically similar amino acid substitutions for such predicted important amino acid residues of VAR2CSA polypeptides and other polypeptides of the invention.

One skilled in the art can also analyze the three-dimensional structure and amino acid sequence in relation to that structure in similar polypeptides. In view of that information, one skilled in the art may predict the alignment of amino acid residues of a VAR2CSA polypeptide with respect to its three dimensional structure. One skilled in the art may choose not to make radical changes to amino acid residues predicted to be on the surface of the protein, since such residues may be involved in important interactions with other molecules. Moreover, one skilled in the art may generate test variants containing a single amino acid substitution at each desired amino acid residue. The variants can then be screened using activity assays as described herein. Such variants could be used to gather information about suitable variants. For example, if one discovered that a change to a particular amino acid residue resulted in destroyed, undesirably reduced, or unsuitable activity, variants with such a change would be avoided. In other words, based on information gathered from such routine experiments, one skilled in the art can readily determine the amino acids where further substitutions should be avoided either alone or in combination with other mutations.

A number of scientific publications have been devoted to the prediction of secondary structure. See Moult J., Curr. Op. in Biotech., 7(4):422-427 (1996), Chou et al., Biochemistry, 13(2):222-245 (1974); Chou et al., Biochemistry, 113(2): 211-222 (1974); Chou et al., Adv. Enzymol. Relat. Areas Mol. Biol, 47:45-148 (1978); Chou et al., Ann. Rev. Biochem., 47:251-276 and Chou et al., Biophys. J., 26:367-384 (1979). Moreover, computer programs are currently available to assist with predicting secondary structure. One method of predicting secondary structure is based upon homology modeling. For example, two polypeptides or proteins, which have a sequence identity of greater than 30%, or similarity greater than 40% often have similar structural topologies. The recent growth of the protein structural data base (PDB) has provided enhanced predictability of secondary structure, including the potential number of folds within a polypeptide's or protein's structure. See Holm et al., Nucl. Acid. Res., 27(1):244-247 (1999). It has been suggested (Brenner et al., Curr. Op. Struct. Biol., 7(3):369-376 (1997)) that there are a limited number of folds in a given polypeptide or protein and that once a critical number of structures have been resolved, structural prediction will gain dramatically in accuracy.

Additional methods of predicting secondary structure include "threading" (Jones, D., Curr. Opin. Struct. Biol., 7(3):377-87 (1997); Sippl et al., Structure, 4(1):15-9 (1996)), "profile analysis" (Bowie et al., Science, 253:164-170 (1991); Gribskov et al., Meth. Enzymol., 183:146-159 (1990); Gribskov et al., Proc. Nat. Acad. Sci., 84(13):4355-4358 (1987)), and "evolutionary linkage" (See Home, supra, and Brenner, supra).

Identity and similarity of related polypeptides can be readily calculated by known methods. Such methods include, but are not limited to, those described in Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part 1, Griffin, A. M., and Griffin, H. G., eds., Humana Press, New Jersey, 1994; Sequence Analysis in Molecular Biology, von Heinje, G., Academic Press, 1987; Sequence Analysis Primer, Gribskov, M. and Devereux, J., eds., M. Stockton Press, New York, 1991; and Carillo et al., SIAM J. Applied Math., 48:1073 (1988).

Preferred methods to determine identity and/or similarity are designed to give the largest match between the sequences tested. Methods to determine identity and similarity are described in publicly available computer programs. Preferred computer program methods to determine identity and similarity between two sequences include, but are not limited to, the GCG program package, including GAP (Devereux et al., Nucl. Acid. Res., 12:387 (1984); Genetics Computer Group, University of Wisconsin, Madison, Wis.), BLASTP, BLASTN, and FASTA (Altschul et al., J. Mol. Biol., 215:403-410 (1990)). The BLASTX program is publicly available from the National Center for Biotechnology Information (NCBI) and other sources (BLAST Manual, Altschul et al. NCB/NLM/NIH Bethesda, Md. 20894; Altschul et al., supra). The well known Smith Waterman algorithm may also be used to determine identity.

Certain alignment schemes for aligning two amino acid sequences may result in the matching of only a short region of the two sequences, and this small aligned region may have very high sequence identity even though there is no significant relationship between the two full length sequences. Accordingly, in a preferred embodiment, the selected alignment method (GAP program) will result in an alignment that spans at least 50 contiguous amino acids of the target polypeptide.

For example, using the computer algorithm GAP (Genetics Computer Group, University of Wisconsin, Madison, Wis.), two polypeptides for which the percent sequence identity is to be determined are aligned for optimal matching of their respective amino acids (the "matched span", as determined by the algorithm). A gap opening penalty (which is calculated as 3 times the average diagonal; the "average diagonal" is the average of the diagonal of the comparison matrix being used; the "diagonal" is the score or number assigned to each perfect amino acid match by the particular comparison matrix) and a gap extension penalty (which is usually {fraction (1/10)} times the gap opening penalty), as well as a comparison matrix such as PAM 250 or BLOSUM 62 are used in conjunction with the algorithm. A standard comparison matrix (see Dayhoff et al., Atlas of Protein Sequence and Structure, vol. 5, supp.3 (1978) for the PAM 250 comparison matrix; Henikoff et al., Proc. Natl. Acad. Sci USA, 89:10915-10919 (1992) for the BLOSUM 62 comparison matrix) is also used by the algorithm.

Preferred parameters for a polypeptide sequence comparison include the following:

Algorithm: Needleman et al., J. Mol. Biol, 48:443-453 (1970); Comparison matrix: BLOSUM 62 from Henikoff et al., Proc. Natl. Acad. Sci. USA, 89:10915-10919 (1992); Gap Penalty: 12, Gap Length Penalty: 4, Threshold of Similarity: 0.

The GAP program is useful with the above parameters. The aforementioned parameters are the default parameters for polypeptide comparisons (along with no penalty for end gaps) using the GAP algorithm.

Preferred parameters for nucleic acid molecule sequence comparisons include the following: Algorithm: Needleman et al., J. Mol Biol., 48:443-453 (1970); Comparison matrix: matches=+10, mismatch=0, Gap Penalty: 50, Gap Length Penalty: 3.

The GAP program is also useful with the above parameters. The aforementioned parameters are the default parameters for nucleic acid molecule comparisons.

Other exemplary algorithms, gap opening penalties, gap extension penalties, comparison matrices, thresholds of similarity, etc. may be used, including those set forth in the Program Manual, Wisconsin Package, Version 9, September, 1997. The particular choices to be made will be apparent to those of skill in the art and will depend on the specific comparison to be made, such as DNA to DNA, protein to protein, protein to DNA; and additionally, whether the comparison is between given pairs of sequences (in which case GAP or BestFit are generally preferred) or between one sequence and a large database of sequences (in which case FASTA or BLASTA are preferred).

The inventors of the present invention has now addressed and found the answers to the following key questions related to the molecular mechanism behind placental adhesion in PM: 1) is the described differential CSA adhesion related to the VAR2CSA sequence 2) what are the exact minimal structural requirements for VAR2CSA binding to CSA 3) what type of chemical interaction exists between VAR2CSA and CSA and finally 4) can this information be used to design an optimal vaccine antigen?

By expressing identical FCR3 and 3d7 VAR2CSA truncations, the present inventors showed that VAR2CSA bind CSA with similar affinity and specificity, regardless of parasite strain origin. These two sequences has a sequence identity of 79.6%. The present inventors further demonstrate that the high CSA binding-affinity is retained in several shorter fragments, and that DBL2X, including small regions from the flanking interdomains, form a compact core that contains the high affinity CSA binding site. In silico present inventors defined putative GAG binding sites in VAR2CSA and by deletion and substitution the present inventors showed that mutations in these sites have no effect on CSPG binding. Using the theory of polyelectrolyte-protein interactions the present inventors have shown that the VAR2CSA-CSA interaction may not, solely, be dependent on ionic interactions. Finally, the present inventors have shown that several short VAR2CSA fragments are capable of inducing the production of adhesion-blocking antibodies and that the anti-adhesive antibodies target the proposed CSA binding region. These data provide the first detailed insight into the biochemical nature of the interaction between a PfEMP1 molecule and its ligand.

Preparation of VAR2CSA Polypeptides and Other Polypeptides of the Invention

The invention also relates to a method of preparing VAR2CSA polypeptides and other polypeptides of the invention as mentioned above. The VAR2CSA polypeptides and other polypeptides of the invention described herein may be produced by means of recombinant nucleic acid techniques. In general, a cloned wild-type VAR2CSA nucleic acid sequence is modified to encode the desired protein. This modified sequence is then inserted into an expression vector, which is in turn transformed or transfected into host cells. Higher eukaryotic cells, in particular cultured mammalian cells, may be used as host cells. Procaryotic cells such as *Lactococcus lactis* or *E. coli* can also be used to express the polypeptides as long as these prokaryotes are able to produce disulfide bonds or the protein is or may be refolded correctly. In addition, Yeast strains can also be used to express the protein, here among *Saccharomyces cerevisiae* and P. *Pichia*.

The amino acid sequence alterations may be accomplished by a variety of techniques. Modification of the nucleic acid sequence may be by site-specific mutagenesis. Techniques for site-specific mutagenesis are well known in the art and are described in, for example, Zoller and Smith (DNA 3:479-488, 1984) or "Splicing by extension overlap", Horton et al., Gene 77, 1989, pp. 61-68. Thus, using the nucleotide and amino acid sequences of VAR2CSA, one may introduce the alteration(s) of choice. Likewise, procedures for preparing a DNA construct using polymerase chain reaction using specific primers are well known to per-sons skilled in the art (cf. PCR Protocols, 1990, Academic Press, San Diego, Calif., USA).

The polypeptides of the present invention can also comprise non-naturally occurring amino acid residues. Non-naturally occurring amino acids include, without limitation, beta-alanine, desaminohistidine, trans-3-methylproline, 2,4-methanoproline, cis-4-hydroxyproline, trans-4-hydroxyproline, N-methylglycine, allo-threonine, methylthreonine, hydroxyethylcys-teine, hydroxyethylhomocysteine, nitroglutamine, homoglutamine, pipecolic acid, thiazolidine carboxylic acid, dehydroproline, 3- and 4-methylproline, 3,3-dimethylproline, tert-leucine, nor-valine, 2-azaphenylalanine, 3-azaphenylalanine, 4-azaphenylalanine, and 4-fluorophenylalanine. Several methods are known in the art for incorporating non-naturally occurring amino acid residues into polypeptides. For example, an in vitro system can be employed wherein nonsense mutations are suppressed using chemically aminoacylated suppressor tRNAs. Methods for synthesizing amino acids and aminoacylating tRNA are known in the art. Transcription and translation of plasmids containing nonsense mutations is carried out in a cell-free system comprising an *E. coli* S30 extract and commercially available enzymes and other reagents. Polypeptides are purified by chromatography. See, for example, Robertson et al., J. Am. Chem. Soc. 113:2722, 1991; Ellman et al., Methods Enzymol. 202:301, 1991; Chung et al., Science 259:806-9, 1993; and Chung et al., Proc. Natl. Acad. Sci. USA 90:10145-9, 1993). In a second method, translation is carried out in *Xenopus* oocytes by microinjection of mutated mRNA and chemically aminoacylated suppressor tRNAs (Turcatti et al., J. Biol. Chem. 271:19991-8, 1996). Within a third method, *E. coli* cells are cultured in the absence of a natural amino acid that is to be replaced (e.g., phenylalanine) and in the presence of the desired non-naturally occurring amino acid(s) (e.g., 2-azaphenylalanine, 3-azaphenylalanine, 4-azaphenylalanine, or 4-fluorophenylalanine). The non-naturally occurring amino acid is incorporated into the polypeptide in place of its natural counterpart. See, Koide et al., Biochem. 33:7470-6, 1994. Naturally occurring amino acid residues can be converted to non-naturally occurring species by in vitro chemical modification. Chemical modification can be combined with site-directed mutagenesis to further expand the range of substitutions (Wynn and Richards, Protein Sci. 2:395-403, 1993).

The nucleic acid construct encoding the VAR2CSA polypeptides and other polypeptides of the invention may suitably be of genomic or cDNA origin, for instance obtained by preparing a genomic or cDNA library and screening for DNA sequences coding for all or part of the polypeptide by hybridization using synthetic oligonucleotide probes in accordance with standard techniques (cf. Sambrook et al., Molecular Cloning: A Laboratory Manual, 2nd. Ed. Cold Spring Harbor Labora-tory, Cold Spring Harbor, N.Y., 1989).

The nucleic acid construct encoding a VAR2CSA polypeptide may also be prepared synthetically by established standard methods, e.g. the phosphoramidite method described by Beaucage and Caruthers, Tetrahedron Letters 22 (1981), 1859-1869, or the method described by Matthes et al., EMBO Journal 3 (1984), 801-805. According to the phosphoramidite method, oligonucleotides are synthesised, e.g. in an automatic DNA synthesiser, purified, annealed, ligated and cloned in suitable vectors. The DNA sequences encoding the Plasmodium falciparum VAR2CSA polypeptides and other polypeptides of the invention may also be prepared by polymerase chain reaction using specific primers, for instance as described in U.S. Pat. No. 4,683,202, Saiki et al., Science 239 (1988), 487-491, or Sambrook et al., supra.

Furthermore, the nucleic acid construct may be of mixed synthetic and genomic, mixed synthetic and cDNA or mixed genomic and cDNA origin prepared by ligating fragments of syn-thetic, genomic or cDNA origin (as appropriate), the fragments corresponding to various parts of the entire nucleic acid construct, in accordance with standard techniques.

The nucleic acid construct is preferably a DNA construct. DNA sequences for use in producing VAR2CSA polypeptides and other polypeptides according to the present invention will typically encode a pre-pro polypeptide at the amino-terminus of VAR2CSA to obtain proper posttranslational processing and secretion from the host cell.

The DNA sequences encoding the Plasmodium falciparum VAR2CSA polypeptides and other polypeptides according to the present invention are usually inserted into a recombinant vector which may be any vector, which may conveniently be subjected to recombinant DNA procedures, and the choice of vector will often depend on the host cell into which it is to be introduced. Thus, the vector may be an autonomously replicating vector, i.e. a vector, which exists as an extrachromosomal entity, the replication of which is independent of chromosomal replication, e.g. a plasmid. Alternatively, the vector may be one which, when introduced into a host cell, is integrated into the host cell genome and replicated together with the chromosome(s) into which it has been integrated.

The vector is preferably an expression vector in which the DNA sequence encoding the Plasmodium falciparum VAR2CSA polypeptides and other polypeptides according to the present invention is operably linked to additional segments required for transcription of the DNA. In general, the expression vector is derived from plasmid or viral DNA, or may contain elements of both. The term, "operably linked" indicates that the segments are arranged so that they function in concert for their intended purposes, e.g. transcription initiates in a promoter and proceeds through the DNA sequence coding for the polypeptide.

Expression vectors for use in expressing VAR2CSA polypeptides and other polypeptides according to the present invention will comprise a promoter capable of directing the transcription of a cloned gene or cDNA. The promoter may be any DNA sequence, which shows transcriptional activity in the host cell of choice and may be derived from genes encoding proteins either homologous or heterologous to the host cell.

Examples of suitable promoters for directing the transcription of the DNA encoding the Plasmodium falciparum VAR2CSA polypeptide in mammalian cells are the SV40 promoter (Subramani et al., Mol. Cell Biol. 1 (1981), 854-864), the MT-1 (metallothionein gene) promoter (Palmiter et al., Science 222 (1983), 809-814), the CMV promoter (Boshart et al., Cell 41:521-530, 1985) or the adenovirus 2 major late promoter (Kaufman and Sharp, Mol. Cell. Biol, 2:1304-1319, 1982).

An example of a suitable promoter for use in insect cells is the polyhedrin promoter (U.S. Pat. No. 4,745,051; Vasuvedan et al., FEBS Lett. 311, (1992) 7-11), the P10 promoter (3.M. Vlak et al., J. Gen. Virology 69, 1988, pp. 765-776), the Autographa californica polyhedrosis virus basic protein promoter (EP 397 485), the baculovirus immediate early gene 1 promoter (U.S. Pat. Nos. 5,155,037; 5,162,222), or the baculovirus 39K delayed-early gene promoter (U.S. Pat. Nos. 5,155,037; 5,162,222).

Examples of suitable promoters for use in yeast host cells include promoters from yeast glycolytic genes (Hitzeman et al., J. Biol. Chem. 255 (1980), 12073-12080; Alber and Kawasaki, J. Mol. Appl. Gen. 1 (1982), 419-434) or alcohol dehydrogenase genes (Young et al., in Genetic Engineering of Microorganisms for Chemicals (Hollaender et al, eds.), Plenum Press, New York, 1982), or the TPI1 (U.S. Pat. No. 4,599,311) or ADH2-4c (Russell et al., Nature 304 (1983), 652-654) promoters.

Examples of suitable promoters for use in filamentous fungus host cells are, for instance, the ADH3 promoter (McKnight et al., The EMBO J. 4 (1985), 2093-2099) or the tpiA promoter. Examples of other useful promoters are those derived from the gene encoding A. oryzae TAKA amylase, Rhizomucor miehei aspartic proteinase, A. niger neutral alpha-amylase, A. niger acid stable alpha-amylase, A. niger or A. awamori glucoamylase (gluA), Rhizomucor miehei lipase, A. oryzae alkaline protease, A. oryzae triose phosphate isomerase or A. nidulans acetamidase. Preferred are the TAKA-amylase and gluA promoters. Suitable promoters are mentioned in, e.g. EP 238 023 and EP 383 779.

The DNA sequences encoding the Plasmodium falciparum VAR2CSA polypeptides and other polypeptides according to the present invention may also, if necessary, be operably connected to a suitable terminator, such as the human growth hormone terminator (Palmiter et al., Science 222, 1983, pp. 809-814) or the TPI1 (Alber and Kawasaki, J. Mol. Appl. Gen. 1, 1982, pp. 419-434) or ADH3 (McKnight et al., The EMBO J. 4, 1985, pp. 2093-2099) terminators. Expression vectors may also contain a set of RNA splice sites located downstream from the promoter and upstream from the insertion site for the VAR2CSA sequence itself. Preferred RNA splice sites may be obtained from adenovirus and/or immunoglobulin genes. Also contained in the expression vectors is a polyadenylation signal located downstream of the insertion site. Particularly preferred polyadenylation signals include the early or late polyadenylation signal from SV40 (Kaufman and Sharp, ibid.), the polyadenylation signal from the adenovirus 5 Elb region, the human growth hormone gene terminator (DeNoto et al. Nucl. Acids Res. 9:3719-3730, 1981) or the polyadenylation signal from Plasmodium falciparum, human or bovine genes. The expression vectors may also include a noncoding viral leader sequence, such as the adenovirus 2 tripartite leader, located between the promoter and the RNA splice sites; and enhancer sequences, such as the SV40 enhancer.

To direct the Plasmodium falciparum VAR2CSA polypeptides and other polypeptides of the present invention into the secretory pathway of the host cells, a secretory signal sequence (also known as a leader sequence, prepro sequence or pre sequence) may be provided in the recombinant vector. The secretory signal sequence is joined to the DNA sequences encoding the *Plasmodium falciparum* VAR2CSA polypeptides and other polypeptides according to the present invention in the correct reading frame. Secretory signal sequences are commonly positioned 5' to the DNA sequence encoding the peptide. The secretory signal sequence may be that, normally associated with the protein or may be from a gene encoding another secreted protein.

For secretion from yeast cells, the secretory signal sequence may encode any signal peptide, which ensures efficient direction of the expressed *Plasmodium falciparum* VAR2CSA polypeptides and other polypeptides according to the present invention into the secretory pathway of the cell. The signal peptide may be naturally occurring signal peptide, or a functional part thereof, or it may be a synthetic peptide. Suitable signal peptides have been found to be the alpha-factor signal peptide (cf. U.S. Pat. No. 4,870,008), the signal peptide of mouse salivary amylase (cf. O. Hagenbuchle et al., Nature 289, 1981, pp. 643-646), a modified carboxypeptidase signal peptide (cf. L. A. Valls et al., Cell 48, 1987, pp. 887-897), the yeast BAR1 signal peptide (cf. WO 87/02670), or the yeast aspartic protease 3 (YAP3) signal peptide (cf. M. Egel-Mitani et al., Yeast 6, 1990, pp. 127-137).

For efficient secretion in yeast, a sequence encoding a leader peptide may also be inserted downstream of the signal sequence and upstream of the DNA sequence encoding the *Plasmodium falciparum* VAR2CSA polypeptides and other polypeptides according to the present invention. The function of the leader peptide is to allow the expressed peptide to be directed from the endoplasmic reticulum to the Golgi apparatus and further to a secretory vesicle for secretion into the culture medium (i.e. exportation of the *Plasmodium falciparum* VAR2CSA polypeptides and other polypeptides according to the present invention across the cell wall or at least through the cellular membrane into the periplasmic space of the yeast cell). The leader peptide may be the yeast alpha-factor leader (the use of which is described in e.g. U.S. Pat. Nos. 4,546,082, 4,870,008, EP 16 201, EP 123 294, EP 123 544 and EP 163 529). Alternatively, the leader peptide may be a synthetic leader peptide, which is to say a leader peptide not found in nature. Synthetic leader peptides may, for instance, be constructed as described in WO 89/02463 or WO 92/11378.

For use in filamentous fungi, the signal peptide may conveniently be derived from a gene encoding an *Aspergillus* sp. amylase or glucoamylase, a gene encoding a *Rhizomucor miehei* lipase or protease or a *Humicola lanuginosa* lipase. The signal peptide is preferably derived from a gene encoding *A. oryzae* TAKA amylase, *A. niger* neutral alpha-amylase, *A. niger* acid-stable amylase, or *A. niger* glucoamylase. Suitable signal peptides are disclosed in, e.g. EP 238 023 and EP 215 594.

For use in insect cells, the signal peptide may conveniently be derived from an insect gene (cf. WO 90/05783), such as the lepidopteran Manduca sexta adipokinetic hormone precursor signal peptide (cf. U.S. Pat. No. 5,023,328).

The procedures used to ligate the DNA sequences coding for the *Plasmodium falciparum* VAR2CSA polypeptides and other polypeptides according to the present invention, the promoter and optionally the terminator and/or secretory signal sequence, respectively, and to insert them into suitable vectors containing the information necessary for replication, are well known to persons skilled in the art (cf., for instance, Sambrook et al., Molecular Cloning: A Laboratory Manual, Cold Spring Harbor, N.Y., 1989).

Methods of transfecting mammalian cells and expressing DNA sequences introduced in the cells are described in e.g. Kaufman and Sharp, J. Mol. Biol. 159 (1982), 601-621; Southern and Berg, J. Mol. Appl. Genet. 1 (1982), 327-341; Loyter et al., Proc. Natl. Acad. Sci. USA 79 (1982), 422-426; Wigler et al., Cell 14 (1978), 725; Corsaro and Pearson, Somatic Cell Genetics 7 (1981), 603, Graham and van der Eb, Virology 52 (1973), 456; and Neumann et al., EMBO J. 1 (1982), 841-845.

Cloned DNA sequences are introduced into cultured mammalian cells by, for example, calcium phosphate-mediated transfection (Wigler et al., Cell 14:725-732, 1978; Corsaro and Pearson, Somatic Cell Genetics 7:603-616, 1981; Graham and Van der Eb, Virology 52d:456-467, 1973) or electroporation (Neumann et al., EMBO J. 1:841-845, 1982). To identify and select cells that express the exogenous DNA, a gene that confers a selectable phenotype (a selectable marker) is generally introduced into cells along with the gene or cDNA of interest. Preferred selectable markers include genes that confer resistance to drugs such as neomycin, hygromycin, and methotrexate. The selectable marker may be an amplifiable selectable marker. A preferred amplifiable selectable marker is a dihydrofolate reductase (DHFR) sequence. Selectable markers are reviewed by Thilly (Mammalian Cell Technology, Butterworth Publishers, Stoneham, Mass., incorporated herein by reference). The person skilled in the art will easily be able to choose suitable selectable markers.

Selectable markers may be introduced into the cell on a separate plasmid at the same time as the gene of interest, or they may be introduced on the same plasmid. If on the same plasmid, the selectable marker and the gene of interest may be under the control of different promoters or the same promoter, the latter arrangement producing a dicistronic message. Constructs of this type are known in the art (for example, Levinson and Simonsen, U.S. 4,713,339). It may also be advantageous to add additional DNA, known as "carrier DNA," to the mixture that is introduced into the cells.

After the cells have taken up the DNA, they are grown in an appropriate growth me-dium, typically 1-2 days, to begin expressing the gene of interest. As used herein the term "appropriate growth medium" means a medium containing nutrients and other components required for the growth of cells and the expression of the *Plasmodium falciparum* VAR2CSA polypeptide of interest. Media generally include a carbon source, a nitrogen source, essential amino acids, essential sugars, vitamins, salts, phospholipids, protein and growth factors. Drug selection is then applied to select for the growth of cells that are expressing the selectable marker in a stable fashion. For cells that have been transfected with an amplifiable selectable marker the drug concentration may be increased to select for an increased copy number of the cloned sequences, thereby in-creasing expression levels. Clones of stably transfected cells are then screened for expression of the *Plasmodium falciparum* VAR2CSA polypeptide of interest.

The host cell into which the DNA sequences encoding the *Plasmodium falciparum* VAR2CSA polypeptides and other polypeptides according to the present invention is introduced may be any cell, which is capable of producing the posttranslational modified polypeptides and includes yeast, fungi and higher eucaryotic cells.

Examples of mammalian cell lines for use in the present invention are the COS-1 (ATCC CRL 1650), baby hamster kidney (BHK) and 293 (ATCC CRL 1573; Graham et al., J. Gen. Virol. 36:59-72, 1977) cell lines. A preferred BHK cell line is the tk-ts13 BHK cell line (Waechter and Baserga, Proc. Natl. Acad. Sci. USA 79:1106-1110, 1982, incorporated herein by reference), hereinafter referred to as BHK 570 cells. The BHK 570 cell line has been deposited with the American Type Culture Collection, 10801 University Boulevard, Manassas, Va. 20110-2209, under ATCC accession number CRL 10314. A tk-ts13 BHK cell line is also available from the ATCC under accession number CRL 1632. In addition, a number of other cell lines may be used within the present invention, including Rat Hep I (Rat hepatoma; ATCC CRL 1600), Rat Hep II (Rat hepatoma; ATCC CRL 1548), TCMK (ATCC CCL 139), Human lung (ATCC HB 8065), NCTC 1469 (ATCC CCL 9.1), CHO (ATCC CCL 61) and DUKX cells (Urlaub and Chasin, Proc. Natl. Acad. Sci. USA 77:4216-4220, 1980).

Examples of suitable yeasts cells include cells of *Saccharomyces* spp. or *Schizosaccharomyces* spp., in particular strains of *Saccharomyces cerevisiae* or *Saccharomyces kluyveri*. Methods for transforming yeast cells with heterologous DNA and producing heterologous poly-peptides there from are described, e.g. in U.S. Pat. Nos. 4,599,311, 4,931,373, 4,870,008, 5,037,743, and 4,845,075, all of which are hereby incorporated by reference. Transformed cells are selected by a phenotype determined by a selectable marker, commonly drug resistance or the ability to grow in the absence of a particular nutrient, e.g. leucine. A preferred vector for use in yeast is the POT1 vector disclosed in U.S. Pat. No. 4,931,373. The DNA sequences encoding the *Plasmodium falciparum* VAR2CSA polypeptides and other polypeptides according to the present invention may be preceded by a signal sequence and optionally a leader sequence, e.g. as described above. Further examples of suitable yeast cells are strains of *Kluyveromyces*, such as *K. lactis, Hansenula*, e.g. *H. polymorpha*, or *Pichia*, e.g. *P. pastoris* (cf. Gleeson et al., J. Gen. Microbiol. 132, 1986, pp. 3459-3465; U.S. Pat. No. 4,882,279).

Examples of other fungal cells are cells of filamentous fungi, e.g. *Aspergillus* spp., *Neurospora* spp., *Fusarium* spp. or *Trichoderma* spp., in particular strains of *A. oryzae, A. nidulans* or *A. niger*. The use of *Aspergillus* spp. for the expression of proteins is described in, e.g., EP 272 277, EP 238 023, EP 184 438 The transformation of *F. oxysporum* may, for instance, be carried out as described by Malardier et al., 1989, Gene 78: 147-156. The transformation of *Trichoderma* spp. may be performed for instance as described in EP 244 234.

When a filamentous fungus is used as the host cell, it may be transformed with the DNA construct of the invention, conveniently by integrating the DNA construct in the host chromosome to obtain a recombinant host cell. This integration is generally considered to be an advantage as the DNA sequence is more likely to be stably maintained in the cell. Integration of the DNA constructs into the host chromosome may be performed according to conventional methods, e.g. by homologous or heterologous recombination.

Transformation of insect cells and production of heterologous polypeptides therein may be performed as described in U.S. Pat. Nos. 4,745,051; 4,879,236; 5,155,037; 5,162, 222; EP 397,485) all of which are incorporated herein by reference. The insect cell line used as the host may suitably be a Lepidoptera cell line, such as *Spodoptera frugiperda* cells or *Trichoplusia ni* cells (cf. U.S. Pat. No. 5,077,214). Culture conditions may suitably be as described in, for instance, WO 89/01029 or WO 89/01028, or any of the aforementioned references.

The transformed or transfected host cell described above is then cultured in a suitable nutrient medium under conditions permitting expression of the *Plasmodium falciparum* VAR2CSA polypeptide after which all or part of the resulting peptide may be recovered from the culture. The medium used to culture the cells may be any conventional medium suitable for growing the host cells, such as minimal or complex media containing appropriate supplements. Suitable media are available from commercial suppliers or may be prepared according to published recipes (e.g. in catalogues of the American Type Culture Collection). The *Plasmodium falciparum* VAR2CSA polypeptide produced by the cells may then be recovered from the culture medium by conventional procedures including separating the host cells from the medium by centrifugation or filtration, precipitating the proteinaqueous components of the supernatant or filtrate by means of a salt, e.g. ammonium sulfate, purification by a variety of chromatographic procedures, e.g. ion exchange chromatography, gelfiltration chromatography, affinity chromatography, or the like, dependent on the type of polypeptide in question.

Transgenic animal technology may be employed to produce the VAR2CSA polypeptides and other polypeptides of the invention. It is preferred to produce the proteins within the mammary glands of a host female mammal. Expression in the mammary gland and subsequent secretion of the protein of interest into the milk overcomes many difficulties encountered in isolating proteins from other sources. Milk is readily collected, available in large quantities, and biochemically well characterized. Furthermore, the major milk proteins are present in milk at high concentrations (typically from about 1 to 15 g/l).

From a commercial point of view, it is clearly preferable to use as the host a species that has a large milk yield. While smaller animals such as mice and rats can be used (and are preferred at the proof of principle stage), it is preferred to use livestock mammals including, but not limited to, pigs, goats, sheep and cattle. Sheep are particularly preferred due to such factors as the previous history of transgenesis in this species, milk yield, cost and the ready availability of equipment for collecting sheep milk (see, for example, WO 88/00239 for a comparison of factors influencing the choice of host species). It is generally desirable to select a breed of host animal that has been bred for dairy use, such as East Friesland sheep, or to introduce dairy stock by breeding of the transgenic line at a later date. In any event, animals of known, good health status should be used.

To obtain expression in the mammary gland, a transcription promoter from a milk protein gene is used. Milk protein genes include those genes encoding caseins (see U.S. Pat. No. 5,304,489), beta lactoglobulin, a lactalbumin, and whey acidic protein. The beta lactoglobulin (BLG) promoter is preferred. In the case of the ovine beta lactoglobulin gene, a region of at least the proximal 406 bp of 5' flanking sequence of the gene will generally be used, although larger portions of the 5' flanking sequence, up to about 5 kbp, are preferred, such as a ~4.25 kbp DNA segment encompassing the 5' flanking promoter and non coding portion of the beta lactoglobulin gene (see Whitelaw et al., Biochem. J. 286: 31 39 (1992)). Similar fragments of promoter DNA from other species are also suitable.

Other regions of the beta lactoglobulin gene may also be incorporated in constructs, as may genomic regions of the gene to be expressed. It is generally accepted in the art that constructs lacking introns, for example, express poorly in comparison with those that contain such DNA sequences (see Brinster et al., Proc. Natl. Acad. Sci. USA 85: 836 840

(1988); Palmiter et al., Proc. Natl. Acad. Sci. USA 88: 478 482 (1991); Whitelaw et al., Transgenic Res. 1: 3 13 (1991); WO 89/01343; and WO 91/02318, each of which is incorporated herein by reference). In this regard, it is generally preferred, where possible, to use genomic sequences containing all or some of the native introns of a gene encoding the protein or polypeptide of interest, thus the further inclusion of at least some introns from, e.g, the beta lactoglobulin gene, is preferred. One such region is a DNA segment that provides for intron splicing and RNA polyadenylation from the 3' non coding region of the ovine beta lactoglobulin gene. When substituted for the natural 3' non coding sequences of a gene, this ovine beta lactoglobulin segment can both enhance and stabilize expression levels of the protein or polypeptide of interest. Within other embodiments, the region surrounding the initiation ATG of the VAR2CSA sequence is replaced with corresponding sequences from a milk specific protein gene. Such replacement provides a putative tissue specific initiation environment to enhance expression. It is convenient to replace the entire VAR2CSA pre pro and 5' non coding sequences with those of, for example, the BLG gene, although smaller regions may be replaced.

For expression of VAR2CSA polypeptides and other polypeptides according to the present invention in transgenic animals, a DNA segment encoding VAR2CSA is operably linked to additional DNA segments required for its expression to produce expression units. Such additional segments include the above mentioned promoter, as well as sequences that provide for termination of transcription and polyadenylation of mRNA. The expression units will further include a DNA segment encoding a secretory signal sequence operably linked to the segment encoding modified VAR2CSA. The secretory signal sequence may be a native secretory signal sequence or may be that of another protein, such as a milk protein (see, for example, von Heijne, Nucl. Acids Res. 14: 4683 4690 (1986); and Meade et al., U.S. Pat. No. 4,873,316, which are incorporated herein by reference).

Construction of expression units for use in transgenic animals is conveniently carried out by inserting a VAR2CSA sequence into a plasmid or phage vector containing the additional DNA segments, although the expression unit may be constructed by essentially any sequence of ligations. It is particularly convenient to provide a vector containing a DNA segment encoding a milk protein and to replace the coding sequence for the milk protein with that of a VAR2CSA variant; thereby creating a gene fusion that includes the expression control sequences of the milk protein gene. In any event, cloning of the expression units in plasmids or other vectors facilitates the amplification of the VAR2CSA sequence. Amplification is conveniently carried out in bacterial (e.g. E. coli) host cells, thus the vectors will typically include an origin of replication and a selectable marker functional in bacterial host cells. The expression unit is then introduced into fertilized eggs (including early stage embryos) of the chosen host species. Introduction of heterologous DNA can be accomplished by one of several routes, including microinjection (e.g. U.S. Pat. No. 4,873,191), retroviral infection (Jaenisch, Science 240: 1468 1474 (1988)) or site directed integration using embryonic stem (ES) cells (reviewed by Bradley et al., Bio/Technology 10: 534 539 (1992)). The eggs are then implanted into the oviducts or uteri of pseudopregnant females and allowed to develop to term. Offspring carrying the introduced DNA in their germ line can pass the DNA on to their progeny in the normal, Mendelian fashion, allowing the development of transgenic herds. General procedures for producing transgenic animals are known in the art (see, for example, Hogan et al., Manipulating the Mouse Embryo: A Laboratory Manual, Cold Spring Harbor Laboratory, 1986; Simons et al., Bio/Technology 6: 179 183 (1988); Wall et al., Biol. Reprod. 32: 645 651 (1985); Buhler et al., Bio/Technology 8: 140 143 (1990); Ebert et al., Bio/Technology 9: 835 838 (1991); Krimpenfort et al., Bio/Technology 9: 844 847 (1991); Wall et al., J. Cell. Biochem. 49: 113 120 (1992); U.S. Pat. Nos. 4,873,191; 4,873,316; WO 88/00239, WO 90/05188, WO 92/11757; and GB 87/00458). Techniques for introducing foreign DNA sequences into mammals and their germ cells were originally developed in the mouse (see, e.g., Gordon et al., Proc. Natl. Acad. Sci. USA 77: 7380 7384 (1980); Gordon and Ruddle, Science 214: 1244 1246 (1981); Palmiter and Brinster, Cell 41: 343 345 (1985); Brinster et al., Proc. Natl. Acad. Sci. USA 82: 4438 4442 (1985); and Hogan et al. (ibid.)). These techniques were subsequently adapted for use with larger animals, including livestock species (see, e.g., WO 88/00239, WO 90/05188, and WO 92/11757; and Simons et al., Bio/Technology 6: 179 183 (1988)). To summarize, in the most efficient route used to date in the generation of transgenic mice or livestock, several hundred linear molecules of the DNA of interest are injected into one of the pro nuclei of a fertilized egg according to established techniques. Injection of DNA into the cytoplasm of a zygote can also be employed.

Production in transgenic plants may also be employed. Expression may be generalised or directed to a particular organ, such as a tuber (see, Hiatt, Nature 344:469 479 (1990); Edelbaum et al., J. Interferon Res. 12:449 453 (1992); Sijmons et al., Bio/Technology 8:217 221 (1990); and EP 0 255 378).

VAR2CSA Purification

The VAR2CSA polypeptides and other polypeptides of the invention may be recovered from cell culture medium or milk. The VAR2CSA polypeptides and other polypeptides of the present invention may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing (IEF), differential solubility (e.g., ammonium sulfate precipitation), or extraction (see, e.g., Protein Purification, J.-C. Janson and Lars Ryden, editors, VCH Publishers, New York, 1989). Preferably, they may be purified by affinity chromatography on an anti-VAR2CSA antibody column. Additional purification may be achieved by conventional chemical purification means, such as high performance liquid chromatography. Other methods of purification, including barium citrate precipitation, are known in the art, and may be applied to the purification of the novel VAR2CSA polypeptides and other polypeptides described herein (see, for example, Scopes, R., Protein Purification, Springer-Verlag, N.Y., 1982).

For therapeutic purposes it is preferred that the VAR2CSA polypeptides and other polypeptides of the invention are substantially pure. Thus, in a preferred embodiment of the invention the and other polypeptides of the invention are purified to at least about 90 to 95% homogeneity, preferably to at least about 98% homogeneity. Purity may be assessed by e.g. gel electrophoresis and amino-terminal amino acid sequencing.

The term "isolated polypeptide" refers to a polypeptide of the present invention that (1) has been separated from at least about 50 percent of polynucleotides, lipids, carbohydrates or other materials (i.e., contaminants) with which it is naturally associated. Preferably, the isolated polypeptide is substantially free from any other contaminating polypeptides or other contaminants that are found in its natural environment, which would interfere with its therapeutic, diagnostic, prophylactic or research use.

The term "microorganism" as used herein refers to bacteria, fungi, archaea, protists; microscopic plants and animals (such as green algae or plankton), the planarian and amoeba. Included within this definition are pathogenic microorganisms.

Administration and Pharmaceutical Compositions
Combination Treatments

The VAR2CSA polypeptide, derivative, or conjugate as defined in the present specification may be administered simultaneously or sequentially with one or more other cancer agent, and/or be used in a combination treatment with other known therapies. The factors may be supplied in single-dosage form wherein the single-dosage form contains both compounds, or in the form of a kit-of-parts comprising a preparation of a VAR2CSA polypeptide as a first unit dosage form and a preparation of the one or more other compound as a second unit dosage form. Whenever a first or second or third, etc., unit dose is mentioned throughout this specification this does not indicate the preferred order of administration, but is merely done for convenience purposes.

Suitable other cancer agents or therapies that may be used in combination with a VAR2CSA polypeptide includes antibodies already on the market or in development, including Vemurafenib (Hoffmann-La Roche), human monoclonal antibodies against MCSP, Therapeutical (Micromet Inc) anti-MCSP using BITE antibody platform technology, and Adoptive transfer of cytotoxic T cells with specificity for MCSP.

By "simultaneous" dosing of a preparation of a VAR2CSA polypeptide and a preparation of one or more other compound is meant administration of the compounds in single-dosage form, or administration of a first agent followed by administration of a second agent with a time separation of no more than 15 minutes, preferably 10, more preferred 5, more preferred 2 minutes. Either factor may be administered first.

By "sequential" dosing is meant administration of a first agent followed by administration of a second agent with a time separation of more than 15 minutes. Either of the two unit dosage form may be administered first. Preferably, both products are injected through the same intravenous access.

Another object of the present invention is to provide a pharmaceutical formulation comprising a VAR2CSA polypeptide which is present in a serum/plasma concentration from 0 mg/ml to 1 mg/ml, and wherein the formulation has a pH from 2.0 to 10.0. The formulation may further comprise a buffer system, preservative(s), tonicity agent(s), chelating agent(s), stabilizers and surfactants. In some embodiments of the invention the pharmaceutical formulation is an aqueous formulation, i.e. formulation comprising water. Such formulation is typically a solution or a suspension. In a further embodiment of the invention the pharmaceutical formulation is an aqueous solution. The term "aqueous formulation" is defined as a formulation comprising at least 50% w/w water. Likewise, the term "aqueous solution" is defined as a solution comprising at least 50% w/w water, and the term "aqueous suspension" is defined as a suspension comprising at least 50% w/w water.

In other embodiments the pharmaceutical formulation is a freeze-dried formulation, whereto the physician or the patient adds solvents and/or diluents prior to use.

In other embodiments the pharmaceutical formulation is a dried formulation (e.g. freeze-dried or spray-dried) ready for use without any prior dissolution.

In a further aspect the invention relates to a pharmaceutical formulation comprising an aqueous solution of a VAR2CSA polypeptide, and a buffer, wherein the VAR2CSA polypeptide is present in a serum/plasma concentration from 0-1 mg/ml or above, and wherein the formulation has a pH from about 2.0 to about 10.0.

In a other embodiments of the invention the pH of the formulation is selected from the list consisting of 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, and 10.0.

In a further embodiment of the invention the buffer is selected from the group consisting of sodium acetate, sodium carbonate, citrate, glycylglycine, histidine, glycine, lysine, arginine, sodium dihydrogen phosphate, disodium hydrogen phosphate, sodium phosphate, and tris(hydroxymethyl)-aminomethan, bicine, tricine, malic acid, succinate, maleic acid, fumaric acid, tartaric acid, aspartic acid or mixtures thereof. Each one of these specific buffers constitutes an alternative embodiment of the invention.

In a further embodiment of the invention the formulation further comprises a pharmaceutically acceptable preservative. In a further embodiment of the invention the preservative is selected from the group consisting of phenol, o-cresol, m-cresol, p-cresol, methyl p-hydroxybenzoate, propyl p-hydroxybenzoate, 2-phenoxyethanol, butyl p-hydroxybenzoate, 2-phenylethanol, benzyl alcohol, chlorobutanol, and thiomerosal, bronopol, benzoic acid, imidurea, chlorohexidine, sodium dehydroacetate, chlorocresol, ethyl p-hydroxybenzoate, benzethonium chloride, chlorphenesine (3p-chlorphenoxypropane-1,2-diol) or mixtures thereof. In a further embodiment of the invention the preservative is present in a concentration from 0.1 mg/ml to 20 mg/ml. In a further embodiment of the invention the preservative is present in a concentration from 0.1 mg/ml to 5 mg/ml. In a further embodiment of the invention the preservative is present in a concentration from 5 mg/ml to 10 mg/ml. In a further embodiment of the invention the preservative is present in a concentration from 10 mg/ml to 20 mg/ml. Each one of these specific preservatives constitutes an alternative embodiment of the invention. The use of a preservative in pharmaceutical compositions is well-known to the skilled person. For convenience reference is made to Remington: The Science and Practice of Pharmacy, 19th edition, 1995.

In a further embodiment of the invention the formulation further comprises an isotonic agent. In a further embodiment of the invention the isotonic agent is selected from the group consisting of a salt (e.g. sodium chloride), a sugar or sugar alcohol, an amino acid (e.g. L-glycine, L-histidine, arginine, lysine, isoleucine, aspartic acid, tryptophan, threonine), an alditol (e.g. glycerol (glycerine), 1,2-propanediol (propyleneglycol), 1,3-propanediol, 1,3-butanediol) polyethyleneglycol (e.g. PEG400), or mixtures thereof. Any sugar such as mono-, di-, or polysaccharides, or water-soluble glucans, including for example fructose, glucose, mannose, sorbose, xylose, maltose, lactose, sucrose, trehalose, dextran, pullulan, dextrin, cyclodextrin, soluble starch, hydroxyethyl starch and carboxymethylcellulose-Na may be used. In some embodiments the sugar additive is sucrose. Sugar alcohol is defined as a C4-C8 hydrocarbon having at least one —OH group and includes, for example, mannitol, sorbitol, inositol, galactitol, dulcitol, xylitol, and arabitol. In some embodiments the sugar alcohol additive is mannitol. The sugars or sugar alcohols mentioned above may be used individually or in combination. There is no fixed limit to the amount used, as long as the sugar or sugar alcohol is soluble in the liquid preparation and does not adversely effect the stabilizing effects achieved using the methods of the invention. In some embodiments, the sugar or sugar alcohol concentration is between about 1 mg/ml and about 150 mg/ml. In a further embodiment of the invention the isotonic agent is present in a concentration from 1 mg/ml to 50 mg/ml. In a further embodiment of the invention the isotonic agent is present in a concentration from 1 mg/ml to 7 mg/ml. In a further embodiment of the invention the isotonic agent is present in a concentration from 8 mg/ml to 24 mg/ml. In a further embodiment of the invention the isotonic agent is present in a concentration from 25 mg/ml to 50 mg/ml. Each one of these specific isotonic agents constitutes an alternative embodiment of the invention. The use of an isotonic agent in pharmaceutical compositions is well known to the skilled person. For convenience reference is made to *Remington: The Science and Practice of Pharmacy*, 19$^{th}$ edition, 1995.

In a further embodiment of the invention the formulation further comprises a chelating agent. In a further embodiment of the invention the chelating agent is selected from salts of ethylenediaminetetraacetic acid (EDTA), citric acid, and aspartic acid, and mixtures thereof. In a further embodiment of the invention the chelating agent is present in a concentration from 0.1 mg/ml to 5 mg/ml. In a further embodiment of the invention the chelating agent is present in a concentration from 0.1 mg/ml to 2 mg/ml. In a further embodiment of the invention the chelating agent is present in a concentration from 2 mg/ml to 5 mg/ml. Each one of these specific chelating agents constitutes an alternative embodiment of the invention. The use of a chelating agent in pharmaceutical compositions is well-known to the skilled person. For convenience reference is made to *Remington: The Science and Practice of Pharmacy*, 19$^{th}$ edition, 1995.

In a further embodiment of the invention the formulation further comprises a stabilizer. The use of a stabilizer in pharmaceutical compositions is well-known to the skilled person. For convenience reference is made to *Remington: The Science and Practice of Pharmacy*, 19$^{th}$ edition, 1995.

More particularly, compositions of the invention are stabilized liquid pharmaceutical compositions whose therapeutically active components include a polypeptide that possibly exhibits aggregate formation during storage in liquid pharmaceutical formulations. By "aggregate formation" is intended a physical interaction between the polypeptide molecules that results in formation of oligomers, which may remain soluble, or large visible aggregates that precipitate from the solution. By "during storage" is intended a liquid pharmaceutical composition or formulation once prepared, is not immediately administered to a subject. Rather, following preparation, it is packaged for storage, either in a liquid form, in a frozen state, or in a dried form for later reconstitution into a liquid form or other form suitable for administration to a subject. By "dried form" is intended the liquid pharmaceutical composition or formulation is dried either by freeze drying (i.e., lyophilization; see, for example, Williams and Polli (1984) J. Parenteral Sci. Technol. 38:48-59), spray drying (see Masters (1991) in Spray-Drying Handbook (5th ed; Longman Scientific and Technical, Essex, U.K.), pp. 491-676; Broadhead et al. (1992) Drug Devel. Ind. Pharm. 18:1169-1206; and Mumenthaler et al. (1994) Pharm. Res. 11:12-20), or air drying (Carpenter and Crowe (1988) Cryobiology 25:459-470; and Roser (1991) Biopharm. 4:47-53). Aggregate formation by a polypeptide during storage of a liquid pharmaceutical composition can adversely affect biological activity of that polypeptide, resulting in loss of therapeutic efficacy of the pharmaceutical composition. Furthermore, aggregate formation may cause other problems such as blockage of tubing, membranes, or pumps when the polypeptide-containing pharmaceutical composition is administered using an infusion system.

The pharmaceutical compositions of the invention may further comprise an amount of an amino acid base sufficient to decrease aggregate formation by the polypeptide during storage of the composition. By "amino acid base" is intended an amino acid or a combination of amino acids, where any given amino acid is present either in its free base form or in its salt form. Where a combination of amino acids is used, all of the amino acids may be present in their free base forms, all may be present in their salt forms, or some may be present in their free base forms while others are present in their salt forms. In some embodiments, amino acids to use in preparing the compositions of the invention are those carrying a charged side chain, such as arginine, lysine, aspartic acid, and glutamic acid. Any stereoisomer (i.e., L, D, or DL isomer) of a particular amino acid (e.g. glycine, methionine, histidine, imidazole, arginine, lysine, isoleucine, aspartic acid, tryptophan, threonine and mixtures thereof) or combinations of these stereoisomers, may be present in the pharmaceutical compositions of the invention so long as the particular amino acid is present either in its free base form or its salt form. In some embodiments the L-stereoisomer is used. Compositions of the invention may also be formulated with analogues of these amino acids. By "amino acid analogue" is intended a derivative of the naturally occurring amino acid that brings about the desired effect of decreasing aggregate formation by the polypeptide during storage of the liquid pharmaceutical compositions of the invention. Suitable arginine analogues include, for example, aminoguanidine, ornithine and N-monoethyl L-arginine, suitable methionine analogues include ethionine and buthionine and suitable cysteine analogues include S-methyl-L cysteine. As with the other amino acids, the amino acid analogues are incorporated into the compositions in either their free base form or their salt form. In a further embodiment of the invention the amino acids or amino acid analogues are used in a concentration, which is sufficient to prevent or delay aggregation of the protein.

In a further embodiment of the invention methionine (or other sulphuric amino acids or amino acid analogous) may be added to inhibit oxidation of methionine residues to methionine sulfoxide when the polypeptide acting as the therapeutic agent is a polypeptide comprising at least one methionine residue susceptible to such oxidation. By "inhibit" is intended minimal accumulation of methionine oxidized species over time. Inhibiting methionine oxidation results in greater retention of the polypeptide in its proper molecular form. Any stereoisomer of methionine (L, D, or DL isomer) or combinations thereof can be used. The amount to be added should be an amount sufficient to inhibit oxidation of the methionine residues such that the amount of methionine sulfoxide is acceptable to regulatory agencies. Typically, this means that the composition contains no more than about 10% to about 30% methionine sulfoxide. Generally, this can be achieved by adding methionine such that the ratio of methionine added to methionine residues ranges from about 1:1 to about 1000:1, such as 10:1 to about 100:1.

In a further embodiment of the invention the formulation further comprises a stabilizer selected from the group of high molecular weight polymers or low molecular compounds. In a further embodiment of the invention the stabilizer is selected from polyethylene glycol (e.g. PEG 3350), polyvinyl alcohol (PVA), polyvinylpyrrolidone, carboxy-/hydroxycellulose or derivates thereof (e.g. HPC, HPC-SL, HPC-L and HPMC), cyclodextrins, sulphur-containing substances as monothioglycerol, thioglycolic acid and 2-methylthioethanol, and different salts (e.g. sodium chloride). Each one of these specific stabilizers constitutes an alternative embodiment of the invention.

The pharmaceutical compositions may also comprise additional stabilizing agents, which further enhance stability of a therapeutically active polypeptide therein. Stabilizing agents of particular interest to the present invention include, but are not limited to, methionine and EDTA, which protect the polypeptide against methionine oxidation, and a nonionic surfactant, which protects the polypeptide against aggregation associated with freeze-thawing or mechanical shearing.

In a further embodiment of the invention the formulation further comprises a surfactant. In a further embodiment of the invention the surfactant is selected from a detergent, ethoxylated castor oil, polyglycolyzed glycerides, acetylated monoglycerides, sorbitan fatty acid esters, polyoxypropylene-polyoxyethylene block polymers (eg. poloxamers such as PLURONIC F68 surfactant, poloxamer 188 and 407, TRITON X-100 poloxamer), polyoxyethylene sorbitan fatty acid esters, polyoxyethylene and polyethylene derivatives such as alkylated and alkoxylated derivatives (tweens, e.g. TWEEN-20, TWEEN-40, TWEEN-80 and BRIJ-35 surfactants), monoglycerides or ethoxylated derivatives thereof, diglycerides or polyoxyethylene derivatives thereof, alcohols, glycerol, lectins and phospholipids (eg. phosphatidyl serine, phosphatidyl choline, phosphatidyl ethanolamine, phosphatidyl inositol, diphosphatidyl glycerol and sphingomyelin), derivates of phospholipids (eg. dipalmitoyl phosphatidic acid) and lysophospholipids (eg. palmitoyl lysophosphatidyl-L-serine and 1-acyl-sn-glycero-3-phosphate esters of ethanolamine, choline, serine or threonine) and alkyl, alkoxyl (alkyl ester), alkoxy (alkyl ether)-derivatives of lysophosphatidyl and phosphatidylcholines, e.g. lauroyl and myristoyl derivatives of lysophosphatidylcholine, dipalmitoylphosphatidylcholine, and modifications of the polar head group, that is cholines, ethanolamines, phosphatidic acid, serines, threonines, glycerol, inositol, and the positively charged DODAC, DOTMA, DCP, BISHOP, lysophosphatidylserine and lysophosphatidylthreonine, and glycerophospholipids (eg. cephalins), glyceroglycolipids (eg. galactopyransoide), sphingoglycolipids (eg. ceramides, gangliosides), dodecylphosphocholine, hen egg lysolecithin, fusidic acid derivatives—(e.g. sodium tauro-dihydrofusidate etc.), long-chain fatty acids and salts thereof C6-C12 (eg. oleic acid and caprylic acid), acylcarnitines and derivatives, $N^\alpha$-acylated derivatives of lysine, arginine or histidine, or side-chain acylated derivatives of lysine or arginine, $N^\alpha$-acylated derivatives of dipeptides comprising any combination of lysine, arginine or histidine and a neutral or acidic amino acid, $N^\alpha$-acylated derivative of a tripeptide comprising any combination of a neutral amino acid and two charged amino acids, DSS (docusate sodium, CAS registry no [577-11-7]), docusate calcium, CAS registry no [128-49-4]), docusate potassium, CAS registry no [7491-09-0]), SDS (sodium dodecyl sulfate or sodium lauryl sulfate), sodium caprylate, cholic acid or derivatives thereof, bile acids and salts thereof and glycine or taurine conjugates, ursodeoxycholic acid, sodium cholate, sodium deoxycholate, sodium taurocholate, sodium glycocholate, N-Hexadecyl-N,N-dimethyl-3-ammonio-1-propanesulfonate, anionic (alkyl-aryl-sulphonates) monovalent surfactants, zwitterionic surfactants (e.g. N-alkyl-N,N-dimethylammonio-1-propanesulfonates, 3-cholamido-1-propyldimethylammonio-1-propanesulfonate, cationic surfactants (quaternary ammonium bases) (e.g. cetyl-trimethylammonium bromide, cetylpyridinium chloride), non-ionic surfactants (eg. Dodecyl β-D-glucopyranoside), poloxamines (eg. Tetronic's), which are tetrafunctional block copolymers derived from sequential addition of propylene oxide and ethylene oxide to ethylenediamine, or the surfactant may be selected from the group of imidazoline derivatives, or mixtures thereof. Each one of these specific surfactants constitutes an alternative embodiment of the invention.

The use of a surfactant in pharmaceutical compositions is well known to the skilled person. For convenience reference is made to Remington: The Science and Practice of Pharmacy, 19th edition, 1995.

It is possible that other ingredients may be present in the peptide pharmaceutical formulation of the present invention. Such additional ingredients may include wetting agents, emulsifiers, antioxidants, bulking agents, tonicity modifiers, chelating agents, metal ions, oleaginous vehicles, proteins (e.g., human serum albumin, gelatine or proteins) and a zwitterion (e.g., an amino acid such as betaine, taurine, arginine, glycine, lysine and histidine). Such additional ingredients, of course, should not adversely affect the overall stability of the pharmaceutical formulation of the present invention.

Pharmaceutical compositions containing a VAR2CSA polypeptide according to the present invention may be administered to a patient in need of such treatment at several sites, for example, at topical sites, for example, skin and mucosal sites, at sites which bypass absorption, for example, administration in an artery, in a vein, in the heart, and at sites which involve absorption, for example, administration in the skin, under the skin, in a muscle or in the abdomen.

Topical administration may be a particular advantage in the treatment of conditions associated with local inflammation, such as in the treatment of inflammation associated with burn or other conditions associated with the skin. Accordingly, in some embodiments administration is by topical administration.

In some particular embodiments, eye droplets may be used in conditions associated with the eye, such as keratitis, such as diffuse lamellar keratitis (DLK).

Administration of pharmaceutical compositions according to the invention may be through several routes of administration, for example, lingual, sublingual, buccal, in the mouth, oral, in the stomach and intestine, nasal, pulmonary, for example, through the bronchioles and alveoli or a combination thereof, epidermal, dermal, transdermal, vaginal, rectal, ocular, for examples through the conjunctiva, uretal, and parenteral to patients in need of such a treatment.

Compositions of the current invention may be administered in several dosage forms, for example, as solutions, suspensions, emulsions, microemulsions, multiple emulsion, foams, salves, pastes, plasters, ointments, tablets, coated tablets, rinses, capsules, for example, hard gelatine capsules and soft gelatine capsules, suppositories, rectal capsules, drops, gels, sprays, powder, aerosols, inhalants, eye drops, ophthalmic ointments, ophthalmic rinses, vaginal pessaries, vaginal rings, vaginal ointments, injection solution, in situ transforming solutions, for example in situ gelling, in situ setting, in situ precipitating, in situ crystallization, infusion solution, and implants.

Compositions of the invention may further be compounded in, or attached to, for example through covalent, hydrophobic and electrostatic interactions, a drug carrier, drug delivery system and advanced drug delivery system in order to further enhance stability of the VAR2CSA polypeptide, increase bioavailability, increase solubility, decrease adverse effects, achieve chronotherapy well known to those skilled in the art, and increase patient compliance or any combination thereof. Examples of carriers, drug delivery systems and advanced drug delivery systems include, but are not limited to, polymers, for example cellulose and derivatives, polysaccharides, for example dextran and derivatives, starch and derivatives, poly(vinyl alcohol), acrylate and methacrylate polymers, polylactic and polyglycolic acid and block co-polymers thereof, polyethylene glycols, carrier proteins, for example albumin, gels, for example, thermogelling systems, for example block co-polymeric systems well known to those skilled in the art, micelles, liposomes, microspheres, nanoparticulates, virus like particles, bacteria like particles, liquid crystals and dispersions thereof, L2 phase and dispersions there of, well known to those skilled in the art of phase behaviour in lipid-water systems, polymeric micelles, multiple emulsions, self-emulsifying, self-microemulsifying, cyclodextrins and derivatives thereof, and dendrimers.

Compositions of the current invention are useful in the formulation of solids, semisolids, powder and solutions for pulmonary administration of the VAR2CSA polypeptide, using, for example a metered dose inhaler, dry powder inhaler and a nebulizer, all being devices well known to those skilled in the art.

Compositions of the current invention are specifically useful in the formulation of controlled, sustained, protracting, retarded, and slow release drug delivery systems. More specifically, but not limited to, compositions are useful in formulation of parenteral controlled release and sustained release systems (both systems leading to a many-fold reduction in number of administrations), well known to those skilled in the art. Even more preferably, are controlled release and sustained release systems administered subcutaneous. Without limiting the scope of the invention, examples of useful controlled release system and compositions are hydrogels, oleaginous gels, liquid crystals, polymeric micelles, microspheres, nanoparticles, Methods to produce controlled release systems useful for compositions of the current invention include, but are not limited to, crystallization, condensation, co-crystallization, precipitation, co-precipitation, emulsification, dispersion, high pressure homogenisation, encapsulation, spray drying, microencapsulating, coacervation, phase separation, solvent evaporation to produce microspheres, extrusion and supercritical fluid processes. General reference is made to Handbook of Pharmaceutical Controlled Release (Wise, D. L., ed. Marcel Dekker, New York, 2000) and Drug and the Pharmaceutical Sciences vol. 99: Protein Formulation and Delivery (MacNally, E. J., ed. Marcel Dekker, New York, 2000).

Parenteral administration may be performed by subcutaneous, intramuscular, intraperitoneal or intravenous injection by means of a syringe, optionally a pen-like syringe. Alternatively, parenteral administration can be performed by means of an infusion pump. A further option is a composition, which may be a solution or suspension for the administration of the VAR2CSA polypeptide in the form of a nasal or pulmonal spray. As a still further option, the pharmaceutical compositions containing the VAR2CSA polypeptide of the invention can also be adapted to transdermal administration, e.g. by needle-free injection or from a patch, optionally an iontophoretic patch, or transmucosal, e.g. buccal, administration.

The term "stabilized formulation" refers to a formulation with increased physical stability, increased chemical stability or increased physical and chemical stability.

The term "physical stability" of the protein formulation as used herein refers to the tendency of the protein to form biologically inactive and/or insoluble aggregates of the protein as a result of exposure of the protein to thermo-mechanical stresses and/or interaction with interfaces and surfaces that are destabilizing, such as hydrophobic surfaces and interfaces. Physical stability of the aqueous protein formulations is evaluated by means of visual inspection and/or turbidity measurements after exposing the formulation filled in suitable containers (e.g. cartridges or vials) to mechanical/physical stress (e.g. agitation) at different temperatures for various time periods. Visual inspection of the formulations is performed in a sharp focused light with a dark background. The turbidity of the formulation is characterized by a visual score ranking the degree of turbidity for instance on a scale from 0 to 3 (a formulation showing no turbidity corresponds to a visual score 0, and a formulation showing visual turbidity in daylight corresponds to visual score 3). A formulation is classified physical unstable with respect to protein aggregation, when it shows visual turbidity in daylight. Alternatively, the turbidity of the formulation can be evaluated by simple turbidity measurements well known to the skilled person. Physical stability of the aqueous protein formulations can also be evaluated by using a spectroscopic agent or probe of the conformational status of the protein. The probe is preferably a small molecule that preferentially binds to a non-native conformer of the protein. One example of a small molecular spectroscopic probe of protein structure is Thioflavin T. Thioflavin T is a fluorescent dye that has been widely used for the detection of amyloid fibrils. In the presence of fibrils, and perhaps other protein configurations as well, Thioflavin T gives rise to a new excitation maximum at about 450 nm and enhanced emission at about 482 nm when bound to a fibril protein form. Unbound Thioflavin T is essentially non-fluorescent at the wavelengths.

Other small molecules can be used as probes of the changes in protein structure from native to non-native states. For instance the "hydrophobic patch" probes that bind preferentially to exposed hydrophobic patches of a protein. The hydrophobic patches are generally buried within the tertiary structure of a protein in its native state, but become exposed as a protein begins to unfold or denature. Examples of these small molecular, spectroscopic probes are aromatic, hydrophobic dyes, such as anthracene, acridine, phenanthroline or the like. Other spectroscopic probes are metal-amino acid complexes, such as cobalt metal complexes of hydrophobic amino acids, such as phenylalanine, leucine, isoleucine, methionine, and valine, or the like.

The term "chemical stability" of the protein formulation as used herein refers to chemical covalent changes in the protein structure leading to formation of chemical degradation products with potential less biological potency and/or potential increased immunogenic properties compared to the native protein structure. Various chemical degradation products can be formed depending on the type and nature of the native protein and the environment to which the protein is exposed. Elimination of chemical degradation can most probably not be completely avoided and increasing amounts of chemical degradation products is often seen during storage and use of the protein formulation as well-known by the person skilled in the art. Most proteins are prone to deamidation, a process in which the side chain amide group in glutaminyl or asparaginyl residues is hydrolysed to form a free carboxylic acid. Other degradations pathways involves formation of high molecular weight transformation products where two or more protein molecules are covalently bound to each other through transamidation and/or disulfide interactions leading to formation of covalently bound dimer, oligomer and polymer degradation products (Stability of Protein Pharmaceuticals, Ahern. T. J. & Manning M. C., Plenum Press, New York 1992). Oxidation (of for instance methionine residues) can be mentioned as another variant of chemical degradation. The chemical stability of the protein formulation can be evaluated by measuring the amount of the chemical degradation products at various time-points after exposure to different environmental conditions (the formation of degradation products can often be accelerated by for instance increasing temperature). The amount of each individual degradation product is often determined by separation of the degradation products depending on molecule size and/or charge using various chromatography techniques (e.g. SEC-HPLC and/or RP-HPLC).

Hence, as outlined above, a "stabilized formulation" refers to a formulation with increased physical stability, increased chemical stability or increased physical and chemical stability. In general, a formulation must be stable during use and storage (in compliance with recommended use and storage conditions) until the expiration date is reached.

In some embodiments of the invention the pharmaceutical formulation comprising the VAR2CSA polypeptide is stable for more than 6 weeks of usage and for more than 3 years of storage. In other embodiments of the invention the pharmaceutical formulation comprising the VAR2CSA polypeptide is stable for more than 4 weeks of usage and for more than 3 years of storage. In a further embodiment of the invention the pharmaceutical formulation comprising the VAR2CSA polypeptide is stable for more than 4 weeks of usage and for more than two years of storage. In an even further embodiment of the invention the pharmaceutical formulation comprising the VAR2CSA polypeptide is stable for more than 2 weeks of usage and for more than two years of storage.

Indications for Use of VAR2CSA Polypeptide and Conjugates Thereof

The VAR2CSA polypeptides or conjugates thereof may be used in a wide range of indications associated with expression, such as inappropriate expression of CSA, such as in various cancers, such as metastatic cancers including melanomas, such as C32 melanoma, sarcomas, lung carcinomas, oligodendrocytomas, human brain tumours including gliomas, leukaemia, such as lymphoblastic leukemia and acute myeloid leukemia, and carcinoma, such as squamous cell carcinomas and breast carcinomas, renal cell carcinomas, chondrosarcomas, and pancreatic cell carcinomas. The VAR2CSA polypeptides or conjugates thereof may also be used for cancer stem cells and accordingly target the cells before development into a cancer. Other conditions associated with expression, such as inappropriate expression of CSA are conditions of the cartilage and/or the development of scar tissue.

The VAR2CSA polypeptides or conjugates thereof may be used in identifying, tracking and targeting distant micrometastasis in vivo. Virtually all primary tumours, including cancers of the hematopoietic system, have the potential of developing into metastatic disease, which is highly associated with poor therapeutic outcome of the patients.

The VAR2CSA polypeptides or conjugates thereof may be used to target compounds that prevent degradation of or repair extracellular CSPG such as growth hormones, anti-inflammatory compounds or protein inhibitors, to cartilage tissue, joints, and neural tissue.

The VAR2CSA polypeptides or conjugates thereof may be used to target compounds that enhance degradation or prevent production of extracellular CSPG such as chondroitinase ABC, which cut the sugar chains of the protein core of CSPG molecules. Xylocides, which reduce CSPG production, or drugs that inhibit enzymes important for CSPG production such as chondroitin synthase or chondroitin polymerizing factor (such as 4-fluoro-glucosamine, p-nitrophenyl-beta-D-xyloxide, 4-methyl-umbelliferyl-beta-D-xylopyranoside), to damaged neural tissue.

VAR2CSA conjugated to a nucleic acid, here among small interfering RNA (siRNA), antisense peptide nucleic acids (PNA), small hairpin RNA (shRNA) and locked nucleic acids (LNA), can be used to remove RNA encoding CSA presenting molecules.

Conjugates of VAR2CSA Polypeptide

Therapeutic or Diagnostic Effector Moiety, Such as Cytotoxic and Detecting Moieties In some aspects of the present invention, there are provided VAR2CSA polypeptides, fusion protein or conjugate as defined in the present disclosure, further comprising a therapeutic effector moiety, such as an inflammatory agent, a steroid hormone, a cytotoxic or detecting agent or moiety, such as an organic molecule, radionuclide, or cytotoxic enzyme.

In some aspects of the present invention, the VAR2CSA polypeptide or VAR2CSA fusion protein according to the present invention comprises a sequence as defined by one or more sequences selected from SEQ ID NO 57-59, and 71 or a functional variant or fragment thereof.

In some embodiments the VAR2CSA polypeptide or VAR2CSA fusion protein according to the present invention may comprise a protease inhibitor, such as basic pancreatic trypsin inhibitor (BPTI) in the terminal, such as the N-terminal of the protein sequence, such as a sequence defined by SEQ ID NO:57.

In some embodiments the VAR2CSA polypeptide or VAR2CSA fusion protein according to the present invention may comprise a toxin protein sequence, such as a sequence as defined by one or more sequences selected from SEQ ID NO 58, 59 and 71, such as a toxin protein sequence have an optimized to be less immunogenic, such as a sequence defined by SEQ ID NO:59. In some embodiments the signal sequence KDEL of SEQ ID NO 58 or 59 is present in a VAR2CSA fusion protein according to the present invention and in some embodiments the signal sequence KDEL of SEQ ID NO 58 or 59 is absent in a VAR2CSA fusion protein according to the present invention. Accordingly, the signal sequence KDEL may be optional for the constructs according to the present invention.

Non-limiting examples of cytotoxic moieties which may be fused or conjugated to VAR2CSA polypeptides according to the invention, are chemotherapeutics selected from calicheamycin, cisplatin, adriamycin, auristatin, doxorubicin, maytansinoid, taxol, ecteinascidin, geldanamycin, methotrexate and their derivatives, and combinations thereof and the like suitable for cancer therapy. Examples of cytotoxic proteins fused to VAR2CSA polypeptides are *Pseudomonas* exotoxin A, diphtheria toxin, ricin toxin, pokeweed antiviral protein, saporin, gelonin and variants hereof.

Conjugates of albumin with doxorubicin for use in cancer have been described (Kratz et al, Med Chem 45: 5523-33, 2002) and with metotrexate in rheumatoid arthritis (Wunder et al, Immunol 170:4793-4801, 2003). Compounds that increase reactive oxygen species, i.e. Piperlongumine have also been described (Raj et al, Nature 475: 231-234, 2011). Also, therapeutic enzymes, agents that induce apoptosis, and the like in order to provide for targeted cytotoxicity, i.e. killing of tumor cells, may be used.

The VAR2CSA polypeptides described herein may mediate killing of cells by inducing complement dependent cytotoxicity (CDC) mediated lysis, antibody dependent cellular cytotoxicity (ADCC) mediated lysis, apoptosis, homotypic adhesion, and/or phagocytosis, such as by inducing CDC mediated lysis and/or ADCC mediated lysis. The VAR2CSA polypeptides described herein may interact with components of the immune system, preferably through ADCC or CDC. However, VAR2CSA polypeptides of the invention may also exert an effect simply by binding to tumor antigens on the cell surface, thus, e.g. blocking proliferation of the cells.

According to the invention, the term "therapeutic effector moiety" means any molecule, which may exert a therapeutic effect. According to the invention, a therapeutic effector molecule is preferably selectively guided to a cell, which expresses CSA and includes anticancer agents, radioisotopes, toxins, cytostatic or cytolytic drugs, etc. Anticancer agents comprise, for example, Anthracyclins (doxorubicin, daunorubicin, epirubicin, idarubicin, valrubicin, mitoxantrone), Platinum and non-platinum based alkylating agents (cisplatin, carboplatin, oxaliplatin, mechlorethamine, cyclophosphamide, chlorambucil, ifosfamide, busulfan, carmustine, dacarbazine, lomustine, procarbazine), Vinca alkaloids (vincristine, vinblastine, vinorelbine, vindesine), Taxanes (taxol and decetaxel), Topoisomerase I inhibitors (camptothecin, irinotecan, topotecan), Topoisomerase II inhibitors (amsacrine, etoposide, etoposide phosphate, teniposide and other alkaloid-derivates naturally occurring in the root of American Mayapple (*Podophyllum peltatum*)), Non-anthracyclin cytotoxic antibiotics (dactinomycin, bleomycin, plicamycin and mitomycins), Anti-steroids (such as aminoglutethimide), Nucleoside analogues (cytarabidine, fluorouracil and mercaptopurine), Antimetabolites (methotrexate and thioguanine), dichlorodiphenyltrichloroethane analogues (like mitotane), and reactive oxygen species (ROS)-inducing compounds (including but not limited to piperlongumine, and beta-phenylethyl isothiocyanate). Other anticancer agents are described, for example, in Goodman and Gilman, "The Pharmacological Basis of Therapeutics", 8th Edition, 1990, McGraw-Hill, Inc., in particular Chapter 52 (Antineoplastic Agents (Paul Calabresi and Bruce A. Chabner). Toxins may be proteins such as pokeweed antiviral protein, cholera toxin, pertussis toxin, ricin, gelonin, abrin, diphtheria exotoxin or *Pseudomonas* exotoxin. Toxin residues may also be high energy-emitting radionuclides such as cobalt-60. A VAR2CSA polypeptide may be used together with cell-penetrating peptides (CPP) to facilitate transport of the VAR2CSA polypeptide and any thereto-linked molecule across cell plasma membranes. Cell-penetrating peptides have found numerous applications in medicine as drug delivery agents in the treatment of different diseases including cancer and virus inhibitors. Examples on CPP include but are not limited to: trans-activating transcriptional activator (Tat) from human immunodeficiency virus; pep-1 (CHARIOT peptide); R8, azo-R8; SMoC. (Okuyama M et al. Nat Methods. 2007 February; 4(2):153-9M; Soane L and Fiskum G J Neurochem. 2005 October; 95(1):230-43; Loudet A et al. Org Biomol Chem. 2008 Dec. 21; 6(24):4516-22).

Radionuclides

A VAR2CSA polypeptides, a fusion protein or conjugate according to the aspects described herein coupled to a polyaminopolycarboxylate chelator may be used to provide a radiolabeled polypeptide consisting of a radiochelate of the VAR2CSA polypeptide, fusion protein or conjugate coupled to the chelator and a radionuclide suitable for medical imaging, the radionuclide being selected from the group consisting of $^{61}$Cu, $^{64}$Cu, $^{66}$Ga, $^{67}$Ga, $^{68}$Ga, $^{110}$In, $^{111}$In, $^{44}$Sc, $^{89}$Zr and $^{86}$Y, or with a radionuclide suitable for therapy, the radionuclide being selected from the group consisting of $^{225}$Ac, $^{212}$Bi, $^{213}$Bi, $^{67}$Cu, $^{166}$Ho, $^{177}$Lu, $^{212}$Pb, $^{149}$Pm, $^{153}$Sm, $^{227}$Th and $^{90}$Y, wherein the radionuclide is complexed with the VAR2CSA polypeptide, such as via a chelator.

Accordingly VAR2CSA polypeptides, a fusion protein or conjugate according to the aspects described herein may be used for radioimaging of cancer cells, including solid tumors or metastases, such as in melanoma patients.

In embodiments thereof, the polypeptide may also be radiolabeled with non-metal radioisotopes using so called indirect labelling. Thus, for labelling with for example $^{18}$F, $^{76}$Br, different iodine isotopes and $^{211}$At, intermediate "linker molecules" are used for labelling. Such a linker molecule should contain two functional moieties, one providing rapid and efficient radiolabeling, and another enabling rapid and efficient coupling to the proteins, e.g. to amine groups, or preferably to the thiol group of a unique cysteine. For example a malemide group reacts with thiol groups to form a stable thioether bond. The "linker molecule" may first be reacted with the radiolabel and subsequently with the thiol or the selenothiol group of the protein.

Other alternative detecting moieties includes fluorophores or fluorochromes such as any one selected from Hydroxycoumarin, Aminocoumarin, Methoxycoumarin, CASCADE BLUE, PACIFIC BLUE, PACIFIC ORANGE, LUCIFER YELLOW, NBD, R-Phycoerythrin (PE), PE-Cy5 conjugates, PE-Cy7 conjugates, RED 613, PerCP, TRU RED, FLUOR X, Fluorescein, BODIPY-FL, TRITC, X-Rhodamine, Lissamine Rhodamine B, TEXAS RED, Allophycocyanin (APC), and APC-Cy7 conjugates.

Such conjugates with detecting moieties include fluorophores or fluorochromes may be used for imaging of cancer cells or tumors.

Steroid Hormones or Anti-Inflammatory Agents

In some embodiments according to the invention the VAR2CSA polypeptides are conjugated with an anti-inflammatory agent, including steroid hormones.

Cartilage and scar tissue is known to contain CSPG in high amounts. Accordingly, it may be attractive to direct anti-inflammatory agents such as non-steroid anti-inflammatory compounds, disease modifying anti-rheumatic drugs (such as methotrexate, azathioprine, sulfasalazine, ciclosporine, pennicillamine, leflunomide, or gold), biological anti-rheumatic drugs (such as Tumor Necrosis Factor inhibitors, interleukin-1-receptor antagonists, CD20-antibody, Insulin Growth Factor 1) and steroid hormones or alternative compounds to such tissues.

In some embodiments according to the invention the VAR2CSA polypeptides are conjugated with an anti-inflammatory agent, such as non-steroid anti-inflammatory compounds, disease modifying anti-rheumatic drugs (such as methotrexate, azathioprine, sulfasalazine, ciclosporine, pennicillamine, leflunomide, or gold), biological anti-rheumatic drugs (such as Tumor Necrosis Factor inhibitors, interleukin-1-receptor antagonists, CD20-antibody, Insulin Growth Factor 1) and steroid hormones or alternative compounds to such tissues.

Conjugates with CSPG4

In some embodiments according to the invention the VAR2CSA polypeptides are conjugated with CSPG4.

It is assumed that conjugates of VAR2CSA polypeptides with CSPG4 may be used as an immunization agent. For the purpose of this use, it is assumed that the VAR2CSA polypeptide may function as a chaperone that could facilitate a display of CSPG4 to T-cells in a conformation that would provide antibodies. Accordingly, it is assumed that VAR2CSA polypeptides conjugated with CSPG4 may be used in a vaccine.

As used herein the term "CSPG4" refers to the 2322 amino acid full length human Chondroitin sulfate proteoglycan 4 identified by Uniprot as Q6UVK1 (CSPG4_HUMAN) as well as variants, functional fragments, and orthologs thereof. CSPG4 may also be referred to as melanoma-associated chondroitin sulfate proteoglycan (MCSP), High Molecular Weight-Melanoma Associated Antigen (HMW-MAA) or neuron-glial antigen 2 (NG2).

Targeting of CD44 or Other Proteoglycans

For the purpose of use of conjugates of VAR2CSA polypeptides in the treatment of cancer indications, it is assumed that the conjugates according to the present invention may be used to target not only CSPG4 expressing tumor cells, but also CD44 expressing cells, such as cancer stem cells, and cells expressing proteoglycans exemplified but not limited to those of Table 1. This targeting is mediated through the binding to CSA on the CD44 antigen. Accordingly, the conjugates according to the present invention may be used to target CSPG4 negative but CD44 positive cells. This may be used as an alternative to or simultaneously with the targeting of CSPG4 expressing tumor cells.

Use in Isolation of Cancer Stem Cells Through Binding to CD44, and/or CSPG4, and/or Other Proteoglycans, Such as Those in Table 1.

The specific and high affinity binding of the VAR2CSA polypeptides according to the present invention, such as in the form of conjugates of VAR2CSA polypeptides, may be used to isolate stem cells, such as cancer stem cells expressing CD44 and/or CSPG4.

Use in Isolation or Detection of Circulating Tumor Cells (CTC) Through Binding to CSA-Containing Proteoglycans The specific and high affinity binding of the VAR2CSA polypeptides according to the present invention, such as in the form of conjugates of VAR2CSA polypeptides, may be used to isolate or detect CTCs of epithelial and non-epithelial origin, which express one or more CSA-containing proteoglycans, such as those described in Table 1.

Anti-Idiotypic Antibodies

As an alternative or supplement to the use of VAR2CSA polypeptides, it is also possible to use anti-idiotypic antibodies or even mimotopes that mimic VAR2CSA. The technologies for preparing anti-idiotypic antibodies that mimic an antigen epitope are known in the art and entail provision of a first monoclonal antibody binding VAR2CSA polypeptides followed by subsequent production of a second antibody that binds the idiotype of said first antibody.

Mimotopes can be isolated from libraries of random peptides that are screened in phage display against antibodies that bind VAR2CSA polypeptides specifically.

Anti-idiotypic antibodies may also be prepared by immunization with inhibitory host or patient derived antibodies against VAR2CSA in order to obtain and screen for polyclonal and/or monoclonal antibodies, such as human antibodies against and inhibiting the host derived antibodies. Although VAR2CSA generally is an evolutionary refined malaria protein unlikely to cause autoimmune reactions in the patient, such an immune reaction cannot be excluded after a period of treatment. An anti-idiotypic antibody used in combination with or as an alternative to VAR2CSA polypeptides may then be used.

Specific Embodiments of the Invention

As described herein the present invention relates to an isolated protein fragment of VAR2CSA, which fragment consist of a sequential amino acid sequence of
  a) ID1, and
  b) DBL2Xb, and optionally
  c) ID2a.

In some embodiments the isolated protein fragment of VAR2CSA according to the present invention comprises ID2a.

In some embodiments the isolated protein fragment of VAR2CSA according to the present invention do not comprise ID2a.

In some embodiments the isolated protein fragment of VAR2CSA according to the present invention further comprises an amino acid sequence in the N- or C-terminal, or within the sequence of the protein fragment of VAR2CSA of not more than 100 amino acids, such as not more than 90 amino acids, such as not more than 80 amino acids, such as not more than 70 amino acids, such as not more than 60 amino acids, such as not more than 50 amino acids, such as not more than 40 amino acids, such as not more than 30 amino acids, such as not more than 20 amino acids, such as not more than 18 amino acids, such as not more than 16 amino acids, such as not more than 14 amino acids, such as not more than 12 amino acids, such as not more than 10 amino acids, such as not more than 8 amino acids, such as not more than 6 amino acids, such as not more than 4 amino acids, such as not more than 2 amino acids derived from any part of a VAR2CSA polypeptide as defined herein, which is not part of ID1, DBL2Xb, or ID2a.

In some embodiments the isolated protein fragment of VAR2CSA according to the present invention further comprises an amino acid sequence in the N- or C-terminal, or within the sequence of the protein fragment of VAR2CSA of not more than 100 amino acids, such as not more than 90 amino acids, such as not more than 80 amino acids, such as not more than 70 amino acids, such as not more than 60 amino acids, such as not more than 50 amino acids, such as not more than 40 amino acids, such as not more than 30 amino acids, such as not more than 20 amino acids, such as not more than 18 amino acids, such as not more than 16 amino acids, such as not more than 14 amino acids, such as not more than 12 amino acids, such as not more than 10 amino acids, such as not more than 8 amino acids, such as not more than 6 amino acids, such as not more than 4 amino acids, such as not more than 2 amino acids, which amino acid sequence is not derived from any part of a VAR2CSA polypeptide as defined herein.

In some embodiments the protein fragment according to the present invention binds chondroitin sulfate A (CSA) on proteoglycans (CSPG) with an affinity as measured by a $K_D$ lower than 100 nM, such as lower than 80 nM, such as lower than 70 nM, such as lower than 60 nM, such as lower than 50 nM, such as lower than 40 nM, such as lower than 30 nM, such as lower than 26 nM, such as lower than 24 nM, such as lower than 22 nM, such as lower than 20 nM, such as lower than 18 nM, such as lower than 16 nM, such as lower than 14 nM, such as lower than 12 nM, such as lower than 10 nM, such as lower than 9 nM, such as lower than 8 nM, such as lower than 7 nM, such as lower than 6 nM, or lower than 4 nM.

In some embodiments the protein fragment according to the present invention comprises an amino acid sequence having at least 70% sequence identity with any one amino acid sequence of 1-577 of SEQ ID NO:1, 1-592 of SEQ ID NO:3, 1-579 of SEQ ID NO:4, 1-576 of SEQ ID NO:5, 1-586 of SEQ ID NO:10, 1-579 of SEQ ID NO:11, 1-565 of SEQ ID NO:29, 1-584 of SEQ ID NO:34, 1-569 of SEQ ID NO:36, 1-575 of SEQ ID NO:37, 1-592 of SEQ ID NO:38, 1-603 of SEQ ID NO:41, 1-588 of SEQ ID NO:43, 1-565 of SEQ ID NO:44, 1-589 of SEQ ID NO:45, 1-573 of SEQ ID NO:48, 1-583 of SEQ ID NO:53, or 1-569 of SEQ ID NO:54.

In some embodiments the protein fragment according to the present invention comprises an amino acid sequence having at least 70% sequence identity with an amino acid sequence of 578-640 of SEQ ID NO:1, 593-656 of SEQ ID NO:3, 580-643 of SEQ ID NO:4, 577-640 of SEQ ID NO:5, 587-650 of SEQ ID NO:10, 580-643 of SEQ ID NO:11, 566-628 of SEQ ID NO:29, 585-647 of SEQ ID NO:34, 570-632 of SEQ ID NO:36, 576-639 of SEQ ID NO:37, 593-655 of SEQ ID NO:38, 604-667 of SEQ ID NO:41, 589-652 of SEQ ID NO:43, 566-628 of SEQ ID NO:44, 590-653 of SEQ ID NO:45, 574-637 of SEQ ID NO:48, 584-646 of SEQ ID NO:53, or 570-632 of SEQ ID NO:54.

In some embodiments the protein fragment according to the present invention comprises an amino acid sequence having at least 70% sequence identity with an amino acid sequence of SEQ ID NO:2, 6, 8, 9, 12, 13, 14, 15, 16, 17, 18, 19, 20, 21, 22, 23, 24, 25, 26, 27, 28, 30, 31, 32, 33, 35, 39, 40, 42, 46, 47, 49, 50, 51, or 52.

In some embodiments the protein fragment according to the present invention consists of an amino acid sequence having at least 70% sequence identity with any one amino acid sequence of 1-577 of SEQ ID NO:1, 1-592 of SEQ ID NO:3, 1-579 of SEQ ID NO:4, 1-576 of SEQ ID NO:5, 1-586 of SEQ ID NO:10, 1-579 of SEQ ID NO:11, 1-565 of SEQ ID NO:29, 1-584 of SEQ ID NO:34, 1-569 of SEQ ID NO:36, 1-575 of SEQ ID NO:37, 1-592 of SEQ ID NO:38, 1-603 of SEQ ID NO:41, 1-588 of SEQ ID NO:43, 1-565 of SEQ ID NO:44, 1-589 of SEQ ID NO:45, 1-573 of SEQ ID NO:48, 1-583 of SEQ ID NO:53, or 1-569 of SEQ ID NO:54.

In some embodiments the protein fragment according to the present invention consists of an amino acid sequence selected from the list consisting of SEQ ID NO:1, 3-5, 10, 11, 29, 34, 36-38, 41, 43-45, 48, 53, and 54.

In some embodiments the protein fragment according to the present invention fragment consists of an amino acid sequence having a length of less than 700 amino acids, such as less than 690 amino acids, such as less than 680 amino acids, such as less than 670 amino acids, such as less than 660 amino acids, such as less than 650 amino acids, such as less than 640 amino acids, such as less than 630 amino acids, such as less than 620 amino acids, such as less than 610 amino acids, such as less than 600 amino acids, such as less than 590 amino acids, such as less than 580 amino acids, such as less than 570 amino acids.

In some embodiments the protein fragment according to the present invention is substantially pure.

In some embodiments the protein fragment according to the present invention has a molecular mass of less than about 100 kDa under non-reducing conditions on an SDS-PAGE.

In some embodiments the protein fragment according to the present invention is a recombinant protein.

In some embodiments the protein fragment according to the present invention is non-glycosylated.

The invention further relates to a protein fragment as defined herein, a VAR2CSA polypeptide, or a conjugate according to the invention for the treatment of any indications associated with a condition involving expression, such as inappropriate expression of CSA, such as in cancer, arthritis, multiple sclerosis and healing after neural damage, cartilage repair, wound healing, and in psoriasis.

In some embodiments, a VAR2CSA polypeptide, conjugate or fusion protein is or comprises a protein fragment of VAR2CSA according to the present invention.

Accordingly, a VAR2CSA polypeptide, conjugate or fusion protein according to the present invention may comprise an amino acid sequence with at least 70% sequence identity to an amino acid sequence identified by any sequence of SEQ ID NO: 1-75.

In some embodiments a VAR2CSA polypeptide according to the present invention consist of an amino acid sequence selected from SEQ ID NO: 60-70, 72-75.

In some embodiments, the cancer is selected from Cutaneous, Ocular or Conjuctival melanoma. Carcinomas (Triple negative- and metaplastic breast carcinoma, Pancreatic carcinoma, Ovarian carcinoma, Endometrial carcinoma, Hepatocellular carcinoma, Lung carcinoma, Colon carcinoma, Prostate carcinoma, Cervix carcinoma, Testis carcinoma, Basal cell skin carcinoma, Clear cell renal cell carcinoma, Kreatinized head and neck squamous cell carcinoma, Skin squamous cell carcinoma, Vulvar kreatinized squamous cell carcinoma and Vulvar basal cell carcinoma), sarcomas (Breast liposarcoma, Fibrosarcoma, Dedifferentiated chondro- and liposarcoma, Leiomyosarcoma, Liposarcoma, Myxoid liposarcoma, Uterine corpus leiomyosarcoma, Osteosarcoma, Ewing sarcoma and Rhabdomyosarcoma), hematopoietic cancers (Chronic lymphatic leukaemia (CLL), Acute lymphatic leukaemia (ALL), Acute myeloid leukaemia (AML), B-cell, T-cell and large granular lymphoma), tumours of neuroepithelial tissue, such as Astrocytomas (Pleomorphic Xanthoastrocytoma, Fibrillary Astrocytomas, Anaplastic astrocytoma, Glioblastoma Multiforme), Oligodendroglioma, Ependymoma, Choroid plexus tumor, Oligoastrocytoma, gliosarcoma, Ganglioglioma, Retinoblastoma, Neurocytoma, Neuroblastomas (Esthesioneuroblastoma and Ganglioneuroblastoma), Medulloblastoma and Atypical Teratoid Rhabdoid tumors, and any other CSA-expressing cancer subtype.

In some embodiments, the cancer is selected from all CSA-expressing malignancies including carcinomas (including but not limited to Breast carcinoma, Pancreatic carcinoma, Ovarian carcinoma, Endometrial carcinoma, Hepatocellular carcinoma, Lung carcinoma, Colon carcinoma, Prostate carcinoma, Cervix carcinoma, Testis carcinoma, Basal cell skin carcinoma, Clear cell renal cell carcinoma, Head and neck squamous cell carcinoma, Skin squamous cell carcinoma, Vulvar kreatinized squamous cell carcinoma and Vulvar basal cell carcinoma), sarcomas (including but not limited to Fibrosarcoma, Dedifferentiated chondro- and liposarcoma, Leiomyosarcoma, Liposarcoma, Myxoid liposarcoma, Uterine corpus leiomyosarcoma, Osteosarcoma, Ewing sarcoma and Rhabdomyosarcoma, Synovial sarcoma, Solitary Fibrous tumor), hematopoietic cancers (including but not limited to Chronic lymphatic leukaemia (CLL), Acute lymphatic leukaemia (ALL), Acute myeloid leukaemia (AML), B-cell, T-cell and large granular lymphoma), tumours of neuroepithelial tissue, such but not limited to Astrocytomas (Pleomorphic Xanthoastrocytoma, Fibrillary Astrocytomas, Anaplastic astrocytoma, Glioblastoma Multiforme), Oligodendroglioma, Ependymoma, Choroid plexus tumor, Oligoastrocytoma, gliosarcoma, Ganglioglioma, Retinoblastoma, Neurocytoma, Neuroblastomas (Esthesioneuroblastoma and Ganglioneuroblastoma), Medulloblastoma, Atypical Teratoid Rhabdoid tumors and all types of neuroendocrine cancer.

Sequences, Including Sequences of VAR2CSA Polypeptides:

>fcr3 745 amino acids | 640 aa; underlined sequence corresponds to the ID1 domain of FCR3, Sequence in bold corresponds to DBL2Xb domain of FCR3. Remaining sequence is ID2a (SEQ ID NO: 1)

NYIKGDPYFAEYATKLSFILNPSDANNPSGETANHNDEACNCNESGISSVGQAQTSGPSSNKTCI

THSSIKTNKKKECKDVKLGVRENDKDLKICVIEDTSLSGVDNCCCQDLLGILQENCSDNKRGSSS

NDSCDNKNQDECQKKLEKVFASLTNGYKCDKCKSGTSRSKKKWIWKKSSGNEEGLQEEYANTIGL

PPRTQSLYLGNLPKLENVCEDVKDINFDTKEKFLAGCLIVSFHEGKNLKKRYPQNKNSGNKENLC

KALEYSFADYGDLIKGTSIWDNEYTKDLELNLQNNFGKLFGKYIKKNNTAEQDTSYSSLDELRES

WWNTNKKYIWTAMKHGAEMNITTCNADGSVTGSGSSCDDIPTIDLIPQYLRFLQEWVENFCEQRQ

AKVKDVITNCKSCKESGNKCKTECKTKCKDECEKYKKFIEACGTAGGGIGTAGSPWSKRWDQIYK

RYSKHIEDAKRNRKAGTKNCGTSSTTNAAASTDENKCVQSDIDSFFKHLIDIGLTTPSSYLSNVL

DDNICGADKAPWTTYTTYTTTEKCNKERDKSKSQSSDTLVVVNVPSPLGNTPYRYKYACQCKIPT

NEETCDDRKEYMNQWSCGSARTMKRGYKNDNYELCKYNGVDVKPTTVRSNSSKLD

>gi|254952610|gb|ACT97135.1| VAR2CSA [*Plasmodium falciparum*] | 341 aa (SEQ ID NO: 2)

KCDKCKSGTSRSRKIWTWRKSSGNKEGLQEEYANTIGLSPRTQLLYLGNLRKLENVCEDVTDINF

DTKEKFLAGCLIAAFHEGKNLKKRYLEKKKGDNNSKLCKDLKYSFADYGDLIKGTSIWDNDFTKD

LELNLQQIFGKLFRKYIKKKNISTEQDTSYSSLDELRESWWNTNKKYIWLAMKHGAGMNSTTCSC

SGDSSSGENQTNSCDDIPTIDLIPQYLRFLQEWVEHFCEQRQAKVKDVITNCNSCKESGGICNSD

CEKKCKNKCDAYKTFIEDCKGVGGTGTAGSSWVKRWYQIYMRYSKYIEDAKRNRKAGTKSCGTSS

TTNVSVSTDENKCVQS-

>M24 745 amino acids | 656 aa (SEQ ID NO: 3)

DYIKGDPYFAEYATKLSFILNSSDANNPSGETANHNDEVCNPNESEISSVGQAQTSDPSSNKTCN

THSSIKANKKKVCKHVKLGINNNDKVLRVCVIEDTSLSGVENCCFKDLLGILQENCSDNKSGSSS

NGSCNNKNQEACEKNLEKVLASLTNCYKCDKCKSGTSTVNKNWIWKKSSGNKEGLQKEYANTIGL

PPRTHSLYLGNLPKLENVCEDVKDINFDTKEKFLAGCLIAAFHEGKNLKKRYPQNKNDDNNSKLC

KALEYSFADYGDLIKGTSIWDNEYTKDLELNLQQIFGKLFRKYIKKNISTEQDTLYSSLDELRES

WWNTNKKYIWLAMKHGAGMNITTCCGDGSVTGSGSSCDDIPTIDLIPQYLRFLQEWVEHFCKQRQ

EKVKDVINSCNSCKNTSSKTKLGDTCNSDCEKKCKIECEKYKKFIEECRTAVGGTAGSSWSKRWD

QIYKMYSKHIEDAKRNRKAGTKNCGITTGTISGESSGANSGVTTTENKCVQSDIDSFFKHLIDIG

LTTPSSYLSIVLDDNICGDDKAPWTTYTTYTTYTTTEKCNKERDKSKSQQSNTSVVVNVPSPLGN

TPHGYKYACQCKIPTNEETCDDRKEYMNQWISDTSKNPKGSGSTNNDYELYTYNGVKETKLPKKL

NSPKLD

>KMWII 745 amino acids | 643 aa (SEQ ID NO: 4)

DYIKDDPYSKEYTTKLSFILNSSDANTSSGETANHNDEACNCNESEISSVGQAQTSGPSSNKTCI

THSFIKANKKKVCKDVKLGVRENDKVLRVCVIEDTSLSGVDNCCCQDLLGILQENCSDNKRGSSS

NGSCNNKNQDECQKKLEKVFVSLTNGYKCDKCKSGTSTVNKKWIWKKSSGNEKGLQKEYANTIGL

PPRTQSLYLGNLPKLGNVCEDVTDINFDTKEKFLAGCLIAAFHEGKNLKISHEKKKGDNGKKLCK

-continued

ALEYSFADYGDLIKGTSIWDNEYTKDLELNLQKAFGKLFGKYIKKNIASDENTSYSSLDELRESW

WNTNKKYIWTAMKHGAEMNSTMCNADGSVTGSGSSCDDIPTTDFIPQYLRFLQEWVEHFCKQRQE

KVNAVIENCNSCKNTSGERKIGGTCNGDCKTECKNKCEAYKNFIEDCKGGDGTAGSSWVKRWDQI

YKRYSKHIEDAKRNRKAGTKSCGPSSITNASVSTDENKCVQSDIDSFFKHLIDIGLTTPSSYLSI

VLDENNCGEDNAPWTTYTTYTTTEKCNKDKKKSKSQSCNTAVVVNVPSPLGNTPHEYKYACQCKI

PTTEETCDDRKEYMNQWISDTSKKQKGSGSTNNDYELYTYTGVKETKLPKKLNSPKLD

>1248 745 amino acids | 640 aa (SEQ ID NO: 5)

SYVKNDPYSKEYVTKLSFILNPSDANNPSGETANHNDEACNPNESEIASVGQAQTSDRLSQKACI

THSFIGANKKIVCKDVKLGVREKDKDLKICVIEDDSLRGVENCCFKDLLGILQENCSDNKSGSSS

NGSCNNKNQDECQKKLDEALASLHNGYKCDKCKSGTSRSKKIWTWRKFPGNGEGLQKEYANTIGL

PPRTQSLYLGNLRKLENVCKGVTDINFDTKEKFLAGCLIAAFHEGKNLKISNKKKNDDNGKKLCK

DLKYSFADYGDLIKGTSIWDNEYTKDLELNLQKIFGKLFRKYIKKNIASDENTLYSSLDELRESW

WNTNKKYIWLAMKHGTTCSSGSGDNGDGSVTGSGSSCDDMSTIDLIPQYLRFLQEWVEHFCKQRQ

EKVKDVIENCKSCKNTSGERIIGGTCGSDCKTKCKGECDAYKNFIEECKRGDTAGSPWSKRWDQ

IYMRYSKYIEDAKRNRKAGTKNCGTSSTTNAAENKCVQSDIDSFFKHLIDIGLTTPSSYLSIVLD

ENICGDDKAPWTTYTTYTTTEKCNKETDKSKSQSCNTAVVVNVPSPLGNTPHGYKYACECKIPTT

EETCDDRKEYMNQWISDTSKKPKGGRSTNNDYELYTYNGVKETKLPKKSSSSKLD

>gi|254952618|gb|ACT97139.1| VAR2CSA [*Plasmodium falciparum*] | 358 aa (SEQ ID NO: 6)

KCEKCKSEQSKKNNNIWIWRKFPGNGEGLQKEYANTIGLPPRTHSLYLGNLPKLENVCKDVKDIN

FDTKEKFLAGCLIAAFHEGKNLKTTYPQNKNADNNSKLCKDLKYSFADYGDLIKGTSIWDNDFTK

DLELNLQKIFGKLFRKYIKKNIASDENTLYSSLDELRESWWNTNKKYIWLAMKHGAEMNSTMCNG

DGSVTGSSDSGSTTCSGDNGSISCDDIPTIDLIPQYLRFLQEWVEHFCKQRQEKVKPVIENCKSC

KNTSGERIIGGTCGSDCEKKCKGECDAYKKFIEECKGGGGGTGTAGSPWSKRWDQIYKRYSKYIE

DAKRNRKAGTKSCGPSSTTNAAASTTESKCVQS

>gi|254952592|gb|ACT97126.1| VAR2CSA [*Plasmodium falciparum*] | 333 aa (SEQ ID NO: 7)

KCDKCKSEQSKKNNKNWIWKQFPGNGEGLQKEYANTIGLPPRTHSLYLGNLPKLENVCKGVTDIN

FDTKEKFLAGCLIAAFHEGKNLKTSHEKKKGDNGKKLCKDLKYSFADYGDLIKGTSIWDNDFTKD

LELNLQQIFGKLFRKYIKKNISAEQDTSYSSLDELRESWWNTNKKYIWLAMKHGTTCSSGSGDNG

DGSVTGSGSSCDDMPTTDFIPQYLRFLQEWVEHFCKQRQEKVNAVITNCKSCKESGGTCNSDCEK

KCKDECEKYKKFIEECRTAADGTAGSSWSKRWDQIYKMYSKHIEDAKRNRKAGTKNCGTSSTTNA

AENKCVQS

>gi|90193467|gb|ABD92329.1| erythrocyte membrane protein 1 [*Plasmodium falciparum*] 269 aa (SEQ ID NO: 8)

DYIKDDPYSKEYTTKLSFILNSSDANTSSGETANHNDEACNCNESEIASVEQASISDRSSQKAYI

THSSIKTNKKKVCKYVKLGINNNDKVLRVCVIEDTSLSGVENCCFKDLLGILQENCSDNKRGSSF

NDSCNNNNEEACQKKLEKVLASLTNGYKCEKCKSGTSRSKKKWIWKKSSGKEGGLQKEYANTIGL

PPRTQSLYLGNLPKLENVCKGVTDINFDTKEKFLAGCLIAAFHEGKNLKPSHQNKNDDNNSKLCK

DLKYSFADY

>gi|254952616|gb|ACT97138.1| VAR2CSA [*Plasmodium falciparum*] | 333 aa (SEQ ID NO: 9)
KCDKCKSGTSRSKKKWTWRKSSGNKEGLQKEYANTIGLPPRTHSLYLGNLRKLENVCEDVTDINF

DTKEKFLAGCLIAAFHEGKNLKTTYPQNKNDDNNSKLCKALKYSFADYGDLIKGTSIWDNDFTKD

LELNLQKIFGKLFRKYIKKNISTEQHTSYSSLDELRESWWNTNIKKYIWLAMKHGAEMNGTTCSC

SGDSSDDIPTIDLIPQYLRFLQEWVEHFCKQRQAKVNAVINSCNSCKNTSGERKLGGTCGSECKT

ECKNKCDAYKEFIDGTGSGGGTGTAGSSWVKRWDQIYKRYSKYIEDAKRNRKAGSKNCGTSSTTN

AAESKCVQS

>hb31 745 amino acids | 650 aa (SEQ ID NO: 10)
SYVKNNPYSAEYVTKLSFILNSSDANTSSETPSKYYDEVCNCNESEISSVGQAQTSGPSSNKTCI

THSSIKTNKKKVCKDVKLGINNNDKVLRVCVIEDTSLSGVDNCCCQDLLGILQENCSDKNQSGSS

SNGSCNNKNQDECQKKLEKVFASLTNGYKCDKCKSGTSRSKKKWIWRKSSGNEEGLQKEYANTIG

LPPRTQSLYLGNLRKLENVCKGVTDINFDTKEKFLAGCLIAAFHEGKNLKTTYPQNKKKLCKDLK

YSFADYGDLIKGTSIWDNEYTKDLELNLQKAFGKLFRKYIKKNISTEQHTLYSSLDELRESWWNT

NKKYIWLAMKHGAGMNSTTCCGDGSVTGSGSSCDDIPTIDLIPQYLRFLQEWVEHFCKQRQEKVN

AVIENCNSCKECGDTCNGECKTECEKKCKIECEKYKTFIEECVTAVGGTSGSPWSKRWDQIYKRY

SKYIEDAKRNRKAGTKNCGITTGTISGESSGANSGVTTTENKCVQSDIDSFFKHLIDIGLTTPSS

YLSIVLDDNICGADNAPWTTYTTYTTYTTTKNCDIKKKTPKSQPINTSVVVNVPSPLGNTPHGYK

YACQCKIPTTEESCDDRKEYMNQWIIDTSKKQKGSGSTNNDYELYTYNGVKETKLPKKSSSSKLD

>hb32 745 amino acids | 643 aa (SEQ ID NO: 11)
SYVKDDPYSAEYVTKLSFILNSSDANTSSETPSKYYDEVCNCNESEISSVGQAQTSGPSSNKTCI

THSSIKTNKKKVCKDVKLGINNNDKVLRVCVIEDTSLSGVDNCCCQDLLGILQENCSDKNQSGSS

SNGSCNNKNQDECQKKLEKVFASLTNGYKCDKCKSGTSRSKKKWIWRKSSGNEEGLQKEYANTIG

LPPRTQSLYLGNLPKLENVCKGVTDIIYDTKEKFLSGCLIAAFHEGKNLKTSHEKKNDDNGKKLC

KALEYSFADYGDLIKGTSIWDNDFTKDLELNLQKIFGKLFRKYIKKNNTAEQDTSYSSLDELRES

WWNTNKKYIWTAMKHGAGMNSTTCSGDGSVTGSGSSCDDMPTIDLIPQYLRFLQEWVEHFCKQRQ

EKVKDVITNCNSCKECGDTCNGECKTECKTKCKGECEKYKNFIEECNGTADGGTSGSSWSKRWDQ

IYKRYSKYIEDAKRNRKAGTKNCGTSSTTNAAASTTENKCVQSDIDSFFKHLIDIGLTTPSSYLS

NVLDDNICGEDKAPWTTYTTYTTKNCDIQKKTPKPQSCDTLVVVNVPSPLGNTPHGYKYVCECKI

PTTEETCDDRKEYMNQWIIDTSKKQKGSGSTNNDYELYTYNGVQIKQAAGTLKNSKLD

>gi|90193475|gb|ABD92333.1| erythrocyte membrane protein 1 [*Plasmodium falciparum*] 269 aa (SEQ ID NO: 12)
NYIKGDPYSAEYATKLSFILNSSDTENASEKIQKNNDEVCNCNESEIASVEQAPISDRSSQKACI

THSSIKANKKKVCKHVKLGVRENDKDLKICVIEDTSLSGVDNCCCQDLLGILQENCSDNKSGSSS

NGSCNNNEEICQKKLEKVLASLTNGYKCDKCKSGTSTVNKNWIWKKYSGKEGGLQEEYANTIGL

PPRTQSLYLGNLPKLENVCEDVKDINFDTKEKFLAGCLIAAFHEGKNLKTSNKKKNDDNNSKLCK

ALKYSFADY

>gi|254952600|gb|ACT97130.1| VAR2CSA [*Plasmodium falciparum*] | 344 aa (SEQ ID NO: 13)
KCDKCKSGTSTVNKKWIWKKYSGTEGGLQEEYANTIALPPRTQSLYLGNLPKLENVCKDVTDINF

DTKEKFLAGCLIAAFHEGKNLKTTYLEKKKGDNGKKNDDNNSKLCKALKYSFADYGDLIKGTSIW

DNDFTKDLELNLQQIFGKLFRKYIKKNIASDENTLYSSLDELRESWWNTNKKYIWLAMKHGAGMN

STMCNADGSVTGSGSSCDDIPTIDLIPQYLRFLQEWVEHFCKQRQAKVKDVITNCNSCKECGGTC

NGECKTECEKKCKGECDAYKKFIEECKGKADEGTSGSSWSKRWDQIYKRYSKYIEDAKRNRKAGT

KNCGPSSTTSTAESKCVQS

>gi|254952598|gb|ACT97129.1| VAR2CSA [Plasmodium
falciparum] | 334 aa
(SEQ ID NO: 14)
KCDKCKSEQSKKNNNIWIWKKSSGTEGGLQKEYANTIALPPRTQSLYLGNLRKLENVCEDVKDIN

FDTKEKFLAGCLIAAFHEGKNLKKRYLEKKNGDNNSKLCKALKYSFADYGDLIKGTSIWDNEYTK

DLELNLQKIFGKLFRKYIKKNNTAEQHTSYSSLDELRESWWNTNKKYIWLAMKHGTTCSSGSGDN

GSISCDDIPTIDLIPQYLRFLQEWVEHFCEQRQGKVNAVIENCNSCKNTSSKTKLGGTCNGECKT

ECKGECDAYKEFIEKCKGTAAEGTSGSSWVKRWYQIYMRYSKYIEDAKRNRKAGTKNCGTSSTTS

TAESKCVQS

>gi|254952596|gb|ACT97128.1| VAR2CSA [Plasmodium
falciparum] | 332 aa
(SEQ ID NO: 15)
KCDKCKSEQSKKNNNIWIWKKSSGTEGGLQKEYANTIALPPRTQSLYLGNLRKLENVCEDVKDIN

FDTKEKFLAGCLIAAFHEGKNLKKRYLEKKNGDNNSKLCKALKYSFADYGDLIKGTSIWDNEYTK

DLELNLQKIFGKLFRKYIKKNNTAEQDTSYSSLDELRESWWNTNKKYIWTAMKHGTTCSSGSGDN

GSISCDDIPTIDLIPQYLRFLQEWVEHFCEQRQEKVKDVIKNCNSCKECGGTCNGECKTECKNKC

KDECDAYKKFIEECEGKAAEGTSGSSWSKRWDQIYKRYSKYIEDAKRNRKAGTKNCGTSSTTSTA

ENKCVQS

>gi|90193465|gb|ABD92328.1| erythrocyte membrane protein 1
[Plasmodium falciparum] | 267 aa
(SEQ ID NO: 16)
NYIKDDPYSAEYTTKLSFILNSSDTENASEKIQKNNDEVCNPNESGIACVELAQTSGSSSNKTCN

THSFIKANKKKVCKDVKLGINKKDKDLKICVIEDDSLRGVDNCCCQDLLGILQENCSDKNQSGSS

SNGSCNNKNQEACQKKLENVFASLTNGYKCEKCKSEQSKKNNKNWIWKKYSVKEEGLQKEYANTI

ALPPRTQSLYLGNLPKLGNVCKGVTDINFDTKEKFLAGCLIAAFHEGKNLKTTYLQNKKKLCKAL

KYSFADY

>gi|90193477|gb|ABD92334.1| erythrocyte membrane protein 1
[Plasmodium falciparum] | 263 aa
(SEQ ID NO: 17)
DYIKGDPYFAEYATKLSFILNSSDANTSSGETANHNDEACNPNESEIASVEQASISDRSSQKACN

THSSIKANKKKECKHVKLGVRENDKDLKICVIEDTSLSGVDNCCCQDLLGILQENCSDNKRGSSS

NGSCDKNSEEICQKKLDEALASLHNGYKNQKCKSEQSKKNKNKWIWKKSSGNEKGLQKEYANTIG

LPPRTQSLYLGNLPKLENVCEDVTDINFDTKEKFLAGCLIAAFHEGKNLKTTYPQNKNDDNGKKL

CKD

>gi|254952594|gb|ACT97127.1| VAR2CSA [Plasmodium
falciparum] | 338 aa
(SEQ ID NO: 18)
KCDKCKSEQSKKNNNIWIWKKSSGNKKGLQKEYANTIGLPPRTQSLYLGNLPKLENVCKDVTDIN

FDTKEKFLAGCLIAAFHEGKNLKISNEKKNDDNGKKLCKDLKYSFADYGDLIKGTSIWDNEYTKD

LELNLQNNFGKLFRKYIKKNNTAEQHTLYSSLDELRESWWNTNKKYIWLAMKHGTTCSSGSGDNG

DGSVTGSGSSCDDMSTIDLIPQYLRFLQEWVEHFCKQRQEKVNAVIENCNSCKNTSSKTKLGGTC

NGECKTECEKKCKDECEKYKEFIEECKRGDGTAGSPWVKRWDQIYMRYSKYIEDAKRNRKAGTKS

CGTSAAENKCVQS

>gi|254952602|gb|ACT97131.1| VAR2CSA [*Plasmodium falciparum*] | 341 aa (SEQ ID NO: 19)

KCDKCKSEQSKKNNNIWIWKKSSGDEKGLQKEYANTIALPPRTQSLYLGNLPKLENVCKDVTDIN

FDTKEKFLAGCLIAAFHEGKNLKTSHQNKNADNGKKNDDNGKKLCKALKYSFADYGDLIKGTSIW

DNEYTKDLELNLQQIFGKLFRKYIKRNNTAEQHTLYSSLDELRESWWNTNKKYIWLAMKHGTTCS

SGSGDNGDGSVTGSGSSCDDMSTIDLIPQYLRFLQEWVEHFCKQRQEKVKDVITNCNSCKECGGT

CGSDCKTKCEAYKKFIEECNGTADGGTSGSSWSKRWDQIYKRYSKYIEDAKRNRKAGTKNCGPSS

GANSGVTTTENKCVQS

>gi|254952660|gb|ACT97160.1| VAR2CSA [*Plasmodium falciparum*] | 352 aa (SEQ ID NO: 20)

KCEKCESEQSKKNNKYWIWKKSSGNGEGLQEEYANTIALPPRTHSLCLVCLHEKEGKKTQELKNI

RTNSELLKERIIAAFHEGKNLKTSPQNKNDNGKKLCKDLKYSFADYGDLIKGTSIWDNEYTKDLE

LNLQKIFGKLFRKYIKKNNTAEQHTLYSSLDELRESWWNTNKKYIWLAMKHGAGMNSTMCNADGS

VTGSSDSGSTTCCGDNGSISCDDMPTIDLIPQYLRFLQEWVEHFCEQRQEKVNAVITNCKSCKEC

GGTCNSDCEKKCKAYKEFIEKCKGGGTEGTSGSSWSKRWDQIYKRHSKHIEDAKRNRKAGTKNCG

ITTGTISGESSGANSGVTTTENKCVQS

>gi|254952652|gb|ACT97156.1| VAR2CSA [*Plasmodium falciparum*] | 344 aa (SEQ ID NO: 21)

KCDKCKSGTSRSRKIWTWRKFRGNGEGLQKEYANTIGLSPRTQLLYLVCLHEKGKKTQELKNIST

NSELLKEWIIAAFHEGKNLKTTYPQKKNDDNGKKLCKALKYSFADYGDLIKGTSIWDNDFTKDLE

LNLQKIFGKLFRKYIKKNIASDENTSYSSLDELRESWWNTNKKYIWTAMKHGAGMNGTTCCGDGS

VTGSSDSGSTTCCGDGSVTGSGSSCDDIPTIDLIPQYLRFLQEWVEHFCEQRQEKVKDVITNCKS

CKESEKKCKNKCDAYKEFIDGTGSGGGTGTAGSSWSKRWDQIYMRYSKYIEDAKRNRKAGTKNCG

TSSGANSGVTTTENKCVQS

>gi|254952622|gb|ACT97141.1| VAR2CSA [*Plasmodium falciparum*] | 350 aa (SEQ ID NO: 22)

KCEKCKSEQSKKNNKIWTWRKFPGNGEGLQKEYANTIGLSPRTQLLYLVCLHEKGKKTQHKTIST

NSELLKEWIIAAFHEGKNLKKRYLEKKKGDNNSKLCKDLKYSFADYGDLIKGTSIWDNDFTKDLE

LNLQQIFGKLFRKYIKKNIASDENTSYSSLDELRESWWNTNKKYIWTAMKHGAGMNSTMCNGDGS

VTGSSDSGSTTCSGDNGSISCDDIPTIDLIPQYLRFLQEWVEHFCEQRQEKVKDVIKNCNSCKEC

GGTCNGECKTECKNKCKDECEKYKNFIEVCTGGDGTAGSPWSKRWYQIYMRYSKYIEDAKRNRKA

GTKSCGTSSGANSGVTTTESKCVQS

>gi|254952626|gb|ACT97143.1| VAR2CSA [*Plasmodium falciparum*] | 359 aa (SEQ ID NO: 23)

KCEKCKSEQSKKNNKNWIWRKFPGNGEGLQKEYANTIGLPPRTHSLYLVCLHEKGKKTQELKNIR

TNSELLKEWIIAAFHEGKNLKKRYHQNNNSGNKKKLCKALEYSFADYGDLIKGTSIWDNEYTKDL

ELNLQQIFGKLFRKYIKKNISTEQDTLYSSLDELRESWWNTNKKYIWLAMKHGAGMNSTTCCGDG

SVTGSSDSGSTTCSGDNGSISCDDMPTIDLIPQYLRFLQEWVEHFCEQRQEKVKDVIENCKSCKN

TSGERIIGGTCNGECKTECEKKCKAACEAYKTFIEECEGKAAEGTSGSSWSKRWYQIYMRYSKYI

EDAKRNRKAGTKNCGKSSGANSGVTTTENKCVQS

-continued

>gi|90193469|gb|ABD92330.1| erythrocyte membrane protein 1
[*Plasmodium falciparum*] 270 aa (SEQ ID NO: 24)

NYIKDDPYSKEYVTKLSFIPNSSDANNPSGETANHNDEVCNPNESEISSVEHAQTSVLLSQKAYI

THSSIKANKKKVCKYVKLGVRENDKDLKICVIEDDSLRGVENCCFKDFLRILQENCSDNKRESSS

NGSCNNNNEEACEKNLDEALASLTNCYKNQKCKSGTSTVNNNKWIWKKSSGKEGGLQKEYANTIG

LPPRTQSLCLVVCLDEKEGKTQELKNIRTNSELLKEWIIAAFHEGKNLKKRYHQNKNDDNNSKLC

KALKYSFADY

>gi|254952644|gb|ACT97152.1| VAR2CSA [*Plasmodium falciparum*] | 334 aa (SEQ ID NO: 25)

KCDKCKSEQSKKNNKYWIWKKYSVKEGGLQKEYANTIALPPRTQSLCLVVCLDEKEGKTQELKNI

RTNSELLKERIIAAFHEGKNLKTYHEKKKGDDGKKLCKDLKYSFADYGDLIKGTSIWDNDFTKDL

ELNLQKIFGKLFRKYIKKNNTAEQHTSYSSLDELRESWWNTNKKYIWTAMKHGAEMNGTTCSCSG

DSSNDIPTIDLIPQYLRFLQEWVEHFCEQRQAKVNAVIKNCSCKECGGTCNGECKTECKTKCKG

ECEKYKEFIEKCEGQAAEGTSGSSWSKRWYQIYMRYSKYIEDAKRNRKAGTKNCGTSSGANSGVT

TTENKCVQS

>gi|254952642|gb|ACT97151.1| VAR2CSA [*Plasmodium falciparum*] | 351 aa (SEQ ID NO: 26)

KCDKCKSEQSKKNNKNWIWKKYSGTEGGLQKEYANTIALPPRTQSLYLVCLHEKEEKTQELKNIS

TNSELLKEWIIAAFHEGKNLKISPQNKNDNGKNLCKDLKYSFADYGDLIKGTSIWDNDFTKDLEL

NLQQIFGKLFRKYIKKNNTAEQDTLYSSLDELRESWWNTNKKYIWTAMKHGAGMNGTTCCGDGSV

TGSSDSGSTTCCGDGSVTGSGSSCDDIPTIDLIPQYLRFLQEWVEHFCEQRQAKVKDVIKNCNSC

KECGGTCNGECKTECEKKCKGECEAYKKFIEKCNGGGEGTSGSSWSKRWDQIYMRYSKYIEDAK

RNRKAGTKNCGTSSTTNAAENKCVQS

>gi|254952658|gb|ACT97159.1| VAR2CSA [*Plasmodium falciparum*] | 353 aa (SEQ ID NO: 27)

KCDKCKSGTSTVNKKWIWKKFPGKEGGLQEEYANTIALPPRTQSLCLVVCLDEKEGKTQHKTIST

NSELLKEWIIAAFHEGKNLKISNKKKNDENNSKLCKDLKYSFADYGDLIKGTSIWDNDFTKDLEL

NLQKIFGKLFRKYIKKNNTAEQDTSYSSLDELRESWWNINKKYIWLAMKHGTTCSSGSGDNGDGS

VTGSSDSGSTICCGDGSVTGSGSSCDDIPTIDLIPQYLRFLQEWVEHFCKQRQAKVKDVIENCKS

CKNTSSKTKLGDTCNSDCKTKCKVACEKYKEFIEKCVSAAGGTSGSSWVKRWDQIYMRYSKYIED

AKRNRKAGTKNCGPSSTTSTAESKCVQS

>gi|254952640|gb|ACT97150.1| VAR2CSA [*Plasmodium falciparum*] | 327 aa (SEQ ID NO: 28)

KCDKCKSGTSTVNKKWIWKKYSGKEGGLQKEYANTIGLPPRTQSLCLVCLHEKEGKTQELKNIST

NSELLKEWIIAAFHEGKNLKISNKKKNDDNGKKLCKDLKYSFADYGDLIKGTSIWDNDFTKDLEL

NLQKIFGKLFRKYIKKNNTAEQDTLYSSLDELRESWWNTNKKYIWTAMKHGAGMNSTTCSCSGDS

SNDIPTIDLIPQYLRFLQEWVEHFCKQRQEKVNAVITNCKSCKESGGTCNSDCEKKCKIECEKYK

NFIEKCVTAAGGTSGSSWSKRWDQIYKMYSKYIEDAKRNRKAGTKNCGPSSTTNAAASTDENKCV

QS

>dd2full 745 amino acids | 628 aa (SEQ ID NO: 29)

NYIKGDPYFAEYATKLSFILNSSDTENASETPSKYYDEACNCNESEIASVGQAQTSGPSSNKTCI

THSSIKTNKKKECKDVKLGINNNDKVLRVCVIEDTSLSGVDNCCCQDLLGILQENCSDNKRGSSS

NGSCDKNSEEICQKKLEKVFASLTNGYKCDKCKSGTSRSKKKWIWKKSSGNEEGLQKEYANTIGL

PPRTQSLCLVCLHEKEGKTQHKTISTNSELLKEWIIAAFHEGKNLKTSHEKKNDDNGKKLCKALE

YSFADYGDLIKGTSIWDNEYTKDLELNLQKIFGKLFRKYIKKNNTAEQHTSYSSLDELRESWWNT

NKKYIWTAMKHGAGMNGTTCSCSGDSSNDMPTIDLIPQYLRFLQEWVEHFCKQRQEKVNAVIENC

NSCKESGGTCNSDCKTECKNKCEAYKEFIEDCKGGGTGTAGSPWSKRWDQIYKRYSKHIEDAKRN

RKAGTKNCGTSSTTNAAASTDENKCVQSDVDSFFKHLIDIGLTTPSSYLSNVLDDNICGADKAPW

TTYTTYTTTKNCDIQKKTPKSQSCDTLVVVNVPSPLGNTPHEYKYACECKIPTTEETCDDRKEYM

NQWSCGSAQTVRGRSGKDDYELYTYNGVKETKPLGTLKNSKLD

>gi|254952636|gb|ACT97148.1| VAR2CSA [*Plasmodium
falciparum*] | 350 aa
                                           (SEQ ID NO: 30)
KCEKCKSEQSKKNNKNWIWRKFRGTEGGLQEEYANTIGLPPRTQSLCLVVCLDEKGKKTQELKNI

RTNSELLKEWIIAAFHEGKNLKPSHQNKNSGNKENLCKALKYSFADYGDLIKGTSIWDNDFTKDL

ELNLQKIFGKLFRKYIKKNNTAEQHTSYSSLDELRESWWNTNKKYIWTAMKHGAEMNGTTCNADG

SVTGSSDSGSTTCSGDNGSISCDDIPTIDLIPQYLRFLQEWVEHFCKQRQEKVNAVINSCNSCKN

TSSKTKLGDTCNSDCKTKCKIECEKYKTFIEKCVTAAGGTSGSPWSKRWDQIYKRYSKYIEDAKR

NRKAGTKNCGPSSTTSTAESKCVQS

>gi|254952638|gb|ACT97149.1| VAR2CSA [*Plasmodium
falciparum*] | 330 aa
                                           (SEQ ID NO: 31)
KCDKCKSEQSKKNNKNWIWRKYSGNGEGLQKEYANTIGLPPRTHSLYLVCLHEKEGKTQELKNIR

TNSELLKEWIIAAFHEGKNLKTTYLENKNDENKKKLCKALKYSFADYGDLIKGTSIWDNDFTKDL

ELNLQKIFGKLFRKYIKKNIASDENTLYSSLDELRESWWNTNKKYIWTAMKHGAEMNGTTCSSGS

GDNGSISCDDIPTIDLIPQYLRFLQEWVGHFCKQRQEKVNAVITNCNSCKESGGTCNSDCEKKCK

IECEKYKKFIEECRTAAGGTSGSPWSKRWDQIYKMYSKYIEDAKRNRKAGTKNCGPSSTTSTAES

KCVQS

>gi|254952628|gb|ACT97144.1| VAR2CSA [*Plasmodium
falciparum*] | 334 aa
                                           (SEQ ID NO: 32)
KCDKCKSEQSKKNNKNWIWRKYSGNGEGLQKEYANTIGLPPRTHSLYLVCLHEKEGKTQHKTIST

NSELLKEWIIAAFHEGKNLKKRYPQNNNSGNKKKLCKDLKYSFADYGDLIKGTSIWDNEYTKDLE

LNLQKAFGKLFRKYIKKNIASDENTLYSSLDELRESWWNTNKKYIWLAMKHGAEMNGTMCNADGS

VTGSGSSCDDMSTIDLIPQYLRFLQEWVEHFCEQRQAKVKDVINSCKSCKESGDTCNSDCEKKCK

NKCDAYKTFIEEFCTADGGTAGSPWSKRWDQIYKRYSKYIEDAKRNRKAGTKNCGTSSGANSGVT

TTENKCVQS

>gi|254952630|gb|ACT97145.1| VAR2CSA [*Plasmodium
falciparum*] | 350 aa
                                           (SEQ ID NO: 33)
KCDKCKSGTSTVNKNWIWKKYSGKEEGLQKEYANTIALPPRTHSLYLVCLHEKGKKTQELKNIRT

NSELLKEWIIAAFHEGKNLKTSPQNNNSGNKKKLCKALKYSFADYGDLIKGTSIWDNDFTKDLEL

NLQKIFGKLFRKYIKKNNTAEQHTSYSSLDELRESWWNTNKKYIWLAMKHGAEMNGTTCCGDGSV

TGSSDSGSTTCSGDNGSISCDDMPTTDFIPQYLRFLQEWVEHFCKQRQEKVKHVMESCKSCKECG

DTCNGECKTECEKKCKNKCEAYKTFIEKCVSADGGTSGSSWSKRWDQIYMRYSKYIEDAKRNRKA

GTKNCGTSSTTNAAASTAENKCVQS

>P13 745 amino acids | 647 aa
                                           (SEQ ID NO: 34)
DYIKDDPYSAEYATKLSFILNPSDANTSSGETANHNDEVCNCNESEIASVELAPISDSSSNKTCI

THSFIGANKKKECKDVKLGVREKDKDLKICVIEDDSLRGVENCCCQDLLGILQENCSDNKSGSSS

-continued

NGSCDKNSEDECQKKLENVFASLKNGYKCDKCKSGTSTVNKKWIWRKYSGNGEGLQKEYANTIGL

PPRTHSLYLVCLHEKEGKTQHKTISTNSELLKEWIIAAFHEGKNLKTSHQNNNSGNKKKLCKALK

YSFADYGDLIKGTSIWDNDFTKDLELNLQKIFGKLFRKYIKKNIASDENTSYSSLDELRESWWNT

NKKYIWLAMKHGAEMNSTMCNGDGSVTGSSDSGSTTCSGDNGSISCDDIPTIDLIPQYLRFLQEW

VEHFCKQRQEKVKDVITNCKSCKESGDTCNSDCEKKCKNKCEAYKKFIEERRTAAQGTAESSWVK

RWDQIYMRYSKYIEDAKRNRKAGTKSCGPSSTTNAAASTAENKCVQSDIDSFFKHLIDIGLTTPS

SYLSIVLDDNICGADNAPWTTYTTYTTTKNCDIKKKTPKPQSCDTLVVVNVPSPLGNTPHEYKYA

CQCRTPNKQESCDDRKEYMNQWSSGSAQTVRGRSTNNDYELYTYNGVKETKPLGTLKNSKLD

>gi|254952608|gb|ACT97134.1| VAR2CSA [Plasmodium
falciparum] | 341 aa
(SEQ ID NO: 35)
KCDKCKSGTSTVNKKWIWRKSSGNKEGLQKEYANTIGLPPRTQSLYLGNLPKLENVCEDVKDINF

DTKEKFLAGCLIVSFHEGKNLKTSHEKKNDDNGKKLCKALEYSFADYGDLIKGTSIWDNEYTKDL

ELNLQKIFGKLFRKYIKKNNTAEQDTSYSSLDELRESWWNTNKKYIWTAMKHGAGMNITTCCGDG

SSGENQTNSCDDIPTIDLIPQYLRFLQEWVEHFCKQRQEKVNAVVTNCKSCKESGGTCNGECKTK

CKNKCEVYKTFIDNVGDGTAGSPWVKRWDQIYKRYSKHIEDAKRNRKAGTKNCGITTGTISGESS

GATSGVTTTENKCVQS

>7g8 745 amino acids | 632 aa
(SEQ ID NO: 36)
NYIKDDPYSKEYVTKLSFIPNSSDANTSSEKIQKNNDEVCNPNESGISSVEQAQTSGPSSNKTCI

THSSIKANKKKECKDVKLGVRENDKDLKICVIEDTSLSGVDNCCCQDLLGILQENCSDNKRGSSS

NDSCDNKNQDECQKKLDEALESLHNGYKNQKCKSGTSTVNKKWIWKKSSGNKEGLQKEYANTIGL

PPRTQSLYLGNLPKLENVSKGVTDIIYDTKEKFLAGCLIVSFHEGKNLKTSHEKKNDDNGKKLCK

ALEYSFADYGDLIKGTSIWDNEYTKDLELNLQKAFGKLFRKYIKKNISAEQDTSYSSLDELRESW

WNTNKKYIWIAMKHGAGMNGTTCCGDGSSGENQTNSCDDIPTIDLIPQYLRFLQEWVEHFCEQRQ

AKVKDVITNCKSCKNTSGERKIGGTCNGECKTKCKNKCEAYKTFIEHCKGGDGTAGSSWVKRWDQ

IYKRYSKHIEDAKRNRKAGTKSCGTSTAENKCVQSDIDSFFKHLIDIGLTTPSSYLSIVLDENNC

GEDICAPWTTYTTTKNCDIQKDKSKSQSSDTLVVVNVPSPLGNTPHGYKYACQCKIPTTEETCDD

RKEYMNQWSCGSARTMKRGYKNDNYELCKYNGVDVKPTTVRSSSTKLD

>Indo 745 amino acids | 639 aa
(SEQ ID NO: 37)
DYIKGDPYSAEYVTKLSFIPNSSDANNPSEKIQKNNDEVCNCNESEISSVGQASISDPSSNKTCN

THSSIKANKKKVCKDVKLGVRENDKVLKICVIEHTSLRGVDNCCFKDLLGILQEPRIDKNQSGSS

SNGSCDKNSEEACEKNLEKVLASLTNGYKCDKCKSGTSRSKKKWIWKKYSGKEGGLQEEYANTIG

LPPRTQSLCLVVCLDEKEGKTQELKNISTNSELLKEWIIAAFPEGKNLKPSPEKKKGDNGKKLCK

DLKYSFADYGDLIKGTSIWDNEYTKDLELNLQKIFGKLFRKYIKKNIASDENTLYSSLDELRESW

WNTNKKYIWLAMKHGAGMNSTMCNADGSVTGSGSSCDDMPTIDLIPQYLRFLQEWVEHFCKQRQE

KVKPVIENCNSCKNTSSERKIGGTCNSDCKTECKNKCEVYKKFIEDCKGGDGTAGSSWSKRWDQI

YKRYSKYIEDAKRNRKAGTKNCGPSSTTNAAENKCVQSDIDSFFKHLIDIGLTTPSSYLSTVLDD

NICGEDNAPWTTYTTYTTTKNCDKDKKKSKSQSCDTLVVVNVPSPLGNTPHEYKYACECRTPNKQ

ESCDDRKEYMNQWISDNIKNPKGSGSGKDYYELYTYNGVDVKPTIVRSSSTKLD

>MC 745 amino acids | 655 aa
(SEQ ID NO: 38)
DYIKGDPYFAEYATKLSFILNSSDANTSSGETANHNDEACNCNESEISSVEHASISDPSSNKTCN

THSSIKANKKKVCKHVKLGVRENDKDLRVCVIEHTSLSGVENCCFKDFLRILQENCSDNKSGSSS

NGSCDKNNEEACEKNLEKVFASLTNCYKCEKCKSEQSKKNNKKWTWRKSSGNKGGLQEEYANTIG

LPPRTQSLCLVVCLDEKEGKKTQELKNIRTNSELLKEWIIAAFHEGKNLKPSHEKKNDDNGKKND

DNNSKLCKDLKYSFADYGDLIKGTSIWDNEYTKDLELNLQKIFGKLFRKYIKKNIASDENTLYSS

LDELRESWWNTNKKYIWLAMKHGAEMNGTTCNADGSVTGSGSSCDDIPTIDLIPQYLRFLQEWVE

HFCKQRQAKVKDVIENCKSCKESGNKCKTECKNKCEAYKKFIENCKGGDGTAGSSWVKRWDQIYM

RYSKYIEDAKRNRKAGTKNCGPSSITNVSASTDENKCVQSDIDSFFKHLIDIGLTTPSSYLSIVL

DDNICGDDKAPWTTYTTYTTYTTYTTYTTYTTTKNCDKERDKSKSQSCNTAVVVNVPSPLGN

TPHEYKYACECRTPSNKELCDDRKEYMNQWSSGSAQTVRDRSGKDYYELYTYNGVKETKLPKKLN

SSKLD

>gi|254952650|gb|ACT97155.1| VAR2CSA [*Plasmodium falciparum*] | 347 aa (SEQ ID NO: 39)

KCDKCKSEQSKKNNKYWIWKKSSVKEEGLQKEYANTIALPPRTHSLCLVVCLDEKGKKTQELKNI

STNSELLKERIIAAFHEGKNLKTTYLEKKNADNNSKLCKALKYSFADYGDLIKGTSIWDNEYTKD

LELNLQQIFGKLFRKYIKKNNTAEQHTLYSSLDELRESWWNTNKKYIWLAMKHGAGMNGTTCCGD

GSVTGSSDSGSTTCSGDNGSISCDDMPTTDFIPQYLRFLQEWVEHFCKQRQEKVKDVIENCNSCK

NNLGKTEINEKCKTECKNKCEAYKNFIEKFCTADGGTSGSPWSKRWDQIYKRYSKYIEDAKRNRK

AGTKNCGTSSTTSTAENKCVQS

>gi|254952648|gb|ACT97154.1| VAR2CSA [*Plasmodium falciparum*] | 335 aa (SEQ ID NO: 40)

KCEKCKSGTSTVNKYWIWRKSSGNKEGLQKEYANTIALPPRTHSLCLVVCLDEKEGKTQELKNIS

TNSELLKERIIAAFHEGENLKTSHEKKKGDDGKKNADNNSKLCKALKYSFADYGDLIKGTSIWDN

EYTKDLELNLQKIFGKLFRKYIKKNIASDENTSYSSLDELRESWWNTNKKYIWLAMKHGAGMNGT

TCSCSGDSSDDMPTTDFIPQYLRFLQEWVEHFCKQRQENVNAVIENCNSCKECGGTCNSDCEKKC

KTECKNKCEAYKNFIEKFCTADGGTSGYSWSKRWDQIYKRYSKYIEDAKRNRKAGTKSCGTSSTT

STAESKCVQS

>ghana2 745 amino acids | 667 aa (SEQ ID NO: 41)

SYVKNNPYSKEYVTKLSFILNPSDANNPSETPSKYYDEVCNCNESGIACVGQAQTSGPSSNKTCI

THSFIGANKKKVCKDVKLGVREKDKDLKICVIEDTYLSGVDNCCFKDFLGMLQENCSDNKSGSSS

NGSCNNKNQDECEKNLDEALASLTNGYKCEKCKSGTSTVNKYWIWRKSSGNKEGLQKEYANTIAL

PPRTHSLCLVVCLDEKEGKTQHKTISTNSELLKEWIIAAFHEGKNLKTSHEKKKGDDGKKNADNN

SKLCKALKYSFADYGDLIKGTSIWDNDFTKDLELNLQKIFGKLFRKYIKKNIASDENTSYSSLDE

LRESWWNTNKKYIWLAMKHGAGMNSTTCCGDGSVTGSSDSGSTTCCGDGSVTGSGSSCDDMPTTD

FIPQYLRFLQEWVEHFCKQRQENVNAVIENCNSCKECGGTCNSDCEKKCKTECKGECDAYKEFIE

KCNGGAAEGTSGSSWSKRWDQIYKRYSKYIEDAKRNRKAGTKNCGTSSTTSTAESKCVQSDIDSF

FKHLIDIGLTTPSSYLSIVLDENICGADNAPWTTYTTYTTYTTYTTTEKCNKETDKSKLQQCNTS

VVVNVPSPLGNTPHGYKYVCECRTPNKQETCDDRKEYMNQWISDNTKNPKGSRSTNNDYELYTYN

GVQIKPTTVRSNSTKLD

>gi|254952634|gb|ACT97147.1| VAR2CSA [*Plasmodium falciparum*] | 348 aa (SEQ ID NO: 42)

KCDKCKSEQSKKNNKNWIWKKSSGNEKGLQKEYANTIGLPPRTQSLCLVVCLDEKEGKTQELKNI

RTNSELLKEWIIAAFHEGKNLKTSHEKKKGDNNSKLCKDLKYSFADYGDLIKGTSIWDNEYTKDL

ELNLQNNFGKLFRKYIKKNIASDENTSYSSLDELRESWWNTNKKYIWLAMKHGAGMNSTTCSSGS

-continued

```
GSTTCSSGSGSTTCSSGSGDSCDDMPTIDLIPQYLRFLQEWVEHFCKQRQEKVNAVIKNCNSCKE

SGGTCNGECKTECKNKCEAYKTFIEEFCTADGGTSGSPWSKRWDQIYKMYSKHIEDAKRNRKAGT

KNCGPSSTTNVSVSTDENKCVQS
```

>ghana1 745 amino acids | 652 aa (SEQ ID NO: 43)

```
DYIKDDPYFAEYVTKLSFILNSSDANNPSGETANHNDEVCNPNESGIASVEQAQTSDPSSNKTCN

THSSIKANKKKVCKHVKLGVRENDKDLKICVIEHTSLSGVENCCCQDFLRILQENCSDNKSGSSS

NGSCNNKNQEACEKNLEKVLASLTNCYKCDKCKSEQSKKNNKNWIWKKSSGNEKGLQKEYANTIG

LPPRTQSLCLVVCLDEKEGKTQELKNIRTNSELLKEWIIAAFHEGKNLKKRYPQNKNDDNNSKLC

KDLKYSFADYGDLIKGTSIWDNEYTKDLELNLQNNFGKLFRKYIKKNISTEQDTLYSSLDELRES

WWNTNKKYIWLAMKHGAGMNSTTCSSGSGSTTCSSGSGSTTCSSGSGDSCDDMPTTDFIPQYLRF

LQEWVEHFCKQRQEKVNAVIKNCNSCKESGGTCNGECKTECKNKCEAYKTFIEEFCTADGGTSGS

PWSKRWDQIYKMYSKHIEDAKRNRKAGTKNCGPSSTTNVSVSTDENKCVQSDIDSFFKHLIDIGL

TTPSSYLSIVLDDNICGEDKAPWTTYTTYTTTKKCNKETDKSKSQSCNTAVVVNVPSPLGNTPHG

YKYACECKIPTTEETCDDRKEYMNQWIIDTSKKQKGSGSGKDDYELYTYNGVDVKPTTVRSNSTK

LD
```

>V1S1 745 amino acids | 628 aa (SEQ ID NO: 44)

```
DYIKDDPYSAQYTTKLSFILNPSDANTSSEKIQKNNDEACNCNESGISSVGQAQTSGPSSNKTCI

THSSIKANKKKVCKDVKLGINNNDKVLRVCVIEDTSLSGVDNCCCQDLLGILQENCSDNKRGSSS

NGSCNNNNEEACEKNLDEAPASLHNGYKNQKCKSGTSRSKKKWIWKKSSGNEKGLQEEYANTIGL

PPRTQSLCLVCLHEKEGKTQHKTISTNSELLKEWIIAAFHEGKNLKTSHEKKNDDNGKKLCKALE

YSFADYGDLIKGTSIWDNEYTKDLELNLQKAFGKLFRKYIKKNNTAEQDTSYSSLDELRESWWNT

NKKYIWIAMKHGAGMNGTTCSCSGDSSNDMPTIDLIPQYLRFLQEWVEHFCEQRQAKVKDVITNC

KSCKESGNKCKTECKTKCKDECEKYKTFIEDCNGGGTGTAGSSWVKRWDQIYKRYSKHIEDAKRN

RKAGTKNCGPSSITNAAASTDENKCVQSDIDSFFKHLIDIGLTTPSSYLSNVLDENSCGDDKAPW

TTYTTYTTTKNCDIQKDKSKSQPINTSVVVNVPSPLGNTPYRYKYACECKIPTTEESCDDRKEYM

NQWSCGSARTMKRGYKNDNYELCKYNGVDVKPTTVRSNSSKLD
```

>raj116_var25 745 amino acids | 653 aa (SEQ ID NO: 45)

```
DYIKGDPYFAEYATKLSFILNPSDTENASETPSKYYDEACNPNESEIASVEQAQTSGPSSNKTCI

THSSIKTNKKKECKDVKLGVRENDKDLKICVIEDTSLSGVDNCCFKDLLGILQENCSDNKRGSSS

NDSCNNNNEEACEKNLDEALASLTNGYKCDKCKSGTSTVNKKWTWRKSSGNEEGLQKEYANTIGL

PPRTQSLCLVCLHEKEGKTKHKTISTNSELLKEWIIAAFHEGKNLKTSHEKKNDDNGKKLCKALE

YSFADYGDLIKGTSIWDNEYTKDLELNLQKAFGKLFRKYIKKNNTAEQDTSYSSLDELRESWWNT

NKKYIWTAMKHGAEMNGTTCSSGSGDNGDSSITGSSDSGSTTCSGDNGSISCDDIPTTDFIPQYL

RFLQEWVEHFCEQRQAKVKDVINSCNSCNESGGTCNGECKTKCKDECEKYKKFIEDCNGGDGTAG

SSWVKRWDQIYKRYSKHIEDAKRNRKAGTKNCGPSSITNAAASTDENKCVQSDVDSFFKHLIDIG

LTTPSSYLSIVLDENSCGDDKAPWTTYTTYTTTEKCNKERDKSKSQSSDTLVVVNVPSPLGNTPH

EYKYACECKIPTNEETCDDRKDYMNQWISDTSKKQKGSGSGKDYYELYTYNGVQIKQAAGRSSST

KLD
```

>gi|31323048|gb|AAP37940.1| var2csa [*Plasmodium falciparum*] | 490 aa (SEQ ID NO: 46)

KCDKCKSEQSKKNNNKWIWKKYSGNGEGLQKEYANTIGLPPRTQSLCLVCLHEKEGKTQHKTIST

NSELLKEWIIAAFHEGKNLKKRYPQNKNDDNNSKLCKALEYSFADYGDLIKGTSIWDNEYTKDLE

LNLQKAFGKLFRKYIKKNNTAEQDTSYSSLDELRESWWNTNKKYIWTAMKHGAEMNGTTCSSGSG

DNGDSSCDDIPTIDLIPQYLRFLQEWVEHFCKQRQAKVKDVINSCNSCKNTSGERKIGGTCNSDC

EKKCKVACDAYKTFIEECRTAVGGTAGSSWVKRWDQIYKRYSKHIEDAKRNRKAGTKNCGPSSTT

NAAENKCVQSDIDSFFKHLIDIGLTTPSSYLSNVLDENSCGADKAPWTTYTTYTTYTTYTTT

EKCNKERDKSKSQQSNTSVVVNVPSPLGNTPHEYKYACECKIPTTEETCDDRKEYMNQWIIDNIK

NPKGSGSTDNDYELTMGVQIKQAAGRSSSTKLD

>gi|254952620|gb|ACT97140.1| VAR2CSA [*Plasmodium falciparum*] | 335 aa (SEQ ID NO: 47)

KCEKCKSGTSTVNNKWIWRKSSGKEGGLQKEYANTIGLPPRTQSLYLGNLPKLENVCKGVTDIIY

DTKEKFLSGCLIAAFHEGKNLKTTYLEKKNDDNGKKLCKALEYSFADYGDLIKGTSIWDNEYTKD

LELNLQKIFGKLFRKYIKKNNTAEQDTSYSSLDELRESWWNTNKKYIWIAMKHGAGMNGTTCSSG

SGDSSNDIPTTDFIPQYLRFLQEWVENFCEQRQAKVKPVIENCNSCKESGGTCNGECKTKCKVAC

DAYKKFIDGTGSGGGSRPTGIAGSSWSKRWDQIYKRYSKHIEDAKRNRKAGTKNCGPSSITNVSV

STDENKCVQS

>T2C6 745 amino acids | 637 aa (SEQ ID NO: 48)

NYIKDDPYSKEYVTKLSFIPNSSDANTSSEKIQKNNDEVCNPNESGISSVEQAQTSDPSSNKTCI

THSSIKANKKKECKDVKLGVRENDKDLKICVIEHTSLSGVDNCCFKDFLRMLQEPRIDKNQRGSS

SNGSCDKNSEEACEKNLDEALASLTNGYKCDKCKSEQSKKNNNKWIWKKFPGKEGGLQEEYANTI

GLPPRTQYLCLVVCLDEKEGKTQELKNIRTNSELLKEWIIAAFHEGKNLKTTYPQKKNDDNGKKL

CKDLKYSFADYGDLIKGTSIWDNEYTKNVELNLQNNFGKLFRKYIKKNNTAEQDTSYSSLDELRE

SWWNTNKKYIWLAMKHGAEMNSTTCCGDGSVTGSGSSCDDIPTIDLIPQYLRFLQEWVEHFCKQR

QAKVKDVITNCNSCKESGNKCKTECKNKCKDECEKYKKFIEACGTAVGGTGTAGSPWSKRWDQIY

KRYSKHIEDAKRNRKAGTKNCGPSSTTNAAENKCVQSDIDSFFKHLIDIGLTTPSSYLSIVLDDN

ICGADKAPWTTYTTYTTENCDIQKKTPKSQSCDTLVVVNVPSPLGNTPHGYKYACQCRTPNKQES

CDDRKEYMNQWIIDNTKNPKGSGSGKDYYELCKYNGVKETKPLGTLKNSKLD

>gi|254952632|gb|ACT97146.1| VAR2CSA [*Plasmodium falciparum*] | 330 aa (SEQ ID NO: 49)

KCDKCKSEQSKKNNNKWIWRKFPGKEGGLQKEYANTIGLPPRTQSLCLVCLHEKEGKTQHKTIST

NSELLKEWIIAAFHEGKNLKTTYLEKKNAENKKKLCKALKYSFADYGDLIKGTSIWDNEYTKDLE

LNLQKIFGKLFRKYIKKNNTAEQDTSYSSLDELRESWWNTNKKYIWTAMKHGAGMNGTMCNADGS

VTGSGSSCDDMPTTDFIPQYLRFLQEWVEHFCKQRQAKVKDVIENCKSCKESGNKCKTECKNKCD

AYKTFIEECGTAVGGTAGSSWVKRWDQIYKRYSKHIEDAKRNRKAGTKNCGTSSTTNAAASTAEN

KCVQS

>gi|90193487|gb|ABD92339.1| erythrocyte membrane protein 1 [*Plasmodium falciparum*] 269 aa (SEQ ID NO: 50)

NYIKDDPYSKEYVTKLSFILNSSDAENASETPSKYYDEACNCNESGISSVEQASISDRSSQKACN

THSFIGANKKKVCKHVKLGVRENDKDLKICVIEDDSLRGVENCCFKDFLRMLQEPRIDKNQRGSS

SNDSCNNNEEACEKNLDEALASLHNGYKNQKCKSEQSKKNNNKWIWKKSSGKEGGLQKEYANTI

-continued

GLPPRTQSLCLVCLHEKEGKTQHKTISTNSELLKEWIIDAFHEGKNLKTTYLEKKKGDNGKKLCK

ALKYSFADY

>gi|254952646|gb|ACT97153.1| VAR2CSA [*Plasmodium falciparum*] | 347 aa (SEQ ID NO: 51)

KCDKCKSEQSKKNNKNWIWKKSSGKEGGLQKEYANTIALPPRTQSLCLVVCLHEKEGKTQHKTIS

TNSELLKEWIIDAFHEGKNLKTTYLEKQNADNGKKNADNNSKLCKDLKYSFADYGDLIKGTSIWD

NEYTKDLELNLQQIFGKLFRKYIKKNIASDENTLYSSLDELRESWWNTNKKYIWTAMKHGAEMNG

TTCSSGSGDSSSGENQINSCDDIPTIDLIPQYLRFLQEWVEHFCEQRQAKVKDVITNCKSCKESG

GICNSDCKTKCKGECEKYKKFIEKCKGGGTEGTSGSSWVKRWYQIYMRYSKYIEDAKRNRKAGTK

SCGTSSGANSGVTTTESKCVQS

>gi|90193485|gb|ABD92338.1| erythrocyte membrane protein 1 [*Plasmodium falciparum*] | 269 aa (SEQ ID NO: 52)

DYIKDDPYSKEYTTKLSFILNSSDANTSSEKIQKNNDEVCNPNESEISSVEQAQTSRPSSNKTCI

THSSIKANKKKVCKDVKLGVRENDKVLRVCVIEHTSLSGVENCCCQDLLGILQENCSDNKRGSSS

NGSCDKNSEEACEKNLDEALASLTNCYKNQKCKSEQSKKNNNKWIWKKSSGNEKGLQKEYANTIG

LPPRTQSLCLVCLHEKEGKTQELKNISTNSELLKEWIIAAFHEGKNLKTTYPQNKNDDNGKKLFK

DLKYSFADY

>MTS1 745 amino acids | 646 aa (SEQ ID NO: 53)

DYIKDDPYSKEYTTKLSFILNSSDANTSSEKIQKNNDEVCNPNESEISSVEQAQTSRPSSNKTCI

THSSIKANKKKVCKDVKLGVRENDKVLRVCVIEHTSLSGVENCCCQDLLGILQENCSDNKRGSSS

NGSCDKNSEEACEKNLDEALASLTNCYKNQKCKSEQSKKNNNKWIWKKSSGKEGGLQKEYANTIG

LPPRTQSLYLGNLPKLENVCKGVTDINFDTKEKFLAGCLIAAFHEGKNLKTTYLEKKNDDNGKKL

CKALEYSFADYGDLIKGTSIWDNEYTKDLELNLQKAFGKLFRKYIKKNNTAEQDTSYSSLDELRE

SWWNTNKKYIWTAMKHGAGMNGTTCSSGSGDSSNDIPTTDFIPQYLRFLQEWVENFCEQRQAKVK

DVIENCNSCKNTSGERKIGDTCNSDCEKKCKDECEKYKKFIEDCKGGDGTAGSSWVKRWDQIYKR

YSKHIEDAKRNRICAGTKNCGITTGTISGESSGATSGVTTTENKCVQSDIDSFFKHLIDIGLTTP

SSYLSNVLDDNICGEDNAPWTTYTTYTTEKCNKETDKSKSQQSNTAVVVNVPSPLGNTPHGYKYA

CECKIPTTEETCDDRKEYMNQWSCGSAQTVRDRSGKDDYELCKYNGVQIKQAAGTLKNSKLD

>Q8I639 (Q8I639_PLAF7) *Plasmodium falciparum* (isolate 3D7), 632 aa extracellular part (SEQ ID NO: 54)

NYIKGDPYFAEYATKLSFILNSSDANNPSEKIQKNNDEVCNCNESGIASVEQEQISDPSSNKTCI

THSSIKANKKKVCKHVKLGVRENDKDLRVCVIEHTSLSGVENCCCQDFLRILQENCSDNKSGSSS

NGSCNNKNQEACEKNLEKVLASLTNCYKCDKCKSEQSKKNNKNWIWKKSSGKEGGLQKEYANTIG

LPPRTQSLCLVVCLDEKGKKTQELKNIRTNSELLKEWIIAAFHEGKNLKPSHEKKNDDNGKKLCK

ALEYSFADYGDLIKGTSIWDNEYTKDLELNLQKIFGKLFRKYIKKNNTAEQDTSYSSLDELRESW

WNTNKKYIWLAMKHGAGMNSTTCCGDGSVTGSGSSCDDIPTIDLIPQYLRFLQEWVEHFCKQRQE

KVKPVIENCKSCKESGGTCNGECKTECKNKCEVYKKFIEDCKGGDGTAGSSWVKRWDQIYKRYSK

YIEDAKRNRKAGTKNCGPSSTTNAAENKCVQSDIDSFFKHLIDIGLTTPSSYLSIVLDDNICGAD

KAPWTTYTTYTTTEKCNKETDKSKLQQCNTAVVVNVPSPLGNTPHGYKYACQCKIPTNEETCDDR

KEYMNQWSCGSARTMKRGYKNDNYELCKYNGVDVKPTTVRSNSSKLD

>Q8I639 (Q8I639_PLAF7) *Plasmodium falciparum* (isolate 3D7), complete 2730 aa extracellular part (SEQ ID NO: 55)

MDKSSIANKIEAYLGAKSDDSKIDQSLKADPSEVQYYGSGGDGYYLRKNICKITVNHSDSGTNDP

CDRIPPPYGDNDQWKCAIILSKVSEKPENVFVPPRRQRMCINNLEKLNVDKIRDKHAFLADVLLT

ARNEGERIVQNHPDINSSNVCNALERSFADIADIIRGIDLWKGINSNLEQNLKQMFAKIRENDKV

LQDKYPKDQNYRKLREDWWNANRQKVWEVITCGARSNDLLIKRGWRTSGKSNGDNKLELCRKCGH

YEEKVPTKLDYVPQFLRWLTEWIEDFYREKQNLIDDMERHREECTSEDHKSKEGTSYCSTCKDKC

KKYCECVKKWKSEWENQKNKYTELYQQNKNETSQKNTSRYDDYVKDFFKKLEANYSSLENYIKGD

PYFAEYATKLSFILNSSDANNPSEKIQKNNDEVCNCNESGIASVEQEQISDPSSNKTCITHSSIK

ANKKKVCKHVKLGVRENDKDLRVCVIEHTSLSGVENCCCQDFLRILQENCSDNKSGSSSNGSCNN

KNQEACEKNLEKVLASLTNCYKCDKCKSEQSKKNNKNWIWKKSSGKEGGLQKEYANTIGLPPRTQ

SLCLVVCLDEKGKKTQELKNIRTNSELLKEWIIAAFHEGKNLKPSHEKKNDDNGKKLCKALEYSF

ADYGDLIKGTSIWDNEYTKDLELNLQKIFGKLFRKYIKKNNTAEQDTSYSSLDELRESWWNINKK

YIWLAMKHGAGMNSTICCGDGSVIGSGSSCDDIPTIDLIPQYLRFLQEWVEHFCKQRQEKVKPVI

ENCKSCKESGGTCNGECKTECKNKCEVYKKFIEDCKGGDTAGSSWVKRWDQIYKRYSKYIEDAK

RNRKAGTKNCGPSSTTNAAENKCVQSDIDSFFKHLIDIGLTTPSSYLSIVLDDNICGADKAPWIT

YTTYTTTEKCNKETDKSKLQQCNTAVVVNVPSPLGNIPHGYKYACQCKIPTNEETCDDRKEYMNQ

WSCGSARTMKRGYKNDNYELCKYNGVDVKPTTVRSNSSKLDDKDVTFFNLFEQWNKEIQYQIEQY

MTNTKISCNNEKNVLSRVSDEAAQPKFSDNERDRNSITHEDKNCKEKCKCYSLWIEKINDQWDKQ

KDNYNKFQRKQIYDANKGSQNKKVVSLSNFLFFSCWEEYIQKYFNGDWSKIKNIGSDTFEFLIKK

CGNDSGDGETIFSEKLNNAEKKCKENESTNNKMKSSETSCDCSEPIYIRGCQPKIYDGKIFPGKG

GEKQWICKDTIIHGDINGACIPPRTQNLCVGELWDKRYGGRSNIKNDTKESLKQKIKNAIQKETE

LLYEYHDKGTAIISRNPMKGQKEKEEKNNDSNGLPKGFCHAVQRSFIDYKNMILGTSVNIYEYIG

KLQEDIKKIIEKGTTKQNGKTVGSGAENVNAWWKGIEGEMWDAVRCAITKINKKQKKNGTFSIDE

CGIFPPTGNDEDQSVSWEKEWSEQFCIERLQYEKNIRDACTNNGQGDKIQGDCKRKCEEYKKYIS

EKKQEWDKQKTKYENKYVGKSASDLLKENYPECISANFDFIENDNIEYKTYYPYGDYSSICSCEQ

VKYYEYNNAEKKNNKSLCHEKGNDRTWSKKYIKKLENGRTLEGVYVPPRRQQLCLYELF-
PIIIKN

KNDITNAKKELLETLQIVAEREAYYLWKQYHAHNDTTYLAHKKACCAIRGSFYDLEDIIKGNDLV

HDEYTKYIDSKLNEIFDSSNKNDIETKRARTDWWENEAIAVPNITGANKSDPKTIRQLVWDAMQS

GVRKAIDEEKEKKKPNENFPPCMGVQHIGIAKPQFIRWLEEWTNEFCEKYTKYFEDMKSNCNLRK

GADDCDDNSNIECKKACANYTNWLNPKRIEWNGMSNYYNKIYRKSNKESEDGKDYSMIMEPTVID

YLNKRCNGEINGNYICCSCKNIGENSTSGTVNKKLQKKETQCEDNKGPLDLMNKVLNKMDPKYSE

HKMKCTEVYLEHVEEQLKEIDNAIKDYKLYPLDRCEDDKSKMKVCDLIGDAIGCKHKTKLDELDE

WNDVDMRDPYNKYKGVLIPPRRRQLCFSRIVRGPANLRNLKEEKEEILKGAQSEGKFLGNYYNED

KDKEKALEAMKNSFYDYEYIIKGSDMLTNIQFKDIKRKLDRLLEKETNNTEKVDDWWETNKKSIW

NAMLCGYKKSGNKIIDPSWCTIPTTETPPQFLRWIKEWGTNVCIQKEEHKEYVKSKCSNVTNLGA

QESESKNCTSEIKKYQEWSRKRSIQWEAISEGYKKYKGMDEFKNTFKNIKEPDANEPNANEYLKK

HCSKCPCGFNDMQEITKYTNIGNEAFKQIKEQVDIPAELEDVIYRLKHHEYDKGNDYICNKYKNI

NVNMKKNNDDTWTDLVKNSSDINKGVLLPPRRKNLELKIDESDICKYKRDPKLFKDFIYSSAISE

VERLKKVYGEAKTKVVHAMKYSFADIGSIIKGDDMMENNSSDKIGKILGDGVGQNEKRKKWWDMN

-continued

KYHIWESMLCGYKHAYGNISENDRKMLDIPNNDDEHQFLRWFQEWTENFCTKRNELYENMVTACN

SAKCNTSNGSVDKKECTEACKNYSNFILIKKKEYQSLNSQYDMNYKETKAEKKESPEYFKDKCNG

ECSCLSEYFKDETRWKNPYETLDDTEVKNNCMCKPPPPASNNTSDILQKTIPEGIALALGSIAFL

FMKKKPKTPVDLLRVLDIPKGDYGIPTPKSSNRYIPYASDRYKGKTYIYMEGDTSGDDDKYIWDL

>FCR3 (SEQ ID NO: 56) complete 2734 aa extracellular part
(577 aa highlighted corr. ID1-DBL2b)

MDSTSTIANKIEEYLGAKSDDSKIDELLKADPSEVEYYRSGGDGDYLKNNICKITVNHSDSGKYD

PCEKKLPPYDDNDQWKCQQNSSDGSGKPENICVPPRRERLCTYNLENLKEDKIRDNNAFLADVLL

TARNEGEKIVQNHPDTNSSNVCNALERSFADLADIIRGTDQWKGTNSNLEKNLKQMFAKIRENDK

VLQDKYPKDQKYTKLREAWWNANRQKVWEVITCGARSNDLLIKRGWRTSGKSDRKKNFELCRKCG

HYEKEVPTKLDYVPQFLRWLTEWIEDFYREKQNLIDDMERHREECTREDHKSKEGTSYCSTCKDK

CKKYCECVKKWKTEWENQENKYKDLYEQNKNKTSQKNTSRYDDYVKDFFEKLEANYSSLENYIKG

DPYFAEYATKLSFILNPSDANNPSGETANHNDEACNCNESGISSVGQAQTSGPSSNKTCITHSSI

KTNKKKECKDVKLGVRENDKDLKICVIEDTSLSGVDNCCCQDLLGILQENCSDNKRGSSSNDSCD

NKNQDECQKKLEKVFASLTNGYKCDKCKSGTSRSKKKWIWKKSSGNEEGLQEEYANTIGLPPRTQ

SLYLGNLPKLENVCEDVKDINFDTKEKFLAGCLIVSFHEGKNLKKRYPQNKNSGNKENLCKALEY

SFADYGDLIKGTSIWDNEYTKDLELNLQNNFGKLFGKYIKKNNTAEQDTSYSSLDELRESWWNTN

KKYIWTAMKHGAEMNITTCNADGSVTGSGSSCDDIPTIDLIPQYLRFLQEWVENFCEQRQAKVKD

VITNCKSCKESGNKCKTECKTKCKDECEKYKKFIEACGTAGGGIGTAGSPWSKRWDQIYKRYSKH

IEDAKRNRKAGTKNCGTSSTTNAAASTDENKCVQSDIDSFFKHLIDIGLTTPSSYLSNVLDDNIC

GADKAPWTTYTTYTTTEKCNKERDKSKSQSSDTLVVVNVPSPLGNTPYRYKYACQCKIPTNEETC

DDRKEYMNQWSCGSARTMKRGYKNDNYELCKYNGVDVKPTTVRSNSSKLDGNDVTFFNLFEQWNK

QYMTNANISCIDEKEVLDSVSDEGTPKVRGGYEDGRNNNTDQGTNCKEKCKCYKLWIEKINDQWG

EIQYQIEKQKDNYNKFRSKQIYDANKGSQNKKVVSLSNFLFFSCWEEYIQKYENGDWSKIKNIGS

DTFEFLIKKCGNNSAHGEEIFNEKLKNAEKKCKENESTDTNINKSETSCDLNATNYIRGCQSKTY

DGKIFPGKGGEKQWICKDTIIHGDTNGACIPPRTQNLCVGELWDKSYGGRSNIKNDTKELLKEKI

KNAIHKETELLYEYHDTGTAIISKNDKKGQKGKNDPNGLPKGFCHAVQRSFIDYKNMILGTSVNI

YEHIGKLQEDIKKIIEKGTPQQKDKIGGVGSSTENVNAWWKGIEREMWDAVRCAITKINKKNNNS

IFNGDECGVSPPIGNDEDQSVSWFKEWGEQFCIERLRYEQNIREACTINGKNEKKCINSKSGQGD

KIQGACKRKCEKYKKYISEKKQEWDKQKTKYENKYVGKSASDLLKENYPECISANFDFIENDNIE

YKTYYPYGDYSSICSCEQVKYYKYNNAEKKNNKSLCYEKDNDMTWSKKYIKKLENGRSLEGVYVP

PRRQQLCLYELFPIIIKNEEGMEKAKEELLETLQIVAEREAYYLWKQYNPIGKGIDDANKKACCA

IRGSFYDLEDIIKGNDLVHDEYTKYIDSKLNEIFGSSDTNDIDTKRARTDWWENETITNGTDRKT

IRQLVWDAMQSGVRYAVEEKNENFPLCMGVEHIGIAKPQFIRWLEEWTNEFCEKYTKYFEDMKSK

CDPPKRADTCGDNSNIECKKACANYTNWLNPKRIEWNGMSNYYNKIYRKSNKESEGGKDYSMIMA

PTVIDYLNKRCHGEINGNYICCSCKNIGAYNTTSGTVNKKLQKKETECEEEKGPLDLMNEVLNKM

DKKYSAHKMKCTEVYLEHVEEQLNEIDNAIKDYKLYPLDRCEDDQTKMKVCDLIADAIGCKDKTK

LDELDEWNDMDLRGTYNKHKGVLIPPRRRQLCFSRIVRGPANLRSLNEFKEEILKGAQSEGKFLG

NYYKEHDKEKALEAMKNSFYDYEDIIKGTDMLTNIEFKDIKIKLDRLLEKETNNTKKAEDWWKT

NKKSIWNAMLCGYKKSGNKIIDPSWCTIPTTETPPQFLRWIKEWGTNVCIQKQEHKEYVKSKCSN

VTNLGAQASESNNCTSEIKKYQEWSRKRSIRWETISKRYKKYKRMDILKDVKEPDANTYLREHCS

KCPCGENDMEEMNNNEDNEKEAFKQIKEQVKIPAELEDVIYRIKHHEYDKGNDYICNKYKNIHDR

```
MKKNNGNFVTDNFVKKSWEISNGVLIPPRRKNLFLYIDPSKICEYKKDPKLFKDFIYWSAFTEVE

RLKKAYGGARAKVVHAMKYSFTDIGSIIKGDDMMEKNSSDKIGKILGDTDGQNEKRKKWWDMNKY

HIWESMLCGYREAEGDTETNENCRFPDIESVPQFLRWFQEWSENECDRRQKLYDKLNSECISAEC

TNGSVDNSKCTHACVNYKNYILTKKTEYEIQTNKYDNEFKNKNSNDKDAPDYLKEKCNDNKCECL

NKHIDDKNKTWKNPYETLEDTEKSKCDCPKPLPSPIKPDDLPPQADEPFDPTILQTTIPFGIALA

LGSIAFLFMKVIYIYIYVCCICMYVCMYVCMYVCMYVCMHVCMLCVYVIYVFKICIYIEKE

KRKK

>BPTI, protease inhibitor
                                                       (SEQ ID NO: 57)
RPDFCLEPPYTGPCKARIIRYFYNAKAGLCQTFVYGGCRAKRNNFKSAEDCMRTCGGA >PE38, Pseudomonas exotoxin A (SEQ ID NO: 58), (underlining of
KDEL represent a signal sequence, which may be optional for the
constructs according to the present invention)
RHRQPRGWEQLEQCGYPVQRLVALYLAARLSWNQVDQVIRNALASPGSGGDLGEAIREQPEQARL

ALTLAAAESERFVRQGTGNDEAGAANGPADSGDALLERNYPTGAEFLGDGGDISFSTRGTQNWTV

ERLLQAHRQLEERGYVFVGYHGTFLEAAQSIVFGGVRARSQDLDAIWRGFYIAGDPALAYGYAQD

QEPDARGRIRNGALLRVYVPRSSLPGFYRTSLTLAAPEAAGEVERLIGHPLPLRLDAITGPEEEG

GRLETILGWPLAERTVVIPSAIPTDPRNVGGDLDPSSIPDKEQAISALPDYASQPGKPPRKDEL

>PE38LR, variant of PE38 (SEQ ID NO: 59) (underlining of KDEL
represent a signal sequence, which may be optional for the
constructs according to the present invention)
RHRQPRGWEQLYPTGAEFLGDGGDISFSTRGTQNWTVERLLQAHRQLEERGYVFVGYHGTFLEAA

QSIVFGGVRARSQDLDAIWRGFYIAGDPALAYGYAQDQEPDARGRIRNGALLRVYVPRSSLPGFY

RTSLTLAAPEAAGEVERLIGHPLPLRLDAITGPEEEGGRLETILGWPLAERTVVIPSAIPTDPRN

VGGDLDPSSIPDKEQAISALPDYASQPGKPPRKDEL

Sequences of VAR2CSA polypeptides fused with truncated fragments
of Pseudomonas exotoxin A (PE38)
Fused VAR2CSA-PE38 proteins may have modifications such as a
protease inhibitor (BPTI) in the N-terminal and/or an optimized
PE38 sequence that is less immunogenic (PE38LR)

>BPTI-ID1-ID2aFCR3-PE38LR, (SEQ ID NO: 60) underlined sequence
corresponds to the ID1 domain of FCR3, sequence in bold
corresponds to DBL2Xb domain of FCR3, underlined and bold
sequence is ID2a
RPDFCLEPPYTGPCKARIIRYFYNAKAGLCQTFVYGGCRAKRNNFKSAEDCMRTCGGANYIKGDP

YFAEYATKLSFILNPSDANNPSGETANHNDEACNCNESGISSVGQAQTSGPSSNKTCITHSSIKT

NKKKECKDVKLGVRENDKDLKICVIEDTSLSGVDNCCCQDLLGILQENCSDNKRGSSSNDSCDNK

NQDECQKKLEKVFASLTNGYKCDKCKSGTSRSKKKWIWKKSSGNEEGLQEEYANTIGLPPRTQSL

YLGNLPKLENVCEDVKDINFDTKEKFLAGCLIVSFHEGKNLKKRYPQNKNSGNKENLCKALEYSF

ADYGDLIKGTSIWDNEYTKDLELNLQNNFGKLFGKYIKKNNTAEQDTSYSSLDELRESWWNTNKK

YIWTAMKHGAEMNITTCNADGSVTGSGSSCDDIPTIDLIPQYLRFLQEWVENFCEQRQAKVKDVI

TNCKSCKESGNKCKTECKTKCKDECEKYKKFIEACGTAGGGIGTAGSPWSKRWDQIYKRYSKHIE

DAKRNRKAGTKNCGTSSTTNAAASTDENKCVQSDIDSFFKHLIDIGLTTPSSYLSNVLDDNICGA

DKAPWTTYTTYTTTTEKCNKERDKSKSQSSDTLVVVNVPSPLGNTPYRYKYACQCKIPTNEETCDD

RKEYMNCIWSCGSARTMKRGYKNDNYELCICYNGVDVKPTTVRSNSSKLDRHRQPRGWEQLYPTG

AEFLGDGGDISFSTRGTQNWTVERLLQAHRQLEERGYVFVGYHGTFLEAAQSIVFGGVRARSQDL
```

DAIWRGFYIAGDPALAYGYAQDQEPDARGRIRNGALLRVYVPRSSLPGFYRTSLTLAAPEAAGEV

ERLIGHPLPLRLDAITGPEEEGGRLETILGWPLAERTVVIPSAIPTDPRNVGGDLDPSSIPDKEQ

AISALPDYASQPGKPPRKDEL

>BPTI-ID1-ID2aFCR3-PE38
(SEQ ID NO: 61)
RPDFCLEPPYTGPCKARIIRYFYNAKAGLCQTFVYGGCRAKRNNFKSAEDCMRTCGGANYIKGDP

YFAEYATKLSFILNPSDANNPSGETANHNDEACNCNESGISSVGQAQTSGPSSNKTCITHSSIKT

NKKKECKDVKLGVRENDKDLKICVIEDTSLSGVDNCCCQDLLGILQENCSDNKRGSSSNDSCDNK

NQDECQKKLEKVFASLTNGYKCDKCKSGTSRSKKKWIWKKSSGNEEGLQEEYANTIGLPPRTQSL

YLGNLPKLENVCEDVKDINFDTKEKFLAGCLIVSFHEGKNLKKRYPQNKNSGNKENLCKALEYSF

ADYGDLIKGTSIWDNEYTKDLELNLQNNFGKLFGKYIKKNNTAEQDTSYSSLDELRESWWNTNKK

YIWTAMKHGAEMNITTCNADGSVTGSGSSCDDIPTIDLIPQYLRFLQEWVENFCEQRQAKVKDVI

TNCKSCKESGNKCKTECKTKCKDECEKYKKFIEACGTAGGGIGTAGSPWSKRWDQIYKRYSKHIE

DAKRNRKAGTKNCGTSSTTNAAASTDENKCVQSDIDSFFKHLIDIGLTTPSSYLSNVLDDNICGA

DKAPWTTYTTYTTTEKCNKERDKSKSQSSDTLVVVNVPSPLGNTPYRYKYACQCKIPTNEETCDD

RKEYMNQWSCGSARTMKRGYKNDNYELCKYNGVDVKPTTVRSNSSKLDPEGGSLAALTAHQACHL

PLETFTRHRQPRGWEQLEQCGYPVQRLVALYLAARLSWNQVDQVIRNALASPGSGGDLGEAIREQ

PEQARLALTLAAAESERFVRQGTGNDEAGAANGPADSGDALLERNYPTGAEFLGDGGDISFSTRG

TQNWTVERLLQAHRQLEERGYVEVGYHGTFLEAAQSIVEGGVRARSQDLDAIWRGFYIAGDPALA
YGYAQDQEPDARGRIRNGALLRVYVPRSSLPGFYRTSLTLAAPEAAGEVERLIGHPLPLRLDAIT
GPEEEGGRLETILGWPLAERTVVIPSAIPTDPRNVGGDLDPSSIPDKEQAISALPDYASQPGKPP
RKDEL

>ID1-ID2aFCR3-PE38

(SEQ ID NO: 62)

NYIKGDPYFAEYATKLSFILNPSDANNPSGETANHNDEACNCNESGISSVGQAQTSGPSSNKTCI
THSSIKTNKKKECKDVKLGVRENDKDLKICVIEDTSLSGVDNCCCQDLLGILQENCSDNKRGSSS
NDSCDNKNQDECQKKLEKVFASLTNGYKCDKCKSGTSRSKKKWIWKKSSGNEEGLQEEYANTIGL
PPRTQSLYLGNLPKLENVCEDVKDINFDTKEKFLAGCLIVSFHEGKNLKKRYPQNKNSGNKENLC
KALEYSFADYGDLIKGTSIWDNEYTKDLELNLQNNFGKLEGKYIKKNNTAEQDTSYSSLDELRES
WWNINKKYIWTAMKHGAEMNITTCNADGSVTGSGSSCDDIPTIDLIPQYLRFLQEWVENFCEQRQ
AKVKDVITNCKSCKESGNKCKTECKTKCKDECEKYKKFIEACGTAGGGIGTAGSPWSKRWDQIYK
RYSKHIEDAKRNRKAGTKNCGTSSTTNAAASTDENKCVQSDIDSFFKHLIDIGLTTPSSYLSNVL
DDNICGADKAPWTTYTTYTTTEKCNKERDKSKSQSSDTLVVVNVPSPLGNTPYRYKYACQCKIPT
NEETCDDRKEYMNQWSCGSARTMKRGYKNDNYELCKYNGVDVKPTTVRSNSSKLDPEGGSLAALT
AHQACHLPLETFTRHRQPRGWEQLEQCGYPVQRLVALYLAARLSWNQVDQVIRNALASPGSGGDL
GEAIREQPEQARLALTLAAAESERFVRQGTGNDEAGAANGPADSGDALLERNYPTGAEFLGDGGD
ISFSTRGTQNWTVERLLQAHRQLEERGYVFVGYHGTFLEAAQSIVFGGVRARSQDLDAIWRGFYI
AGDPALAYGYAQDQEPDARGRIRNGALLRVYVPRSSLPGFYRTSLTLAAPEAAGEVERLIGHPLP
LRLDAITGPEEEGGRLETILGWPLAERTVVIPSAIPTDPRNVGGDLDPSSIPDKEQAISALPDYA
SQPGKPPRKDEL

>ID1-ID2aFCR3-PE38LR
(SEQ ID NO: 63)
NYIKGDPYFAEYATKLSFILNPSDANNPSGETANHNDEACNCNESGISSVGQAQTSGPSSNKTCI

THSSIKTNKKKECKDVKLGVRENDKDLKICVIEDTSLSGVDNCCCQDLLGILQENCSDNKRGSSS

NDSCDNKNQDECQKKLEKVFASLTNGYKCDKCKSGTSRSKKKWIWKKSSGNEEGLQEEYANTIGL

PPRTQSLYLGNLPKLENVCEDVKDINFDTKEKFLAGCLIVSFHEGKNLKKRYPQNKNSGNKENLC

KALEYSFADYGDLIKGTSIWDNEYTKDLELNLQNNFGKLFGKYIKKNNTAEQDTSYSSLDELRES

WWNTNKKYIWTAMKHGAEMNITTCNADGSVTGSGSSCDDIPTIDLIPQYLRFLQEWVENFCEQRQ

AKVKDVITNCKSCKESGNKCKTECKTKCKDECEKYKKFIEACGTAGGGIGTAGSPWSKRWDQIYK

RYSKHIEDAKRNRKAGTKNCGTSSTTNAAASTDENKCVQSDIDSFFKHLIDIGLTTPSSYLSNVL

DDNICGADKAPWTTYTTYTTTEKCNKERDKSKSQSSDTLVVVNVPSPLGNTPYRYKYACQCKIPT

NEETCDDRKEYMNQWSCGSARTMKRGYKNDNYELCKYNGVDVKPTTVRSNSSKLDRHRQPRGWEQ

LYPTGAEFLGDGGDISFSTRGTQNWTVERLLQAHRQLEERGYVEVGYHGTFLEAAQSIVEGGVRA

RSQDLDAIWRGFYIAGDPALAYGYAQDQEPDARGRIRNGALLRVYVPRSSLPGFYRTSLTLAAPE

AAGEVERLIGHPLPLRLDAITGPEEEGGRLETILGWPLAERTVVIPSAIPTDPRNVGGDLDPSSI

PDKEQAISALPDYASQPGKPPRKDEL

>BPTI-DBL1-ID2aFCR3-PE38LR
(SEQ ID NO: 64)
RPDFCLEPPYTGPCKARIIRYFYNAKAGLCQTFVYGGCRAKRNNFKSAEDCMRTCGGANHSDSGK

YDPCEKKLPPYDDNDQWKCQQNSSDGSGKPENICVPPRRERLCTYNLENLKFDKIRDNNAFLADV

KIVQNHPDTNSSNVCNALERSFADLADIIRGTDQWKGINSNLEKNLKQMFAKIRENDKVLQDKYP

LLTARNEGEKDQKYTKLREAWWNANRQKVWEVITCGARSNDLLIKRGWRTSGKSDRKKNFELCRK

CGHYEKEVPTKLDYVPQFLRWLTEWIEDFYREKQNLIDDMERHREECTREDHKSKEGTSYCSTCK

DKCKKYCECVKKWKTEWENQENKYKDLYEQNKNKTSQKNTSRYDDYVKDFFEKLEANYSSLENYI

KGDPYFAEYATKLSFILNPSDANNPSGETANHNDEACNCNESGISSVGQAQTSGPSSNKTCITHS

SIKTNKKKECKDVKLGVRENDKDLKICVIEDTSLSGVDNCCCQDLLGILQENCSDNKRGSSSNDS

CDNKNQDECQKKLEKVFASLTNGYKCDKCKSGTSRSKKKWIWKKSSGNEEGLQEEYANTIGLPPR

TQSLYLGNLPKLENVCEDVKDINFDTKEKFLAGCLIVSFHEGKNLKKRYPQNKNSGNKENLCKAL

EYSFADYGDLIKGTSIWDNEYTKDLELNLQNNFGKLFGKYIKKNNTAEQDTSYSSLDELRESWWN

INKKYIWTAMKHGAEMNITTCNADGSVIGSGSSCDDIPTIDLIPQYLRFLQEWVENFCEQRQAKV

KDVITNCKSCKESGNKCKTECKTKCKDECEKYKKFIEACGTAGGGIGTAGSPWSKRWDQIYKRYS

KHIEDAKRNRKAGTKNCGTSSTTNAAASTDENKCVQSDIDSFFKHLIDIGLTTPSSYLSNVLDDN

ICGADKAPWITYTTYTTTEKCNKERDKSKSQSSDTLVVVNVPSPLGNIPYRYKYACQCKIPTNEE

TCDDRKEYMNQWSCGSARTMKRGYKNDNYELCKYNGVDVKPTTVRSNSSKLDRHRQPRGWEQLYP

TGAEFLGDGGDISFSTRGTQNWTVERLLQAHRQLEERGYVFVGYHGTFLEAAQSIVFGGVRARSQ

DLDAIWRGFYIAGDPALAYGYAQDQEPDARGRIRNGALLRVYVPRSSLPGFYRTSLTLAAPEAAG

EVERLIGHPLPLRLDAITGPEEEGGRLETILGWPLAERTVVIPSAIPTDPRNVGGDLDPSSIPDK

EQAISALPDYASQPGKPPRKDEL

>BPTI-DBL1-ID2aFCR3-PE38

(SEQ ID NO: 65)

RPDFCLEPPYTGPCKARIIRYFYNAKAGLCQTFVYGGCRAKRNNFKSAEDCMRTCGGANHSDSGK

YDPCEKKLPPYDDNDQWKCQQNSSDGSGKPENICVPPRRERLCTYNLENLKFDKIRDNNAFLADV

LLTARNEGEKIVQNHPDTNSSNVCNALERSFADLADIIRGTDQWKGTNSNLEKNLKQMFAKIREN

-continued

DKVLQDKYPKDQKYTKLREAWWNANRQKVWEVITCGARSNDLLIKRGWRTSGKSDRKKNFELCRK

CGHYEKEVPTKLDYVPQFLRWLTEWIEDFYREKQNLIDDMERHREECTREDHKSKEGTSYCSTCK

DKCKKYCECVKKWKTEWENQENKYKDLYEQNKNTSQKNTSRYDDYVKDFFEKLEANYSSLENYI

KGDPYFAEYATKLSFILNPSDANNPSGETANHNDEACNCNESGISSVGQAQTSGPSSNKTCITHS

SIKTNKKKECKDVKLGVRENDKDLKICVIEDTSLSGVDNCCCQDLLGILQENCSDNKRGSSSNDS

CDNKNQDECQKKLEKVFASLTNGYKCDKCKSGTSRSKKKWIWKKSSGNEEGLQEEYANTIGLPPR

TQSLYLGNLPKLENVCEDVKDINFDTKEKFLAGCLIVSFHEGKNLKKRYPQNKNSGNKENLCKAL

EYSFADYGDLIKGTSIWDNEYTKDLELNLQNNFGKLFGKYIKKNNTAEQDTSYSSLDELRESWWN

TNKKYIWTAMKHGAEMNITTCNADGSVTGSGSSCDDIPTIDLIPQYLRFLQEWVENFCEQRQAKV

KDVITNCKSCKESGNKCKTECKTKCKDECEKYKKFIEACGTAGGGIGTAGSPWSKRWDQIYKRYS

KHIEDAKRNRKAGTKNCGTSSTTNAAASTDENKCVQSDIDSFFKHLIDIGLTTPSSYLSNVLDDN

ICGADKAPWTTYTTYTTTEKCNKERDKSKSQSSDTLVVVNVPSPLGNTPYRYKYACQCKIPTNEE

TCDDRKEYMNQWSCGSARTMKRGYKNDNYELCKYNGVDVKPTTVRSNSSKLDPEGGSLAALTAHQ

ACHLPLETFTRHRQPRGWEQLEQCGYPVQRLVALYLAARLSWNQVDQVIRNALASPGSGGDLGEA

IREQPEQARLALTLAAAESERFVRQGTGNDEAGAAnGPADSGDALLERNYPTGAEFLGDGGDISF

STRGTQNWTVERLLQAHRQLEERGYVFVGYHGTFLEAAQSIVFGGVRARSQDLDAIWRGFYIAGD

PALAYGYAQDQEPDARGRIRNGALLRVYVPRSSLPGFYRTsLTLAAPEAAGEVERLIGHPLPLRL

DAITGPEEEGGRLETILGWPLAERTVVIPSAIPTDPRNVGGDLDPSSIPDKEQAISALPDYASQP

GKPPRKDEL

>DBL1-ID2aFCR3-PE38LR (SEQ ID NO: 66)
NHSDSGKYDPCEKKLPPYDDNDQWKCQQNSSDGSGKPENICVPPRRERLCTYNLENLKFDKIRDN

NAFLADVLLTARNEGEKIVQNHPDTNSSNVCNALERSFADLADIIRGTDQWKGTNSNLEKNLKQM

FAKIRENDKVLQDKYPKDQKYTKLREAWWNANRQKVWEVITCGARSNDLLIKRGWRTSGKSDRKK

NFELCRKCGHYEKEVPTKLDYVPQFLRWLTEWIEDFYREKQNLIDDMERHREECTREDHKSKEGT

SYCSTCKDKCKKYCECVKKWKTEWENQENKYKDLYEQNKNTSQKNTSRYDDYVKDFFEKLEANY

SSLENYIKGDPYFAEYATKLSFILNPSDANNPSGETANHNDEACNCNESGISSVGQAQTSGPSSN

KTCITHSSIKTNKKKECKDVKLGVRENDKDLKICVIEDTSLSGVDNCCCQDLLGILQENCSDNKR

GSSSNDSCDNKNQDECQKKLEKVFASLTNGYKCDKCKSGTSRSKKKWIWKKSSGNEEGLQEEYAN

TIGLPPRTQSLYLGNLPKLENVCEDVKDINFDTKEKFLAGCLIVSFHEGKNLKKRYPQNKNSGNK

ENLCKALEYSFADYGDLIKGTSIWDNEYTKDLELNLQNNFGKLFGKYIKKNNTAEQDTSYSSLDE

LRESWWNTNKKYIWTAMKHGAEMNITTCNADGSVTGSGSSCDDIPTIDLIPQYLRFLQEWVENFC

EQRQAKVKDVITNCKSCKESGNKCKTECKTKCKDECEKYKKFIEACGTAGGGIGTAGSPWSKRWD

QIYKRYSKHIEDAKRNRKAGTKNCGTSSTTNAAASTDENKCVQSDIDSFFKHLIDIGLTTPSSYL

SNVLDDNICGADKAPWTTYTTYTTTEKCNKERDKSKSQSSDTLVVVNVPSPLGNTPYRYKYACQC

KIPTNEETCDDRKEYMNQWSCGSARTMKRGYKNDNYELCKYNGVDVKPTTVRSNSSKLDRHRQPR

GWEQLYPTGAEFLGDGGDISFSTRGTQNWTVERLLQAHRQLEERGYVFVGYHGTFLEAAQSIVFG

GVRARSQDLDAIWRGFYIAGDPALAYGYAQDQEPDARGRIRNGALLRVYVPRSSLPGFYRTSLTL

AAPEAAGEVERLIGHPLPLRLDAITGPEEEGGRLETILGWPLAERTVVIPSAIPTDPRNVGGDLD

PSSIPDKEQAISALPDYASQPGKPPRKDEL

>DBL1-ID2aFCR3-PE38
(SEQ ID NO: 67)
NHSDSGKYDPCEKKLPPYDDNDQWKCQQNSSDGSGKPENICVPPRRERLCTYNLENLKFDKIRDN

NAFLADVLLTARNEGEKIVQNHPDTNSSNVCNALERSFADLADIIRGTDQWKGTNSNLEKNLKQM

FAKIRENDKVLQDKYPKDQKYTKLREAWWNANRQKVWEVITCGARSNDLLIKRGWRTSGKSDRKK

NFELCRKCGHYEKEVPTKLDYVPQFLRWLTEWIEDFYREKQNLIDDMERHREECTREDHKSKEGT

SYCSTCKDKCKKYCECVKKWKTEWENQENKYKDLYEQNKNKTSQKNTSRYDDYVKDFFEKLEANY

SSLENYIKGDPYFAEYATKLSFILNPSDANNPSGETANHNDEACNCNESGISSVGQAQTSGPSSN

KTCITHSSIKTNKKKECKDVKLGVRENDKDLKICVIEDTSLSGVDNCCCQDLLGILQENCSDNKR

GSSSNDSCDNKNQDECQKKLEKVFASLTNGYKCDKCKSGTSRSKKKWIWKKSSGNEEGLQEEYAN

TIGLPPRTQSLYLGNLPKLENVCEDVKDINFDTKEKFLAGCLIVSFHEGKNLKKRYPQNKNSGNK

ENLCKALEYSFADYGDLIKGTSIWDNEYTKDLELNLQNNFGKLFGKYIKKNNTAEQDTSYSSLDE

LRESWWNTNKKYIWTAMKHGAEMNITTCNADGSVTGSGSSCDDIPTIDLIPQYLRFLQEWVENFC

EQRQAKVKDVITNCKSCKESGNKCKTECKTKCKDECEKYKKFIEACGTAGGGIGTAGSPWSKRWD

QIYKRYSKHIEDAKRNRKAGTKNCGTSSTTNAAASTDENKCVQSDIDSFFKHLIDIGLTTPSSYL

SNVLDDNICGADKAPWTTYTTYTTTEKCNKERDKSKSQSSDTLVVVNVPSPLGNTPYRYKYACQC

KIPTNEETCDDRKEYMNQWSCGSARTMKRGYKNDNYELCKYNGVDVKPTTVRSNSSKLDPEGGSL

AALTAHQACHLPLETFTRHRQPRGWEQLEQCGYPVQRLVALYLAARLSWNQVDQVIRNALASPGS

GGDLGEAIREQPEQARLALTLAAAESERFVRQGTGNDEAGAANGPADSGDALLERNYPTGAEFLG

DGGDISFSTRGTQNWTVERLLQAHRQLEERGYVFVGYHGTFLEAAQSIVFGGVRARSQDLDAIWR

GFYIAGDPALAYGYAQDQEPDARGRIRNGALLRVYVPRSSLPGFYRTSLTLAAPEAAGEVERLIG

HPLPLRLDAITGPEEEGGRLETILGWPLAERTVVIPSAIPTDPRNVGGDLDPSSIPDKEQAISAL

PDYASQPGKPPRKDEL

>ID1-ID2a3D7-PE38
(SEQ ID NO: 68)
LSFILNSSDANNPSEKIQKNNDEVCNCNESGIASVEQEQISDPSSNKTCITHSSIKANKKKVCKH

VKLGVRENDKDLRVCVIEHTSLSGVENCCCQDFLRILQENCSDNKSGSSSNGSCNNKNQEACEKN

LEKVLASLTNCYKCDKCKSEQSKKNNKNWIWKKSSGKEGGLQKEYANTIGLPPRTQSLCLVVCLD

EKGKKTQELKNIRTNSELLKEWIIAAFHEGKNLKPSHEKKNDDNGKKLCKALEYSFADYGDLIKG

TSIWDNEYTKDLELNLQKIFGKLFRKYIKKNNTAEQDTSYSSLDELRESWWNTNKKYIWLAMKHG

AGMNSTTCCGDGSVTGSGSSCDDIPTIDLIPQYLRFLQEWVEHFCKQRQEKVKPVIENCKSCKES

GGTCNGECKTECKNKCEVYKKFIEDCKGGDGTAGSSWVKRWDQIYKRYSKYIEDAKRNRKAGTKN

CGPSSTTNAAENKCVQSDIDSFFKHLIDIGLTTPSSYLSIVLDDNICGADKAPWTTYTTYTTTEK

CNKETDKSKLQQCNTAVVVNVPSPLGNTPHGYKYACQCKIPTNEETCDDRKEYMNQWSCGSARTM

KRGYKNDNYELCKYNGVDVKPTTVRSNSSKLDPEGGSLAALTAHQACHLPLETFTRHRQPRGWEQ

LEQCGYPVQRLVALYLAARLSWNQVDQVIRNALASPGSGGDLGEAIREQPEQARLALTLAAAESE

RFVRQGTGNDEAGAANGPADSGDALLERNYPTGAEFLGDGGDISFSTRGTQNWTVERLLQAHRQL

EERGYVFVGYHGTFLEAAQSIVFGGVRARSQDLDAIWRGFYIAGDPALAYGYAQDQEPDARGRIR

NGALLRVYVPRSSLPGFYRTSLTLAAPEAAGEVERLIGHPLPLRLDAITGPEEEGGRLETILGWP

LAERTVVIPSAIPTDPRNVGGDLDPSSIPDKEQAISALPDYASQPGKPPRKDE

-continued

>ID1-ID2a3D7-PE38LR (SEQ ID NO: 69)

LSFILNSSDANNPSEKIQKNNDEVCNCNESGIASVEQEQISDPSSNKTCITHSSIKANKKKVCKH
VKLGVRENDKDLRVCVIEHTSLSGVENCCCQDFLRILQENCSDNKSGSSSNGSCNNKNQEACEKN

LEKVLASLTNCYKCDKCKSEQSKKNNKNWIWKKSSGKEGGLQKEYANTIGLPPRTQSLCLVVCLD

EKGKKTQELKNIRTNSELLKEWIIAAFHEGKNLKPSHEKKNDDNGKKLCKALEYSFADYGDLIKG

TSIWDNEYTKDLELNLQKIFGKLFRKYIKKNNTAEQDTSYSSLDELRESWWNTNKKYIWLAMKHG

AGMNSTTCCGDGSVTGSGSSCDDIPTIDLIPQYLRFLQEWVEHFCKQRQEKVKPVIENCKSCKES

GGTCNGECKTECKNKCEVYKKFIEDCKGGDGTAGSSWVKRWDQIYKRYSKYIEDAKRNRKAGTKN

CGPSSTTNAAENKCVQSDIDSFFKHLIDIGLTTPSSYLSIVLDDNICGADKAPWTTYTTYTTTEK

CNKETDKSKLQQCNTAVVVNVPSPLGNTPHGYKYACQCKIPTNEETCDDRKEYMNQWSCGSARTM

KRGYKNDNYELCKYNGVDVKPTTVRSNSSKLDRHRQPRGWEQLYPTGAEFLGDGGDISFSTRGTQ

NWTVERLLQAHRQLEERGYVFVGYHGTFLEAAQSIVFGGVRARSQDLDAIWRGFYIAGDPALAYG

YAQDQEPDARGRIRNGALLRVYVPRSSLPGFYRTSLTLAAPEAAGEVERLIGHPLPLRLDAITGP

EEEGGRLETILGWPLAERTVVIPSAIPTDPRNVGGDLDPSSIPDKEQAISALPDYASQPGKPPRK

DEL

>ID1-DBL2bFCR3-PE38LR (SEQ ID NO: 70)

NYIKGDPYFAEYATKLSFILNPSDANNPSGETANHNDEACNCNESGISSVGQAQTSGPSSNKTCI

THSSIKTNKKKECKDVKLGVRENDKDLKICVIEDTSLSGVDNCCCQDLLGILQENCSDNKRGSSS

NDSCDNKNQDECQKKLEKVFASLTNGYKCDKCKSGTSRSKKKWIWKKSSGNEEGLQEEYANTIGL

PPRTQSLYLGNLPKLENVCEDVKDINFDTKEKFLAGCLIVSFHEGKNLKKRYPQNKNSGNKENLC

KALEYSFADYGDLIKGTSIWDNEYTKDLELNLQNNFGKLFGKYIKKNNTAEQDTSYSSLDELRES

WWNTNKKYIWTAMKHGAEMNITTCNADGSVTGSGSSCDDIPTIDLIPQYLRFLQEWVENFCEQRQ

AKVKDVITNCKSCKESGNKCKTECKTKCKDECEKYKKFIEACGTAGGGIGTAGSPWSKRWDQIYK

RYSKHIEDAKRNRKAGTKNCGTSSTTNAAASTDENKCVQSDIDSFFKHLIDIGLTTPSSYLSNVL

DDNICGADKAPWTTYTTYTTTEKCNKERDKSKSQSSDTLVVVNVPSPLGNTPYRYKYRHRQPRGW

EQLYPTGAEFLGDGGDISFSTRGTQNWTVERLLQAHRQLEERGYVFVGYHGTFLEAAQSIVFGGV

RARSQDLDAIWRGFYIAGDPALAYGYAQDQEPDARGRIRNGALLRVYVPRSSLPGFYRTSLTLAA

PEAAGEVERLIGHPLPLRLDAITGPEEEGGRLETILGWPLAERTVVIPSAIPTDPRNVGGDLDPS

SIPDKEQAISALPDYASQPGKPPRKDEL

>DT388, sequence of diphtheria toxin (SEQ ID NO: 71)

MGADDVVDSSKSFVMENFSSYHGTKPGYVDSIQKGIQKPKSGTQGNYDDDWKGFYSTDNKYDAAG

YSVDNENPLSGKAGGVVKVTYPGLTKVLALKVDNAETIKKELGLSLTEPLMEQVGTEEFIKRFGD

GASRVVLSLPFAEGSSSVEYINNWEQAKALSVELEINFETRGKRGQDAMYEYMAQACAGNRVRRS

VGSSLSCINLDWDVIRDKTKTKIESLKEHGPIKNKMSESPNKTVSEEKAKQYLEEFHQTALEHPE

LSELKTVTGTNPVFAGANYAAWAVNVAQVIDSETADNLEKTTAALSILPGIGSVMGIADGAVHHN

TEEIVAQSIALSSLMVAQAIPLVGELVDIGFAAYNFVESIINLFQVVHNSYNRPAYSPGHKTQPM

HEF

-continued

Sequences of VAR2CSA polypeptides fused with truncated fragments of diphtheria toxin >DT388-DBL1-ID2a 3D7

(SEQ ID NO: 72)

MGADDVVDSSKSFVMENFSSYHGTKPGYVDSIQKGIQKPKSGTQGNYDDDWKGFYSTDNKYDAAG
YSVDNENPLSGKAGGVVKVTYPGLTKVLALKVDNAETIKKELGLSLTEPLMEQVGTEEFIKRFGD
GASRVVLSLPFAEGSSSVEYINNWEQAKALSVELEINFETRGKRGQDAMYEYMAQACAGNRVRRS
VGSSLSCINLDWDVIRDKTKTKIESLKEHGPIKNKMSESPNKTVSEEKAKQYLEEFHQTALEHPE
LSELKTVTGTNPVFAGANYAAWAVNVAQVIDSETADNLEKTTAALSILPGIGSVMGIADGAVHHN
TEEIVAQSIALSSLMVAQAIPLVGELVDIGFAAYNFVESIINLFQVVHNSYNRPAYSPGHKTQPM
HEFHSDSGTNDPCDRIPPPYGDNDQWKCAIILSKVSEKPENVFVPPRRQRMCINNLEKLNVDKIR
DKHAFLADVLLTARNEGERIVQNHPDTNSSNVCNALERSFADIADIIRGTDLWKGTNSNLEQNLK
QMFAKIRENDKVLQDKYPKDQNYRKLREDWWNANRQKVWEVITCGARSNDLLIKRGWRTSGKSNG
DNKLELCRKCGHYEEKVPTKLDYVPQFLRWLTEWIEDFYREKQNLIDDMERHREECTSEDHKSKE
GTSYCSTCKDKCKKYCECVKKWKSEWENQKNKYTELYQQNKNETSQKNTSRYDDYVKDFFKKLEA
NYSSLENYIKGDPYFAEYATKLSFILNSSDANNPSEKIQKNNDEVCNCNESGIASVEQEQISDPS
SNKTCITHSSIKANKKKVCKHVKLGVRENDKDLRVCVIEHTSLSGVENCCCQDFLRILQENCSDN
KSGSSSNGSCNNKNQEACEKNLEKVLASLTNCYKCDKCKSEQSKKNNKNWIWKKSSGKEGGLQKE
YANTIGLPPRTQSLCLVVCLDEKGKKTQELKNIRTNSELLKEWIIAAFHEGKNLKPSHEKKNDDN
GKKLCKALEYSFADYGDLIKGTSIWDNEYTKDLELNLQKIFGKLFRKYIKKNNTAEQDT-
SYSSLD
ELRESWWNTNKKYIWLAMKHGAGMNSTTCCGDGSVTGSGSSCDDIPTIDLIPQYLRFLQEWVEHF
CKQRQEKVKPVIENCKSCKESGGTCNGECKTECKNKCEVYKKFIEDCKGGDTAGSSWVKRWDQI
YKRYSKYIEDAKRNRKAGTKNCGPSSTTNAAENKCVQSDIDSFFKHLIDIGLTTPSSYLSIVLDD
NICGADKAPWTTYTTYTTTEKCNKETDKSKLQQCNTAVVVNVPSPLGNTPHGYKYACQCKIPTNE
ETCDDRKEYMNQWSCGSARTMKRGYKNDNYELCKYNGVDVKPTTVRSNSSKLDSGR

>DT388-DBL1-ID2a FCR3

(SEQ ID NO: 73)

MGADDVVDSSKSFVMENFSSYHGTKPGYVDSIQKGIQKPKSGTQGNYDDDWKGFYSTDNKYDAAG
YSVDNENPLSGKAGGVVKVTYPGLTKVLALKVDNAETIKKELGLSLTEPLMEQVGTEEFIKRFGD
GASRVVLSLPFAEGSSSVEYINNWEQAKALSVELEINFETRGKRGQDAMYEYMAQACAGNRVRRS
VGSSLSCINLDWDVIRDKTKTKIESLKEHGPIKNKMSESPNKTVSEEKAKQYLEEFHQTALEHPE
LSELKTVTGINPVFAGANYAAWAVNVAQVIDSETADNLEKTTAALSILPGIGSVMGIADGAVHHN
TEEIVAQSIALSSLMVAQAIPLVGELVDIGFAAYNFVESIINLFQVVHNSYNRPAYSPGHKTQPM
HEFHSDSGKYDPCEKKLPPYDDNDQWKCQQNSSDGSGKPENICVPPRRERLCTYNLENLKFDKIR
DNNAFLADVLLTARNEGEKIVQNHPDTNSSNVCNALERSFADLADIIRGTDQWKGTNSNLEKNLK
QMFAKIRENDKVLQDKYPKDQKYTKLREAWWNANRQKVWEVITCGARSNDLLIKRGWRTSGKSDR
KKNFELCRKCGHYEKEVPTKLDYVPQFLRWLTEWIEDFYREKQNLIDDMERHREECTREDHKSKE
GTSYCSTCKDKCKKYCECVKKWKTEWENQENKYKDLYEQNKNKTSQKNTSRYDDYVKDFFEKLEA
NYSSLENYIKGDPYFAEYATKLSFILNPSDANNPSGETANHNDEACNCNESGISSVGQAQTSGPS
SNKTCITHSSIKTNKKKECKDVKLGVRENDKDLKICVIEDTSLSGVDNCCCQDLLGILQENCSDN
KRGSSSNDSCDNKNQDECQKKLEKVFASLTNGYKCDKCKSGTSRSKKKWIWKKSSGNEEGLQEEY
ANTIGLPPRTQSLYLGNLPKLENVCEDVKDINFDTKEKFLAGCLIVSFHEGKNLKKRYPQNKNSG
NKENLCKALEYSFADYGDLIKGTSIWDNEYTKDLELNLQNNFGKLFGKYIKKNNTAEQDTSYSSL

-continued

DELRESWWNTNKKYIWTAMKHGAEMNITTCNADGSVTGSGSSCDDIPTIDLIPQYLRFLQEWVEN

FCEQRQAKVKDVITNCKSCKESGNKCKTECKTKCKDECEKYKKFIEACGTAGGGIGTAGSPWSKR

WDQIYKRYSKHIEDAKRNRKAGTKNCGTSSTTNAAASTDENKCVQSDIDSFFKHLIDIGLTTPSS

YLSNVLDDNICGADKAPWTTYTTYTTTEKCNKERDKSKSQSSDTLVVVNVPSPLGNTPYRYKYAC

QCKIPTNEETCDDRKEYMNQWSCGSARTMKRGYKNDNYELCKYNGVDVKPTTVRSNSSKLDSGR

>DT388-ID1-ID2a 3D7
(SEQ ID NO: 74)
MGADDVVDSSKSFVMENFSSYHGTKPGYVDSIQKGIQKPKSGTQGNYDDDWKGFYSTDNKYDAAG

YSVDNENPLSGKAGGVVKVTYPGLTKVLALKVDNAETIKKELGLSLTEPLMEQVGTEEFIKRFGD

GASRVVLSLPFAEGSSSVEYINNWEQAKALSVELEINFETRGKRGQDAMYEYMAQACAGNRVRRS

VGSSLSCINLDWDVIRDKTKTKIESLKEHGPIKNKMSESPNKTVSEEKAKQYLEEFHQTALEHPE

LSELKTVTGTNPVFAGANYAAWAVNVAQVIDSETADNLEKTTAALSILPGIGSVMGIADGAVHHN

TEEIVAQSIALSSLMVAQAIPLVGELVDIGFAAYNFVESIINLFQVVHNSYNRPAYSPGHKTQPM

HEFLSFILNSSDANNPSEKIQKNNDEVCNCNESGIASVEQEQISDPSSNKTCITHSSIKANKKKV

CKHVKLGVRENDKDLRVCVIEHTSLSGVENCCCQDFLRILQENCSDNKSGSSSNGSCNNKNQEAC

EKNLEKVLASLTNCYKCDKCKSEQSKKNNKNWIWKKSSGKEGGLQKEYANTIGLPPRTQSLCLVV

CLDEKGKKTQELKNIRTNSELLKEWIIAAFHEGKNLKPSHEKKNDDNGKKLCKALEYSFADYGDL

IKGTSIWDNEYTKDLELNLQKIFGKLFRKYIKKNNTAEQDTSYSSLDELRESWWNTNKKYIWLAM

KHGAGMNSTTCCGDGSVTGSGSSCDDIPTIDLIPQYLRFLQEWVEHFCKQRQEKVKPVIENCKSC

KESGGTCNGECKTECKNKCEVYKKFIEDCKGGDTAGSSWVKRWDQIYKRYSKYIEDAKRNRKAG

TKNCGPSSTTNAAENKCVQSDIDSFFKHLIDIGLTTPSSYLSIVLDDNICGADKAPWITYTTYTT

TEKCNKETDKSKLQQCNTAVVVNVPSPLGNTPHGYKYACQCKIPTNEETCDDRKEYMNQWSCGSA

RTMKRGYKNDNYELCKYNGVDVKPTTVRSNSSKLDSGR

>DT388-ID1-ID2a FCR3
(SEQ ID NO: 75)
MGADDVVDSSKSFVMENFSSYHGTKPGYVDSIQKGIQKPKSGTQGNYDDDWKGFYSTDNKYDAAG

YSVDNENPLSGKAGGVVKVTYPGLTKVLALKVDNAETIKKELGLSLTEPLMEQVGTEEFIKRFGD

GASRVVLSLPFAEGSSSVEYINNWEQAKALSVELEINFETRGKRGQDAMYEYMAQACAGNRVRRS

VGSSLSCINLDWDVIRDKTKTKIESLKEHGPIKNKMSESPNKTVSEEKAKQYLEEFHQTALEHPE

LSELKTVTGINPVFAGANYAAWAVNVAQVIDSETADNLEKTTAALSILPGIGSVMGIADGAVHHN

TEEIVAQSIALSSLMVAQAIPLVGELVDIGFAAYNFVESIINLFQVVHNSYNRPAYSPGHKTQPM

HEFNYIKGDPYFAEYATKLSFILNPSDANNPSGETANHNDEACNCNESGISSVGQAQTSGPSSNK

TCITHSSIKTNKKKECKDVKLGVRENDKDLKICVIEDTSLSGVDNCCCQDLLGILQENCSDNKRG

SSSNDSCDNKNQDECQKKLEKVFASLTNGYKCDKCKSGTSRSKKKWIWKKSSGNEEGLQEEYANT

IGLPPRTQSLYLGNLPKLENVCEDVKDINFDTKEKFLAGCLIVSFHEGKNLKKRYPQNKNSGNKE

NLCKALEYSFADYGDLIKGTSIWDNEYTKDLELNLQNNFGKLFGKYIKKNNTAEQDTSYSSLDEL

RESWWNTNKKYIWTAMKHGAEMNITTCNADGSVTGSGSSCDDIPTIDLIPQYLRFLQEWVENFCE

QRQAKVKDVITNCKSCKESGNKCKTECKTKCKDECEKYKKFIEACGTAGGGIGTAGSPWSKRWDQ

IYKRYSKHIEDAKRNRKAGTKNCGTSSTTNAAASTDENKCVQSDIDSFFKHLIDIGLTTPSSYLS

NVLDDNICGADKAPWTTYTTYTTTEKCNKERDKSKSQSSDTLVVVNVPSPLGNTPYRYKYACQCK

IPTNEETCDDRKEYMNQWSCGSARTMKRGYKNDNYELCKYNGVDVKPTTVRSNSSKLDSGR

EXAMPLES

Example 1 Production of Truncated Recombinant VAR2CSA Proteins

All protein truncations were produced according to previously defined domain borders (Dahlback M, Jorgensen L M, Nielsen M A, Clausen T M, Ditlev S B, et al. J Biol Chem 286: 15908-15917). For the purpose of simplification we have divided the $CIDR_{PAM}$ domain into two domains ID2a and ID2b, where ID2a is the N-terminal part of $CIDR_{PAM}$ not containing the CIDR-like sequence and ID2b corresponds to the CIDR-like sequence. We also used a new DBL2X border incorporating 93 amino acids of ID2a. For simplification we call this border DBL2Xb, while the old border will be referred to as DBL2Xa. Primers used in cloning are listed in Table 2. Fragments were expressed in baculovirus-infected insect cells as soluble proteins as described in Method 1. Most proteins were produced based on the FCR3 genotype. Some FCR3 fragments did not express and these were instead made based on the 3D7 genotype. The proteins were used interchangeably in the analysis since we show that recombinant VAR2CSA from both genotypes bind equally to CSA. All proteins showed a shift in gel mobility when comparing reduced and non-reduced samples by SDS-PAGE (Method 2). This is consistent with the formation of intra-molecular disulfide bridges. Some proteins formed high-molecular weight complexes detected by non-reduced SDS-PAGE. This is probably due to the formation of inter-molecular disulfide bridges between unpaired cysteines. This was confirmed by reducing the complexes to monomeric protein using DTT.

TABLE 2

| Cloning Primers | | |
|---|---|---|
| Protein | Forward Primer | Reverse Primer |
| FCR3 Primers | | |
| ID1-ID2b | AACTACATCAAGGGCGAC (SEQ ID NO: 76) | CTTGTTGATATTGGTGTC GGT (SEQ ID NO: 77) |
| DBL1X-ID2a | CACAGCGATAGCGGCAAG (SEQ ID NO: 78) | GTCCAGCTTGCTGGAGTT (SEQ ID NO: 79) |
| ID1-ID2a | AACTACATCAAGGGCGAC (SEQ ID NO: 80) | GTCCAGCTTGCTGGAGTT (SEQ ID NO: 81) |
| ID1-DBL2Xa | AACTACATCAAGGGCGAC (SEQ ID NO: 82) | AGCGGCGTTGGTGGTGGA (SEQ ID NO: 83) |
| ID1-DBL2Xb | AACTACATCAAGGGCGAC (SEQ ID NO: 84) | GTACTTGTACCGGTAGGG (SEQ ID NO: 85) |
| DBL1X-DBL2Xb | CACAGCGATAGCGGCAAG (SEQ ID NO: 86) | GTACTTGTACCGGTAGGG (SEQ ID NO: 87) |
| 3d7 Primers | | |
| DBL2X-DBL4ε | CTGACCAACTGCTACAAG (SEQ ID NO: 88) | GGTCCAGAGGGTACAGCT T (SEQ ID NO: 89) |
| ID1-DBL3Eε | CTGTCCTTCATCCTGAAC (SEQ ID NO: 90) | TTCAGCGTTGTTGTACTC GTA (SEQ ID NO: 91) |
| ID1-DBL4Eε | CTGTCCTTCATCCTGAAC (SEQ ID NO: 92) | GTCCAGAGGGTACAGCTT (SEQ ID NO: 93) |
| DBL1X-ID2b | CACTCTGACTCTGGCACC (SEQ ID NO: 94) | AGAGGACTTCATCTTGTT GTTGGT (SEQ ID NO: 95) |
| ID1-ID2b | CTGTCCTTCATCCTGAAC (SEQ ID NO: 96) | AGAGGACTTCATCTTGTT GTTGGT (SEQ ID NO: 97) |
| DBL1X-ID2a | CACTCTGACTCTGGCACC (SEQ ID NO: 98) | GTCCAGCTTAGAGGAGTT (SEQ ID NO: 99) |
| ID1-ID2a | CTGTCCTTCATCCTGAAC (SEQ ID NO: 100) | GTCCAGCTTAGAGGAGTT (SEQ ID NO: 101) |
| DBL1X-DBL2Xa | CACTCTGACTCTGGCACC (SEQ ID NO: 102) | GGCGGCGTTGGTGGTAGA (SEQ ID NO: 103) |
| ID1-DBL2Xa | CTGTCCTTCATCCTGAAC (SEQ ID NO: 104) | GGCGGCGTTGGTGGTAGA (SEQ ID NO: 105) |

TABLE 2-continued

Cloning Primers

| | | |
|---|---|---|
| DBL1X-DBL2Xb | CACTCTGACTCTGGCACC (SEQ ID NO: 106) | GTACTTGTATCCGTGGGG (SEQ ID NO: 107) |
| ID1-DBL2Xb | CTGTCCTTCATCCTGAAC (SEQ ID NO: 108) | GTACTTGTATCCGTGGGG (SEQ ID NO: 109) |

| Protein | Forward | Reverse |
|---|---|---|

Mutating Putative CSA Binding Sites

PCR1
Fragment 1

| | | |
|---|---|---|
| DBL1X-ID2a (DSM Deletion) | CACAGCGATAGCGGCAAG (SEQ ID NO: 110) | GGTGTCGAAGTTGATGTC GGGCAGATTGCCCAGGTA (SEQ ID NO: 111) |
| Alanine sub. K(626,629,630), R(631) | CACAGCGATAGCGGCAAG (SEQ ID NO: 112) | AGC TABLE 3-continued CSA binding affinity of produced VAR2CSA proteins. Affinity is given as a $K_D$ (nM) value determined in kinetics experiments using a quartz crystal microbalance biosensor (Attana A100).

| VAR2CSA Fragment | FCR3 Baculo | FCR3 E. coli | 3D7 Baculo |
|---|---|---|---|
| ID1-DBL3ε | 0.3* | | 8.5 |
| DBL2X-DBL4ε | 2.4* | | 1.2 |
| DBL1-ID2b | 1.5* | | |
| DBL1-ID2a | 8.0 | 3.5 | 29.5 |
| ID1-ID2a | 7.6 | 18.3 | 5.7 |
| DBL1X-DBL2Xb | | 14.6 | |
| DBL1X-DBL2Xa | N/A | | |
| ID1-DBL2Xb | | | 21.8 |
| ID1-DBL2Xa | | | N/A |

*Proteins published in (Dahlbäck et al, JBC, 2011)
N/A: proteins for which no $K_D$ value could be determined, due to a lack of binding to CSA.

Example 3—the Core-CSA Binding Site Lies within the DBL2X Domain

It has been suggested that the minimal CSA binding region in VAR2CSA lies within DBL2X-ID2b, with the need of flanking domains for full affinity binding (Dahlback M, Jorgensen L M, Nielsen M A, Clausen T M, Ditlev S B, et al. J Biol Chem 286: 15908-15917). Here we have analyzed shorter fragments of VAR2CSA to further map the regions required for CSA binding.

The truncated proteins were first screened for binding to a CSA proteoglycan (CSPG) in ELISA and then further purified to obtain monomers for examination on the Quartz Crystal Microbalance (Methods 3, 2 and 4, respectively). The minimal binding region is ID1-DBL2Xb (Table 3). This region showed a binding affinity of 21.8 nM, which is comparable to that of full-length VAR2CSA.

Placental IEs are highly selective for low-sulfated placental CSPG. They do not adhere to any other glycosaminoglycans (GAG), such as heparan sulfate (HS). The same is true for the full-length recombinant VAR2CSA protein. The solid state binding assay showed that the VAR2CSA fragments, containing the minimal CSA binding region, bound specifically to CSA. To confirm this the minimal binding fragments were further tested for binding to a heparan sulfate proteoglycan (HSPG) on the Quartz Crystal Microbalance (Method 4). None of the fragments bound HSPG.

Example 4—Antibodies Induced Against Novel Minimum Binding Regions Induce a Potent Parasite Anti-Adhesive Immune Response A VAR2CSA based vaccine against PM must be able to induce a strong protective immune response. In this, the most important aspect is the formation of anti-VAR2CSA IgG antibodies capable of inhibiting placental sequestration. We have examined the molecular mechanism underlying the VAR2CSA-CSA interaction for the purpose of designing optimal vaccine antigens. To test whether our produced VAR2CSA recombinant fragments showed the capacity to induce an adhesion blocking immune response, they were used in rat immunizations (Method 6).

VAR2CSA fragment-specific serum was tested for ability to inhibit IE adhesion to CSPG (Method 11). Antibodies raised against all CSA-binding fragments were very potent inhibitors of binding. In fact binding was inhibited nearly 100% in all cases. DBL1X-DBL2Xa and ID1-DBL2Xa were not good inhibitors, consistent with the lack of CSA binding of these fragments (Table 3). The data implies that the CSA-binding proteins are properly folded and support the localization of the above-defined minimal binding region.

Example 5—Epitopes Responsible for the Induction of Anti-Adhesive Antibodies Lies within the Minimal Binding Region To examine if the inhibitory anti-FV2 response is directed towards the minimal binding region, we affinity purified FV2 antibodies on four of the previous described VAR2CSA fragments (Method 7). The fragment-specific antibodies were then tested for the capacity to inhibit VAR2CSA expressing parasite binding to CSPG (Method 11). Antibodies purified on immobilized ID1-DBL4E, DBL1X-ID2a and ID1-ID2a, fully inhibited parasite adhesion. Furthermore, the depleted FV2 samples lost a significant portion of their inhibitory capacity. This indicates that epitopes inducing anti-adhesive antibodies are present within these fragments. Antibodies purified on DBL1X-DBL2Xa show a reduced inhibitory capacity, consistent with the lack of CSA binding of this fragment (Table 3). The data suggest that epitopes responsible for induction of inhibitory antibodies are located within the minimal binding region (here illustrated by ID1-ID2a).

Example 6—Mutating Putative GAG Binding Sites in the Minimal Binding Region has No Effect on CSPG Binding Characterizing the nature of the interaction between VAR2CSA and CSA is important for the design of multivalent PM vaccines. In this, a major part is identification of the specific CSA-binding site and characterization of the underlying chemical interactions. Sequence analysis of the minimal CSA-binding region revealed two conserved putative GAG binding sites. One is located in the ID1 region and has the classic Cardin-Weintraub XBBBXXBX (SEQ ID NO:128) motif (Cardin, A. D., and Weintraub, H. J. (1989) *Arteriosclerosis* 9, 21-32) (458-NKKKECKD-465 (SEQ ID NO:129)). Another, in DBL2X, has the same motif in reverse (625-GKNLKKRY-632 (SEQ ID NO:130)). It has also been hypothesized that a dimorphic sequence motif (DSM), found in the N-terminal part of DBL2X, is involved in binding CSA (Sander, A. F., Salanti, A., Laystsen, T., Nielsen, M. A., Magistrado, P., Lusingu, J., Ndam, N. T., and Arnot, D. E. (2009) *PLoS One* 4, e6667). To test whether these putative sites had a function in CSA binding, we substituted basic amino acids in the classic GAG binding sites with alanines and made a ten amino acid (590-KLENVCEDVK-603 (SEQ ID NO:131)) deletion in the middle of a surface exposed loop within the DSM region. All mutations were performed in the DBL1X-ID2a fragment.

Substituting basic amino acids in the putative ID1 and DBL2X GAG binding sites, with alanines had no effect on CSPG binding. No decrease in CSPG binding was seen compared to the wild-type protein in ELISA (Method 3). The construct with four alanine substitutions, Alanine Sub. K(459,460,461,464), shows considerable HSPG binding, which could be caused by a change in protein structure in response to mutation. The two mutants, Alanine Sub. K(626, 629, 630), R(631) and Alanine Sub. K(459,460,461,464), show CSPG binding kinetics similar to the positive control (Method 4). This is evident by similar $K_D$ values and peak responses.

The deletion of the DSM region did not reduce binding to CSPG (Methods 3 and 4). The DSM knock out mutant shows considerable binding to HSPG in ELISA. This is likely caused by an erroneous cloning where 100 amino acids of DBL1X were lost. Importantly CSPG binding was not affected.

Example 7

VAR2CSA Binding to CSPG does not Depend on Ionic Interactions

Mutation of the classic Cardin-Weintraub GAG binding motifs had no effect on CSPG binding. This indicates that the VAR2CSA-CSA binding mechanism differs from the general mode of sulfate binding in classic GAG binding models. There are examples of GAG binding proteins showing little dependence on ionic interactions with the sulfated GAG structure. To test if this was the case, we examined ionic dependence according to the polyelectrolyte theory (Record, M. T., Jr., Lohman, M. L., and De Haseth, P. (1976) *J Mol Biol* 107, 145-158).

Glycosaminoglycans, like DNA, are highly charged polymers often referred to as polyelectrolytes. The negatively charged groups incur a high degree of repulsive energy within each polymer. Monovalent cations, such as $Na^+$, interact with the negatively charged groups to minimize the repulsive energy. Binding of basic amino acids to the sulfate groups displaces the bound cations and leads to the release of free energy. The favorable release of bound $Na^+$ ions is referred to as the polyelectrolyte effect.

The theory states that the binding of a protein to a GAG can be described by:

$$\text{Protein} + \text{GAG}(m \text{ sites}) \leftrightarrow \text{Protein-GAG} + m(1-f)Na^+$$

Where m is the number of $Na^+$ ions released upon binding of a single protein and f is the fraction of anions not shielded by $Na^+$ ions. According to the theory the observed $K_D$ value is related to ionic and non-ionic contributions by:

$$\text{Log } K_{D,observed} = \text{Log } K_{D,nonionic} + m(1-f)\text{Log }[Na^+]$$

Where $K_{D,nonionic}$ is the disassociation constant in the absence of ionic interactions. A plot of Log $K_{D,observed}$ vs Log $[Na^+]$ is linear with a slope of m(1−f). Thus, if the fraction of unshielded anions (f) is known, the number of ionic interactions involved in the binding can be determined. For heparin (1−f) is 0.8 (Olson, S. T., Halvorson, H. R., and Bjork, I. (1991) *J Biol Chem* 266, 6342-6352). The value is not known for CSA, but (1−f) cannot exceed 1. We can therefore estimate the maximal number of ionic interactions involved. Furthermore, when $[Na^+]=1$ M, Log $[Na^+]=0$, which means that at this $Na^+$ concentration Log $K_{D,observed}=\text{Log } K_{D,nonionic}$.

We tested the binding of FV2, DBL1X-ID2a and ID1-ID2a to CSPG in a solid state binding assay at different concentrations of NaCl (150 mM, 200 mM, 250 mM, 300 mM), by performing titrations of binding from 400 nM-1.65 nM protein in a 1:2 dilution series (Method 5). The observed $K_D$ values were determined as the protein concentration giving half-maximum ($B_{max}$) response. This was done using non-linear regression (least squares fit with Hill slope) in GRAPHPAD PRISM software. Higher salt concentrations were not included in the analysis as binding was almost completely inhibited. This is probably due to a change in protein structure. This notion is supported by the fact that Log $K_{D,observed}$ vs Log $[Na^+]$ was linear only between 150 mM and 300 mM, suggesting that other factors play a role at higher concentrations of NaCl.

Log $K_{D,observed}$ vs Log $[Na^+]$ shows a linear relationship. The slope m(1−f) ranges between 2.7 for ID1-ID2a and 3.4 for full-length (FV2). We do not know the value for f, but the maximal number of ionic interactions involved in the binding must be between 2 and 3. It is interesting that the value for the full-length protein is higher than for the short fragments, indicating that this protein makes an extra ionic interaction with CSPG. The $K_D$ values at 150 mM NaCl serves as our reference point, as this is the physiological NaCl concentration. By extrapolating the linear relationship and finding the y-intercept we find that $K_{D,nonionic}=5.9$ μM for FV2, $K_{D,nonionic}=3.4$ μM for DBL1X-ID2a, and $K_{D,nonionic}=0.7$ μM for ID1-ID2a. Comparing the logarithmic values of these and the reference point (150 mM NaCl), we estimate that between 25-35% of the VAR2CSA binding can be accounted for by ionic interactions. This suggests that the high CSA affinity for VAR2CSA cannot be explained by ionic interactions with the sulfated GAG structure alone. The high affinity may be achieved through a complex binding site making a multivalent interaction with the CSA carbohydrate backbone.

Example 8

VAR2CSA Minimal CSA Binding Region Binds Specifically to a Wide Panel of Cancer Cells Many different cancer cells have been associated with high expression of the proteoglycan CSPG4. This molecule was initially described as a marker for melanoma but it has recently been found in many cancer forms, including cancer stem cells. The CS chain(s) attached to CSPG4 is known to be primarily CSA. One of the smallest VAR2CSA fragments (ID1-ID2a) was analyzed for binding to a large panel of various cancer cell lines by flow-cytometry (Method 12a and 12b). The non-CSA binding protein ID1-DBL2Xa was used as a negative control. The VAR2CSA recombinant protein (ID1-ID2a) binds strongly at 75 nM to all cancer cell lines transcribing CSPG4 (microarray data) including cutaneous Melanoma (C32, MeWo), Lung carcinoma (A549), Breast carcinoma (HCC1395), Osteosarcoma (U2OS, MNNG/HOS), Rhabdomyosarcoma (RH30) (Table 4 and 5). This protein also binds strongly to cutaneous T-cell lymphoma, which does not express CSPG4 (Table 4). The negative control protein ID1-DBL2Xa did not bind to any of the cell lines tested (Table 4). In addition, ID1-ID2a did not interact with human red blood cells, which were used as control cells. Wild type and GAG-deficient Chinese hamster ovary (CHO) cells were also analyzed for ID1-ID2a interaction. The strong interaction seen for ID1-ID2a with wild-type CHO cells was completely abolished when analyzing the CHO-745 cell line, in which the GAG-synthesis is disrupted. The CSA specificity of the interaction was also verified by inhibiting VAR2CSA binding to cells by pre-mixing VAR2CSA with CSA, CSC or HS. CSC and HS did not have any effect on the binding, whereas CSA efficiently abrogated binding of VAR2CSA to the cancer cells.

Following these results, a larger panel of cancer cells were screened by flow cytometry (Table 6 and 7) using the DBL1-ID2a or ID1-ID2a fragment of VAR2CSA. The main purpose of this screening is to identify cell lines suitable for xenograft modeling in vivo.

TABLE 4

Staining of cancer cell lines and negative control cells using the minimal binding domain of VAR2CSA (ID1-ID2a). Cells were incubated with medium alone (blank) or recombinant proteins (ID1-DBL2 or ID1-ID2a) at 75 nM for 30 minutes, followed by incubation with anti-V5-FITC (Invitrogen) at 1:800, cells were washed thrice between each incubation. Shown are the mean FITC fluorescence values recorded from a minimum of 5000 cells using a FC500 flowcytometer (Becton Dickinson).

| Cell type | Blank | ID1-DBL2Xa | ID1-ID2a |
|---|---|---|---|
| C32 | 5.77 | 6.94 | 63.81 |
| MyLa 2059 | 5.61 | 5.61 | 145.35 |
| MyLa 1850 | 5.87 | 5.6 | 137.86 |
| Cho WT | 3.09 | 4.35 | 34.79 |
| Cho 745 | 4.24 | 4.29 | 4.38 |
| PBMC | 1.34 | 1.36 | 1.67 |
| Erythrocytes | 1.11 | 1.17 | 1.07 |

TABLE 5

Staining of cancer cell lines using recombinant VAR2CSA Cells were incubated with medium alone (blank) or recombinant proteins (DBL1-ID2a or ID1-ID2a) at 75 nM for 30 minutes, followed by incubation with anti-V5-FITC (Invitrogen) at 1:800, cells were washed thrice between each incubation. Shown are the medium score of FITC fluorescence intensity recorded from a minimum of 4 high power field images using a HAL100 Zeiss microscope.

| Cell type | Blank | DBL1-ID2a |
|---|---|---|
| U2OS | NS | +++ |
| MG63 | NS | ++++ |
| MDA-MB-231 | NS | +++ |
| TC32 | NS | + |
| TC71 | NS | ++ |
| MNNG | NS | +++ |
| CHLA9 | NS | ++ |
| CHLA10 | NS | ++ |
| RH30 | NS | +++ |
| RH18 | NS | ++ |
| PC3 | NS | +++ |

NS: No staining; +: weak; ++: medium; +++: strong; ++++: Very strong.

TABLE 6

Screening of diverse human cancer cell lines for binding of recombinant VAR2CSA (using DBL1-ID2a or ID1-ID2a). Binding was measured by flow cytometry as described in METHOD 12.

| Cell line | Control | 75 nM VAR2CSA | 150 nM VAR2CSA | Comments |
|---|---|---|---|---|
| MeWo | NS | +++ | ++++ | Melanoma (Fibroblast morphology, derived from lymphnode) |
| A549 | NS | +++ | +++ | Lung Adenocarcinoma (K-RasG12S) |
| HCC1395 | NS | +++ | ++++ | Invasive ductal breast carcinoma TNM stage 1 grade 3; no lymphnode metastasis; Her2-neg, ER-neg, PR-neg (Triple-negative) |
| RH30 | NS | +++ | ++++ | Rhabdomyosarcoma (TPp53 negativ; PAX7-FOXO1A fusion positive; highly genomic instable (>50 chromosome rearangements)) |
| MNNG | NS | +++ | +++ | Osteosarcoma from 13 year old female caucasian (TPR-Met positive) |
| U2OS | NS | +++ | +++ | Osterosarcoma from 15 year old female caucasian (IGF-R1 and IGFR-II positive; TPp53 wt, pRb wt, p16-neg; highly aneuploid) |
| H1792 | NS | ++ | ++ | Lung Adenocarcinoma (K-RasG12S: TPp53het)) |
| MDA-MD-435 | NS | ++ | +++ | Breast carcinoma of melanocytic origin (ER-neg, Her2-pos, PR-pos) |
| MG63 | NS | +++ | ++++ | Osteosarcoma |
| TC32 | NS | ++ | ++ | Ewing's sarcoma |
| CHLA9 | NS | ++ | ++ | Ewing's sarcoma |
| CHLA10 | NS | ++ | ++ | Ewing's sarcoma |
| TC71 | NS | ++ | ++ | Ewing's sarcoma |
| HOS | NS | +++ | ++++ | Osteosarcoma |
| PC3 | NS | ++ | ++ | Prostate carcinoma |
| SKNMC | NS | ++ | +++ | Ewing's sarcoma |
| MCF-7 | NS | + | ++ | Breast carcinoma |

NS: No staining; +: weak; ++: medium; +++: strong; ++++: Very strong.

TABLE 7

Screening of more human cell cancer cell lines for binding of recombinant VAR2CSA (using DBL1-ID2a or ID1-ID2a) Binding was measured by flow cytometry as described in METHOD 12. Values shown are mean fluorescence intensity using protein concentration of 200 nM.

| Cell type | Negative control | ID1-ID2a | Comments |
| --- | --- | --- | --- |
| GP202 | 21.63 | 111.37 | Gastric Carcinoma |
| NCI-N87 | 7.18 | 207.72 | Gastric Carcinoma |
| MKN45 | 4.22 | 55.4 | Gastric Carcinoma |
| MKN28 | 6.9 | 103.84 | Gastric Carcinoma |
| AGS | 7.25 | 18.21 | Gastric Carcinoma |
| KatoIII | 7.33 | 18.76 | Gastric Carcinoma |
| SNU-1 | 4.33 | 155.79 | Gastric Carcinoma |
| SNU-638 | 8.47 | 8.49 | Gastric Carcinoma |
| IPA220 | 7.72 | 13.67 | Gastric Carcinoma |
| MDA-231 | 3.39 | 63.43 | Triple negative Breast |
| T47D | 3.63 | 48.13 | Luminal Breast |
| LNCap | 6.58 | 24.86 | Prostate |
| PC3 | 5.2 | 29.82 | Prostate |
| Ovc316 | 1.89 | 7.24 | Ovarian cancer stem cells |

| Cell type | Blank | DBL1-ID2a | |
| --- | --- | --- | --- |
| NALM-6 | 6.19 | 8.22 | Acute lymphatic leukaemia (ALL) |
| 697 | 3.23 | 30.36 | ALL |
| AMO-1 | 2.68 | 35.22 | Myelomatosis |
| KMM-1 | 2.82 | 16.1 | Myelomatosis |
| MOLP-8 | 2.44 | 19.24 | Myelomatosis |
| KMS-12-PE | 3.02 | 7.14 | Myelomatosis |
| KMS-12-BM | 2.2 | 3.25 | Myelomatosis |
| U2932 | 4.24 | 16.83 | Diffuse Large B-cell lymphoma (DLBCL) |
| SU-DHL8 | ND | 3.75 | DLBCL |
| SU-DHL5 | 2.19 | 10.28 | DLBCL |
| Oci_Ly19 | 3.38 | 18.96 | DLBCL |
| HBL1 | 6.53 | 39.53 | DLBCL |
| Farage | 2.8 | 3.28 | DLBCL |
| RIVA | 2.26 | 3.32 | DLBCL |
| WSU-FSCCL | 4.89 | 22.32 | Low-grade follicular small cleaved cell lymphoma |
| U-698-M | 2.24 | 2.85 | Lymphoblastic lymphoma del(6)(q15q22) |

Example 9

Recombinant VAR2CSA Binds to Cancer Cells with High Affinity

The binding affinity of the recombinant VAR2CSA fragment DBL1-ID2a to the cancer cell lines, C32 melanoma and two Cho cell lines (described in example 8) was analysed using a Quartz Crystal Microbalance biosensor (ATTANA CELL200 biosensor). A 2-fold dilution series (25-400 nM) of the protein was analysed for binding to the cell surface, with regeneration of the binding surface in between each new protein injection. The binding affinity was estimated to lie in the nano-molar range (Table 8), which is similar to the binding affinity to pure receptor (Table 3).

TABLE 8

Estimated binding affinity ($K_D$) of recombinant DBL1-ID2a (*E. coli*) to cancer cells expressing CSA (C32 and Cho WT) and lack of binding to a CSA-negative cell line (Cho 745)

| Cell type | $K_D$ (nM) |
| --- | --- |
| C32 melanoma cells | 13 |
| Cho WT | 1.4 |
| Cho 745 | N/A |

N/A: $K_D$ could not be determined due to lack of binding to the cells

Example 10

Recombinant VAR2CSA Protein Binds to Cancer Tissue with High Specificity

The binding of recombinant VAR2CSA to primary cancer tissue obtained from human patients is investigated using immunohistochemistry (IHC). The method was developed using human placenta tissue as positive control and Tonsil and liver tissue as negative control. The staining protocol was optimized on the Ventana DISCOVERY XT platform with no epitope retrieval. Paraffin embedded tissue spotted on glass slides was incubated with 0.1-500 nM V5-VAR2CSA (ID1-ID2a) or V5-Control protein (DBL4) for 1 h in room temperature, washed for 8 minutes, incubated with 1:700 mouse anti-V5 antibody for 30 minutes, washed for 8 minutes. Bound anti-V5 was subsequently detected using UltraMap anti-mouse HRP. V5-VAR2CSA stains human placenta in 0.5 nM concentrations with no staining in Tonsil or normal liver. The staining can be completely blocked by adding 200 μg/μl CSA to the reaction buffer. V5-control protein does not stain human placenta tissue at any concentrations tested. A multi-organ tissue micro-array (TMA) representing 24 normal organs showed low or absent staining when stained with 1 nM V5-VAR2CSA, while cancer specimens of breast, colon, Rectum, Prostate, kidney, liver, bladder, pancreas, squamous cell, Lung, Gall bladder, Stomach, Testis, Ovary, Uterus, Adrenal gland, Thyroid and Thymus, hematopoietic system, and the connective tissue (sarcomas) stained positive with intensities equal or higher than human placenta positive control tissue (Table 9).

TABLE 9

Detection of CSA on primary human tumor specimens using recombinant VAR2CSA. Table shows number of positive/total number of cases stained as described in Example 10 for main cancer groups. Positive staining is defined as intensity equal or higher than that observed in placenta tissue.

| Cancer group | Positive ratio |
| --- | --- |
| Bladder carcinoma | 44/56 |
| Prostate carcinoma | 71/76 |
| Breast carcinoma | 64/75 |
| Melanoma | 5/6 |
| Sarcoma | 23/25 |
| Esophagus Squamous cell carcinoma | 2/3 |
| Stomach Adenocarcinoma | 3/3 |
| Colon carcinoma | 2/3 |
| Rectal Adenocarcinoma | 3/3 |
| Liver carcinoma | 3/3 |
| Renal carcinoma | 3/3 |
| Lung carcinoma | 2/3 |

TABLE 9-continued

Detection of CSA on primary human tumor specimens using recombinant VAR2CSA. Table shows number of positive/total number of cases stained as described in Example 10 for main cancer groups. Positive staining is defined as intensity equal or higher than that observed in placenta tissue.

| Cancer group | Positive ratio |
| --- | --- |
| Cervix carcinoma | 3/3 |
| Ovarian carcinoma | 2/3 |
| Diffuse B-cell lymphoma | 1/3 |
| Astrocytoma | 3/3 |
| Pancreatic carcinoma | 3/3 |

Example 11

Inhibition of Transformation-Parameters In Vitro by Recombinant VAR2CSA Proteins The inhibitory effect of un-coupled VAR2CSA on tumor cell morphology in vitro is investigated by three different assays:
  i) The soft agar colony formation assay addresses whether VAR2CSA can inhibit the ability of cancer cells to proliferate in a three dimensional matrix.
  ii) The migration assay addresses whether VAR2CSA can inhibit the ability of cancer cells to migrate vertically towards a chemo-attractant in a boyden chamber.
  iii) The invasion assay addresses whether VAR2CSA can inhibit the ability of cancer cells to invade through an artificial basement membrane.

Soft agar colony formation assay: Cells are treated with 25-100 nM VAR2CSA for 24 hours before seeded in soft agar matrix, and left for 10-12 days at 37° C. Images are captured by phase contrast microscope and quantified by IMAGE software. Recombinant VAR2CSA inhibits soft agar colony formation of MG63 osteosarcoma and RH30 Rhabdomyosarcoma cells in concentrations between 75 and 150 nM.

Basement Membrane Extract (BME)-coated cell invasion assay: To model the invasive process, we utilize the CULTRECOAT 24 Well BME-Coated Cell Invasion platform (Cedarlane) according to the manufacturer's protocols, with the following modifications. Cells are serum starved one day before assays in the presence or absence of 25-100 nM VAR2CSA. On the second day, cells maintained under the above conditions are plated in the top chambers ($1 \times 10^5$ cells/well) of plates, while lower chambers contained either serum depleted media as a negative control, or media supplemented with 10% FBS. Cells are then incubated for another 18 hours. Cells invading through the BME are collected using dissociation buffer containing Calcein AM, which converts into a highly fluorescent compound in living cells. Emitted fluorescence are measured using a fluorescent plate reader, analyzed by the FLUOSTAR software, fitted on a standard curve, and converted into corresponding number of cells.

Migration assay. The Migration assay is essentially the same procedure as the Basement Membrane Extract (BME)-coated cell invasion assay, but without BME.

Migration and Invasion capacity of MG63 osteosarcoma, RH30 Rhabdomyosarcoma, and MDA-MB-231 triple-negative breast cancer are inhibited by 75-150 nM recombinant VAR2CSA.

Example 12

Analyzing Intracellular Signalling Events Controlling Cancer Cell Transformation-Parameters Regulated by CSA-Containing Proteoglycans CSPG4 facilitates proliferation, migration and invasion via a Ras, Rac1 and PI3 kinase-dependent mechanism. Based on the results obtained in EXAMPLE 10, we will investigate intracellular signalling events leading to potential VAR2CSA-mediated inhibition of proliferation, migration and invasion. This is done with state-of-the-art biochemical and molecular biology methods including, but not limited to, Rac1 activation assays, immunoblotting of pathway components and in-cell measurements of reactive oxygen species (ROS) generation. This line of experiments will clarify the signalling pathways affected by VAR2CSA binding to CSA-containing proteoglycans.

Rac1 activity assay: Rac1 activity assays are performed on appropriate human cancer cell lines left untreated or treated with recombinant VAR2CSA, according to the manufacturer's protocols (Thermo Scientific).

Reactive oxygen species (ROS) assays: Crude ROS levels are measured by CM-H2DCFDA (Invitrogen) according to the manufacturer's guidelines. Superoxide levels will be measured using dihydroethidium (DHE). In the presence of the superoxide anion $O_2^-$, dihydroethidium is rapidly oxidized to oxyethidium, which binds DNA and emits light in the 570-580 nm ranges when excited at 488 nm. For cell culture, after appropriate treatments, cells are washed in Hank's Balanced Salt Solution (HBSS), incubated for 30-60 minutes in HBSS containing 10 µM DHE, washed in HBSS and directly analyzed for oxyethidium fluorescence with an epi-fluorescence HAL100 microscope (Zeiss). For tumor sections, snap-frozen tumors are cut in 20 µm sections using a cryostat, washed and DHE-treated as described for cell lines, mounted on cover slides and analyzed as for cell lines. Oxyethidium emission are analyzed and quantified using IMAGE software. For all tumor specimens, hematoxylin and eosin (H&E) staining are performed side-by-side to verify tissue integrity and pathology, using standard methods. Preliminary data indicates that recombinant VAR2CSA inhibits ROS-generation in MG63 and U2OS cells.

Immunodetection. For immunoblotting, proteins separated by SDS-PAGE and transferred to a nitrocellulose membrane are detected with relevant primary and appropriate secondary antibodies, ECL Western blotting reagents (Thermo Scientific), and film (Kodak and Covance (HA). For microscopy, cells are fixed in 4% formaldehyde, incubated with appropriate primary antibodies, incubated with appropriate secondary FITC-conjugated antibodies and analyzed by microscopy as described in EXAMPLE 9. Human cancer cell lines (MDA-MB-231, MG63, U205, TC32, TC71 and RH30) were serum starved for 24 h with recombinant VAR2CSA (ID1-ID2a) or Control protein (DBL4), and lysates prepared at 0, 1, 2, 3, 4, 5, 6 and 12 h after serum was added back to the cells. Using this approach, 100 nM VAR2CSA efficiently inhibited proto-oncogene tyrosine-protein kinase Src phosphorylation on 1416, Focal Adhesion Kinase (FAK) phosphorylation at T397, Extracellular-Signal-regulated Kinase (ERK) 1- and 2-phosphorylation at Thr202/Tyr204 for human ERK1 and Thr185/Tyr187 for human ERK2. This suggests that recombinant VAR2CSA inhibits canonical ERK signaling in cancer cells.

Example 13

Unbiased Analysis of Intracellular Signalling Events Modified by Recombinant VAR2CSA The broad impact of VAR2CSA on intracellular signalling events can be analysed using expression microarray technology. MG63 osteosarcoma cells were serum starved for 24 h with no treatment, VAR2CSA or Control (DBL4) and RNA was harvested after 1 h serum addition. The total RNA was quality tested (RIN<8), used as a template for AFFYMETRIX probe construction and hybridized to the AFFYMETRIX U133APLUS2.0 chip system. This readout provides a snapshot of activated or inactivated signalling pathways after 1 h of serum was added back. Preliminary data confirmed an inhibitory effect on ERK signalling.

Example 14

Inhibition of Cancer Cell Growth In Vivo by Recombinant VAR2CSA Proteins

Based on the results from the in vitro analysis appropriate cell lines will be selected for in vivo subcutaneous and metastatic xenograft models in immuno-compromised mice. The in vivo study addresses five main questions:
  i) can i.v. or i.p. administrated recombinant VAR2CSA trace and bind human cancer cells in vivo?
  ii) can i.v. or i.p. administration of recombinant VAR2CSA inhibit tumor formation in vivo?
  iii) can i.v. or i.p. administration of recombinant VAR2CSA inhibit growth of established tumors in vivo?
  iv) can i.v. or i.p. administration of recombinant VAR2CSA inhibit metastatic spread of human cancer cells in vivo?
  v) does i.v. or i.p. administration of recombinant VAR2CSA change CSA-containing proteoglycan-governed signaling events in human cancer cells in vivo (post mortem pathology and biochemistry)?

In vivo models: Selected human cancer cell lines representing cancer types showing a strong binding to VAR2CSA are inoculated subcutaneously into Rag2m or SCID immuno-compromised mice at approximately $5 \times 10^6$ cells/animal. When the tumor is established, the mice receive the first injection of vehicle (Saline) and recombinant VAR2CSA (1 mg/Kg). Treatment is repeated once a week throughout an experimental period of approximately 30 days. Animal weights and tumor volumes are measured every second or third day and at termination, tumors are removed and divided into two halves, with one half snap-frozen in liquid nitrogen and the other half fixed in paraffin. Snap-frozen tumors are processed for (DHE) superoxide detection as described in EXAMPLE 11 (along with corresponding hematoxylin and eosin [H&E] staining of the same tumor specimens).

Example 15

Tracking Micro-Metastasis In Vivo by Tracer-Coupled Recombinant VAR2CSA Peptides Recombinant VAR2CSA will be coupled to different applicable tracer-molecules in collaboration with external partners or outsourced on a contract-based agreement. The traceable recombinant VAR2CSA molecules are analyzed for their ability to track and report micro-metastasis in both xenograft and transgenic mouse models. In vivo models are established as described in EXAMPLE 12. For testing of tracer-coupled VAR2CSA in vivo, mice with metastatic cancer are analyzed by in vivo imaging for the ability of VAR2CSA to track and bind micro-metastasis.

Example 16

Internalization of Recombinant VAR2CSA Proteins

Recombinant VAR2CSA is internalized by cancer cells. This was shown by first conjugating VAR2CSA fragment (DBL1-ID2a) with a fluorophore and then analysing VAR2CSA uptake both by live imaging and on fixed cells. Cancer cell lines (C32 melanoma and MDA-MB-231) were seeded and grown overnight to 60-80% confluency. Cells were incubated with fluorophore-conjugated VAR2CSA for 10-15 min at 4° C. to allow for surface binding of VAR2CSA. Cells were then washed to remove unbound VAR2CSA, and subsequently incubated at 37° C. to initiate internalization for 10 min, 1 h, 2 h, 4 h, and up to 22 h. Fluorophore-conjugated transferrin was used for following classical clathrin-dependent uptake of transferrin ending up in the lysosomes. In addition, for some experiments fluorophore-conjugated dextran was used for detecting lysosomes. The live imaging analysis showed that VAR2CSA starts to reach lysosomes after around 4 h, and after 22 h all VAR2CSA can be localized to the lysosomal compartments. However, colocalization of VAR2CSA and transferrin was scarce, and VAR2CSA was taken up much slower than transferrin. The fact that recombinant VAR2CSA is taken up by cancer cells, allows us to fuse or conjugate VAR2CSA to cytotoxic compounds that become active inside the cancer cell. Table 10 summarizes the result from indicated cancer cell lines tested for internalization of recombinant VAR2CSA.

TABLE 10

Cells were incubated with medium alone (blank) or recombinant proteins (DBL1-ID2a or ID1-ID2a) at 75 nM for 1 h, followed by incubation with anti-V5-FITC (Invitrogen) at 1:800, cells were washed thrice between each incubation. Shown are the medium score of FITC fluorescence intensity at either the plasma membrane or intracellular structures recorded from a minimum of 4 high power field images using a HAL100 Zeiss microscope.

| Cell line | Plasma membrane localization (after 1 h) | Intracellular localization (after 1 h) |
|---|---|---|
| U2OS | + | ++++ |
| RH30 | + | +++ |
| MG63 | + | ++++ |
| MeWo | + | ++++ |
| HOS | + | +++ |
| MDA-MB-231 | + | ++++ |
| SKNMC | ++++ | (+) |
| RH18 | + | +++ |
| TC71 | + | ++ |
| TC3 | + | ++ |

Scoring system is: +: weak;, ++: medium; +++: strong; ++++: Very strong.

Example 17

Fused VAR2CSA-Toxin Protein Kills Cancer Cells

DBL1-ID2a and ID1-ID2a VAR2CSA gene fragments have been fused to *Pseudomonas* exotoxin A and diptheria toxin as various constructs (SEQ ID NO:60-70, 72). These fused VAR2CSA-toxin proteins are expressed in E. coli. The protein construct called BPTI-ID1-ID2aFCR3-PE38LR (SEQ ID NO:60), which is based on ID1-ID2a from VAR2CSA and PE38 has been successfully produced and analysed for binding to cancer cells (Table 11) as well as cytotoxic activity as described in Method 13.

Preliminary data show that this fused VAR2CSA-toxin protein binds to CSA-expressing cancer cells and is able to induce cell death (IC50 for the U2OS cell line is below 1 nM.

TABLE 11

Binding of VAR2CSA-PE38 to cancer cells analysed by flow cytometry
Binding of DBL1-ID2a (naked protein) and ID1-ID2a-PE38 at 200 nM to Myla2059 cells (T cell lymphoma) was detected with anti-PENTA HIS antibody and anti-mouse-FITC antibody and analysed by flow cytometry. Binding is given as mean fluorescence intensity (MFI).

|  | DBL1-ID2a | ID1-ID2a-PE38 | Control[c] |
|---|---|---|---|
| Binding to cells | 24.7 | 12.4 | 2.3 |
| Binding to treated cells[a] | 4.4 | 2.5 | 2.5 |
| Inhibition of binding[b] | 3.2 | 2.1 | — |

[a]cells were treated with chondroitinase ABC to remove CS chains from cell surface,
[b]protein was mixed with soluble CSA (400 ug/m) prior to addition to cells,
[c]control equals cells stained with the first and second layer of antibodies only.

Example 18

Analyzing the Anti-Tumor Effect of Cytotoxic Compounds Coupled to Recombinant VAR2CSA Based on the results in EXAMPLE 14 recombinant VAR2CSA will be sought coupled to relevant cytotoxic compounds and tested in vivo for performance. Coupling of relevant compounds to VAR2CSA will be performed in collaboration with external partners or outsourced on a contract-based agreement. In particular we analyze whether these VAR2CSA:compound-fusions can:
  i) be delivered specifically to the tumor environment in vivo.
  ii) be up-concentrated and retained specifically in the tumor environment in vivo.
  iii) specifically kill tumor cells with minimal damage to normal tissues in vivo.

In vivo models are established as described in EXAMPLE 12. The mice are treated with cytotoxic VAR2CSA conjugates, and the effect is assayed as described for un-conjugated protein in EXAMPLE 12.

Example 19

Purification of CSA-Expressing Stem Cells from Heterogeneous Cell Populations

Pluripotent stem cells have been reported to express high levels of CSPG4. Stem cells also express other CSA-containing proteoglycans, such as CD44, which VAR2CSA can bind to. Accordingly, recombinant VAR2CSA will be conjugated to an appropriate resin (beads), mixed with a heterogeneous but stem cell or cancer stem cell-containing cell population and sought purified by conventional centrifugation protocols. Purified cells will be analyzed for expression of diverse stem cell markers including CD44, CD31, CD4, OCT4, SOX2, Nestin and Nanog, by immunoblotting (as in EXAMPLE 11), microscopy and FACS (as in EXAMPLE 9). A common trait of cancer stem cells is high expression of Aldehyde dehydrogenase 1A (ALDH1 High). This can be conveniently measured using the ALDEFLUOR® Kit (Stem Cell Technologies). Recombinant VAR2CSA binding to MDA-MB-231 detects a subpopulation of ALDH1 High cells, suggesting that VAR2CSA can bind human cancer stem cells.

Example 20

Identification and Targeting of CD44-Expressing Cancer Stem Cells

CD44 is currently the most popular marker for cancer stem cells and it is a CSA-containing proteoglycan that can bind recombinant VAR2CSA. By using the same approaches as in EXAMPLE 12-15, it will be investigated whether un-modified and modified recombinant VAR2CSA peptides can locate, bind, purify and potentially kill the highly resistant CD44-positive cancer stem cells.

Example 21

Detection of Circulating Tumor Cells

We will examine whether recombinant VAR2CSA can be used as a prognostic marker for cancer recurrences. Cancer cells spread through the blood system after detachment from the primary tumor. A subsequent risk of the occurrence of circulating tumor cells (CTCs) is extravasation and metastasis. Current assays used for detecting CTCs have a poor sensitivity and cannot be directly correlated with risk of metastases. Using VAR2CSA-coupled magnetic beads and flow cytometry, we will investigate the prognostic value of detecting CS expressing cancer cells in the blood flow. This method could be used as a fast and painless examination of patients.

Example 22

Identification of Potential CSPG Molecules that were Targeted by VAR2CSA

Recombinant VAR2CSA protein (DBL1-ID2a) with a V5-tag was screened for binding to a panel of transfected HEK293 cells expressing >3000 human membrane receptors. A set of 25 receptors have been identified as potential targets of VAR2CSA (Table 12). The interaction between VAR2CSA and these receptors will be further verified by analysis of the binding specificity through inhibition with CSA and HS, both in the HEK293 system and in ELISA.

TABLE 12

Receptors that were experimentally identified as potential targets of VAR2CSA.

| Gene ID | Name | UniProt/SwissProt |
|---|---|---|
| BCAN | Brevican | PGCB HUMAN, Q96GW7 |
| BDKRB2 | Bradykinin receptor B2 | BKRB2 HUMAN, P30411 |

TABLE 12-continued

Receptors that were experimentally identified as potential targets of VAR2CSA.

| Gene ID | Name | UniProt/SwissProt |
| --- | --- | --- |
| CA9 | Carbonic anhydrase IX | CAH9 HUMAN, Q16790 |
| CCR10 | chemokine (C-C motif) receptor 10 | CCR10 HUMAN, P46092 |
| CD44 | CD44 molecule (Indian blood group) | CD44 HUMAN, P16070 |
| CDH8 | Cadherin 8, type 2 | CADH8 HUMAN, P55286 |
| CFB | Complement factor B | CFAB HUMAN, P00751 |
| GABBR2 | gamma-aminobutyric acid (GABA) B receptor, 2 | GABR2 HUMAN, O75899 |
| GPC3 | Glypican 3 | GPC3 HUMAN, P51654 |
| GPC5 | Glypican 5 | GPC5 HUMAN, P78333 |
| GPR65 | G-protein coupled receptor 65 | PSYR HUMAN, Q8IYL9 |
| GPRC5B | G protein-coupled receptor, family C, group 5, member B | GPC5B HUMAN, Q9NZH0 |
| KCNA2 | potassium voltage-gated channel, shaker-related subfamily, member 2 | KCNA2 HUMAN, P16389 |
| PKD2 | polycystic kidney disease 2 (autosomal dominant) | PKD2 HUMAN, Q13563 |
| PODXL2 | podocalyxin-like 2 | PDXL2 HUMAN, Q9NZ53 |
| PTPRG | protein tyrosine phosphatase, receptor type, G | PTPRG HUMAN, P23470 |
| S100A9 | S100 calcium binding protein A9 | S10A9 HUMAN, P06702 |
| SDC1 | Syndecan 1 | SDC1 HUMAN, P18827 |
| SDC4 | Syndecan 4 | SDC4 HUMAN, P31431 |
| STX2 | Syntaxin 2 | STX2 HUMAN, P32856 |
| STXBP5 | syntaxin binding protein 5 (tomosyn) | STXB5 HUMAN, Q5T5C0 |
| TGFBR3 | transforming growth factor, beta receptor III | TGBR3 HUMAN, Q03167 |
| TMEFF1 | transmembrane protein with EGF-like and two follistatin-like domains 1 | TEFF1 HUMAN, Q8IYR6 |
| TMEFF2/TENB2 | transmembrane protein with EGF-like and two follistatin-like domains 2 | TEFF2 HUMAN, Q9UIK5 |
| TMEM154 | Transmembrane protein 154 | (None) |
| BCAN | Brevican | PGCB HUMAN, Q96GW7 |
| BDKRB2 | Bradykinin receptor B2 | BKRB2 HUMAN, P30411 |
| CA9 | Carbonic anhydrase IX | CAH9 HUMAN, Q16790 |
| CCR10 | chemokine (C-C motif) receptor 10 | CCR10 HUMAN, P46092 |
| CD44 | CD44 molecule (Indian blood group) | CD44 HUMAN, P16070 |
| CDH8 | Cadherin 8, type 2 | CADH8 HUMAN, P55286 |
| CFB | Complement factor B | CFAB HUMAN, P00751 |
| GABBR2 | gamma-aminobutyric acid (GABA) B receptor, 2 | GABR2 HUMAN, O75899 |
| GPC3 | Glypican 3 | GPC3 HUMAN, P51654 |
| GPC5 | Glypican 5 | GPC5 HUMAN, P78333 |
| GPR65 | G-protein coupled receptor 65 | PSYR HUMAN, Q8IYL9 |
| GPRC5B | G protein-coupled receptor, family C, group 5, member B | GPC5B HUMAN, Q9NZH0 |
| KCNA2 | potassium voltage-gated channel, shaker-related subfamily, member 2 | KCNA2 HUMAN, P16389 |
| PKD2 | polycystic kidney disease 2 (autosomal dominant) | PKD2 HUMAN, Q13563 |
| PODXL2 | podocalyxin-like 2 | PDXL2 HUMAN, Q9NZ53 |
| PTPRG | protein tyrosine phosphatase, receptor type, G | PTPRG HUMAN, P23470 |
| S100A9 | S100 calcium binding protein A9 | S10A9 HUMAN, P06702 |
| SDC1 | Syndecan 1 | SDC1 HUMAN, P18827 |
| SDC4 | Syndecan 4 | SDC4 HUMAN, P31431 |
| STX2 | Syntaxin 2 | STX2 HUMAN, P32856 |
| STXBP5 | syntaxin binding protein 5 (tomosyn) | STXB5 HUMAN, Q5T5C0 |
| TGFBR3 | transforming growth factor, beta receptor III | TGBR3 HUMAN, Q03167 |
| TMEFF1 | transmembrane protein with EGF-like and two follistatin-like domains 1 | TEFF1 HUMAN, Q8IYR6 |
| TMEFF2/TENB2 | transmembrane protein with EGF-like and two follistatin-like domains 2 | TEFF2 HUMAN, Q9UIK5 |
| TMEM154 | Transmembrane protein 154 | (None) |
| THBD | Thrombomodulin | TRBM HUMAN, P07204 |
| CSPG5 | chondroitin sulfate proteoglycan 5 (neuroglycan C) | CSPG5 HUMAN, O95196 |
| STXBP5 | syntaxin binding protein 5 (tomosyn) | STXB5 HUMAN, Q5T5C0 |

DISCUSSION

Malaria is one of the most common infectious diseases and one of the largest global health problems. Pregnant women are especially vulnerable to infection, despite previously acquired immunity. In this study we have addressed key questions related to the molecular mechanism behind the VAR2CSA-CSA interaction in PM.

Previous work has suggested that the minimal CSA binding region in VAR2CSA is DBL2X-ID2b, with the need for DBL1X or DBL3X for full affinity binding (Dahlback, M., Jorgensen, L. M., Nielsen, M. A., Clausen, T. M., Ditlev, S. B., Resende, M., Pinto, V. V., Arnot, D. E., Theander, T.

G., and Salanti, A. *J Biol Chem* 286, 15908-15917). In continuation of this work we made further truncations of VAR2CSA, focusing on the DBL2X region. We show that the core CSA-binding site lies within the DBL2X domain including small parts of the flanking interdomain regions. The binding does not depend on the ID2b region, or on the DBL1X or DBL3X flanking domains, as previously suggested. This is evident by the specific CSPG binding of ID1-ID2a and ID1-DBL2Xb (Table 3). The minimal binding region is ID1-DBL2Xb, which bound CSPG with characteristics comparable to that of full-length VAR2CSA.

It is interesting that these new data maps the core-CSA binding site onto a single domain. Binding of DBL2X (and any other single DBL domain) to CSA has previously been shown to be non-specific and of weak affinity (Resende, M., Ditlev, S. B., Nielsen, M. A., Bodevin, S., Bruun, S., Pinto, V. V., Clausen, H., Turner, L., Theander, T. G., Salanti, A., and Dahlback, M. (2009) *Int J Parasitol* 39, 1195-1204). It is clear that the ID1 and parts of the ID2a interdomains are essential for CSA binding. DBL1X-DBL2Xa and ID1-DBL2Xa did not bind CSPG. The two C-terminal DBL2X borders (DBL2Xa and DBL2Xb) differ by 93 amino acids. Since deletion of these amino acids eliminates binding they must be important for CSA binding.

The ID1-DBL2Xb minimal binding region is much smaller than full-length VAR2CSA, having a molecular weight of only 62 kDa. It is unlikely that further substantial truncations of VAR2CSA will be functional in binding CSA. Our data redefines DBL2X as a larger functional domain, incorporating parts of the flanking ID1 and ID2a interdomains.

A VAR2CSA based vaccine against PM must be able to induce a strong protective immune response. In this, the most important aspect is the generation of IgG antibodies capable of inhibiting placental-specific parasite adhesion. To test the immunogenic characteristics of our produced fragments, we used them in the immunization of rats. Sera raised against all fragments containing the CSA binding site inhibited parasite adhesion to CSA. Importantly, sera raised against ID1-ID2a resulted in almost complete inhibition. This suggests that the minimal CSA binding fragments retain the capacity for inducing a strong anti-adhesive immune response. This conclusion was further supported by the fact that antibodies purified from anti-FV2 serum on ID1-ID2a retained most of the adhesion blocking activity, and that the anti-ID1-ID2a antibody depleted anti-FV2 sample lost most of its activity. This indicates that epitopes required for the induction of adhesion blocking antibodies are located within this region.

In this study we have tested anti-VAR2CSA sera in homologous inhibition of FCR3 parasites binding to CSA. It is important that a vaccine is capable of inhibiting placental adhesion regardless of parasite strain origin. A major concern in vaccine development is therefore the high interclonal diversity among parasite variants. While recombinant full-length VAR2CSA is very immunogenic the antibodies produced are not cross-inhibitory (Avril, M., Hathaway, M. J., Srivastava, A., Dechavanne, S., Hommel, M., Beeson, J. G., Smith, J. D., and Gamain, B. *PLoS One* 6, e16622). A recent study shows that DNA-vaccination with ID1-DBL2X from FCR3, induces antibodies that are cross-inhibitory, inhibiting CSA adhesion of other laboratory strains as well as parasites isolated in the field (Bordbar, B., Tuikue-Ndam, N., Bigey, P., Doritchamou, J., Scherman, D., and Deloron, P. Vaccine). This supports the use of this small fragment in a PM vaccine.

Cardin and Weintraub predicted that a GAG binding site would take one of two forms (Cardin, A. D., and Weintraub, H. J. (1989) *Arteriosclerosis* 9, 21-32). These are X-B-B-X-B-X (SEQ ID NO: 132) and X-B-B-B-X-X-B-X (SEQ ID NO:128), where X is any hydropathic residue and B is any basic residue, with a preference for arginine. Both of these describe a binding site for a sulfated disaccharide. While many interactions may occur, the ionic interaction between negatively charged sulfates and basic amino acids are thought to be most important. We mutated two such sites within the minimal binding region; 625-GKNLKKRY-632 (SEQ ID NO:130) in DBL2X and 458-NKKKECKD-465 (SEQ ID NO:129) in ID1. We also deleted a large region within a dimorphic sequence motif (DSM) located in the N-terminal part of DBL2X, as this has been suggested to have a function in binding. Deletion of the DSM region had no affect on CSA binding. Neither did any substitutions in the putative GAG binding sites. This is a clear indication that these sites have little or no function in CSA binding.

It has been shown that the minimal binding requirement for the human CSA receptor is a dodecasaccharide with 2-4 C4 sulfated GalNAc monosaccharides (Alkhalil, A., Achur, R. N., Valiyaveettil, M., Ockenhouse, C. F., and Gowda, D. C. (2000) J Biol Chem 275, 40357-40364). It is remarkable that the VAR2CSA expressing parasites, in vivo, are very specific for CSA carrying only 2-8% C4 sulfated disaccharide units. To examine if the VAR2CSA-CSA complex formation is dependent on ionic interactions, we tested binding at different salt concentrations. Binding of ID1-ID2a, DBL1X-ID2a and FV2 in 150 mM-300 mM NaCl show a linear relationship when plotting Log ($K_{D,observed}$) vs. Log [Na$^+$]. We find that binding depends on a maximum of 2-3 ionic interactions. It is interesting that the value for the full-length protein is higher than for the shorter fragments, indicating that this protein makes an additional ionic interaction with CSA. We have in this study screened for fragments containing the CSA specific high-affinity binding region. It is possible that more interactions occur in downstream regions of the protein, but that the core site lies within DBL2X. Extrapolating and finding the Y intercept ([Na$^+$]=1 M, Log [Na$^+$]=0) tells us that $K_{D,nonionic}$=5.9 µM for FV2, $K_{D,nonionic}$=3.4 µM for DBL1X-ID2a, and $K_{D,nonionic}$=0.7 µM for ID1-ID2a. This indicates that only 25-30% of the VAR2CSA-CSA binding can be accounted for by ionic interactions. This is in contrast to other GAG binding proteins, which have shown up to 80-90% dependency on ionic interactions in similar assays (Faller, B., Mely, Y., Gerard, D., and Bieth, J. G. (1992) Biochemistry 31, 8285-8290; Hileman, R. E., Fromm, J. R., Weiler, J. M., and Linhardt, R. J. (1998) Bioessays 20, 156-167).

Our data suggest that the VAR2CSA-CSA interaction does not conform to conventional GAG-protein interactions. We hypothesize that the high CSA affinity is achieved through a multivalent interaction, which may include multiple binding sites making nonionic interactions with the CSA carbohydrate backbone. Some of the interaction is ionic and some degree of sulfation is needed for VAR2CSA binding. It is therefore likely that there is an interaction between basic amino acids and sulfates, but that this is not the determining factor in the affinity.

In this study we have defined a small single-domain VAR2CSA fragment that can be produced in eukaryotic cells as a functional CSA-binding protein, and has the capacity to induce highly adhesion-blocking antibodies. This fragment has the potential to be a powerful candidate for a vaccine against PM.

The data identifies a small recombinant part of VAR2CSA that binds specifically to CSA thereby mediating placental binding of infected erythrocytes. We show that this VAR2CSA fragment also binds specifically to cancer cells, through an interaction with CSA presented on CSPG4 or other protein backbones that were identified in this study. In addition, we find that binding of VAR2CSA polypeptides, based on this small fragment, to cancer cells inhibits migration and invasion of the cells. These VAR2CSA polypeptides also inhibit canonical ERK signaling, and we find that VAR2CSA polypeptides that are fused to a toxin efficiently kill the cancer cells.

METHODS

METHOD 1—Cloning and Protein Expression in Insect Cells

VAR2CSA sequence fragments were amplified from codon optimized FCR3 (GenBank accession no. GU249598) or 3D7 (GenBank accession no. JQ247428) VAR2CSA genes using specific primers (Table 2). Simple fragments were amplified in a one-step PCR. Amino acid substitution constructs were made in a two-step PCR. First PCR amplified two fragments from the codon optimized FCR3 template, containing overlapping complimentary ends. Second PCR amplified the total construct, using the two overlapping fragments as template with primers specific for the outer borders. All fragments were sequenced for verification. Fragments were cloned into the baculovirus vector pAcGP67-A (BD Biosciences), modified to contain a V5 and His tag at the C-terminal. The proteins were expressed in baculovirus-infected insect cells as soluble protein secreted into the cell culture supernatant. Briefly, linearized BAK-PAK6 Baculovirus DNA (BD Biosciences) was co-transfected with the pAcGP67-A plasmids, into Sf9 insect cells for generation of recombinant virus particles. 10 ml of the second amplification was used to infect HIGH FIVE cells in 400 ml serum-free medium (10486, GIBCO) at a density of $1 \times 10^6$ cells/ml. The secreted recombinant protein was harvested from the supernatant 3 days after initial infection. The supernatant was filtered (0.2 µm), dialyzed and concentrated before protein purification.

METHOD 2—Protein Purification and SDS-PAGE

The filtered supernatant containing the secreted recombinant protein was dialyzed using an AKTA cross-flow (GE Healthcare). The dialysis was performed in 10 mM $NaH_2PO_4$ (pH 7.4, Sigma-Aldrich) and 500 mM NaCl. The resulting solution was filtered (0.2 µm) and imidiazole was added to a final concentration of 15 mM. The protein was then purified on a 1-ml HisSelect column (H8286, Sigma-Aldrich). Bound protein was eluted with 10 mM $NaH_2PO_4$ (pH 7.4), 500 mM NaCl, and 500 mM imidiazole. Proteins needed for Quartz Crystal Microbalance measurements and SAXS were further purified to obtain monomers by size exclusion chromatography using a HiLoad 16/60 SUPERDEX 200 column (GE Healthcare) in 20 mM Tris (pH 8) and 200 mM NaCl. The purity and structural integrity of the protein was verified by SDS-PAGE.

METHOD 3—ELISA

FALCON microtiter plates (351172, BD Biosciences) were incubated at a concentration of 3 µg/ml for CSPG (bovine) (D8428, Sigma) or HSPG (H4777, Sigma) and 100 µg/ml for CSA (C9819, Sigma), CSC (400675, Seikagaku), and CSB (C3788, Sigma) overnight at 4° C. The plates were then blocked with TSM binding buffer (20 mM Tris, 150 mM NaCl, 2 mM $CaCl_2$), 0.05% TWEEN-20 surfactant, 1% BSA, PH7.4 at 25° C.) for 2 hours at 37° C. on a shaker. A 2-fold dilution series (1.56 mM-100 mM) of protein was prepared in TSM binding buffer and added to the plates, which was incubated 1 hr at 37° C. on a shaker. All measurements were performed in triplicates. The plates were washed three times in TSM washing buffer (20 mM Tris, 150 mM NaCl, 2 mM $CaCl_2$), 0.05% TWEEN-20 surfactant, PH7.4 at 25° C.). The plates were then incubated with 1:3000 anti-V5-HRP antibody (R96125, Invitrogen) in TSM binding buffer 1 hr at 37° C. on a shaker. The plates were washed three times in TSM washing buffer. Finally the plates were developed with o-phenylenediamine substrate (DAKO) for 15 min. The reaction was quenched with 2.5M $H2504$. Absorbance was measured at 490 nm.

METHOD 4—Quartz Crystal Microbalance (ATTANA A100 biosensor)

Experiments were performed on an ATTANA A100 biosensor (Attana AB), using gold plated 10 MHz, AT-cut quartz crystal, polystyrene chips (3611-3103 Attana AB). All buffers and reagents were filtered to 0.2 µm. The ligand was CSPG (Bovine) (D8428, Sigma) or HSPG (H4777, Sigma), coated at a concentration of 1004/ml. Coating was done in steady state by adding ligand solution and incubation 30 minutes at room temperature. This was followed by blocking the plate with PBS containing 0.1% Ig-free BSA (BSA-50, Rockland), 30 minutes at room temperature. The ATTANA A100 biosensor was washed with 1% SDS prior to every experiment, using the manufacturers predefined daily wash program. Following the wash, the running buffer was switched to PBS at a flow rate of 25 µl/min, at 25° C., and the machine was allowed to stabilize at a maximum change in frequency of 0.5 Hz/min. Once stabilized PBS was injected multiple times to show that the injection process minimally affected the baseline. Prior to sample injection PBS was injected as a blank. Analyte was injected in a 1:3 dilution series (0.25 µg/ml-60 µg/ml) starting with the lowest concentration. Association time was set to 84 seconds and disassociation time to 5 minutes. Due to high affinity of binding it was not possible to regenerate binding surface following injections. The data collected was processed in the ATTESTER Evaluation software (Attana AB). Curves were fitted in a simple 1:1 model. $k_{on}$ and $k_{off}$ were determined by curve fitting and $K_D$ was calculated based $K_D = k_{off}/k_{on}$.

METHOD 5—Salt Titration Assay

The ionic dependency of VAR2CSA-CSA binding was tested in an ELISA based binding assay. CSPG was coated at 3 µg/ml. A 1:2 dilution series (400-1.56 nM) of protein was added in several different NaCl concentrations (150 mM, 200 mM, 250 mM, and 300 mM). All experiments were performed in triplicates. The $K_D$ values were calculated for each titration series in GRAPHPAD PRISM software using non-linear regression (Least squares fit with hill slope).

METHOD 6—Animal Immunizations and Serum Extraction

All animal immunizations complied with national and European regulations. Wistar rats were injected subcutaneously with 30 µg recombinant protein in Freunds complete adjuvant (F5881, Sigma-Aldrich). The immunization was boosted three times at 3-week intervals with 15 protein in Freunds incomplete adjuvant (F5506, Sigma-Aldrich). Blood samples were taken one week after each boost, and serum was extracted by centrifugation.

METHOD 7—IgG Affinity Purification

Pools of sera from rats immunized with full-length FCR3 VAR2CSA (FV2) were affinity purified on 1 ml NHS-activated HP column (HiTrap NHS-activated HP, 17-0716-01, GE Healthcare), containing immobilized multidomain FCR3 proteins (DBL1X-DBL2Xa, DBL1X-ID2a, ID1-ID2a, or ID1-DBL4g) and full-length FV2. Purification was done according to the manufacturer's protocol. In short, coupling of ligand to column was done by adding 1 ml 1:1 solution of coupling buffer (0.2 M $NaHCO_3$, 0.5 M NaCl, pH 8.3) and ligand (concentration 0.5-10 mg/ml) to the column. The column was sealed and incubated for 30 min at room temperature, followed by incubation at 4° C. overnight. The column was washed with 6 ml Buffer A (0.5 M ethanolamine, 0.5 M NaCl, pH 8.3), 6 ml Buffer B (0.1 M acetate, 0.5 M NaCl, pH 4) and finally 6 ml Buffer A. After an incubation period of 30 min at room temperature, the washing was repeated in reverse order (Buffer B, A, B). 8-10 ml PBS was injected to adjust the pH before purifying the serum. The sample was passed through the column 3-5 times. The column was washed with 10 ml PBS before antibodies were eluted with 10 ml elution buffer (0.1 M citric acid, pH 2.7).

METHOD 8—*P. falciparum* Parasite Cultures

*P. falciparum* FCR3 type parasites were maintained in culture using 5% hematocrit (Human Blood-group 0 Rh+) in parasite medium RPMI-1640 (BE12115F, Lonza) supplemented with 25 mM $NaHCO_3$, 0.125 µg/ml gentamicin sulfate (BE02012E, Lonza), 0.125 µg/ml AlbuMAX II (11021029, Invitrogen) and 2% normal human serum. IEs were repeatedly panned on BeWo cells (CCL98, ATCC) to maintain the CSA adhering phenotype. Furthermore, isolates were tested to be mycoplasma negative and were regularly genotyped by PCR using nested GLURP (Glutamate-rich protein) and MSP-2 (Merozoite surface protein 2) primers.

METHOD 9—Purification of Late Stage Trophozoites

Parasite cultures were enriched for late trophozoite and schizont stage in a strong magnetic field using a MACS CS-column (130-041-305, Miltenyi Biotec) and a VARIO-MACS magnet (Miltenyi Biotec). In brief, the parasite culture suspension was applied to the column. The column was then washed with 2% fetal calf serum (F6178, Sigma-Aldrich) in PBS. Late-stage infected erythrocytes were elute from the column after separation from the magnet, spun down and resuspended in 2% fetal calf serum in PBS and diluted to a concentration of $2\times10^6$ IEs/ml.

METHOD 10—Flow Cytometry (FCM)

Antibody binding to native VAR2CSA on the purified late-stage trophozoites infected erythrocytes, was measured by flow cytometry (FCM). 100 µl purified late-stage parasites at a concentration of $2\times10^5$ IEs/ml in PBS with 2% FCS were labeled with serum (depleted for non-specific binding by pre-incubation with non-infected erythrocytes) in a final concentration of 1:10. The cells were washed three times in PBS with 2% FCS. The cells were then further labeled with ethidium bromide (15585011, Invitrogen) in a final concentration of 2 µg/ml and a 1:100 dilution of FITC labeled secondary anti-rat-IgG antibody (62-9511, Invitrogen). As negative controls, late-stage parasites were also incubated with serum from rats immunized with an antigen other than VAR2CSA and with secondary antibodies alone. Data from 5000 ethidium bromide positive IEs were collected using a FC500 flow cytometer (Beckmann Coulter). Finally the median fluorescence intensity was determined using the WINLIST 5.0 software (Verify Software House).

METHOD 11—Inhibition of Parasites Binding CSPG

Serum antibodies were analyzed for their ability to inhibit IE binding to CSPG. This was done in a 96-well plate format using a robot-standardized washing method. Wells were coated with 2 µg/ml CSPG (D8428, Sigma-Aldrich). A total of $2\times10^5$ tritium labeled (Hypoxanthine Monohydrochloride, PerkinElmer, NET177005MC) late-stage IEs in 100 µL were added in triplicates to the wells. The labeled IEs were then incubated with serum for 90 min at 37° C. Unbound IEs were washed away by a pipetting robot (Beckman Coulter). The proportion of adhering IEs was determined by liquid scintillation counting on a TOPCOUNT NXT (Perkin-Elmer).

METHOD 12a—Cancer Cell Binding Assays

Flow-cytometry (FCM) was used to test the reactivity of the VAR2CSA minimal binding polypeptide to CSPG expressed on the surface of various cell lines. Cells were cultured in RPMI supplemented with 10% foetal calf serum (CHO cells, C32), Hams F12 (BeWo), kept in 5% carbon dioxide at 37° C. or purified from a human blood sample in CPD buffer (red blood cells). Aliquots of cells ($1\times10^5$) were sequentially exposed to the VAR2CSA minimal binding polypeptide (150, 75 or 37 nM) and a-V5-FITC (1:800) (Invitrogen) diluted in FACS2 (PBS+2% FCS) for 30 minutes at +4 C in dark with smooth agitation. As negative controls a truncated version of the minimal binding polypeptide and FACS2 buffer were used. Intact cells were gated based on the forward and side scatter signal. Data were acquired using a FC500 flow-cytometer (Beckman Coulter) from a minimum of 5000 cells. All samples relating to a particular cell line were processed and analyzed in a single assay.

METHOD 12b—Cancer Cell Binding Assays

As an alternative to the flow-cytometry assay above, cells were incubated with VAR2CSA minimal binding polypeptide and a-V5-FITC (1:500)(Invitrogen) diluted in HBSS. VAR2CSA polypeptide was used at the same concentrations as written above. Following a-V5-FITC staining cells were washed 3 times in HBSS, collected in Enzyme-free cell detachment buffer (Invitrogen) and analyzed on a FACSCALIBUR device (BD Biosciences) for FL-1 signal intensity.

Abbreviations CIDR, cysteine-rich inter-domain region; CSA, chondroitin sulfate A; CSPG, chondroitin sulfate proteoglycan; DBL, Duffy binding-like domain; FCM, flow-cytometry; FV2, full-length ecto-domain of the VAR2CSA protein without N-terminal segment; HSPG, heparan sulfate proteoglycan; ID, inter-domain; IE, *P. falciparum*-infected erythrocyte; NTS, N-terminal segment; PM, placental malaria; PfEMP1, *Plasmodium falciparum* erythrocyte membrane protein 1; PM, placental malaria.

METHOD 13—Cytotoxicity Test In Vitro of Fused VAR2CSA-Toxin Proteins

Cancer cell lines were seeded in a 96-well plate, with 500.0 cells/well one day before the experiment. On the day of experiment a 10-fold dilution series (ranging from 10 µg/ml to 0.01 ng/ml) of fused VAR2CSA-toxin, and control protein (VAR2CSA without toxin) was added to separate wells. Similar dilution series, which also contained 400 µg/ml of CSA, was made for both proteins and added to separate wells. The cells with proteins were incubated for 72 hours at 37° C. Cell death was analyzed by a MTT cell proliferation assay, where readout is absorbance at 570 nm.

METHOD 14—Staining of Paraffin-Embedded Human Tissue Samples

The binding of recombinant VAR2CSA to primary cancer tissue obtained from human patients is investigated using immunohistochemistry (IHC). Paraffin embedded tissue spotted on glass slides subjected no antigen retrieval was incubated with 0.1-500 nM V5-VAR2CSA variants or V5-Control protein (DBL4) for 1 h in room temperature, washed for 8 minutes, incubated with 1:700 mouse anti-V5 antibody for 30 minutes, washed for 8 minutes. Bound anti-V5 was subsequently detected using UltraMap anti-mouse HRP using the Ventana DISCOVERY XT platform.

The invention claimed is:

1. A conjugate or a fusion protein comprising an isolated VAR2CSA polypeptide and a diagnostic effector moiety, wherein said VAR2CSA polypeptide comprises a wild-type ID1-DBL2Xb sequence having at least 70% sequence identity to the full-length sequence set forth in SEQ ID NO: 1 and has the functional activity of binding to chondroitin sulfate A (CSA), or a wild-type ID1-DBL2Xb sequence in the form of a functional fragment of SEQ ID NO: 1 that is between 570 and 640 amino acids in length, wherein the functional fragment has the functional activity of binding to CSA, wherein said diagnostic effector moiety is a magnetic bead capable of being detected upon binding of said conjugate to CSA expressed on cancer cells.

2. The conjugate or the fusion protein of claim 1, wherein ID1 of the ID1-DBL2Xb sequence consists of an amino acid sequence of a wild-type VAR2CSA with at least 70% sequence identity to the amino acid sequence identified by amino acids 1-152 of SEQ ID NO: 1 and DBL2Xb of the ID1-DBL2Xb sequence consists of an amino acid sequence of a wild-type VAR2CSA with at least 70% sequence identity to the amino acid sequence identified by amino acids 153-577 of SEQ ID NO: 1, and wherein said functional fragment has the functional activity of binding to CSA.

3. The conjugate or the fusion protein of claim 2, wherein ID1 of the ID1-DBL2Xb sequence consists of amino acids 1-152 of SEQ ID NO: 1 and DBL2Xb of the ID1-DBL2Xb sequence consists of amino acids 153-577 of SEQ ID NO: 1.

4. The conjugate or the fusion protein of claim 1, wherein the VAR2CSA polypeptide has at least 75% sequence identity to the full-length sequence set forth in SEQ ID NO: 1.

5. A composition comprising the conjugate or the fusion protein of claim 1.

6. A diagnostic composition comprising the conjugate or the fusion protein of claim 1.

7. The composition of claim 5 further comprising a cancer cell.

8. The composition of claim 7, wherein said cancer cell is a CSA-expressing cancer cell.

9. The composition of claim 8, wherein said CSA-expressing cancer cell is bound to the conjugate or the fusion protein.

10. The composition of claim 8, wherein said CSA-expressing cancer cell is selected from the group consisting of a melanoma cell, a lung carcinoma cell, a breast carcinoma cell, an osteocarcinoma cell, a rhabdomyosarcoma cell and a cutaneous T-cell lymphoma cell.

11. The composition of claim 8, wherein said CSA-expressing cancer cell is a melanoma cell.

12. The composition of claim 11, wherein said melanoma cell further expresses CSPG4.

13. A conjugate or a fusion protein comprising an isolated VAR2CSA polypeptide and a diagnostic effector moiety,
    wherein said VAR2CSA polypeptide comprises amino acid residues 1-577 of SEQ ID NO: 1,
    wherein said diagnostic effector moiety is a magnetic bead capable of being detected upon binding of said conjugate to CSA on cancer cells.

* * * * *